(12) United States Patent
Hansen et al.

(10) Patent No.: US 12,048,732 B2
(45) Date of Patent: Jul. 30, 2024

(54) METHODS OF TREATING BREAST CANCER

(71) Applicant: Blaze Bioscience, Inc., Seattle, WA (US)

(72) Inventors: Stacey J. Hansen, Seattle, WA (US); Julia E. Novak, Seattle, WA (US)

(73) Assignee: Blaze Bioscience, Inc., Seattle, WA (US)

( * ) Notice: Subject to any disclaimer, the term of this patent is extended or adjusted under 35 U.S.C. 154(b) by 0 days.

(21) Appl. No.: 16/093,508

(22) PCT Filed: Apr. 14, 2017

(86) PCT No.: PCT/US2017/027812
§ 371 (c)(1),
(2) Date: Oct. 12, 2018

(87) PCT Pub. No.: WO2017/181149
PCT Pub. Date: Oct. 19, 2017

(65) Prior Publication Data
US 2019/0282661 A1   Sep. 19, 2019

Related U.S. Application Data

(60) Provisional application No. 62/485,830, filed on Apr. 14, 2017, provisional application No. 62/323,522, filed on Apr. 15, 2016.

(51) Int. Cl.
| | | |
|---|---|---|
| A61K 38/17 | (2006.01) |
| A61K 9/00 | (2006.01) |
| A61K 31/337 | (2006.01) |
| A61K 31/502 | (2006.01) |
| A61K 31/517 | (2006.01) |
| A61K 31/519 | (2006.01) |
| A61K 31/555 | (2006.01) |
| A61K 31/704 | (2006.01) |
| A61K 33/243 | (2019.01) |
| A61K 47/64 | (2017.01) |
| A61K 49/00 | (2006.01) |
| A61P 35/00 | (2006.01) |
| C07K 14/00 | (2006.01) |
| C07K 14/435 | (2006.01) |

(52) U.S. Cl.
CPC ........ *A61K 38/1767* (2013.01); *A61K 9/0019* (2013.01); *A61K 31/337* (2013.01); *A61K 31/502* (2013.01); *A61K 31/517* (2013.01); *A61K 31/519* (2013.01); *A61K 31/555* (2013.01); *A61K 31/704* (2013.01); *A61K 33/243* (2019.01); *A61K 47/6415* (2017.08); *A61K 49/0032* (2013.01); *A61K 49/0056* (2013.01); *A61P 35/00* (2018.01); *C07K 14/00* (2013.01); *C07K 14/43522* (2013.01)

(58) Field of Classification Search
CPC ............ A61K 2123/00; A61K 2121/00; A61K 38/00; A61K 38/1767; A61K 49/00; A61K 49/0056; A61K 49/0032; A61K 31/00; A61K 31/704; A61K 31/555; A61K 31/519; A61K 31/517; A61K 31/502; A61K 31/337; A61K 9/00; A61K 9/0019; A61K 33/00; A61K 33/243; A61K 47/00; A61K 47/6415; A61P 35/00; C07K 14/00; C07K 14/43522
USPC .......... 424/1.11, 1.49, 1.65, 1.69, 1.81, 1.85, 424/1.89, 9.1, 9.2, 9.3, 9.4, 9.5, 9.6; 514/1, 1.1, 19.2, 19.3, 19.4, 19.5, 19.6, 514/21.3; 530/300, 324
See application file for complete search history.

(56) References Cited

U.S. PATENT DOCUMENTS

| | | |
|---|---|---|
| 4,414,148 A | 11/1983 | Jansen et al. |
| 4,444,744 A | 4/1984 | Goldenberg |
| 4,569,789 A | 2/1986 | Blattler et al. |
| 4,659,839 A | 4/1987 | Nicolotti et al. |
| 4,671,958 A | 6/1987 | Rodwell et al. |
| 4,680,338 A | 7/1987 | Sundoro |
| 4,699,784 A | 10/1987 | Shih et al. |
| 5,051,364 A | 9/1991 | Isacke et al. |
| 5,212,290 A | 5/1993 | Vogelstein et al. |
| 5,223,253 A | 6/1993 | Hall et al. |
| 5,236,844 A | 8/1993 | Basset et al. |

(Continued)

FOREIGN PATENT DOCUMENTS

| | | |
|---|---|---|
| AU | 2014323563 A1 | 4/2016 |
| AU | 2020200116 A1 | 1/2020 |

(Continued)

OTHER PUBLICATIONS

Sharma et al, J. Adv. Pharm. Technol. Res., vol. 1, No. 2, pp. 109-126) (Year: 2010).*
Susan G. Komen, 2014 Breast Cancer Fact Sheet, Jun. 10, 2014, 4 pages, https://www.komensandiego.org/wp-content/uploads/2014/04/2014-Breast-Cancer-Fact-Sheet-6-10-14-FINAL.pdf (Year: 2014).*
Ivanovic et al, World Journal of Surgical Oncology, vol. 13, No. 153, 6 pages (Year: 2015).*

(Continued)

*Primary Examiner* — D. L. Jones
(74) *Attorney, Agent, or Firm* — DLA Piper LLP; Melissa Harwood

(57) ABSTRACT

Compositions and formulations comprising chlorotoxin conjugate compounds are provided, including native and modified variants of chlorotoxin peptide conjugated to detectable agents or active agents. Methods of detecting and treating ductal carcinoma in situ breast cancer, invasive ductal carcinoma breast cancer, lobular carcinoma in situ, invasive lobular carcinoma, and triple-negative breast cancer with chlorotoxin conjugate compounds are also provided, including methods of imaging tumor tissues and cells.

32 Claims, 29 Drawing Sheets

Specification includes a Sequence Listing.

(56) References Cited

U.S. PATENT DOCUMENTS

| | | | |
|---|---|---|---|
| 5,314,992 A | 5/1994 | Guyre et al. |
| 5,591,829 A | 1/1997 | Matsushita |
| 5,626,862 A | 5/1997 | Brem et al. |
| 5,688,773 A | 11/1997 | Chiocca et al. |
| 5,750,376 A | 5/1998 | Weiss et al. |
| 5,756,340 A | 5/1998 | Hammock et al. |
| 5,866,570 A | 2/1999 | Liang et al. |
| 5,905,027 A | 5/1999 | Ullrich et al. |
| 5,935,795 A | 8/1999 | Lin et al. |
| 5,968,479 A | 10/1999 | Ito et al. |
| 5,985,822 A | 11/1999 | Edelman et al. |
| 6,028,174 A | 2/2000 | Ullrich et al. |
| 6,130,101 A | 10/2000 | Mao et al. |
| 6,319,891 B1 | 11/2001 | Sontheimer et al. |
| 6,403,625 B1 | 6/2002 | Nagao et al. |
| 6,429,187 B1 | 8/2002 | Sontheimer et al. |
| 6,514,481 B1 | 2/2003 | Prasad et al. |
| 6,555,652 B1 | 4/2003 | Itoh et al. |
| 6,610,547 B1 | 8/2003 | Klaveness et al. |
| 6,667,156 B2 | 12/2003 | Lyons et al. |
| 6,767,635 B1 | 7/2004 | Bahr et al. |
| 6,849,714 B1 | 2/2005 | Bridon et al. |
| 6,870,029 B2 | 3/2005 | Sontheimer et al. |
| 6,926,896 B2 | 8/2005 | Bosslet et al. |
| 6,972,326 B2 | 12/2005 | Haugland et al. |
| 7,094,868 B2 | 8/2006 | Samoylova et al. |
| 7,252,998 B2 | 8/2007 | Skerra et al. |
| 7,462,446 B2 | 12/2008 | Zhang et al. |
| 7,678,759 B2 | 3/2010 | Sontheimer et al. |
| 7,904,868 B2 | 3/2011 | Feilchenfeld et al. |
| 8,227,439 B2 | 7/2012 | O'Neill et al. |
| 8,470,607 B2 | 6/2013 | Jacoby et al. |
| 8,778,310 B2 | 7/2014 | Zhang et al. |
| 9,018,347 B2 | 4/2015 | Sentissi |
| 9,944,683 B2 | 4/2018 | Olson |
| 10,156,559 B2 | 12/2018 | Olson et al. |
| 10,822,381 B2 | 11/2020 | Olson |
| 11,826,399 B2 | 11/2023 | McGonigle et al. |
| 2001/0007025 A1 | 7/2001 | Bennett et al. |
| 2002/0065216 A1 | 5/2002 | Sontheimer et al. |
| 2002/0146749 A1 | 10/2002 | Lyons et al. |
| 2003/0021810 A1 | 1/2003 | Sontheimer et al. |
| 2003/0105000 A1 | 6/2003 | Pero et al. |
| 2003/0201208 A1 | 10/2003 | Koch et al. |
| 2003/0216322 A1 | 11/2003 | Samoylova et al. |
| 2003/0232013 A1 | 12/2003 | Sieckman et al. |
| 2004/0101822 A1 | 5/2004 | Wiesner et al. |
| 2004/0102381 A1 | 5/2004 | Ekwuribe et al. |
| 2004/0105980 A1 | 6/2004 | Sudarshan et al. |
| 2004/0141981 A1 | 7/2004 | Sontheimer et al. |
| 2004/0180846 A1 | 9/2004 | Huang et al. |
| 2005/0142062 A1 | 6/2005 | Sontheimer et al. |
| 2005/0261191 A1 | 11/2005 | Barasch et al. |
| 2006/0019256 A1 | 1/2006 | Clarke et al. |
| 2006/0019347 A1 | 1/2006 | Cho et al. |
| 2006/0088899 A1 | 4/2006 | Alvarez et al. |
| 2006/0166892 A1 | 7/2006 | Alvarez et al. |
| 2007/0071764 A1 | 3/2007 | Sullivan et al. |
| 2007/0154965 A1 | 7/2007 | Zhang et al. |
| 2007/0237714 A1 | 10/2007 | Alvarez |
| 2007/0275902 A1 | 11/2007 | Gonda et al. |
| 2008/0153745 A1 | 6/2008 | Tian |
| 2008/0153746 A1 | 6/2008 | Alvarez et al. |
| 2008/0279780 A1 | 11/2008 | Zhang et al. |
| 2009/0004105 A1 | 1/2009 | Cheng et al. |
| 2009/0028788 A1 | 1/2009 | Achilefu |
| 2009/0123946 A1 | 5/2009 | Birkenmeyer et al. |
| 2009/0123970 A1 | 5/2009 | Tu et al. |
| 2009/0124022 A1 | 5/2009 | Birkenmeyer et al. |
| 2009/0176274 A1 | 7/2009 | Tu et al. |
| 2009/0203598 A1 | 8/2009 | McCarty et al. |
| 2009/0220430 A1 | 9/2009 | Rajopadhye et al. |
| 2009/0263894 A1 | 10/2009 | Birkenmeyer et al. |
| 2009/0269777 A1 | 10/2009 | Birkenmeyer et al. |
| 2009/0304592 A1 | 12/2009 | O'Neill et al. |
| 2009/0311224 A1 | 12/2009 | Lee et al. |
| 2010/0098637 A1 | 4/2010 | Orringer et al. |
| 2010/0105150 A1 | 4/2010 | Adamczyk et al. |
| 2010/0210546 A1 | 8/2010 | Alvarez et al. |
| 2010/0215575 A1 | 8/2010 | O'Neill et al. |
| 2010/0215576 A1 | 8/2010 | Sontheimer et al. |
| 2011/0027177 A1 | 2/2011 | Jacoby et al. |
| 2011/0055751 A1 | 3/2011 | Morrison et al. |
| 2011/0091380 A1 | 4/2011 | Jacoby et al. |
| 2011/0311445 A1 | 12/2011 | Alvarez et al. |
| 2012/0156131 A1 | 6/2012 | Alvarez |
| 2012/0183544 A1 | 7/2012 | Sontheimer et al. |
| 2013/0028836 A1 | 1/2013 | Sentissi et al. |
| 2013/0045163 A1 | 2/2013 | O'Neill et al. |
| 2013/0195760 A1 | 8/2013 | Olson |
| 2014/0179560 A1 | 6/2014 | Olson et al. |
| 2014/0241993 A1 | 8/2014 | Zhang et al. |
| 2015/0030537 A1 | 1/2015 | Sentissi et al. |
| 2015/0080721 A1 | 3/2015 | Novak et al. |
| 2015/0316536 A1 | 11/2015 | Olson et al. |
| 2015/0374860 A1 | 12/2015 | O'Neill et al. |
| 2016/0096869 A1 | 4/2016 | Hansen et al. |
| 2017/0304342 A1 | 10/2017 | Cox et al. |
| 2020/0188536 A1 | 6/2020 | Hansen et al. |

FOREIGN PATENT DOCUMENTS

| | | |
|---|---|---|
| CN | 1180316 A | 4/1998 |
| CN | 1924006 A | 3/2007 |
| CN | 101003788 A | 7/2007 |
| CN | 101270158 A | 9/2008 |
| CN | 101381405 A | 3/2009 |
| CN | 101824084 A | 9/2010 |
| CN | 101921769 A | 12/2010 |
| CN | 102844044 A | 12/2012 |
| CN | 103097403 A | 5/2013 |
| CN | 104877016 A | 9/2015 |
| EP | 0155396 A2 | 9/1985 |
| EP | 0188256 A2 | 7/1986 |
| EP | 1430131 B1 | 11/2005 |
| EP | 2182004 A1 | 5/2010 |
| EP | 3046572 A1 | 7/2016 |
| JP | H08505615 A | 6/1996 |
| JP | H08325291 A | 12/1996 |
| JP | H0971599 A | 3/1997 |
| JP | H09127115 A | 5/1997 |
| JP | 2002542206 A | 12/2002 |
| JP | 2005537234 A | 12/2005 |
| JP | 2008538506 A | 10/2008 |
| JP | 2009280567 A | 12/2009 |
| JP | 2009300110 A | 12/2009 |
| JP | 2010085108 A | 4/2010 |
| JP | 2013532126 A | 8/2013 |
| WO | WO-8802117 A1 | 3/1988 |
| WO | WO-9311222 A1 | 6/1993 |
| WO | WO-9415615 A1 | 7/1994 |
| WO | WO-9724619 A1 | 7/1997 |
| WO | WO-9802743 A1 | 1/1998 |
| WO | WO-9929715 A1 | 6/1999 |
| WO | WO-0009502 A1 | 2/2000 |
| WO | WO-0062807 A1 | 10/2000 |
| WO | WO-0062810 A1 | 10/2000 |
| WO | WO-03000203 A2 | 1/2003 |
| WO | WO-03008583 A2 | 1/2003 |
| WO | WO-03101474 A1 | 12/2003 |
| WO | WO-03101475 A1 | 12/2003 |
| WO | WO-2005002604 A1 | 1/2005 |
| WO | WO-2005053611 A2 | 6/2005 |
| WO | WO-2005099774 A2 | 10/2005 |
| WO | WO-2005107793 A2 | 11/2005 |
| WO | WO-2005099774 A3 | 3/2006 |
| WO | WO-2006040574 A2 | 4/2006 |
| WO | WO-2005053611 A3 | 5/2006 |
| WO | WO-2006095164 A1 | 9/2006 |
| WO | WO-2006110581 A2 | 10/2006 |
| WO | WO-2006110582 A1 | 10/2006 |
| WO | WO-2006115633 A2 | 11/2006 |
| WO | WO-2006116156 A2 | 11/2006 |
| WO | WO-2007044994 A2 | 4/2007 |

(56) References Cited

FOREIGN PATENT DOCUMENTS

| WO | WO-2007047458 A2 | 4/2007 | |
|---|---|---|---|
| WO | WO-2007117467 A2 | 10/2007 | |
| WO | WO-2007137163 A2 | 11/2007 | |
| WO | WO-2007117467 A3 | 1/2008 | |
| WO | WO-2008075968 A1 | 6/2008 | |
| WO | WO-2008088422 A2 | 7/2008 | |
| WO | WO-2008155134 A1 | 12/2008 | |
| WO | WO-2009021136 A1 | 2/2009 | |
| WO | WO-2009029760 A1 | 3/2009 | |
| WO | WO-2009049184 A2 | 4/2009 | |
| WO | WO-2009052390 A1 | 4/2009 | |
| WO | WO-2009052392 A1 | 4/2009 | |
| WO | WO-2009052400 A1 | 4/2009 | |
| WO | WO-2009062520 A1 | 5/2009 | |
| WO | WO-2009108762 A2 | 9/2009 | |
| WO | WO-2009114776 A2 | 9/2009 | |
| WO | WO-2009117018 A1 | 9/2009 | |
| WO | WO-2009133362 A2 | 11/2009 | |
| WO | WO-2009140599 A1 | 11/2009 | |
| WO | WO-2009156456 A1 | 12/2009 | |
| WO | WO-2010029760 A1 | 3/2010 | |
| WO | WO-2011057295 A2 | 5/2011 | |
| WO | WO-2011073340 A1 | 6/2011 | |
| WO | WO-2011094671 A2 | 8/2011 | |
| WO | WO-2011097533 A1 | 8/2011 | |
| WO | WO-2011142858 A2 | 11/2011 | |
| WO | WO-2012022742 A1 | 2/2012 | |
| WO | WO-2012039741 A1 | 3/2012 | |
| WO | 2013003507 A1 | 1/2013 | |
| WO | WO-2014013730 A1 | 1/2014 | |
| WO | WO-2014074785 A1 | 5/2014 | |
| WO | WO-2014093403 A1 | 6/2014 | |
| WO | WO-2015042202 A1 * | 3/2015 | ............... C12N 9/96 |
| WO | 2017136769 A1 | 8/2017 | |
| WO | WO-2017181149 A1 | 10/2017 | |
| WO | 2019055840 A1 | 3/2019 | |

OTHER PUBLICATIONS

Altschul, et al. Optimal sequence alignment using affine gap costs. Bull Math Biol. 1986;48(5-6):603-16.

Barton, G.J. Protein secondary structure prediction. Curr Opin Struct Biol. Jun. 1995;5(3):372-6.

Berge S.M. et al., "Pharmaceutical Salts," Journal of Pharmaceutical Science, 66:1-19,1997.

Butte, et al. Near-infrared imaging of brain tumors using the Tumor Paint BLZ-100 to achieve near-complete resection of brain tumors. Neurosurg Focus. Feb. 2014;36(2):E1. doi: 10.3171/2013.11.FOCUS13497.

Cordes, et al. Sequence space, folding and protein design. Curr Opin Struct Biol. Feb. 1996;6(1):3-10.

Fidel et al. Preclinical Validation of the Utility of BLZ-100 in Providing Fluorescence Contrast for Imaging Spontaneous Solid Tumors. Cancer Res. Oct. 15, 2015;75(20):4283-91.

Freer, P. Mammographic breast density: impact on breast cancer risk and implications for screening. Radiographics 35.2 (2015): 302-315.

Harrington, et al. Real time, near-infrared detection of breast cancer using BLZ-100 in patients undergoing surgical tumor resection. Apr. 2017. Poster presentation. Abstract 256376. The american society of breast surgeons. Annual 18th meeting . . . .

Henikoff et al. Amino acid substitution matrices from protein blocks. PNAS USA 89(22):10915-10919 (1992).

Hinchcliffe, et al. Intranasal insulin delivery and therapy. Adv Drug Deliv Rev. Feb. 1, 1999;35(2-3):199-234.

Manning, et al., Stability of protein pharmaceuticals: an update. Pharm Res. Apr. 2010;27(4):544-75. doi: 10.1007/s11095-009-0045-6. Epub Feb. 9, 2010.

Needleman et al. A general method applicable to the search for similarities in the amino acid sequence of two proteins. Journal of molecular biology 48(3):443-453 (1970).

Patton, et al. Inhaled insulin. Adv Drug Deliv Rev. Feb. 1, 1999;35(2-3):235-247.

PCT/US2017/027812 International Search Report dated Sep. 22, 2017.

PCT/US2017/027812 Written Opinion of the International Searching Authority dated Sep. 22, 2017.

Pearson, et al. Improved Tools for Biological Sequence Comparison. Proc. Nat'l Acad. Sci. USA. 85 (1988): 2444-48.

Pearson. Rapid and sensitive sequence comparison with FASTP and FASTA. Methods Enzymol. 1990;183:63-98.

Penault-Llorca, et al., Pathological and molecular diagnosis of triple-negative breast cancer: a clinical perspective. Ann Oncol. Aug. 2012;23 Suppl 6:vi19-22.

Pettit, et al. The development of site-specific drug-delivery systems for protein and peptide biopharmaceuticals. Trends Biotechnol. Aug. 1998;16(8):343-9.

"Pharma Times" Excipients Special, Official Monthly Newsmagazine of Indian Pharmaceutical Association. 45(3); Mar. 2013: 1-18.

Pramanick, et al., "Excipient Selection in Parenteral Formulation Development", Pharma Times, vol. 45., No. 3, Mar. 2013.

Sellers, Peter H. On the Theory and Computation of Evolutionary Distances. SIAM J. Appl. Math., 1974; 26(4), 787-793.

Tomao et al. Triple-negative breast cancer: new perspectives for targeted therapies. Onco Targets Ther. Jan. 16, 2015;8:177-93.

Akcan, et al. Chemical re-engineering of chlorotoxin improves bioconjugation properties for tumor imaging and targeted therapy. J Med Chem. Feb. 10, 2011;54(3):782-787. doi: 10.1021/jm101018r. Epub Jan. 6, 2011.

European search report and opinion dated Mar. 4, 2020 for EP Application No. 17783337.3.

Nora Graf, et al. Platinum(IV)-chlorotoxin (CTX) Conjugates for Targeting Cancer Cells. J Inorg Biochem. May 2012;110:58-63. doi: 10.1016/j.jinorgbio.2012.02.012. Epub Feb. 23, 2012.

Paborji, et al., Chemical and Physical Stability of Chimeric L6, a Mouse-Human Monoclonal Antibody. Pharmaceutical Research, 11(5); May 1994: 764-771.

Adelstein, et al. Radiotoxicity of iodine-125 and other auger-electron-emitting radionuclides: background to therapy. Cancer Biother Radiopharm. Jun. 2003;18(3):301-16.

Akabani, et al. Dosimetry and radiographic analysis of 131I-labeled anti-tenascin 81C6 murine monoclonal antibody in newly diagnosed patients with malignant gliomas: a phase II study. J Nucl Med. Jun. 2005;46(6):1042-51.

Akabani, et al. Dosimetry of 131I-labeled 81C6 monoclonal antibody administered into surgically created resection cavities in patients with malignant brain tumors. J Nucl Med. Apr. 1999;40(4):631-8.

Alander, et al. A review of indocyanine green fluorescent imaging in surgery. Int J Biomed Imaging. 2012;2012:940585. doi: 10.1155/2012/940585. Epub Apr. 22, 2012.

Aldrich, et al., Concentration of Indocyanine Green Does Not Significantly Influence Lymphatic Function as Assessed by Near-Infrared Imaging. Lymphatic Research and Biology vol. 10, No. 1, 2012; 5 pages.

Amersham Biosciences. CyDye Mono-reactive NHS Esters: Reagents for the labelling of biological compounds with Cy monofunctional dyes. Amersham Biosciences, 2002, 20 pages.

Amersham Biosciences. Labelling of proteins with CyDye N-hydroxysuccinimide esters for fluorescent applications on the LEADseeker homogeneous imaging system. Amersham Biosciences, Jan. 2001, Issue No. L8, 4 pages.

Appelbaum, et al. Treatment of malignant lymphoma in 100 patients with chemotherapy, total body irradiation, and marrow transplantation. J Clin Oncol. Sep. 1987;5(9):1340-7.

Ashitate, et al., Endocrine-Specific NIR Fluorophores for Adrenal Gland Targeting. Chem Commun (Camb). Aug. 11, 2016; 52(67): 10305-10308. doi:10.1039/c6cc03845j.

Baker, et al. Effects of a epithelial Cl channel blocker on whole cell voltage clamp and patch clamp recordings from a human astrocytoma in culture. Proceedings of the Physiological Society, J. Physiol., vol. 438, Feb. 15-16, 1991, 4 pages.

Bandaranayake, et al. Daedalus: a robust, turnkey platform for rapid production of decigram quantities of active recombinant proteins in

(56) References Cited

OTHER PUBLICATIONS human cell lines using novel lentiviral vectors. Nucleic Acids Res. Nov. 2011;39(21):e143. doi: 10.1093/nar/gkr706. Epub Sep. 12, 2011.

Banks, et al. Delta sleep-inducing peptide crosses the blood-brain-barrier in dogs: some correlations with protein binding. Pharmacol Biochem Behav. Nov. 1982;17(5):1009-14.

Banks, William A. Characteristics of compounds that cross the blood-brain barrier. BMC Neurol. 2009; 9(Suppl 1): S3. Published online Jun. 12, 2009. doi: 10.1186/1471-2377-9-S1-S3.

Berendsen, Herman. A glimpse of the Holy Grail? Science. Oct. 23, 1998;282(5389):642-3.

Berezin, et al. Rational approach to select small peptide molecular probes labeled with fluorescent cyanine dyes for in vivo optical imaging. Biochemistry. Apr. 5, 2011;50(13):2691-700. doi: 10.1021/bi2000966. Epub Mar. 8, 2011.

Berlier, J.E., et al., Quantitative Comparison of Long-Wavelength Alexa Fluor Dyes to Cy Dyes: Fluorscence of the Dyes and Their Bioconjugates, The Journal of Histochemistry & Cytochemistry 51(12) :1699-1712, 2003.

Bertolini, et al. Inhibition of angiogenesis and induction of endothelial and tumor cell apoptosis by green tea in animal models of human high-grade non-Hodgkin's lymphoma. Leukemia, Aug. 2000, vol. 14, No. 8, pp. 1477-1482.

Bigner, et al. Iodine-131-labeled antitenascin monoclonal antibody 81C6 treatment of patients with recurrent malignant gliomas: phase I trial results. J Clin Oncol. Jun. 1998;16(6):2202-12.

Blaze Bioscience and Fred Hutchinson Cancer Research Center Enter into Collaboration and Option Agreement in Support of Optides Discovery Program. Seattle, WA. On Jul. 3, 2013. Contact person: Julie Rathbun.

Blaze Bioscience Announces Initiation of First-in-Human Phase 1 Clinical Study of BLZ-100. In Seattle, WA and Melbourne, AU on Dec. 19, 2013. Contact person: Julie Rathburn.

Blaze Bioscience Announces Presentation at the 2014 Wedbush PacGrow Life Sciences Management Access Conference. In New York on Aug. 13, 2014. Contact person: Media—Lauren Nelson.

Blaze Bioscience Announces Two Poster Presentations at AACR-SNMMI Conference and Award of NCI SBIR Contract Advancing Tumor PaintTM Technology. In Seattle, WA. On Feb. 27, 2013. Contact person: Julie Rathbun.

Blaze Bioscience Licenses Tumor Paint Technology from Fred Hutchinson Cancer Research Center. In Seattle, WA. On Oct. 18, 2011. Contact Person: Heather Franklin.

Bodey, et al. Failure of cancer vaccines: the significant limitations of this approach to immunotherapy. Anticancer Res. Jul.-Aug. 2000;20(4):2665-76.

Bowie, et al. Deciphering the message in protein sequences: tolerance to amino acid substitutions. Science. Mar. 16, 1990;247(4948):1306-10.

Bradley, et al. Limits of cooperativity in a structurally modular protein: response of the Notch ankyrin domain to analogous alanine substitutions in each repeat. J Mol Biol. Nov. 22, 2002;324(2):373-86.

Brem, et al. Placebo-controlled trial of safety and efficacy of intraoperative controlled delivery by biodegradable polymers of chemotherapy for recurrent gliomas. The Polymer-brain Tumor Treatment Group. Lancet. Apr. 22, 1995;345(8956):1008-12.

Bremer, et al. Protein Delivery with Infusion Pumps. In Protein Delivery: Physical Systems, Sanders and Hendren (eds.), pp. 239-254 (Plenum Press 1997).

Brismar, et al. Inward Rectifying Potassium Channels in Human Malignant Glioma Cells. Brain Res 480 (1-2), 249-258. Feb. 20, 1989.

Brismar, et al. Potassium and sodium channels in human malignant glioma cells. Brain Res. Feb. 20, 1989;480(1-2):259-67.

Britton, et al. Prostate cancer: the contribution of nuclear medicine. BJU International, vol. 86, Issue s1, pp. 135-142.

Burger, et al. Topographic anatomy and CT correlations in the untreated glioblastoma multiforme. J Neurosurg. May 1988;68(5):698-704.

Burgess, et al. Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

Buskens, et al. Adenocarcinomas of the Gastro-Esophageal Junction: A Comparative Study of the Gastric Cardia and the Esophagus with Respect to Cyclooxygenase-2 Expression. Abstract. 2003. Publishing ID: 850, Abstract ID: 101362. 1 page. Accessed on Jan. 28, 2004. URL:< http://ddw03.agora.com/planner/displayabstract.asp?presentationid=11913>.

Butterworth, et al. Preparation of Ultrafine Silica- and PEG-Coated Magnetite Particles. Colloids and Surfaces A: Physicochemical and Engineering Aspects 179:93-102, 2001.

Castro, et al. Gene therapy for Parkinson's disease: recent achievements and remaining challenges. Histol Histopathol. Oct. 2001;16(4):1225-38.

Cheng, et al. Recent advances in diagnosis and treatment of gliomas using chlorotoxin-based bioconjugates. Am J Nucl Med Mol Imaging. Aug. 15, 2014;4(5):385-405. eCollection 2014.

Chien, et al. The two-hybrid system: a method to identify and clone genes for proteins that interact with a protein of interest. Proc Natl Acad Sci U S A. Nov. 1, 1991;88(21):9578-82.

Chui, et al. The role of potassium channels in Schwann cell proliferation in Wallerian degeneration of explant rabbit sciatic nerves. J Physiol. Jan. 1989; 408: 199-222.

Chuthapisith, et al. Annexins in human breast cancer: Possible predictors of pathological response to neoadjuvant chemotherapy. Eur J Cancer. May 2009;45(7):1274-81. doi: 10.1016/j.ejca.2008.12.026. Epub Jan. 24, 2009.

Citrin, et al. In vivo tumor imaging in mice with near-infrared labeled endostatin. Mol Cancer Ther. Apr. 2004;3(4):481-8.

Colman. Effects of amino acid sequence changes on antibody-antigen interactions. Res Immunol. Jan. 1994;145(1):33-6.

Co-pending U.S. Appl. No. 16/706,585, filed Dec. 6, 2019.

Culard, et al. Characterization and subcellular localization of calcium-dependent phospholipid binding proteins (annexins) in normal human skin and reconstituted epidermis. J Invest Dermatol. Apr. 1992;98(4):436-41.

CyDye TM mono-reactive NHS-Esters. Amersham Biosciences, 2002, pp. 1-20.

Daly, et al. Pumiliotoxin alkaloids: a new class of sodium channel agents. Abstract of Biochem Pharmacol. Jul. 15, 1990;40(2):315-26. 1 page.

Database Geneseq [Online] Oct. 16, 2008 (Oct. 16, 2008), "Alpha-scorpion toxin family member CTX toxin peptide analog, SEQ:473.", XP002714000, retrieved from EBI accession No. GSP:ATD17606 Database accession No. ATD17606 * sequence.

Davis, C. Geoffrey. The many faces of epidermal growth factor repeats. New Biol. May 1990;2(5):410-9.

Davis, R., Treating Kids' Cancer With Science and a Pocket Full of Hope. Joe's Big Idea. Sep. 13, 2013.

Davis, R., Why Painting Tumors Could Make Brain Surgeons Better. Joe's Big Idea. Sep. 12, 2013.

De Muralt, et al. Reactivity of antiglioma monoclonal antibodies for a large panel of cultured gliomas and other neuroectoderm derived tumors. Anticancer Res. Jan.-Feb. 1983;3(1):1-6.

Deane, et al. An alternative pathway of B cell activation: stilbene disulfonates interact with a Cl-binding motif on AEn-related proteins to stimulate mitogenesis. Eur J Immunol. May 1992;22(5):1165-71.

DeBin, et al. Chloride channel inhibition by the venom of the scorpion Leiurus quinquestriatus. Toxicon. 1991;29(11):1403-8.

DeBin, et al. Purification and characterization of chlorotoxin, a chloride channel ligand from the venom of the scorpion. Am J Physiol. Feb. 1993;264(2 Pt 1):C361-9.

Dermer, Gerald B. Another Anniversary for the War on Cancer. Nature Biotechnology 12, 320 (1994). doi:10.1038/nbt0394-320.

Dernell, et al. Principles of treatment for soft-tissue sarcoma. Clin Tech Small Anim Pract. Feb. 1998;13(1):59-64.

(56) References Cited

OTHER PUBLICATIONS

Dernell, et al. Tumor Paint technology detects naturally occurring solid tumors in dods. In: Proceedings of the 105th Annual Meeting of the American Association for Cancer Research; Apr. 5-9, 2014; San Diego, CA. Philadelphia (PA): AACR; Cancer Res 2014;74(19 Suppl):Abstract # 4936. doi:10.1158/1538-7445.AM2014-4936.

Deroose, et al. Radiotherapy for soft-tissue sarcomas after isolated limb perfusion and surgical resection: Essential for local control in all patients? Ann Surg Oncol. Feb. 2011;18(2):321-7. doi: 10.1245/s10434-010-1400-x. Epub Nov. 4, 2010.

Deshane, et al. Chlorotoxin inhibits glioma cell invasion via matrix metalloproteinase-2. J Biol Chem. Feb. 7, 2003;278(6):4135-44. Epub Nov. 25, 2002.

Dibiase, et al. Oral delivery of microencapsulated proteins. Pharm Biotechnol. 1997;10:255-88.

dictionary.com. Definition of the word "Moiety". pp. 1-3 (last accessed Aug. 26, 2010). URL:< http://dictionary.reference.com/browse/moiety>.

Drexler, Hans G. Recent results on the biology of Hodgkin and Reed-Sternberg cells. II. Continuous cell lines. Leuk Lymphoma. Jan. 1993;9(1-2):1-25.

Eck, et al. Gene-Based Therapy. Chapter 5. Goodman & Gilman's The Pharmacological Basis of Therapeutics. 9th Edition. pp. 77-101.

Egleton, R.D. and Davis, T.P., Development of Neuropeptide Drugs that Cross the Blood-Brain Barrier, J. Am. Soc. Exp. Neuro Therapeutics 2:44-53 (2005).

Entrez Genome. ANXA2 annexin A2 [*Homo sapiens*]. Gene ID: 302, updated on Aug. 26, 2010. Retreived on Sep. 7, 2010. URL:< http://www.ncbi.nlm.nih.gov/gene/302>.

Epstein, et al. Morphological and virological investigations on cultured Burkitt tumor lymphoblasts (strain Raji). J Natl Cancer Inst. Oct. 1966;37(4):547-59.

European search report and search opinion dated Oct. 15, 2013 for EP Application No. 11780950.9.

Evans, et al. Design of nonpeptidal ligands for a peptide receptor: cholecystokinin antagonists. J Med Chem. Jul. 1987;30(7):1229-39.

Extended European Search Report and Search Opinion dated May 29, 2017 for European Patent Application No. EP14846407.6.

Extended European Search Report dated Apr. 6, 2010 for European Patent Application No. EP09176234.4.

Extended European Search Report dated Jul. 30, 2010 for European Patent Application No. EP09150772.3.

Extended European Search Report dated Nov. 23, 2010 for European Patent Application No. EP08837002.8.

Fauchere, Jean-Luc. Elements for the rational design of peptide drugs. Advances in Drug Research, vol. 15, Academic Press, 1986, pp. 29-69.

Fields, et al. A novel genetic system to detect protein-protein interactions. Letters to Nature. Nature 340 (Jul. 20, 1989): 245-246. doi:10.1038/340245a0.

Fischer, et al. Pyrrolopyrrole cyanine dyes: a new class of near-infrared dyes and fluorophores. Chemistry. 2009; 15(19):4857-64. doi: 10.1002/chem.200801996.

Fiveash, et al. Safety and tolerance of multiple weekly intracavitary injections of 131I-chlorotoxin (TM-601): Preliminary results of a prospective clinical trial in patients with recurrent glioblastoma multiforme. Poster. Journal of Clinical Oncology, 2006 ASCO Annual Meeting Proceedings. Abstact No. 1555. 1 page.

Fiveash, et al. Tumor Specific Targeting of Intravenous 131I-chlorotoxin (TM-601) in Patients With Recurrent Glioma. International Journal of Radiation Oncology, ASTRO. Nov. 1, 2007, vol. 69, Issue 3, Supplement, pp. S257-S258.

Flower, et al. Structure and sequence relationships in the lipocalins and related proteins. Protein Sci. May 1993;2(5):753-61.

Freshney, R. Ian. Culture of animal cells: a manual of basic technique. A.R. Liss, 1983. 4 pages.

Friedman, et al. Temozolomide and treatment of malignant glioma. Clin Cancer Res. Jul. 2000;6(7):2585-97.

Goetz, et al. The neutrophil lipocalin NGAL is a bacteriostatic agent that interferes with siderophore-mediated iron acquisition. Mol Cell. Nov. 2002;10(5):1033-43.

Goldstein, et al. The blood-brain barrier. Sci Am. Sep. 1986;255(3):74-83.

Gordon, et al. The Comparative Oncology Trials Consortium: Using spontaneously occurring cancers in dogs to inform the cancer drug development pathway. PLoS Med. Oct. 2009;6(10):e1000161. doi: 10.1371/journal.pmed.1000161. Epub Oct. 13, 2009.

Gorecki, Dariusz C. Prospects and problems of gene therapy: an update. Expert Opin Emerg Drugs. Oct. 2001;6(2):187-98.

Gorman, et al. The hope and the hype. Time, 1998, 151(19):40-44.

Gray, et al. A voltage-gated chloride conductance in rat cultured astrocytes. Proc R Soc Lond B Biol Sci. Aug. 22, 1986;228(1252):267-88.

Griffith, C., One Doctor's Quest to Save People by Injecting Them With Scorpion Venom. Brendan I. Koerner Science. Jun. 24, 2014.

Grimes, et al. TM-601 targets human cancer cells via a phosphatidylinositol phosphate in lamellipodia, J. Clin. Oncol., ASCO Annual Meeting Proceedings Part I, Abstract 9556 (2005).

Grissimer, et al. Calcium-activated potassium channels in resting and activated human T lymphocytes. Expression levels, calcium dependence, ion selectivity, and pharmacology. J Gen Physiol. Oct. 1993;102(4):601-30.

Grossman, et al. Current management of glioblastoma multiforme. Semin Oncol. Oct. 2004;31(5):635-44.

Gunn, J. et al., Smart Superparamagnetic Imaging Probes for Brain Tumor Research, in D.B. Baer and C.T. Campbell (eds.), Joint Institute for Nanoscience Annual Report, Nov. 2004, 2005, pp. 3.65-3.66.

Gura, Trisha. Systems for identifying new drugs are often faulty. Science. Nov. 7, 1997;278(5340):1041-2.

Hajjar, et al. Annexin II: a mediator of the plasmin/plasminogen activator system. Trends Cardiovasc Med. Jul. 1999;9(5):128-38.

Hamman, et al. Oral delivery of peptide drugs: barriers and developments. BioDrugs. 2005;19(3):165-77.

Hansen, et al. Evaluation of candidate near-infrared dyes for clinical translation of Tumor Paint technology. Abstract # 71. AACR/SNMMI State-of-the-Art Molecular Imaging in Cancer Biology and Therapy, Feb. 27-Mar. 2, 2013, in San Diego, California.

Hargis, et al. Animal model: Solar dermatosis (keratosis) and solar dermatosis with squamous cell carcinoma. Am J Pathol. Jan. 1979;94(1):193-6.

Hartwell, et al. Integrating genetic approaches into the discovery of anticancer drugs. Science. Nov. 7, 1997;278(5340):1064-8.

Hatton, et al. The Smo/Smo model: hedgehog-induced medulloblastoma with 90% incidence and leptomeningeal spread. Cancer Res. Mar. 15, 2008;68(6):1768-76. doi: 10.1158/0008-5472.CAN-07-5092.

He, et al. A simple and effective "capping" approach to readily tune the fluorescence of near-infrared cyanines. Chem. Sci., 2015,6, 4530-4536. DOI: 10.1039/C5SC00348B.

Hirata, et al., Synthesis and Reactivities of 3-Indocyanine-green-acyl-1,3-thiazolidine-2-thione (ICG-ATT) as a New Near-infrared Fluorescent-labeling Reagent. Bioorganic & Medicinal Chemistry 6 (1998) 2179-2184.

Hockaday, et al., Imaging Glioma Extent with 131I-TM-601, J. Nuc. Med. 46(4): 580-586 (2005).

Holmes, et al. Protein labeling with fluorescent probes. Methods Cell Biol. 2001;63:185-204.

Holsi, et al. Evidence for GABAb-receptors on cultured astrocytes of rat CNS; autoradiographic binding studies. Experimental Brain Reserach. 1990, (80), pp. 621-625.

Holt, et al. Intraoperative near-infrared imaging can distinguish cancer from normal tissue but not inflammation. PLoS One. Jul. 29, 2014;9(7):e103342. doi: 10.1371/journal.pone.0103342. eCollection 2014.

Huang, A., Bright Idea: Making the Case for 'Tumor Paint' Blaze Bioscience's brilliant concept in the fight against cancer. Print Edition. Sep. 2012.

Huang, et al. Potassium channel induction by the Ras/Raf signal transduction cascade. J Biol Chem. Dec. 9, 1994;269(49):31183-9.

(56) References Cited

OTHER PUBLICATIONS

Huys, et al. Structure-function study of a chlorotoxin-chimer and its activity on Kv1.3 channels. J Chromatogr B Analyt Technol Biomed Life Sci. Apr. 15, 2004;803(1):67-73.
Ibragimova, et al. Stability of the beta-sheet of the WW domain: A molecular dynamics simulation study. Biophys J. Oct. 1999;77(4):2191-8.
International Preliminary Examination Report dated May 29, 2001 for International PCT Patent Application No. PCT/US2000/010453.
International Preliminary Report on Patentability dated Apr. 13, 2010 for International PCT Patent Application No. PCT/US2008/079547.
International Preliminary Report on Patentability dated May 29, 2006 for International PCT Patent Application No. PCT/US2004/039325.
International Preliminary Report on Patentability dated Sep. 30, 2008 for International PCT Patent Application No. PCT/2007/008309.
International Preliminary Report on Patentability dated Sep. 30, 2010 for International PCT Patent Application No. PCT/US2008/076740.
International Preliminary Report on Patentability dated Oct. 11, 2006 for International PCT Patent Application No. PCT/US2005/011523.
International Preliminary Report on Patentability dated Nov. 25, 2010 for International PCT Patent Application No. PCT/US2009/044149.
International Search Report and Written Opinion dated Jan. 9, 2009 for International PCT Patent Application No. PCT/US2008/076740.
International Search Report and Written Opinion dated Feb. 9, 2006 for International PCT Patent Application No. PCT/US2005/011523.
International search report and written opinion dated Feb. 10, 2015 for PCT Application No. PCT/US2014/056177.
International Search Report and Written Opinion dated Mar. 27, 2006 for International PCT Patent Application No. PCT/US2004/039325.
International search report and written opinion dated Apr. 8, 2014 for PCT/US2013/074215.
International search report and written opinion dated Apr. 22, 2014 for PCT/US2013/074218.
International search report and written opinion dated Oct. 6, 2010 for PCT/US2006/010170.
International Search Report and Written Opinion dated Oct. 19, 2009 for International PCT Patent Application No. PCT/US2009/044149.
International search report and written opinion dated Nov. 18, 2011 for PCT/US2011/023797.
International Search Report and Written Opinion dated Nov. 20, 2007 for International PCT Patent Application No. PCT/US2007/008309.
International Search Report dated May 7, 1996 for International PCT Patent Application No. PCT/US1996/020403.
International Search Report dated Nov. 13, 2003 for International PCT Patent Application No. PCT/US2003/017410.
Invitation Pursuant to Article 94(3) and Rule 71(1) EPC, mailed Mar. 1, 2010, in corresponding European Application No. 06 739 100.3, filed Mar. 20, 2006, 3 pages.
Jacoby, et al. Potent pleiotropic anti-angiogenic effects of TM601, a synthetic chlorotoxin peptide. Anticancer Res. Jan. 2010;30(1):39-46.
Jalonen, Tuula. Single-channel characteristics of the large-conductance anion channel in rat cortical astrocytes in primary culture. Glia. Nov. 1993;9(3):227-37.
Jiang, T. et al., Tumor Imaging by Means of Proteolytic Activation of Cell-Penetrating Peptides, Proceedings of the National Academy of Sciences USA (PNAS) 101(51):17867-17872, Dec. 2004.
Jianping, Z. Chinese and Foreign Sciences Yearbook. The Second Military Medical Uniersity (SMMU) Press. p. 426 (2004).

Kaiser, Jocelyn. First Pass at Cancer Genome Reveals Complex Landscape. Science Sep. 8, 2006: vol. 313, Issue 5792, pp. 1370. DOI: 10.1126/science.313.5792.1370.
Kastin, et al. Orexin A but not orexin B rapidly enters brain from blood by simple diffusion. J Pharmacol Exp Ther. Apr. 1999;289(1):219-23.
Kaye, et al. A single amino acid substitution results in a retinoblastoma protein defective in phosphorylation and oncoprotein binding. Proc Natl Acad Sci U S A. Sep. 1990;87(17):6922-6.
Kennedy, et al. Tumor Paint technology detects naturally occurring solid tumors in dods. Presentation No. P 578. The Sixth Annual World Molecular Imaging Congress, Sep. 18-21, 2013, Savannah, USA.
Kesavan, et al. Annexin A2 is a molecular target for TM601, a peptide with tumor-targeting and anti-angiogenic effects. J Biol Chem. Feb. 12, 2010;285(7):4366-74. doi: 10.1074/jbc.M109.066092. Epub Dec. 15, 2009.
Kessler, et al. Identification of the putative brain tumor antigen BF7/GE2 as the (de)toxifying enzyme microsomal epoxide hydrolase. Cancer Res. Mar. 1, 2000;60(5):1403-9.
Kimura, et al. A dual-labeled knottin peptide for PET and near-infrared fluorescence imaging of integrin expression in living subjects. Bioconjug Chem. Mar. 17, 2010;21(3):436-44. doi: 10.1021/bc9003102. Epub Feb. 4, 2010.
Kirkin, et al. Melanoma-associated antigens recognized by cytotoxic T lymphocytes. APMIS. Jul. 1998; 106(7):665-79.
Klein, et al. Surface IgM-kappa specificity on a Burkitt lymphoma cell in vivo and in derived culture lines. Cancer Res. Jul. 1968;28(7):1300-10.
Kohler, et al. A bifunctional poly(ethylene glycol) silane immobilized on metallic oxide-based nanoparticles for conjugation with cell targeting agents. J Am Chem Soc. Jun. 16, 2004;126(23):7206-11.
Kraft, et al. Interactions of indocyanine green and lipid in enhancing near-infrared fluorescence properties: the basis for near-infrared imaging in vivo. Biochemistry. Mar. 4, 2014;53(8):1275-83. doi: 10.1021/bi500021j. Epub Feb. 17, 2014.
Kuan, et al. EGFRvIII as a promising target for antibody-based brain tumor therapy. Brain Tumor Pathol. 2000;17(2):71-8.
Kunwar, et al. Cytotoxicity and antitumor effects of growth factor-toxin fusion proteins on human glioblastoma multiforme cells. J Neurosurg. Oct. 1993;79(4):569-76.
Laumonnier, et al. Identification of the annexin A2 heterotetramer as a receptor for the plasmin-induced signaling in human peripheral monocytes. Blood 2006 107:3342-3349; doi: https://doi.org/10.1182/blood-2005-07-2840.
Lazar, et al. Transforming growth factor alpha: mutation of aspartic acid 47 and leucine 48 results in different biological activities. Mol Cell Biol. Mar. 1988;8(3):1247-52.
Lee, et al. Increased vaccine-specific T cell frequency after peptide-based vaccination correlates with increased susceptibility to in vitro stimulation but does not lead to tumor regression. J Immunol. Dec. 1, 1999;163(11):6292-300.
Lee, M. J., et al., Rapid Pharmacokinetic and Biodistribution Studies Using Cholorotoxin-conjugated Iron oxide Nanoparticles: A Novel Non-Radioactive Method, PLoS One 5(3):e9536 1-8 (2010).
Lerman, R., Armed with a poisonous scorpion and glowing tumor paint, Blaze Bioscience takes on cancer. Puget Sound Business Journal, Jul. 9, 2014.
Levin, V.A.. The place of hydroxyurea in the treatment of primary brain tumors, Database accession No. NLM1641655 (abstract), Seminars in Oncology, 19(3):34-39 (1992).
Licha, et al. Hydrophilic cyanine dyes as contrast agents for near-infrared tumor imaging: synthesis, photophysical properties and spectroscopic in vivo characterization. Photochem Photobiol. Sep. 2000;72(3):392-8.
Lippens, et al. NMR sequential assignments and solution structure of chlorotoxin, a small scorpion toxin that blocks chloride channels. Biochemistry. Jan. 10, 1995;34(1):13-21.
Lynch, Patrick M. Chemoprevention with special reference to inherited colorectal cancer. Fam Cancer. 2008;7(1):59-64. Epub Aug. 7, 2007.

(56) References Cited

OTHER PUBLICATIONS

Lyons, et al. Chlorotoxin, a scorpion-derived peptide, specifically binds to gliomas and tumors of neuroectodermal origin. Glia. Aug. 2002;39(2):162-73.
Malinowska, et al. Recombinant chlorotoxin: An inhibitor of gastric Cl-channels. Abstract. Biophysical Journal, 66(2):A100 (1994).
Mamelak, et al. Phase 1/11 Trial of Intracavitary 131I-TM-601 in Adult Patients with Recurrent High-Grade Glioma. Astract. Neuro-Oncology online, 5:340 (2003).
Mamelak, et al. Phase I single-dose study of intracavitary-administered iodine-131-TM-601 in adults with recurrent high-grade glioma. J Clin Oncol. Aug. 1, 2006;24(22):3644-50.
Mamelak, et al. Targeted delivery of antitumoral therapy to glioma and other malignancies with synthetic chlorotoxin (TM-601). Expert Opin Drug Deliv. Mar. 2007;4(2):175-86.
Marshall, et al. Near-Infrared Fluorescence Imaging in Humans with Indocyanine Green: A Review and Update. Open Surg Oncol J. 2010;2(2):12-25.
McFerrin, et al. A role for ion channels in glioma cell invasion. Neuron Glia Biol. Feb. 2006;2(1):39-49.
Mckie, Robin. Cancer research set back a decade: Mislabelling of samples so common that new treatments have been wrecked, warn scientists. The Observer. Jun. 10, 2001. 4 pages.
Mcmichael, et al. Leukocyte Typing III, Oxford University Press, pp. 302-363 and pp. 432-469 (1987).
Mellman, Ira. Where Next for Cancer Immunotherapy? The Scientist, 20(1): 47-56 (2006).
Merck, Chemotherapy: Prevention and Treatment of Cancer: Merck Manual Home Edition, online manual, entry 'methotrexate'. 4 pages. URL:< http://www.merck.com/rnmhe/print/sec15/ch182/ch182f.html>.
Milross, et al. Relationship of mitotic arrest and apoptosis to antitumor effect of paclitaxel. J Natl Cancer Inst. Sep. 18, 1996;88(18):1308-14.
Minowada, et al. Rosette-Forming Human Lymphoid Cell Lines. I. Establishment and Evidence for Origin of Thymus-Derived Lymphocytes. J Natl Cancer Inst (1972) 49 (3): 891-895. DOI: https://doi.org/10.1093/jnci/49.3.891.
Mizrahi, et al. Synthesis, fluorescence and biodistribution of a bone-targeted near-infrared conjugate. Eur J Med Chem. Oct. 2011;46(10):5175-83.
Motta, et al. Canine and feline intracranial meningiomas: An updated review. Vet J. May 2012;192(2):153-65. doi: 10.1016/j.tvjl.2011.10.008. Epub Nov. 21, 2011.
Mousa, et al. Potent anti-angiogenesis efficacy of chlorotoxin and its synergistic interactions with Anti-VEGF targets. American Association for Cancer Research Annual Meeting Proceedings, Abstract #268 (2008). 1 page.
Munz, et al. Differential expression of the calpactin I subunits annexin II and p11 in cultured keratinocytes and during wound repair. Invest Dermatol. Mar. 1997;108(3):307-12.
Muro, et al. Convection-enhanced and local delivery of targeted cytotoxins in the treatment of malignant gliomas. Technology in Cancer Research and Treatment. 2006. 5(3), pp. 201-213.
Newlands, et al. Temozolomide: a review of its discovery, chemical properties, pre-clinical development and clinical trials. Cancer Treat Rev. Jan. 1997;23(1):35-61.
Ngo et al. Computational complexity, protein structure prediction, and the levinthal paradox. In: The Protein Folding Problem and Tertiary Structure Prediction. K. Merz, Jr., et al. Eds. 1994:433-506.
Nolting, et al. Molecular imaging probe development: a chemistry perspective. Am J Nucl Med Imaging. 2012; 2(3): 273-306.
Nolting, et al. Near-Infrared Dyes: Probe Development and Applications in Optical Molecular Imaging. Curr Org Synth. Aug. 2011;8(4):521-534.
Notice of allowance dated Mar. 11, 2014 for U.S. Appl. No. 11/897,721.
Notice of allowance dated Nov. 15, 2013 for U.S. Appl. No. 11/897,721.
Office action dated Jan. 6, 2016 for U.S. Appl. No. 13/673,779.
Office Action dated Jan. 8, 2010 for Canadian Patent Application No. CA2487425.
Office action dated Mar. 12, 2015 for U.S. Appl. No. 13/673,779.
Office action dated Mar. 24, 2010 for U.S. Appl. No. 11/897,721.
Office action dated May 16, 2017 for U.S. Appl. No. 14/855,355.
Office action dated Jun. 23, 2014 for U.S. Appl. No. 14/102,396.
Office action dated Jul. 1, 2016 for U.S. Appl. No. 14/273,374.
Office action dated Jul. 13, 2016 for U.S. Appl. No. 14/855,355.
Office action dated Jul. 21, 2016 for U.S. Appl. No. 14/489,419.
Office action dated Sep. 3, 2015 for U.S. Appl. No. 13/673,779.
Office action dated Sep. 8, 2016 for U.S. Appl. No. 13/673,779.
Office action dated Sep. 15, 2009 for U.S. Appl. No. 11/897,721.
Office action dated Nov. 4, 2016 for U.S. Appl. No. 14/855,355.
Office action dated Dec. 22, 2017 for U.S. Appl. No. 14/855,355.
Ogawa, et al. In vivo molecular imaging of cancer with a quenching near-infrared fluorescent probe using conjugates of monoclonal antibodies and indocyanine green. Cancer Res. Feb. 15, 2009;69(4):1268-72. doi: 10.1158/0008-5472.CAN-08-3116. Epub Jan. 27, 2009.
Ohnishi, et al. Organic alternatives to quantum dots for intraoperative near-infrared fluorescent sentinel lymph node mapping. Mol Imaging. Jul.-Sep. 2005;4(3):172-81.
Ojeda, et al. The role of disulfide bonds in structure and activity of chlorotoxin. Future Med Chem. Oct. 2014;6(15):1617-28. doi: 10.4155/fmc.14.93.
O'Neill, et al. Treatment of Metastatic Tumors. U.S. Appl. No. 61/053,651, filed May 15, 2008.
Pappas, et al. Reduction of glial proliferation by K channel blockers is mediated by changes in pH. NeuroReport. 6(1):193-196, Dec. 1994.
Pappone, et al. Blockers of voltage-gated K channels inhibit proliferation of cultured brown fat cells. Am J Physiol. Apr. 1993;264(4 Pt 1):C1014-9.
Partial European Search Report dated Apr. 8, 2010 for European Patent Application No. EP09150772.3.
Parungo, et al. Intraoperative identification of esophageal sentinel lymph nodes with near-infrared fluorescence imaging. J Thorac Cardiovasc Surg. Apr. 2005;129(4):844-50.
Phillips, et al. Transforming growth factor-alpha-Pseudomonas exotoxin fusion protein (TGF-alpha-PE38) treatment of subcutaneous and intracranial human glioma and medulloblastoma xenografts in athymic mice. Cancer Res. Feb. 15, 1994;54(4):1008-15.
Puro, et al. Retinal glial cell proliferation and ion channels: a possible link. Invest Ophthalmol Vis Sci. Mar. 1989;30(3):521-9.
Ramakrishnan, et al. Targeting tumor vasculature using VEGF-toxin conjugates. Methods Mol Biol. 2001;166:219-34.
Ranade, V.V, "Implants in Drug Delivery," in Drug Delivery Systems, Ranade and Hollinger (eds.), pp. 95-123 (CRC Press 1995).
Ravik, Miroslav. Intracavitary Treatment of Malignant Gliomas: Radioimmunotherapy Targeting Fibronectin. Acta neurochirurgica. Supplement 88(88):77-82 . Feb. 2003.
Rawstron, et al. Quantitation of minimal disease levels in chronic lymphocytic leukemia using a sensitive flow cytometric assay improves the prediction of outcome and can be used to optimize therapy. Blood. Jul. 1, 2001;98(1):29-35.
Reardon, et al. A pilot study: 131I-Antitenascin monoclonal antibody 81c6 to deliver a 44-Gy resection cavity boost. Neuro Oncol. Apr. 2008; 10(2): 182-189. doi: 10.1215/15228517-2007-053.
Reardon, et al. Phase II trial of murine (131)I-labeled antitenascin monoclonal antibody 81C6 administered into surgically created resection cavities of patients with newly diagnosed malignant gliomas. J Clin Oncol. Mar. 1, 2002;20(5):1389-97.
Rescher, et al. Annexins—unique membrane binding proteins with diverse functions. J Cell Sci. Jun. 1, 2004;117(Pt 13):2631-9.
Ricotti, et al. C-Kit Is Expressed in Soft Tissue Sarcoma of Neuroectodermic Origin and Its Ligand Prevents Apoptosis of Neoplastic Cells. Blood 91 (7), 2397-2405. Apr. 1, 1998.
Robinson, W.L., The role of the pathologists in the diagnosis of cancer. The Canadian medical associate journal. Sep. 1934; pp. 298-301.
Rousselle, et al. New advances in the transport of doxorubicin through the blood-brain barrier by a peptide vector-mediated strategy. Mol Pharmacol. Apr. 2000;57(4):679-86.

(56) References Cited

OTHER PUBLICATIONS

Rudikoff, et al. Single amino acid substitution altering antigen-binding specificity. Proc Natl Acad Sci U S A. Mar. 1982;79(6):1979-83.
Rudinger, J. Peptide Hormones. J.A. Parsons, Ed., pp. 1-7 (1976).
Sakamoto, et al. Identification of a new outwardly rectifying Cl-channel that belongs to a subfamily of the ClC Cl-channels. J Biol Chem. Apr. 26, 1996;271(17):10210-6.
Sano, et al., Short PEG-Linkers Improve the Performance of Targeted, Activatable Monoclonal Antibody-Indocyanine Green Optical Imaging Probes. Bioconjug Chem. May 15, 2013; 24(5): 811-816. doi:10.1021/bc400050k.
Schaafsma, et al. The clinical use of indocyanine green as a near-infrared fluorescent contrast agent for image-guided oncologic surgery. J Surg Oncol. Sep. 1, 2011;104(3):323-32. doi: 10.1002/jso.21943. Epub Apr. 14, 2011.
Scifinder CAS# for indocyanine green, printed from web Oct. 18, 2018 (Year: 2018).
Sgouros, George. Bone marrow dosimetry for radioimmunotherapy: theoretical considerations. J Nucl Med. Apr. 1993;34(4):689-94.
Sharma, et al. The role of annexin II in angiogenesis and tumor progression: a potential therapeutic target. Curr Pharm Des. 2007;13(35):3568-75.
Shen, et al. Dosimetry of Phase I/II study of intracavitary administered I-131-TM-601 peptide in patients with recurrent high-grade glioma. 2004. vol. 60, Issue 1, Supplement, p. S259.
Shen, et al. Patient-specific dosimetry of pretargeted radioimmunotherapy using CC49 fusion protein in patients with gastrointestinal malignancies. J Nucl Med. Apr. 2005;46(4):642-51.
Shen, et al. Practical determination of patient-specific marrow dose using radioactivity concentration in blood and body. J Nucl Med. Dec. 1999;40(12):2102-6.
Shen, et al. Radiation dosimetry of 131I-chlorotoxin for targeted radiotherapy in glioma-bearing mice. J Neurooncol. Jan. 2005;71(2):113-9.
Shimizu, et al. Development of novel nanocarrier-based near-infrared optical probes for in vivo tumor imaging. J Fluoresc. Mar. 2012;22(2):719-27. doi: 10.1007/s10895-011-1007-z. Epub Nov. 10, 2011.
Shiue. Identification of candidate genes for drug discovery by differential display. Drug Development Research. New York. 1997; 41:142-159.
Sigma Genosys. Custom Peptide Synthesis: Designing Custom Peptides. 2004. Sigma Genosys. Accessed Dec. 16, 2004. 2 pages. URL:< http://www.sigma-genosys.com/peptide_design.asp>.
Silva, et al. Agents That Bind Annexin A2 Suppress Ocular Neovascularization. J Cell Physiol. Nov. 2010; 225(3): 855-864. doi: 10.1002/jcp.22296.
Skolnick, et al. From genes to protein structure and function: novel applications of computational approaches in the genomic era. Trends Biotechnol. Jan. 2000;18(1):34-9.
Smith, et al. Molecular markers in head and neck squamous cell carcinoma: their biological function and prognostic significance. Ann Otol Rhinol Laryngol. Mar. 2001;110(3):221-8.
Somogyi, et al. Subcellular localization of benzodiazepine/GABAA receptors in the cerebellum of rat, cat, and monkey using monoclonal antibodies. Journal of Neuroscience Jun. 1, 1989, 9 (6) 2197-2209.
Sontheimer, Harald. Voltage-dependent ion channels in glial cells. Glia. Jun. 1994;11(2):156-72.
Soroceanu, et al. Modulation of glioma cell migration and invasion using Cl(-) and K(+) ion channel blockers. J Neurosci. Jul. 15, 1999;19(14):5942-54.
Soroceanu, et al. Use of chlorotoxin for targeting of primary brain tumors. Cancer Res. Nov. 1, 1998;58(21):4871-9.
Stabin, Michael G. Mirdose: personal computer software for internal dose assessment in nuclear medicine. J Nucl Med. Mar. 1996;37(3):538-46.
Steinmeyer, et al. Cloning and functional expression of rat CLC-5, a chloride channel related to kidney disease. J Biol Chem. Dec. 29, 1995;270(52):31172-7.
Stewart, L.A. Chemotherapy in adult high-grade glioma: a systematic review and meta-analysis of individual patient data from 12 randomised trials. Lancet. Mar. 23, 2002;359(9311):1011-8.
Stroud, et al. In vivo bio-imaging using chlorotoxin-based conjugates. Curr Pharm Des. Dec. 2011;17(38):4362-71.
Stupp, et al. Current and future developments in the use of temozolomide for the treatment of brain tumours. Lancet Oncol. Sep. 2001;2(9):552-60.
Sun, et al. In vivo MRI detection of gliomas by chlorotoxin-conjugated superparamagnetic nanoprobes. Small. Mar. 2008;4(3):372-9. doi: 10.1002/smll.200700784.
Sun, et al. Size-controlled synthesis of magnetite nanoparticles. J Am Chem Soc. Jul. 17, 2002;124(28):8204-5.
Sun, et al. Tumor-targeted drug delivery and MRI contrast enhancement by chlorotoxin-conjugated iron oxide nanoparticles. Nanomedicine (Lond). Aug. 2008;3(4):495-505. doi: 10.2217/17435889.3.4.495.
Supplemental Partial European Search Report dated Mar. 11, 2003 for European Patent Application No. EP00926105.
Supplementary European Search Report dated Sep. 24, 2007 for European Patent Application No. EP05763889.2.
Supplementary Partial European Search Report dated Aug. 28, 2007 for European Patent Application No. EP03731504.
Swart, et al. Homing of negatively charged albumins to the lymphatic system: general implications for drug targeting to peripheral tissues and viral reservoirs. Biochem Pharmacol. Nov. 1, 1999;58(9):1425-35.
Syed, et al. Angiostatin receptor annexin II in vascular tumors including angiosarcoma. Hum Pathol. Mar. 2007;38(3):508-13. Epub Jan. 19, 2007.
Taber's Cyclopedic Medical Dictionary, F.A. Davis Company, Philadelphia, 274 (1985). 3 pages.
Tan, et al. Deduction of Functional Peptide Motifs in Scorpion Toxins. J Pept Sci 12 (6), 420-427. Jun. 2006.
Tanaka, et al. Image-guided oncologic surgery using invisible light: completed pre-clinical development for sentinel lymph node mapping. Ann Surg Oncol. Dec. 2006;13(12):1671-81. Epub Sep. 29, 2006.
Tanaka, et al. Redox regulation of annexin 2 and its implications for oxidative stress-induced renal carcinogenesis and metastasis. Oncogene. May 13, 2004;23(22):3980-9.
Tatenhorst, et al. Knockdown of annexin 2 decreases migration of human glioma cells in vitro. Neuropathol Appl Neurobiol. Jun. 2006;32(3):271-7.
Tatikolov, A.S. and Costa, S.M.B., Complexation of polymethine dyes with human serum albumin: a spectroscopic study, Biophys. Chem. 107:33-49 (2004).
Te Velde, et al. The use of fluorescent dyes and probes in surgical oncology. Eur J Surg Oncol. Jan. 2010;36(1):6-15. doi: 10.1016/j.ejso.2009.10.014. Epub Nov. 18, 2009.
The Free Dictionary. American Heritage Medical Dictionary defines the word "systemic". 2007. 1 page.
Thermo Scientific Pierce Fluorescent Products Guide-fluorescent labeling and Detection. ThermoScientific Jan. 2012.
Timmerman, L., Blaze Bioscience, Fred Hutch Spinoff with Zymo Vet at the Helm, Seeks to "Paint" Tumors. Xconomy, Oct. 18, 2011.
Torchilin, et al. Peptide and protein drug delivery to and into tumors: challenges and solutions. Drug Discov Today. Mar. 15, 2003;8(6):259-66.
Transmolecular. A Phase I Imaging and Safety Study of Intravenous 131-I-TM-601 Labeled Chlorotoxin in Patients With Recurrent or Refractory Somatic and/or Cerebral Metastatic Solid Tumors. Clinical Trials NCT00379132. 3 pages (Aug. 2006).
Troyan, et al. The FLARE intraoperative near-infrared fluorescence imaging system: a first-in-human clinical trial in breast cancer sentinel lymph node mapping. Ann Surg Oncol. Oct. 2009;16(10):2943-52. doi: 10.1245/s10434-009-0594-2. Epub Jul. 7, 2009.
Tytgat, et al. Purification and partial characterization of a 'short' insectotoxin-like peptide from the venom of the scorpion *Parabuthus schlechteri*. FEBS Lett. Dec. 28, 1998;441(3):387-91.

(56) References Cited

OTHER PUBLICATIONS

Uchida, et al. Localization and functional characterization of rat kidney-specific chloride channel, CIC-K1. J Clin Invest. Jan. 1995;95(1):104-13.
Ullrich, et al. Biophysical and pharmacological characterization of chloride currents in human astrocytoma cells. Am J Physiol. May 1996;270(5 Pt 1):C1511-21.
Ullrich, et al. Cell cycle-dependent expression of a glioma-specific chloride current: proposed link to cytoskeletal changes. Am J Physiol. Oct. 1997;273(4 Pt 1):C1290-7.
Ullrich, et al. Expression of voltage-activated chloride currents in acute slices of human gliomas. Neuroscience. Apr. 1998;83(4):1161-73.
Ullrich, et al. Human astrocytoma cells express a unique chloride current. Neuroreport. Apr. 10, 1996;7(5):1020-4.
UniProt Database. Accession No. P45639 (accessed 2007).
U.S. Appl. No. 14/855,355 Office Action dated Feb. 9, 2018.
U.S. Appl. No. 14/855,355 Office Action dated Nov. 5, 2018.
U.S. Appl. No. 16/704,955 Office Action dated Aug. 10, 2020.
U.S. Appl. No. 16/704,955 Office Action dated Feb. 4, 2020.
U.S. Appl. No. 16/704,955 Office Action dated Jun. 23, 2020.
U.S. Appl. No. 16/704,955 Office Action dated Jun. 24, 2020.
Vail, D. M. (2004) Veterinary Co-operative oncology group. Vet Comp Oncol 2, 194-213.
Veber, et al. The design of metabolically-stable peptide analogs. Trends in Neurosciences. vol. 8, p. 392-396, 1985.
Veiseh, et al. A ligand-mediated nanovector for targeted gene delivery and transfection in cancer cells. Biomaterials. Feb. 2009;30(4):649-57. doi: 10.1016/j.biomaterials.2008.10.003. Epub Nov. 5, 2008.
Veiseh, et al. Optical and MRI Multifunctional nanoprobe for Targeting Gliomas, Nano Letters 5(6):1003-1008, 2005.
Veiseh, et al. Specific targeting of brain tumors with an optical/magnetic resonance imaging nanoprobe across the blood-brain barrier. Cancer Res. Aug. 1, 2009;69(15):6200-7. doi: 10.1158/0008-5472.CAN-09-1157. Epub Jul. 28, 2009.
Veiseh, et al. Tumor paint: a chlorotoxin: Cy5.5 bioconjugate for intraoperative visualization of cancer foci. Cancer Res. Jul. 15, 2007;67(14):6882-8.
Veiseh, O., et al., Optical and MRI Multifunctional nanoprobe for Targeting Gliomas, Nano Letters 5(6):1003-1008, 2005.
Velde, et al. The use of fluorescent dyes and probes in surgical oncology. Eur J Surg Oncol. Jan. 2010;36(1):6-15. doi: 10.1016/j.ejso.2009.10.014. Epub Nov. 18, 2009.
VivoTag® 680 XL In Vivo Fluorochrome Label. Perkin Elmer, 2010, Product No. NEV11119.
"Voet, et al. Biochemistry. Second Edition. John Wiley & Sons, Inc., pp. 235-241 (1995).".
Weissleder, et al. Shedding light onto live molecular targets. Nat Med. Jan. 2003;9(1):123-8.
Wen, et al. PTEN controls tumor-induced angiogenesis. Proc Natl Acad Sci U S A. Apr. 10, 2001;98(8):4622-7. Epub Mar. 27, 2001.
Wilson, et al. Mitogenic factors regulate ion channels in Schwann cells cultured from newborn rat sciatic nerve. J Physiol. Oct. 1993; 470: 501-520.
Wiranowska, et al. Clathrin-mediated entry and cellular localization of chlorotoxin in human glioma. Cancer Cell Int. Aug. 12, 2011;11:27. doi: 10.1186/1475-2867-11-27.
Wishart, et al. 1H, 13C and 15N chemical shift referencing in biomolecular NMR. J Biomol NMR. Sep. 1995;6(2):135-40.
Woodfork, et al. Inhibition of ATP-sensitive potassium channels causes reversible cell-cycle arrest of human breast cancer cells in tissue culture. J Cell Physiol. Feb. 1995;162(2):163-71.
Written Opinion dated Oct. 22, 2007 for International PCT Patent Application No. PCT/US2006/010170.
Yasuda, et al. Identification of a tumour associated antigen in lung cancer patients with asbestos exposure. Anticancer Res. Jul. 2010;30(7):2631-9.
Ye, et al. Integrin targeting for tumor optical imaging. Theranostics. 2011;1:102-26.
Yewey, et al., "Delivery of Proteins from a Controlled Release Injectable Implant," in Protein Delivery Physical Systems, Sanders and Hendren (eds.), pp. 93-117 (Plenum Press 1997).
Zellner, et al. Disparity in expression of protein kinase C alpha in human glioma versus glioma-derived primary cell lines: therapeutic implications. Clin Cancer Res. Jul. 1998;4(7):1797-802.
Zhang et al., Surface Modification of Superparamagnetic magnetite Nanoparticles and Their Intracellular Uptake, Biomaterial 23:1553 15-61, 2002.
Zhao, et al. Intraoperative fluorescence-guided resection of high-grade malignant gliomas using 5-aminolevulinic acid-induced porphyrins: a systematic review and meta-analysis of prospective studies. PLoS One. May 28, 2013;8(5):e63682. doi: 10.1371/journal.pone.0063682. Print 2013.
Zips et al. New anticancer agents: in vitro and in vivo evaluation. In Vivo 19(1):1-8 (2005).
Atkins et al., "Positive Margins Rates Following Breast-Conserving Surgery for Stage I-III Breast Cancer: Palpable versus Non-Palpable Tumors", Journal of Surgical Research, Sep. 2012, vol. 177, No. 1, pp. 109-115.
Bianchini et al., "Triple-negative breast cancer: challenges and opportunities of a heterogeneous disease", Nature Reviews Clinical Oncology, Nov. 2016, vol. 13, No. 11, pp. 674-690.
Collignon et al., "Triple-negative breast cancer: treatment challenges and solutions", Breast Cancer: Targets and Therapy, May 20, 2016, vol. 8, pp. 93-107.
Hudis et al., "Triple-Negative Breast Cancer: An Unmet Medical Need", The Oncologist, Jan. 1, 2011, 16(suppl 1), pp. 1-11.
Moran et al., "Society of Surgical Oncology—American Society for Radiation Oncology Consensus Guideline on Margins for Breast-Conserving Surgery with Whole-Breast Irradiation in Stages I and II Invasive Breast Cancer", International Journal of Radiation Oncology, Mar. 1, 2014, vol. 88, No. 3, pp. 553-564.
Podo et al., "Triple-negative breast cancer: Present challenges and new perspectives", Molecular Oncology, Apr. 24, 2010, vol. 4, pp. 209-229.
Veiseh., et al, "Cancer Research," Jul. 2007, vol. 67, No. 14, pp. 6882-6888.
Bae T.K., "Intravenous Contrast Medium Administration and Scan Timing at CT," Radiology, 2010, vol. 256(1), pp. 32-61.
Betheme, IV Bolus vs. IV Push: What's the Difference,https://lonestarivmedics.com/iv-bolus-vs-iv-push/, 2021, 4 pages.
Contrast Administration (Bolus vs Infusion), European Society of Cardiology, https://www.escardio.org/Education/Practice-Tools/EACVI-toolboxes/Contrast-Echo/Lectures/Contrast-administration-bolus-vs-infusion, 2021, 5 pages.
European office action dated Jul. 8, 2021 for EP Application No. 17783337.3, 4 Pages.
Examination Report No. 1 for Australian Patent Application No. 2017250359 dated Aug. 26, 2021, 3 Pages.
Lumiprobe, https://www.lumiprobe.com/tech/cyanine-dyes (obtained from website on May 21, 2021 (Year: 2021).
McGonigle S., et al., "Neuropilin-1 Drives Tumor-Specific Uptake of Chlorotoxin," Cell Communication and Signaling, 2019, vol. 17, No. 1, 67, 14 pages.
Britschgi A., et al., "Calcium-activated Chloride Channel ANO1 Promotes Breast Cancer Progression by Activating EGFR and CAMK Signaling," Proceedings of the National Academy of Sciences, Feb. 19, 2013, vol. 110(11), pp. E1026-E1034.
Dardevet L., et al., "Chlorotoxin: A Helpful Natural Scorpion Peptide to Diagnose Glioma and Fight Tumor Invasion," Toxins, Mar. 27, 2015, vol. 7, pp. 1079-1101.
Dogan B.E., et al., "Imaging of Triple-negative Breast Cancer," Annals of Oncology, vol. 23, 2012, pp. vi23-vi29.
Dogan B.E., et al., "Multimodality Imaging of Triple Receptor-negative Tumors with Mammography, Ultrasound, and MRI," American Journal of Roentgenology, Apr. 2010, vol. 194, pp. 1160-1166.
Haglund M.M., et al., "Enhanced Optical Imaging of Human Gliomas and Tumor Margins," Neurosurgery, vol. 38, No. 2, Feb. 1996, pp. 308-317.
Kosaka N., et al., "Near Infrared Fluorescence-Guided Real-Time Endoscopic Detection of Peritoneal Ovarian Cancer Nodules Using

(56) References Cited

OTHER PUBLICATIONS

Intravenously Injected Indocyanine Green," International Journal of Cancer, 2011, vol. 129, pp. 1671-1677.

Lumachi F., et al., "Current Medical Treatment of Estrogen Receptor-positive Breast Cancer," World Journal of Biological Chemistry, Aug. 26, 2015, vol. 6(3), pp. 231-239.

Moon W.K., et al., "Enhanced Tumor Detection Using a Folate Receptor-Targeted Near-Infrared Fluorochrome Conjugate," Bioconjugate Chem, vol. 14 (3), 2003, pp. 539-545.

Strickland R.N., "Tumor Detection in Nonstationary Backgrounds," IEEE Transactions on Medical Imaging, vol. 13 (3), Sep. 1994, pp. 491-499.

Thurber G.M., et al., "Detection limits of Intraoperative Near Infrared Imaging for Tumor Resection," Journal of Surgical Oncology, vol. 102, 2010, pp. 758-764.

Van Dam G.M., et al., "Intraoperative Tumor-Specific Fluorescence Imaging in Ovarian Cancer by Folate Receptor-a Targeting: First in-Human Results," Nature Medicine, Technical Reports, vol. 17 (10), Oct. 2011, pp. 1315-1320.

Wikipedia: "Indocyanine Green," The WayBack Machine, Accessed on Apr. 6, 2022, 6 pages, Retrieved from the Internet: https://web.archive.org/web/20120628074147/https://en.wikipedia.org/wiki/Indocyanine_green.

Yadav B.S., et al., "Biomarkers in triple negative breast cancer: A review," World journal of clinical oncology, Dec. 10, 2015, vol. 6(6), pp. 252-263.

Collignon et al. "Triple-negative breast cancer: treatment challenges and solutions," Breast Cancer (Dove Med Press), May 2016, 8:93-107 https://doi.org/10.2147/BCTT.S69488.

Dent et al. "Pattern of metastatic spread in triple-negative breast cancer. Breast cancer research and treatment," Jun. 2008, 115(2), 423-428. https://doi.org/10.1007/s10549-008-0086-2.

European Patent Application No. 17783337.3 Office Action dated Jun. 21, 2022.

Office Action for Canadian Patent Application No. 3,021,011, mailed Mar. 24, 2023, 4 pages.

Parrish-Novak et al. "Image-Guided Tumor Resection," Cancer journal (Sudbury, Mass.) vol. 21,3 (2015): 206-12. doi:10.1097/PPO.0000000000000113.

\* cited by examiner

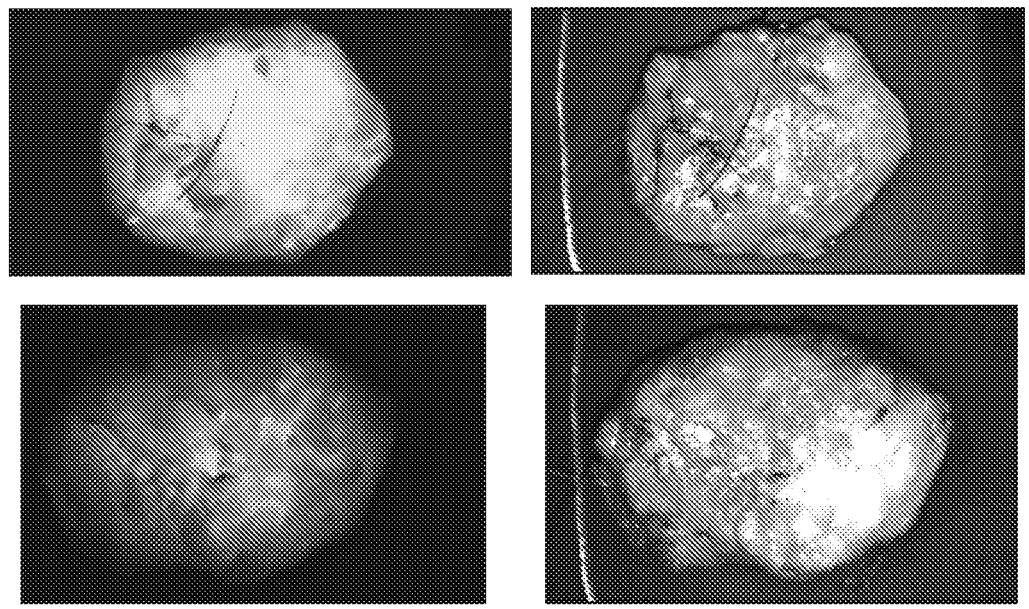
FIG. 1A
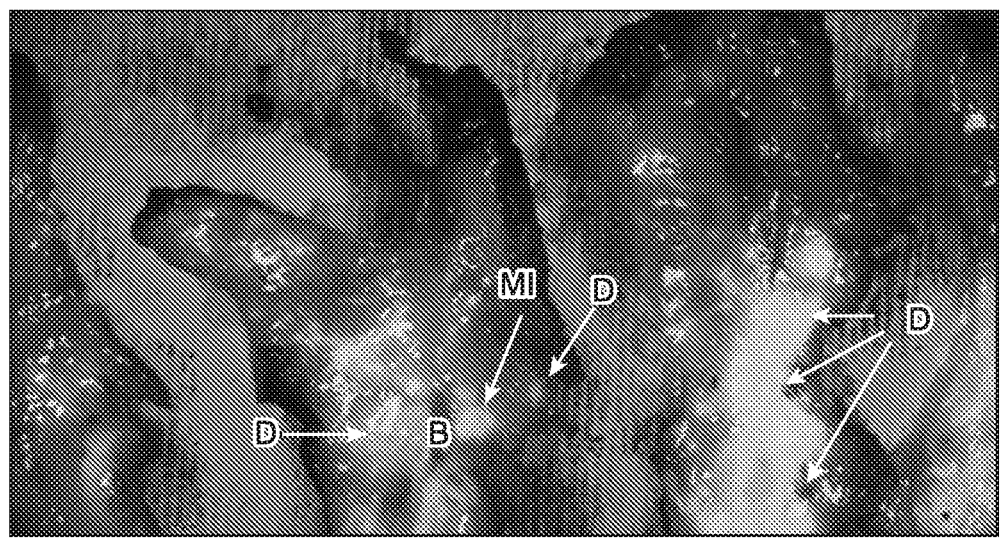
FIG. 1B
FIG. 1

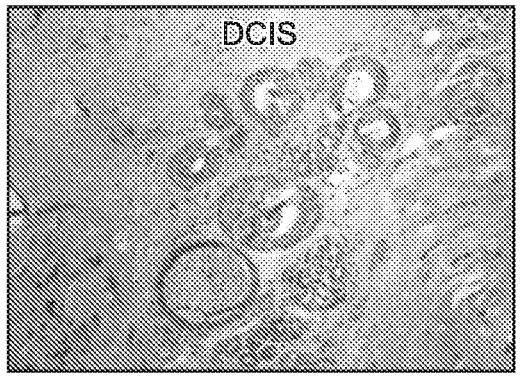
FIG. 1C
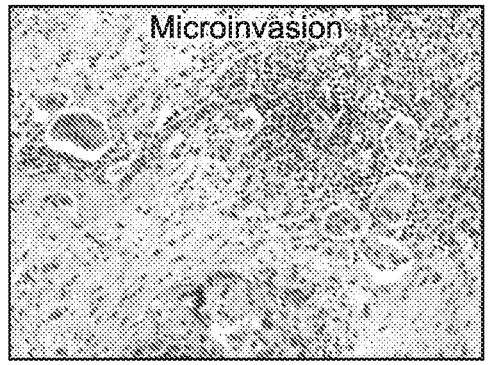
FIG. 1E
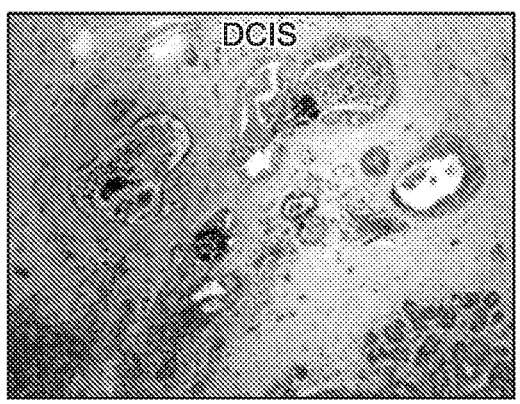
FIG. 1D
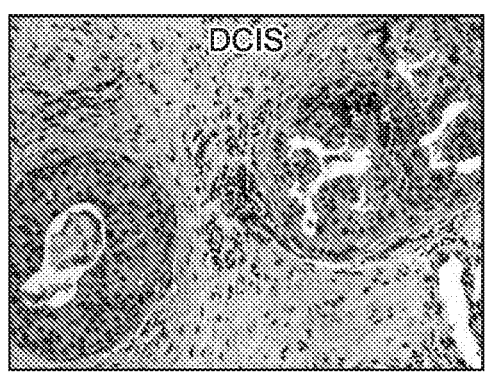
FIG. 1F
FIG. 1

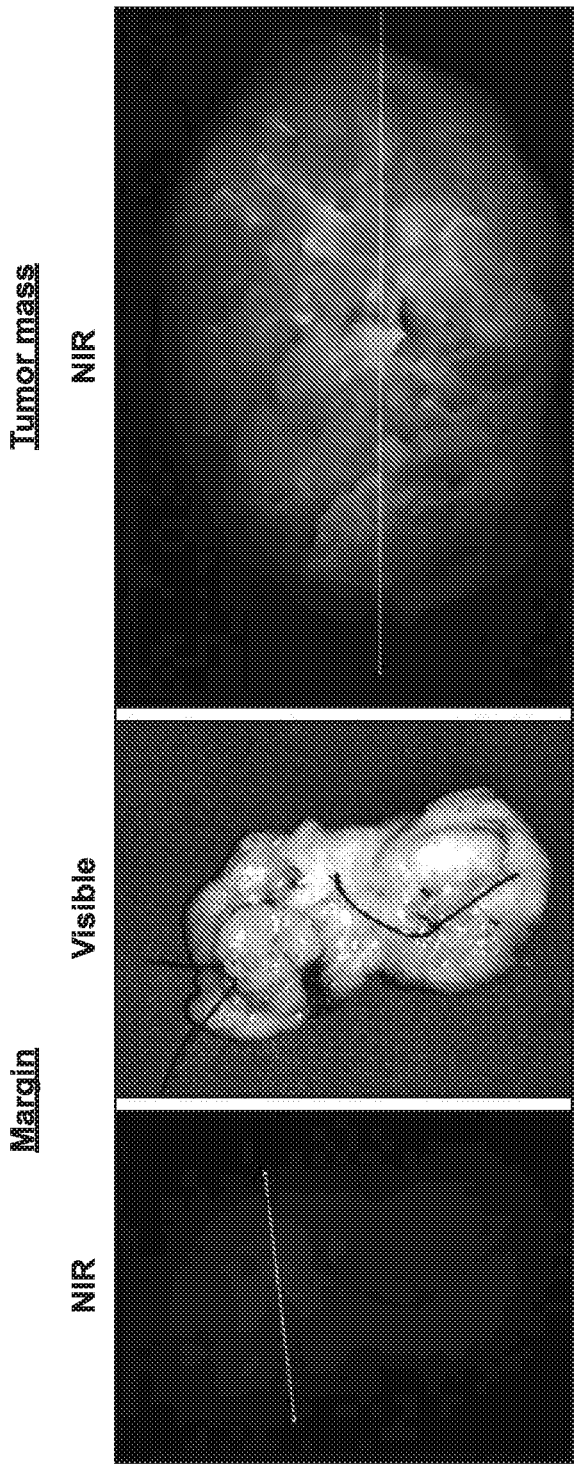
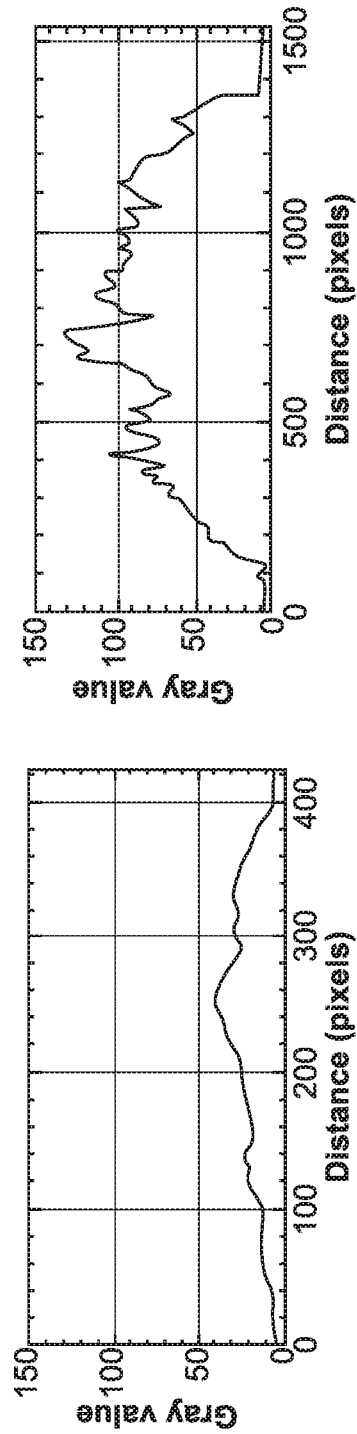
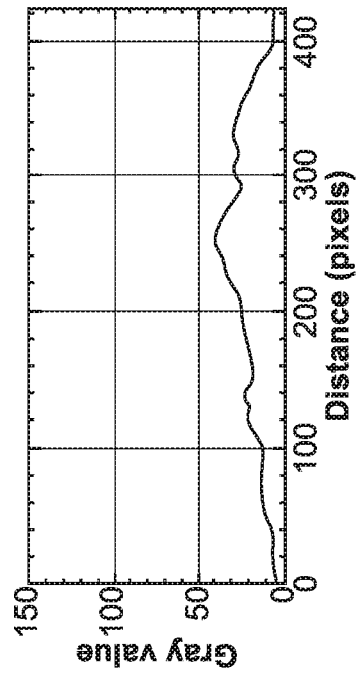
FIG. 1H
FIG. 1I
FIG. 1J
FIG. 1

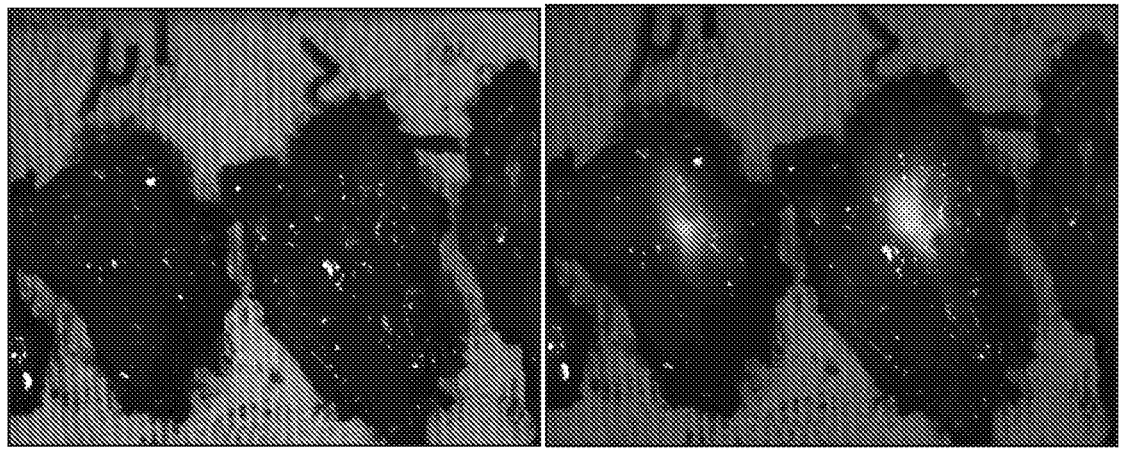
FIG. 2A  FIG. 2B
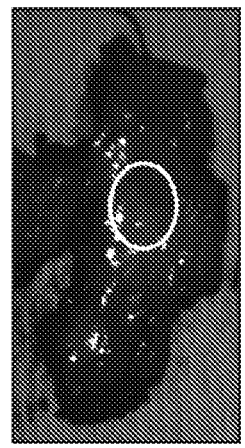
FIG. 2C
FIG. 2

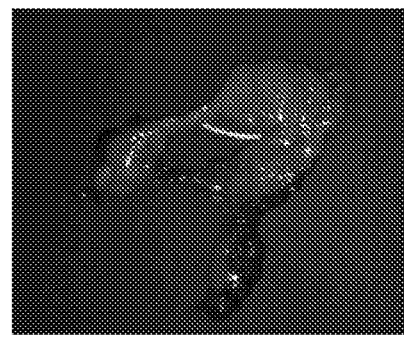
FIG. 7A
FIG. 7B
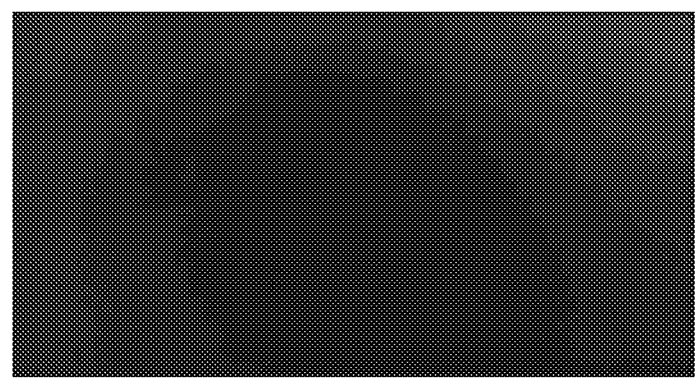
FIG. 7C
FIG. 7

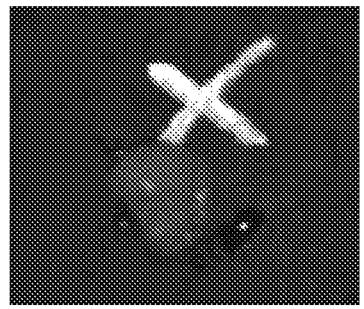
FIG. 8A
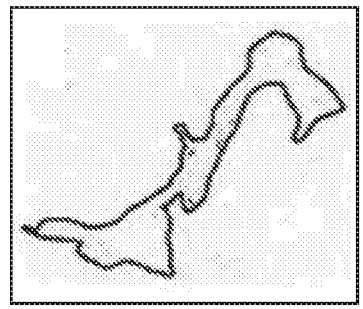
FIG. 8B
FIG. 8C
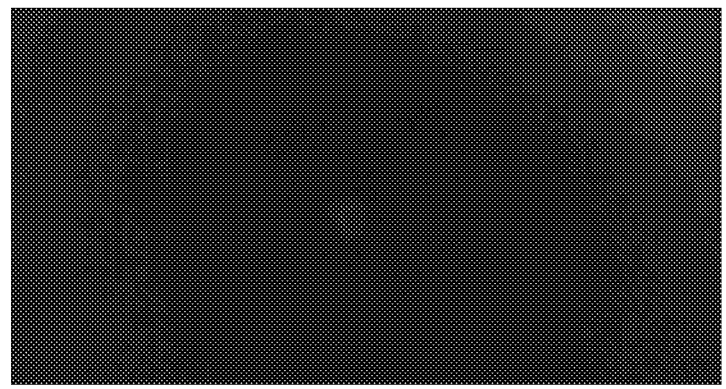
FIG. 8D
FIG. 8

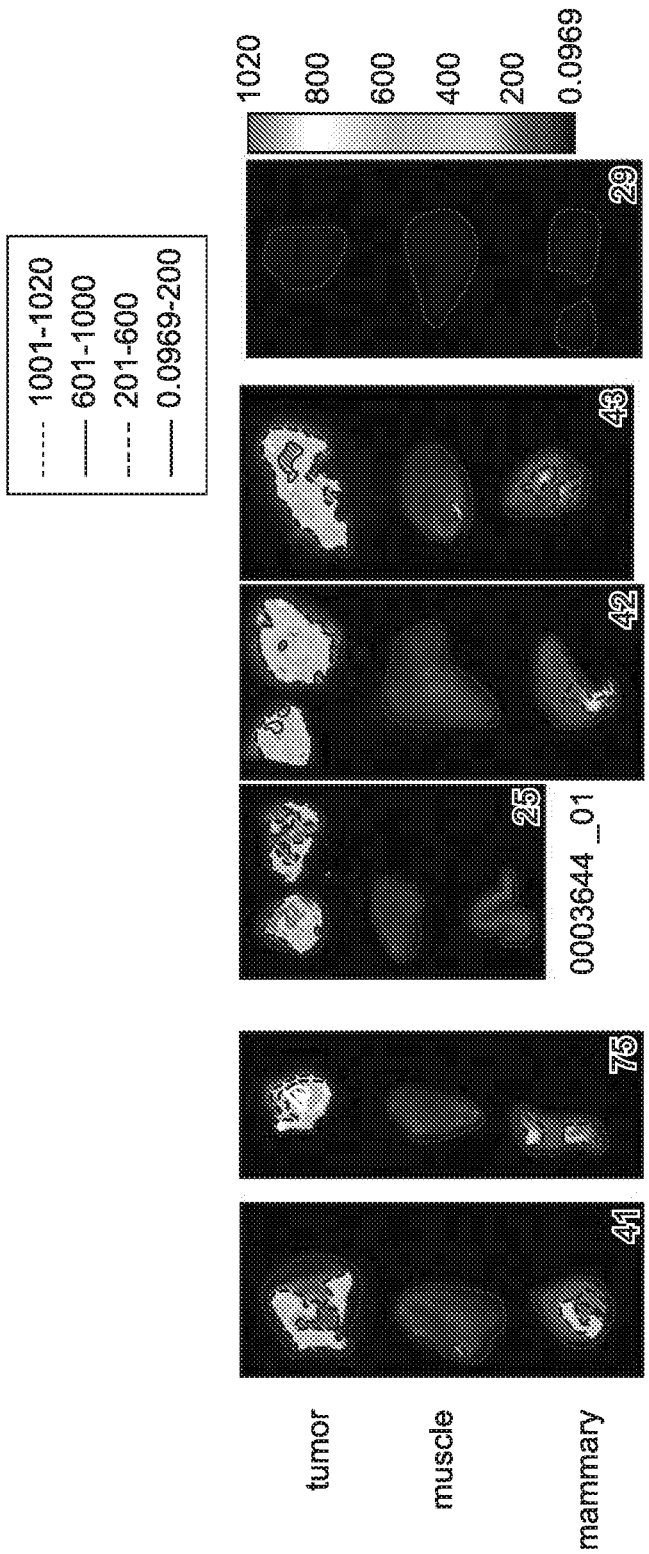
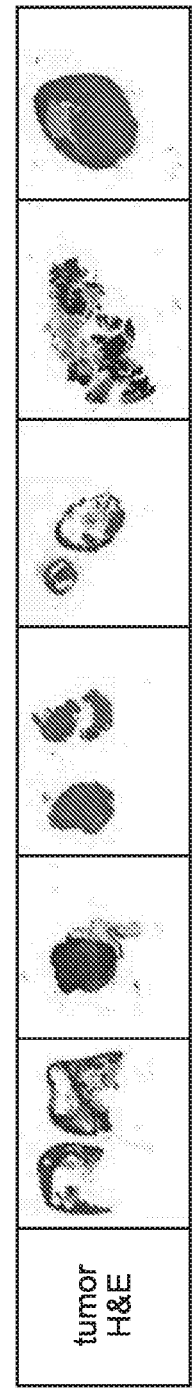
FIG. 11A
FIG. 11B
FIG. 11

Spectrum intraoperative images
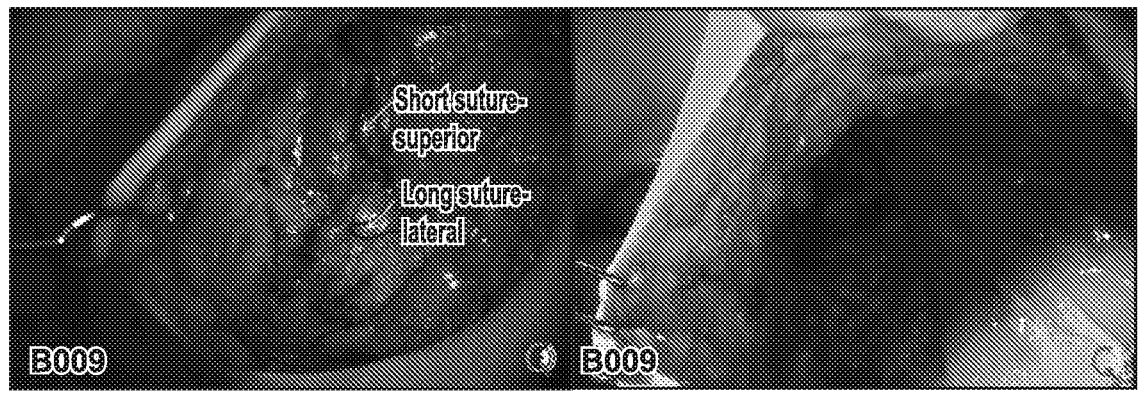
FIG. 16A
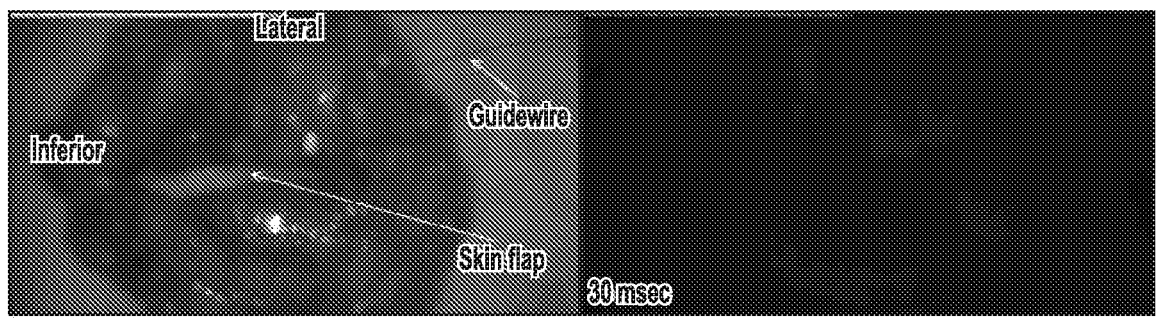
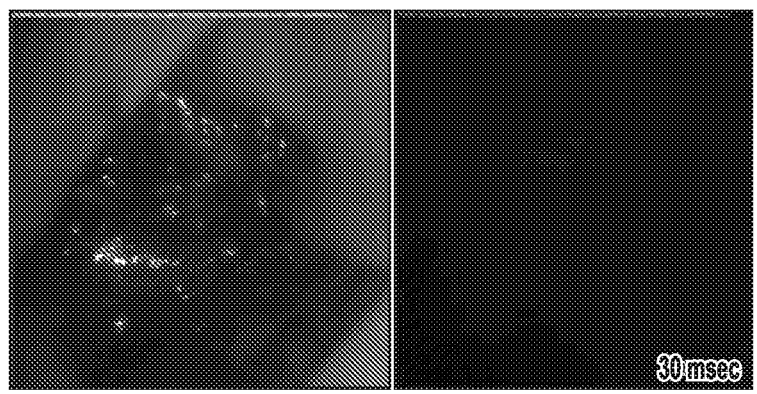
FIG. 16B
FIG. 16

SIRIS lumpectomy specimen ex vivo

Visible light only

NIR only

SIRIS surgical site

Visible light only

NIR only

METHODS OF TREATING BREAST CANCER

CROSS-REFERENCE

This application is a U.S. National Phase Application under 35 U.S.C. § 371 of International Application No. PCT/US2017/027812, filed Apr. 14, 2017, which claims the benefit of U.S. Provisional Application No. 62/323,522, filed Apr. 15, 2016, and U.S. Provisional Application No. 62/485,830, filed Apr. 14, 2017, which are incorporated herein by reference in their entireties for all purposes.

STATEMENT AS TO FEDERALLY SPONSORED RESEARCH

This invention was made with the support of the United States government under Contract number HHSN261201400046C awarded by the National Cancer Institute, National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Apr. 13, 2017, is named 45639-709_601_SL.txt and is 245,114 bytes in size.

BACKGROUND

Breast cancer is a cancer that usually starts in the inner lining of the milk ducts or lobules of the breast. Although breast cancer is rare in men, it is the second most common cancer in women in the United States, with about 230,000 new cases of breast cancer diagnosed each year. Breast cancers exhibit a wide range of morphological phenotypes and specific histopathological types. Treatment usually includes some combination of surgery, drugs (chemotherapy), and radiation, and the extent of surgical resection directly influences patient prognosis. Unfortunately, intraoperative identification of tumor margins or small foci of cancer cells remains imprecise. Residual cancer that is undetected at the time of surgery results in missed opportunity to achieve a complete resection with a single procedure. This can result in additional surgery, additional adjuvant therapy (chemotherapy and/or radiation), and worse outcome for the patient.

SUMMARY

The present disclosure provides peptides and pharmaceutical compositions of peptides for the treatment of triple-negative breast cancer, invasive ductal carcinoma breast cancer, and ductal carcinoma in situ breast cancer. Described herein are peptides that home, target, are directed to, migrate to, or accumulate in triple-negative breast cancer, invasive ductal carcinoma breast cancer, and ductal carcinoma in situ breast cancer.

In various aspects, the present disclosure provides a method of treating a subject with triple-negative breast cancer comprises administering a polypeptide to the subject, wherein the polypeptide is any one of SEQ ID NO: 482-SEQ ID NO: 485 or a fragment thereof.

In various aspects, the present disclosure provides a method of treating a subject with triple-negative breast cancer comprises administering a polypeptide to the subject, wherein the polypeptide has at least 80%, at least 85%, at least 90%, or at least 95% sequence identity with any one of SEQ ID NO: 1-SEQ ID NO: 481 or a fragment thereof.

In various aspects, the present disclosure provides a method of treating a subject with triple-negative breast cancer comprises administering a polypeptide to the subject, wherein the polypeptide has at least 80%, at least 85%, at least 90%, or at least 95% sequence identity with MCMPCFTTDHQMARRCDDCCGGR-GRGKCYGPQCLCR (SEQ ID NO: 9) or a fragment thereof.

In various aspects, the present disclosure provides a method of treating a subject with invasive ductal carcinoma breast cancer comprises administering a polypeptide to the subject, wherein the polypeptide is any one of SEQ ID NO: 482-SEQ ID NO: 485 or a fragment thereof.

In various aspects, the present disclosure provides a method of treating a subject with invasive ductal carcinoma breast cancer comprises administering a polypeptide to the subject, wherein the polypeptide has at least 80%, at least 85%, at least 90%, or at least 95% sequence identity with any one of SEQ ID NO: 1-SEQ ID NO: 481 or a fragment thereof.

In various aspects, the present disclosure provides a method of treating a subject with invasive ductal carcinoma breast cancer comprises administering a polypeptide to the subject, wherein the polypeptide has at least 80%, at least 85%, at least 90%, or at least 95% sequence identity with MCMPCFTTDHQMARRCDDCCGGR-GRGKCYGPQCLCR (SEQ ID NO: 9) or a fragment thereof.

In various aspects, the present disclosure provides a method of treating a subject with ductal carcinoma in situ breast cancer comprises administering a polypeptide to the subject, wherein the polypeptide is any one of SEQ ID NO: 482-SEQ ID NO: 485 or a fragment thereof.

In various aspects, the present disclosure provides a method of treating a subject with ductal carcinoma in situ breast cancer comprises administering a polypeptide to the subject, wherein the polypeptide has at least 80%, at least 85%, at least 90%, or at least 95% sequence identity with any one of SEQ ID NO: 1-SEQ ID NO: 481 or a fragment thereof.

In various aspects, the present disclosure provides a method of treating a subject with ductal carcinoma in situ breast cancer comprises administering a polypeptide to the subject, wherein the polypeptide has at least 80%, at least 85%, at least 90%, or at least 95% sequence identity with MCMPCFTTDHQMARRCDDCCGGR-GRGKCYGPQCLCR (SEQ ID NO: 9) or a fragment thereof.

In various aspects, the present disclosure provides a method of treating a subject with invasive lobular carcinoma breast cancer, the method comprising, administering a polypeptide to the subject, wherein the polypeptide is any one of SEQ ID NO: 482-SEQ ID NO: 485 or a fragment thereof.

In various aspects, the present disclosure provides a method of treating a subject with invasive lobular carcinoma breast cancer, the method comprising, administering a polypeptide to the subject, wherein the polypeptide has at least 80%, at least 85%, at least 90%, or at least 95% sequence identity with any one of SEQ ID NO: 1-SEQ ID NO: 481 or a fragment thereof.

In various aspects, the present disclosure provides a method of treating a subject with invasive lobular carcinoma breast cancer, the method comprising, administering a polypeptide to the subject, wherein the polypeptide has at least 80%, at least 85%, at least 90%, or at least 95% sequence identity with MCMPCFTTDHQMARRCDDCCGGR-GRGKCYGPQCLR (SEQ ID NO: 9) or a fragment thereof.

In various aspects, the present disclosure provides a method of treating a subject with lobular carcinoma in situ breast cancer, the method comprising, administering a polypeptide to the subject, wherein the polypeptide is any one of SEQ ID NO: 482-SEQ ID NO: 485 or a fragment thereof.

In various aspects, the present disclosure provides a method of treating a subject with lobular carcinoma in situ breast cancer, the method comprising, administering a polypeptide to the subject, wherein the polypeptide has at least 80%, at least 85%, at least 90%, or at least 95% sequence identity with any one of SEQ ID NO: 1-SEQ ID NO: 481 or a fragment thereof.

In various aspects, the present disclosure provides a method of treating a subject with lobular carcinoma in situ breast cancer, the method comprising, administering a polypeptide to the subject, wherein the polypeptide has at least 80%, at least 85%, at least 90%, or at least 95% sequence identity with MCMPCFTTDHQMARRCDDCCGGR-GRGKCYGPQCLR (SEQ ID NO: 9) or a fragment thereof.

In other aspects, the fragment of the polypeptide has a length of at least 25 residues.

In other aspects, each amino acid of the polypeptide is independently selected as an L- or D-enantiomer. In further aspects, the polypeptide contains no lysine residues. In some aspects, the polypeptide contains a single lysine residue. In other aspects, the single lysine residue is located at a position corresponding to K-27 of native chlorotoxin, K-23 of native chlorotoxin, or K-15 of native chlorotoxin. In still other aspects, one, two, or three methionine residues of the polypeptide are replaced with other amino acids.

In certain aspects, the N-terminus of the polypeptide is blocked by acetylation or cyclization.

In other aspects, the polypeptide comprises at least 1, at least 2, at least 3, at least 4, at least 5, or at least 6 disulfide bonds.

In some aspects, the polypeptide comprises an isoelectric point of at least 6.0, at least 6.5, at least 7.0, at least 7.5, at least 8.0, at least 8.5, or at least 9.0.

In certain aspects, the polypeptide binds to a breast cancerous tissue or breast cancer cell.

In other aspects, the method further comprises detecting the presence or absence of the polypeptide in a tissue or cell, wherein the presence of the polypeptide in the tissue or cell indicates the presence of a breast cancerous tissue or breast cancer cell. In some aspects, the cancerous tissue or cancer cell is associated with triple-negative breast cancer. In other aspects, the cancerous tissue or cancer cell is associated with invasive ductal carcinoma. In still other aspects, the cancerous tissue or cancer cell is associated with ductal carcinoma in situ breast cancer. In other aspects, the cancerous tissue or cancer cell is associated with invasive lobular carcinoma. In still other aspects, the cancerous tissue or cancer cell is associated with lobular carcinoma in situ breast cancer.

In some aspects, the detecting is performed using fluorescence imaging.

In other aspects, the method further comprises surgically removing the breast cancerous tissue or breast cancer cell from the human subject. In certain aspects, the polypeptide is intravenously administered about 1 hr, about 2 hrs, about 3 hrs, about 4 hrs, about 5 hrs, about 6 hrs, about 7 hrs, about 8 hrs, about 9 hrs, about 10 hrs, about 11 hrs, about 12 hrs, about 13 hrs, about 14 hrs, about 15 hrs, about 16 hrs, about 17 hrs, about 18 hrs, about 19 hrs, about 20 hrs, about 21 hrs, about 22 hrs, about 23 hrs, about 24 hrs, about 36 hrs, about 48 hrs, about 60 hrs, or about 72 hrs prior surgically removing the breast cancerous tissue or breast cancer cell from the human subject.

In some aspects, the polypeptide is administered at a dosage sufficient to treat triple-negative breast cancer in the human subject. In further aspects, the polypeptide is administered at a dosage sufficient to treat invasive ductal carcinoma in the human subject. In still further aspects, the polypeptide is administered at a dosage sufficient to treat ductal carcinoma in situ in the human subject. In other aspects, the polypeptide is administered at a dosage sufficient to treat invasive lobular carcinoma in the human subject. In still other aspects, the polypeptide is administered at a dosage sufficient to treat lobular carcinoma in situ in the human subject.

In other aspects, the polypeptide is conjugated to an agent. In some aspects, the polypeptide is conjugated to the agent via a cleaveable linker or non-cleavable linker. In certain aspects, the polypeptide comprises a single lysine residue and the agent is conjugated to the polypeptide at the single lysine residue. In other aspects, the polypeptide comprises no lysine residues and the agent is conjugated to the polypeptide at the N-terminus of the polypeptide.

In some aspects, the polypeptide and agent comprise the structure of Formula (IV), or a pharmaceutically acceptable salt thereof:

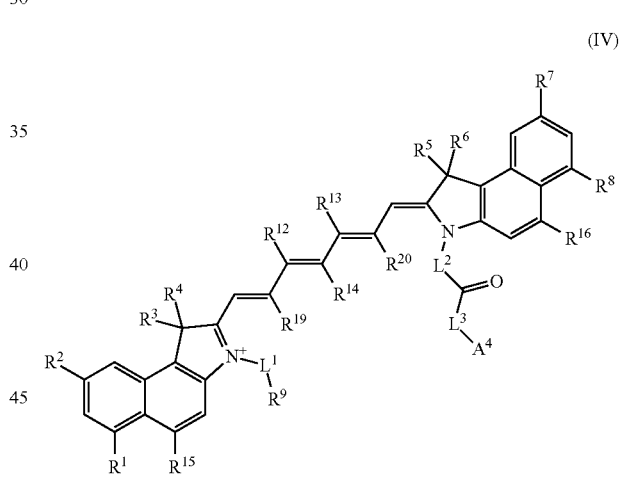

(IV)

wherein: $R^1$, $R^2$, $R^3$, $R^4$, $R^5$, $R^6$, $R^7$, $R^8$, $R^{15}$, and $R^{16}$ are each independently selected from hydrogen, $C_1$-$C_6$ alkyl, $C_1$-$C_6$ alkylene-COOH, sulfonate, $C_1$-$C_6$ alkylene-sulfonate, —COOH, —SO$_2$—NH$_2$, or $C_1$-$C_6$ alkoxy; $R^9$ is hydrogen, sulfonate, amine, or —COOH; $L^1$ is $C_3$-$C_6$ alkylene; $L^2$ is $C_1$-$C_{10}$ alkylene; $L^3$ is a bond, —O—, —NR$^{10}$—, —NR$^{10}$—$C_1$-$C_6$ alkylene-, —O—NR$^{10}$—, —NR$^{10}$—$C_1$-$C_6$ alkylene-(O—$C_1$-$C_6$ alkylene)$_n$-, —NR$^{10}$-L$^4$-, —NR$^{10}$—$C_1$-$C_6$ alkylene-NR$^{11}$—(C(=O)—$C_1$-$C_6$ alkylene-O—)$_m$—, or —NR$^{10}$—$C_1$-$C_6$ alkylene-NR$^{10}$—$C_1$-$C_6$ alkylene-NR$^{10}$—$C_1$-$C_6$ alkylene-; L$^4$ is a bond, -heterocyclyl-, or -heterocyclyl-$C_1$-$C_6$ alkylene-; $R^{10}$ is hydrogen or $C_1$-$C_6$ alkyl; $R^{11}$ is hydrogen or $C_1$-$C_6$ alkyl; $R^{12}$ and $R^{13}$ are independently selected from hydrogen, $C_1$-$C_6$ alkyl, or $R^{12}$ and $R^{13}$ are joined together along with the other atoms to which they are attached to form a 5-membered or 6-membered carbocyclic or heterocyclic ring; $R^{14}$ is hydrogen or $C_1$-$C_6$ alkylene, -(L$^5$)-aryl, -(L$^5$)-aryl-R$^{21}$, -(L$^5$)-heteroaryl, -(L$^5$)-heteroaryl- $R^{21}$, —$NR^{17}R^{18}$, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring; $L^5$ is a bond, $C_1$-$C_{10}$ alkylene, —O—, —$NR^{10}$—; $R^{17}$ and $R^{18}$ are each independently hydrogen or aryl; $R^{19}$ and $R^{20}$ are independently selected from hydrogen, $C_1$-$C_6$ alkyl, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring; $R^{21}$ is hydrogen, sulfonate, or —COOH; n is 0, 1, 2, or 3; m is 0, 1, 2, or 3; p is 0, 1, 2, or 3; q is 0, 1, 2, or 3; and $A^4$ is the polypeptide. In further aspects, $R^3$, $R^4$, $R^5$, $R^6$ are each independently methyl; $R^1$, $R^2$, $R^7$, $R^8$, $R^{15}$, and $R^{16}$ are each independently hydrogen; $R^{12}$, $R^{13}$, $R^{14}$, $R^{19}$, and $R^{20}$ are each independently hydrogen; $R^9$ is sulfonate; $R^{10}$ is hydrogen; $L^1$ is butylene; $L^2$ is pentylene; or $L^3$ is selected from a bond, —O—, —$NR^{10}$—, —$NR^{10}$—$C_1$-$C_6$ alkylene-, —O—$NR^{10}$—, or —$NR^{10}$-$L^4$-.

In some aspects, the polypeptide and agent comprise the structure of any one of Formulas (IX), (X), (XI), (XII), (XIII), (XIV), (XV), or (XVI), wherein $A^4$ is the polypeptide:

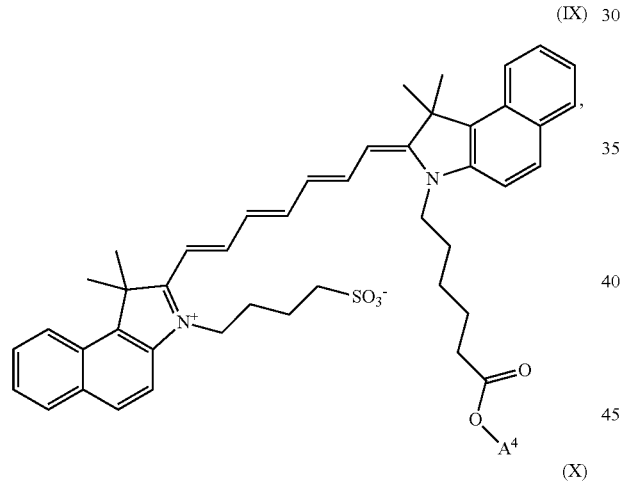

(IX)

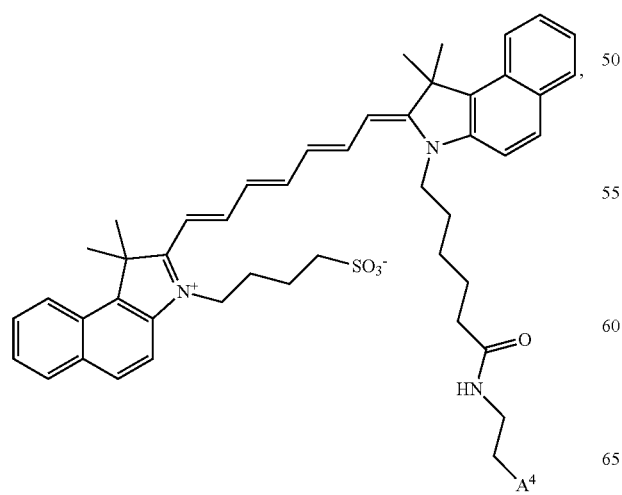

(X)

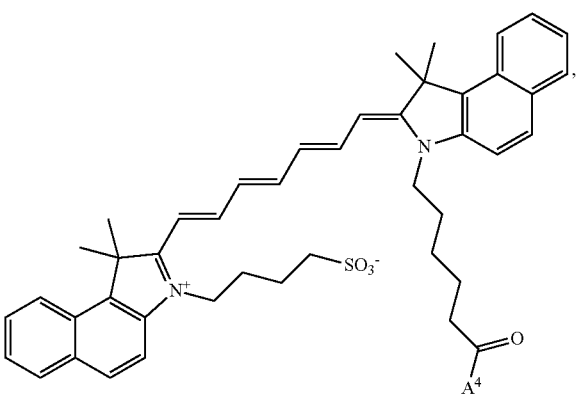

(XI)

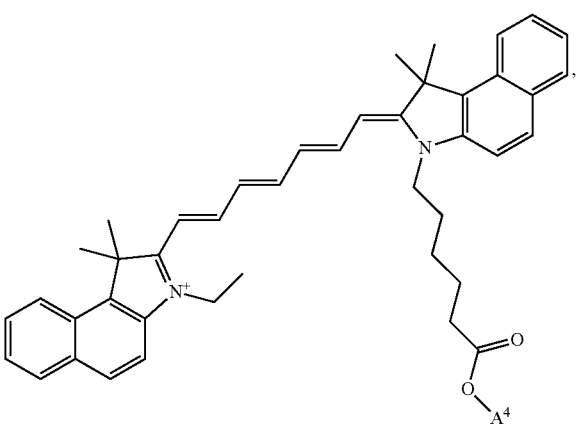

(XII)

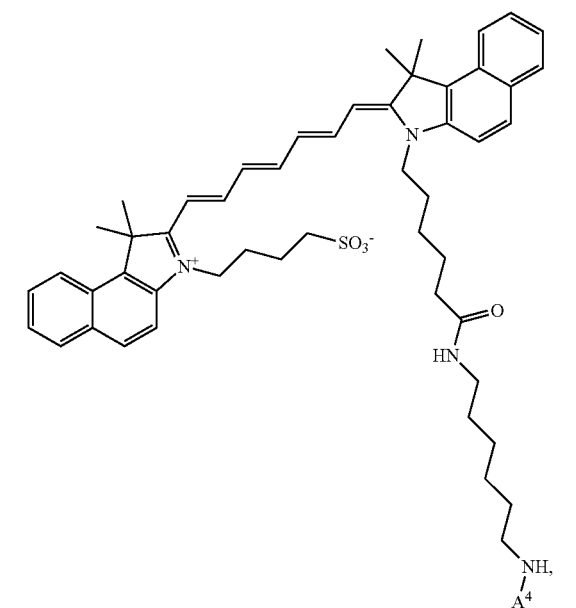

(XIII)

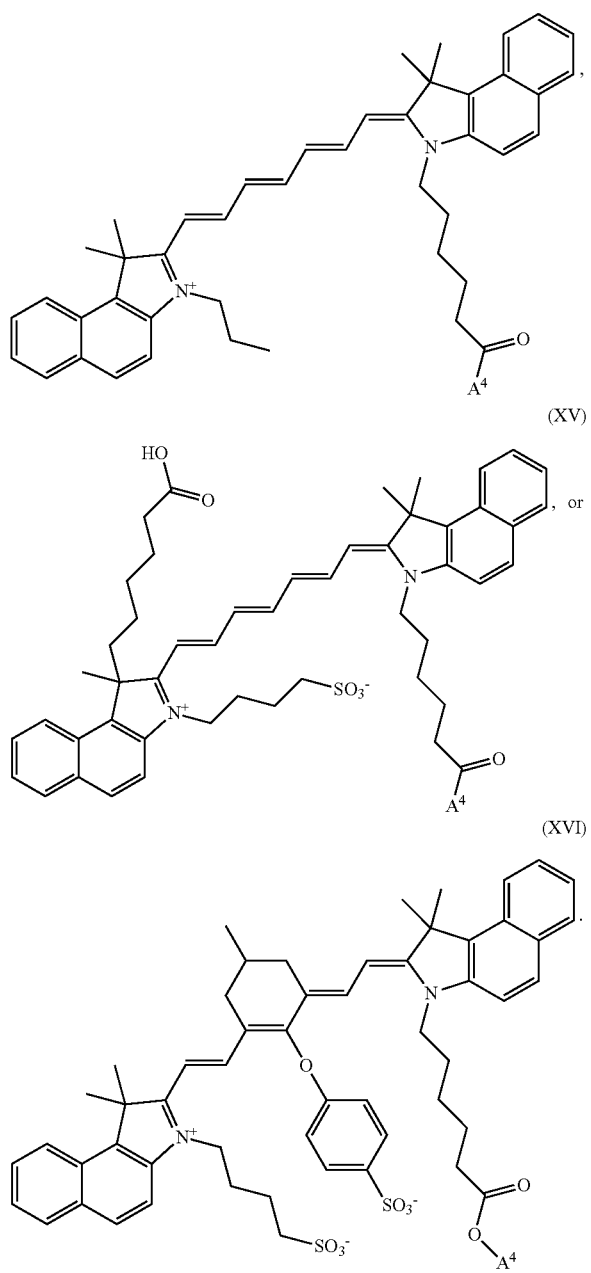

In certain aspects, the polypeptide is conjugated to a detectable agent. In other aspects, the polypeptide is conjugated to the detectable agent via a cleavable linker or a non-cleavable linker. In some aspects, the detectable agent comprises a dye, a fluorophore, a fluorescent biotin compound, a luminescent compound, a chemiluminescent compound, a radioisotope, a paramagnetic metal ion, or a combination thereof.

In other aspects, the polypeptide is conjugated to a therapeutic agent. In some aspects, the polypeptide is conjugated to the therapeutic agent via a cleavable linker or a non-cleavable linker. In certain aspects, the therapeutic agent comprises a radioisotope, toxin, enzyme, sensitizing drug, radiosensitizer, nucleic acid, interfering RNA, antibody, antibody fragment, aptamer, anti-angiogenic agent, cisplatin, carboplatin, oxaliplatin, anti-metabolite, mitotic inhibitor, growth factor inhibitor, cytotoxin, microtubule disrupting agent, DNA modifying agent, maytansine derivative, auristatin derivative, dolostatin derivative, monomethyl auristatin E, monomethyl auristatin F, DM1, calicheamicin, duocarmycin derivative, campthotecin, pyrrolobenzodiazepine, paclitaxel, cyclophosphamide, chlorambucil, melphlan, bufulfan, carmustine, ifosfamide, temozolomide, topotecan, fluorouracil, vincristine, vinblastine, procarbazine, dacarbazine, altretamine, methotrexate, pemetrexed, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomycin, tamoxifen, flutamide, leuprolide, goserelin, aminogluthimide, anastrozole, amsacrine, asparaginase, mitoxantrone, mitotane, amifostine, lenalidomide, imatinib, abiraterone, erlotinib, enzalutimide, everolimus palbociclib, pomalidomide, sunitinib, sorafenib, imatinib, gefitinib, afatinib, axitinib, crizotinib, vismoegib, dabrefenib, vemurafenib, bevacizumab, vorozol and other aromatase inhibitors, lapitinib, cetuximab, panitumumab, bicalutamide, anthracyclines, platinums, poly(ADP-ribose) polymerase (PARP) inhibitors (such as olaparib, veliparib, iniparib, niraparib, rucaparib); trastuzumab, lapatinib, carboplatin, taxane, gemcitabine, epirubicin, apatinib, cediranib, capecitabine, 7-hydroxystaurosporine (UCN-01), bortezomib, denaciclib, panobinostat, dasatinib, LGK974, or a combination thereof.

In other aspects, administering the polypeptide comprises intravenously administering a composition comprising the polypeptide and a pharmaceutically acceptable carrier. In some aspects, the composition comprises a pH within a range from about 6 to about 7.5. In certain aspects, the composition comprises an ionic strength less than or equal to about 50 mM. In some aspects, the composition further comprises a buffer comprising histidine, tris, HEPES, ethylene diamine, or a combination thereof. In other aspects, the composition further comprises a sugar alcohol. In certain aspects, the composition comprises from about 0 mM to about 50 mM histidine, from about 0 mM to about 20 mM tris, about 20 mM methionine, from about 3% to about 10% sugar alcohol, and a pH within a range from about 6 to about 7.5.

In some aspects, a method of imaging an organ or body region of a subject comprises administering to the subject a compound comprising a polypeptide conjugated to a detectable marker, wherein the polypeptide comprises: a) any one of SEQ ID NO: 482-SEQ ID NO: 485 or a fragment thereof; b) at least 80%, at least 85%, at least 90%, or at least 95% sequence identity with any one of SEQ ID NO: 1-SEQ ID NO: 481 or a fragment thereof; or at least at least 80%, at least 85%, at least 90%, or at least 95% sequence identity with MCMPCFTTDHQMARRCDDCCGGR-GRGKCYGPQCLCR (SEQ ID NO: 9) or a fragment thereof; and imaging a breast, breast tissue or breast cell of the subject.

In other aspects, the method further comprises detecting the presence or absence of the compound in a tissue or cell, wherein the presence of the compound in the tissue or cell indicates the presence of a triple-negative breast cancer in a diseased region, tissue, structure, or cell of the subject. In further aspects, the method further comprises detecting the presence or absence of the compound in a tissue or cell, wherein the presence of the compound in the tissue or cell indicates the presence of invasive ductal carcinoma breast cancer in a diseased region, tissue, structure, or cell of the subject. In still further aspects, the method further comprises detecting the presence or absence of the compound in a tissue or cell, wherein the presence of the compound in the tissue or cell indicates the presence of ductal carcinoma in situ breast cancer in the diseased region, tissue, structure or cell of the subject. In other aspects, the method further comprises detecting the presence or absence of the compound in a tissue or cell, wherein the presence of the compound in the tissue or cell indicates the presence of a breast cancerous tissue or breast cancer cell invasive lobular carcinoma breast cancer in a diseased region, tissue, structure, or cell of the subject. In still other aspects, the method further comprises detecting the presence or absence of the compound in a tissue or cell, wherein the presence of the compound in the tissue or cell indicates the presence of lobular carcinoma in situ breast cancer in the diseased region, tissue, structure or cell of the subject.

In other aspects, the method further comprises performing surgery on the subject.

In some aspects, the method further comprises treating the triple-negative breast cancer. In other aspects, the method further comprises treating the invasive ductal carcinoma breast cancer. In certain aspects, the method further comprises treating the ductal carcinoma in situ breast cancer. In other aspects, the method further comprises treating the invasive lobular carcinoma breast cancer. In still other aspects, the method further comprises treating the lobular carcinoma in situ cancer. In some aspects, the method further comprises treating the diseased region, tissue, structure, or cell of the subject.

In other aspects, the surgery comprises removing the triple-negative breast cancer. In further aspects, the surgery comprises removing the invasive ductal carcinoma breast cancer. In some aspects, the surgery comprises removing the ductal carcinoma in situ breast cancer. In other aspects, the surgery comprises removing the lobular ductal carcinoma breast cancer. In still other aspects, the surgery comprises removing the lobular carcinoma in situ breast cancer. In certain aspects, the surgery comprises removing the diseased region, tissue, structure or cell of the subject.

In some aspects, the method further comprises imaging the triple-negative breast cancer after surgical removal. In other aspects, the method further comprises imaging the invasive ductal carcinoma breast cancer after surgical removal. In certain aspects, the method further comprises imaging the ductal carcinoma in situ breast cancer after surgical removal. In other aspects, the method further comprises imaging the invasive lobular carcinoma breast cancer after surgical removal. In still other aspects, the method further comprises imaging the lobular carcinoma in situ breast cancer after surgical removal. In some aspects, the method further comprises imaging the diseased region, tissue, structure, or cell of the subject after surgical removal.

In some aspects, the method further comprises imaging the tumor bed. In further aspects, the method further comprises detecting residual tumor. In still further aspects, the method further comprises surgical removal of the residual tumor.

In other aspects, the fragment of the polypeptide has a length of at least 25 residues.

In other aspects, each amino acid of the polypeptide is independently selected as an L- or D-enantiomer. In further aspects, the polypeptide contains no lysine residues. In some aspects, the polypeptide contains a single lysine residue. In other aspects, the single lysine residue is located at a position corresponding to K-27 of native chlorotoxin, K-23 of native chlorotoxin, or K-15 of native chlorotoxin. In still other aspects, one, two, or three methionine residues of the polypeptide are replaced with other amino acids.

In certain aspects, the N-terminus of the polypeptide is blocked by acetylation or cyclization.

In other aspects, the polypeptide comprises at least 1, at least 2, at least 3, at least 4, at least 5, or at least 6 disulfide bonds.

In some aspects, the polypeptide comprises an isoelectric point of at least 6.0, at least 6.5, at least 7.0, at least 7.5, at least 8.0, at least 8.5, or at least 9.0.

In certain aspects, the polypeptide binds to a breast cancerous tissue or breast cancer cell.

In some aspects, the detecting is performed using fluorescence imaging.

In other aspects, the method further comprises surgically removing the breast cancerous tissue or breast cancer cell from the human subject. In certain aspects, the compound is intravenously administered about 1 hr, about 2 hrs, about 3 hrs, about 4 hrs, about 5 hrs, about 6 hrs, about 7 hrs, about 8 hrs, about 9 hrs, about 10 hrs, about 11 hrs, about 12 hrs, about 13 hrs, about 14 hrs, about 15 hrs, about 16 hrs, about 17 hrs, about 18 hrs, about 19 hrs, about 20 hrs, about 21 hrs, about 22 hrs, about 23 hrs, about 24 hrs, about 36 hrs, about 48 hrs, about 60 hrs, or about 72 hrs prior surgically removing the breast cancerous tissue or breast cancer cell from the human subject.

In certain aspects, the polypeptide comprises a single lysine residue and the detectable agent is conjugated to the polypeptide at the single lysine residue. In other aspects, the polypeptide comprises no lysine residues and the detectable agent is conjugated to the polypeptide at the N-terminus of the polypeptide.

In some aspects, the polypeptide and the detectable agent comprise the structure of Formula (IV), or a pharmaceutically acceptable salt thereof:

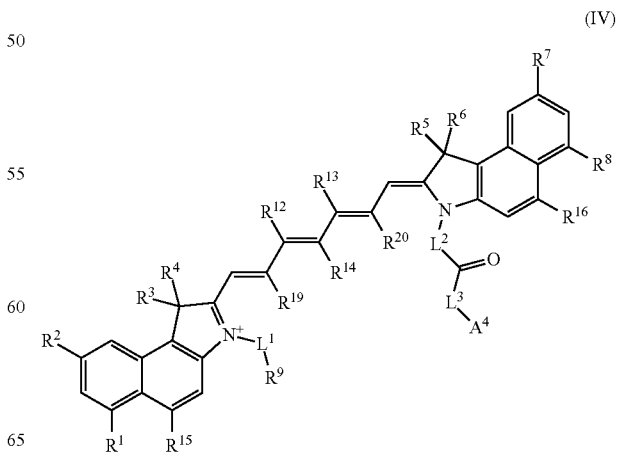

(IV)

wherein: $R^1$, $R^2$, $R^3$, $R^4$, $R^5$, $R^6$, $R^7$, $R^8$, $R^{15}$, and $R^{16}$ are each independently selected from hydrogen, $C_1$-$C_6$ alkyl, $C_1$-$C_6$ alkylene-COOH, sulfonate, $C_1$-$C_6$ alkylene-sulfonate, —COOH, —SO$_2$—NH$_2$, or $C_1$-$C_6$ alkoxy; $R^9$ is hydrogen, sulfonate, amine, or —COOH; $L^1$ is $C_3$-$C_6$ alkylene; $L^2$ is $C_1$-$C_{10}$ alkylene; $L^3$ is a bond, —O—, —NR$^{10}$—, —NR$^{10}$—$C_1$-$C_6$ alkylene-, —O—NR$^{10}$—, —NR$^{10}$—$C_1$-$C_6$ alkylene-(O—$C_1$-$C_6$ alkylene)$_n$-, —NR$^{10}$-L$^4$-, —NR$^{10}$—$C_1$-$C_6$ alkylene-NR$^{11}$—(C(=O)—$C_1$-$C_6$ alkylene-O—)$_m$—, or —NR$^{10}$—$C_1$-$C_6$ alkylene-NR$^{10}$—$C_1$-$C_6$ alkylene-NR$^{10}$—$C_1$-$C_6$ alkylene-; $L^4$ is a bond, -heterocyclyl-, or -heterocyclyl-$C_1$-$C_6$ alkylene-; $R^{10}$ is hydrogen or $C_1$-$C_6$ alkyl; $R^{11}$ is hydrogen or $C_1$-$C_6$ alkyl; $R^{12}$ and $R^{13}$ are independently selected from hydrogen, $C_1$-$C_6$ alkyl, or $R^{12}$ and $R^{13}$ are joined together along with the other atoms to which they are attached to form a 5-membered or 6-membered carbocyclic or heterocyclic ring; $R^{14}$ is hydrogen or $C_1$-$C_6$ alkylene, -(L$^5$)-aryl, -(L$^5$)-aryl-R$^{21}$, -(L$^5$)-heteroaryl, -(L$^5$)-heteroaryl-R$^{21}$, —NR$^{17}$R$^{18}$, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring; $L^5$ is a bond, $C_1$-$C_{10}$ alkylene, —O—, —NR$^{10}$—; $R^{17}$ and $R^{18}$ are each independently hydrogen or aryl; $R^{19}$ and $R^{20}$ are independently selected from hydrogen, $C_1$-$C_6$ alkyl, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring; $R^{21}$ is hydrogen, sulfonate, or —COOH; n is 0, 1, 2, or 3; m is 0, 1, 2, or 3; p is 0, 1, 2, or 3; q is 0, 1, 2, or 3; and $A^4$ is the polypeptide. In further aspects, $R^3$, $R^4$, $R^5$, $R^6$ are each independently methyl; $R^1$, $R^2$, $R^7$, $R^8$, $R^{15}$, and $R^{16}$ are each independently hydrogen; $R^{12}$, $R^{13}$, $R^{14}$, $R^{19}$, and $R^{20}$ are each independently hydrogen; $R^9$ is sulfonate; $R^{10}$ is hydrogen; $L^1$ is butylene; $L^2$ is pentylene; or $L^3$ is selected from a bond, —O—, —NR$^{10}$—, —NR$^{10}$—$C_1$-$C_6$ alkylene-, —O—NR$^{10}$—, or —NR$^{10}$-L$^4$-.

In some aspects, the polypeptide and the detectable agent comprise the structure of any one of Formulas (IX), (X), (XI), (XII), (XIII), (XIV), (XV), or (XVI), wherein $A^4$ is the polypeptide:

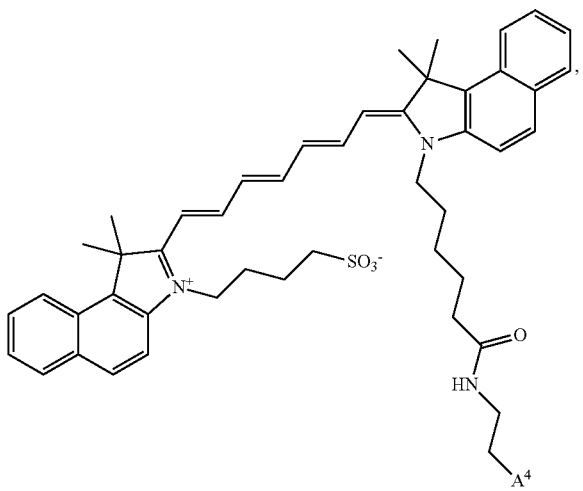
(X)

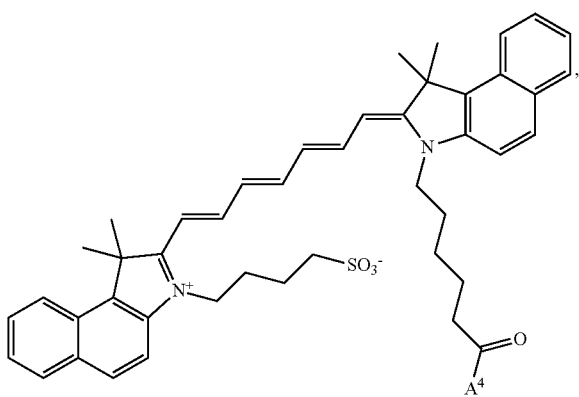
(XI)

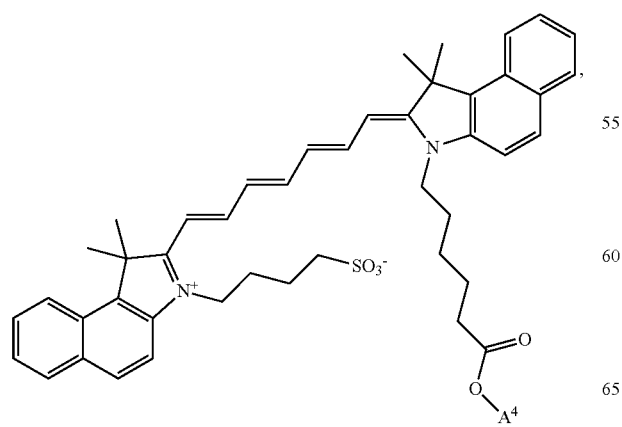
(IX)

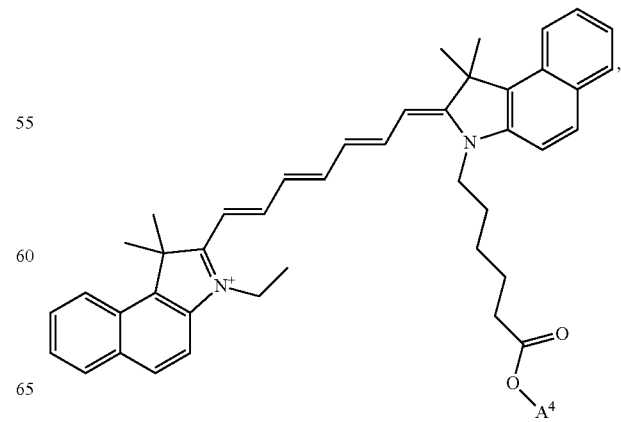
(XII)

(XIII)

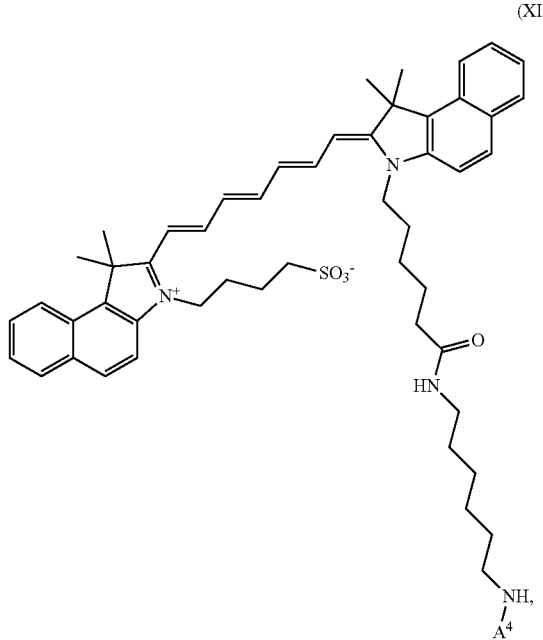

(XIV)

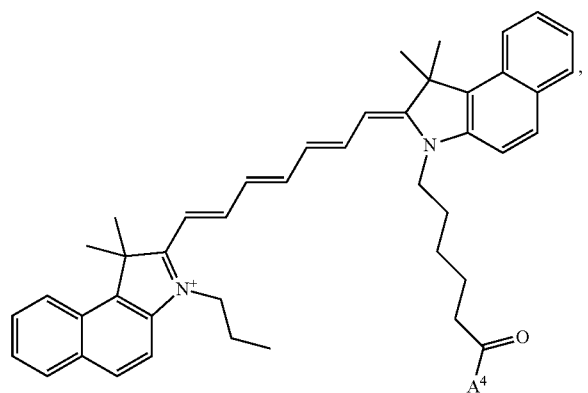

(XV)

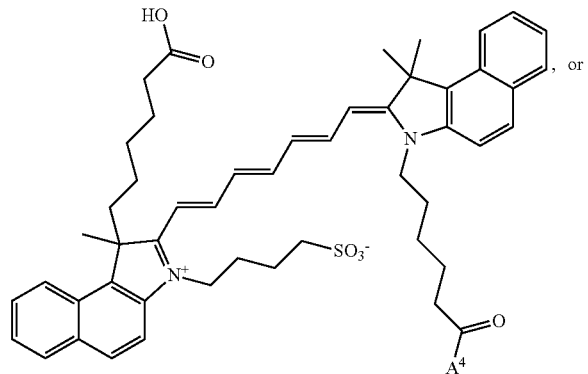

(XVI)

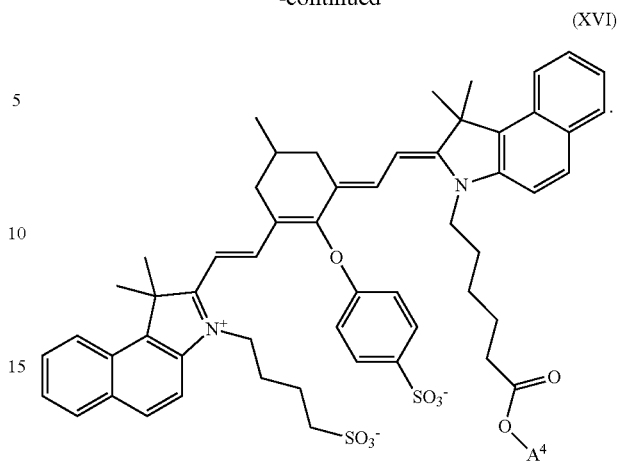

In other aspects, the polypeptide is conjugated to the detectable agent via a cleavable linker or a non-cleavable linker. In some aspects, the detectable agent comprises a dye, a fluorophore, a fluorescent biotin compound, a luminescent compound, a chemiluminescent compound, a radioisotope, a paramagnetic metal ion, or a combination thereof.

In other aspects, the polypeptide is further conjugated to a therapeutic agent. In some aspects, the polypeptide is conjugated to the therapeutic agent via a cleavable linker or non-cleavable linker. In certain aspects, the therapeutic agent comprises a radioisotope, toxin, enzyme, sensitizing drug, radiosensitizer, nucleic acid, interfering RNA, antibody, antibody fragment, aptamer, anti-angiogenic agent, cisplatin, carboplatin, oxaliplatin, anti-metabolite, mitotic inhibitor, growth factor inhibitor, cytotoxin, microtubule disrupting agent, DNA modifying agent, maytansine derivative, auristatin derivative, dolostatin derivative, monomethyl auristatin E, monomethyl auristatin F, DM1, calicheamicin, duocarmycin derivative, campthotecin, pyrrolobenzodiazepine, paclitaxel, cyclophosphamide, chlorambucil, melphlan, bufulfan, carmustine, ifosfamide, temozolomide, topotecan, fluorouracil, vincristine, vinblastine, procarbazine, dacarbazine, altretamine, methotrexate, pemetrexed, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomycin, tamoxifen, flutamide, leuprolide, goserelin, aminogluthimide, anastrozole, amsacrine, asparaginase, mitoxantrone, mitotane, amifostine, lenalidomide, imatinib, abiraterone, erlotinib, enzalutimide, everolimus palbociclib, pomalidomide, sunitinib, sorafenib, imatinib, gefitinib, afatinib, axitinib, crizotinib, vismoegib, dabrefenib, vemurafenib, bevacizumab, vorozol and other aromatase inhibitors, lapitinib, cetuximab, panitumumab, bicalutamide, anthracyclines, platinums, poly(ADP-ribose) polymerase (PARP) inhibitors (such as olaparib, veliparib, iniparib, niraparib, rucaparib); trastuzumab, lapatinib, carboplatin, taxane, gemcitabine, epirubicin, apatinib, cediranib, capecitabine, 7-hydroxystaurosporine (UCN-01), bortezomib, denaciclib, panobinostat, dasatinib, LGK974, or a combination thereof.

In other aspects, administering the polypeptide comprises intravenously administering the compound, wherein the compound is administered in a composition comprising the compound and a pharmaceutically acceptable carrier. In some aspects, the composition comprises a pH within a range from about 6 to about 7.5. In certain aspects, the composition comprises an ionic strength less than or equal to about 50 mM. In some aspects, the composition further comprises a buffer comprising histidine, tris, HEPES, ethylene diamine, or a combination thereof. In other aspects, the composition further comprises a sugar alcohol. In certain aspects, the composition comprises from about 0 mM to about 50 mM histidine, from about 0 mM to about 20 mM tris, about 20 mM methionine, from about 3% to about 10% sugar alcohol, and a pH within a range from about 6 to about 7.5.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows near-infrared (NIR) images of the ex vivo lumpectomy specimen on the left, and corresponding white light images of the lumpectomy specimen on the right, which were taken prior to gross sectioning. Fluorescence signal, corresponding to lighter and brighter areas in the NIR images, is indicative of the presence of Compound 76 in tumor tissues.

FIG. 1B shows an NIR image overlay with the white light image of ex vivo gross sectioned lumpectomy specimen from subject BOO 1 at a 30 millisecond (ms) calculated exposure time. Fluorescence signal, corresponding to lighter and brighter areas in the NIR images, is indicative of the presence of Compound 76 in tumor tissues. The Ds with accompanying arrows indicate areas of DCIS. The MI with accompanying arrow indicates an area with microinvasion. The B indicates the biopsy site.

FIG. 1C shows an haematoxylin and eosin (H&E) staining of a fluorescent region of the ex vivo lumpectomy specimen as shown in FIG. 1B from subject B001, indicating ductal carcinoma in situ (DCIS) tumor pathology.

FIG. 1D shows an H&E staining of a fluorescent region of the ex vivo tumor mass as shown in FIG. 1B from subject B001, indicating ductal carcinoma in situ (DCIS) tumor pathology.

FIG. 1E shows an H&E staining of a fluorescent region of the ex vivo tumor mass as shown in FIG. 1B from subject B001, indicating microinvasive ductal carcinoma tumor pathology.

FIG. 1F shows an H&E staining of a region of the ex vivo lumpectomy specimen as shown in FIG. 1B from subject B001, indicating ductal carcinoma in situ (DCIS) tumor pathology.

FIG. 1H shows an NIR image of the tumor margin and the corresponding visible light image on the left, and the lumpectomy specimen NIR image on the right, which were taken prior to gross sectioning using a 30 ms calculated exposure time. Fluorescence signal, corresponding to lighter and brighter areas in the NIR images, is indicative of the presence of Compound 76 in tumor tissues.

FIG. 1I shows a line plot analysis of the fluorescent signal intensity of the ex vivo tumor margin tissue through the line as shown in FIG. 1H.

FIG. 1J shows a line plot analysis of the fluorescent signal intensity of the ex vivo lumpectomy specimen through the line as shown in FIG. 1H.

FIG. 2 shows images of ex vivo breast tissue after administration of Compound 76 to a human subject (subject B002) diagnosed with breast cancer.

FIG. 2A shows a white light image of ex vivo breast tissue from a human subject (subject B002) diagnosed with breast cancer, wherein 12 mg of Compound 76 was administered to the human subject (subject B002) before excision of the breast tissue.

FIG. 2B shows a NIR image overlay with the white light image of FIG. 2A. Fluorescence signal, corresponding to lighter and brighter areas in the NIR image, is indicative of the presence of Compound 76 in tumor tissues. Both these images are of ex vivo breast tissue from a human subject (subject B002) diagnosed with breast cancer, wherein 12 mg of Compound 76 was administered to the human subject (subject B002) before excision of the breast tissue using a 20 ms calculated exposure time.

FIG. 2C shows a NIR image overlay with a white light image of ex vivo breast tissue from a human subject (subject B002) diagnosed with breast cancer, wherein 12 mg of Compound 76 was administered to the human subject (subject B002) before excision of the breast tissue using a 20 ms exposure time. Fluorescence signal, corresponding to lighter and brighter areas in the NIR image, is indicative of the presence of Compound 76 in tumor tissues.

FIG. 7 shows images of breast tissue from a human subject diagnosed with breast cancer, wherein no Compound 76 was administered to the human subject before excision of the breast tissue.

FIG. 7A shows a white light image of ex vivo breast tissue from a human subject diagnosed with breast cancer, wherein no Compound 76 was administered to the human subject before excision of the breast tissue.

FIG. 7B shows a NIR image of ex vivo breast tissue from a human subject diagnosed with breast cancer, wherein no Compound 76 was administered to the human subject before excision of the breast tissue. The NIR image was exposed for 30 ms calculated exposure time.

FIG. 7C shows a NIR image of ex vivo breast tissue from a human subject diagnosed with breast cancer, wherein no Compound 76 was administered to the human subject before excision of the breast tissue. The NIR image was exposed for 135 ms calculated exposure time.

FIG. 8 shows ex vivo images of normal breast tissue from a human subject, wherein 12 mg of Compound 76 was administered to the human subject before excision of the normal breast tissue.

FIG. 8A shows a white light image of ex vivo normal breast tissue from a human subject, wherein 12 mg of Compound 76 was administered to the human subject before excision of the normal breast tissue.

FIG. 8B shows an H&E stain of ex vivo normal breast tissue from a human subject, wherein 12 mg of Compound 76 was administered to the human subject before excision of the normal breast tissue.

FIG. 8C shows a NIR image of ex vivo normal breast tissue from a human subject, wherein 12 mg of Compound 76 was administered to the human subject before excision of the normal breast tissue. The NIR image was exposed for 30 ms calculated exposure time.

FIG. 8D shows a NIR image of ex vivo normal breast tissue from a human subject, wherein 12 mg of Compound 76 was administered to the human subject before excision of the normal breast tissue. The NIR image was exposed for 135 ms calculated exposure time.

FIG. 11 shows images of tumor, muscle, and mammary tissue from mice that received a xenograft of breast cancer tissue derived from a patient with breast cancer.

FIG. 11A shows NIR images of tumors excised from mice on the top row with control NIR images of corresponding excised normal muscle below in the middle row and corresponding excised normal mammary fat pad below in the bottom row. The tumors are from breast cancer tissue derived from a human patient, which was grafted into the mice. The first five panels on the left are from mice that received an injection of Compound 76 before tissue excision, and the panel on right is from a mouse that did not receive an injection of Compound 76 before tissue excision.

FIG. 11B shows H&E staining of tumors excised from mice below the corresponding NIR image of the tumors shown in FIG. 11A. The tumors are from breast cancer tissue derived from a human patient, which was grafted into the mice. The first five panels on the left are from mice that received an injection of Compound 76 before tissue excision, and the panel on right is from a mouse that did not receive an injection of Compound 76 before tissue excision.

FIG. 16 illustrates representative Spectrum and SIRIS images from intra-operative imaging.

FIG. 16A illustrates fluorescence signal from intra-operative imaging using the Spectrum in subject B009. Fluorescence signal, corresponding to lighter and brighter areas in the mastectomy tissue in situ, is indicative of the presence of Compound 76 in tumor tissues and was observed faintly towards the middle of the image.

FIG. 16B illustrates fluorescence signal from intra-operative imaging using the SIRIS on lumpectomy specimens ex vivo and at the surgical site in subject B010. Fluorescence signal, corresponding to lighter and brighter areas in the NIR images, is indicative of the presence of Compound 76 in tumor tissues.

FIG. 22A illustrates fluorescence signal in the surgical site. Fluorescence signal, corresponding to lighter and brighter areas in the NIR images, is indicative of the presence of Compound 76 in tumor tissues.

FIG. 22B illustrates fluorescence signal in the inferior lateral margin wrap that was excised from the surgical site in FIG. 22A. Fluorescence signal, corresponding to lighter and brighter areas in the NIR image, is indicative of the presence of Compound 76 in tumor tissues.

DETAILED DESCRIPTION

Figures 1, 1G:
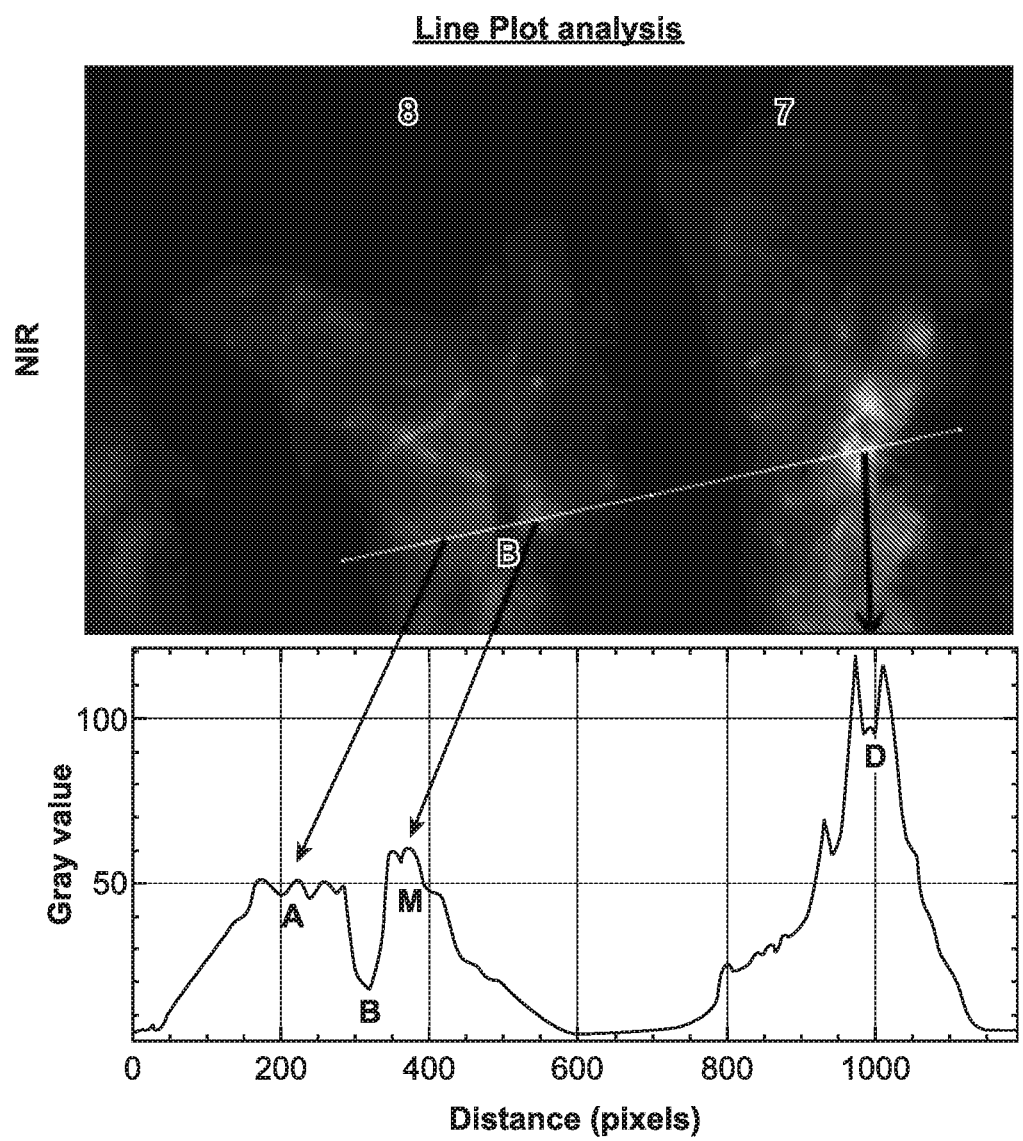
FIG. 1 shows images and graphs of fluorescent signal intensity of ex vivo tissue, wherein 12 mg of Compound 76 was administered to the human subject (subject B001) before excision of the tissue.
FIG. 1G shows a line plot analysis graph of the ex vivo lumpectomy specimen as shown in FIG. 1B, which shows the fluorescent signal (lighter and brighter areas) intensity corresponding to Compound 76 in tumor tissues (through the line on the above NIR image of the tumor mass) was increased in the microinvasive carcinoma "M" and DCIS "D" compared to the non-tumor adipose tissue "A". The biopsy site is marked "B". NIR image above the line plot analysis graph used a 30 ms calculated exposure time.

The present disclosure provides compositions and methods for the detection and/or treatment of certain types of breast cancer. The compositions described herein comprise peptide conjugates comprising a detectable label, which are suitable for the detection and treatment of breast cancer. In some aspects, the type of breast cancer is invasive ductal carcinoma (IDC). In other aspects, the type of breast cancer is triple negative breast cancer (TNBC). In still other aspects, the type of breast cancer is ductal carcinoma in situ (DCIS). In still other aspects, the type of breast cancer is invasive lobular carcinoma (ILC). In other aspects, the type of breast cancer is lobular carcinoma in situ (LCIS). In certain aspects, the compositions are provided in combination with a pharmaceutically acceptable carrier, which can be administered to a subject by any route of administration. Following administration of the compositions described herein, the peptides or peptide conjugates bind selectively to cancer cells. The cancer cells can then be detected, for example, by imaging or other visualization or detection method suitable for detecting the detectable label of the peptide conjugate. In further aspects, the presently described compositions can be used to treat the type of breast cancer by way of a therapeutic agent, which is attached to the conjugate and which acts on the cancer cells following binding by the peptide portion of the conjugate. These and other aspects are described in detail herein.

Breast cancer can begin in different areas of the breast, such as in the milk ducts, the lobules (glands that produce breast milk), or the tissue found in between, including but not limited to stromal tissue (fatty and fibrous connective tissue), and can be non-invasive, invasive, recurrent, or metastatic. These characteristics can be used to determine the type of breast cancer. For example, IDC is an invasive breast cancer that originates in the milk ducts, whereas DCIS breast cancer also originates in the milk ducts, but has not become non-invasive.

Additionally, breast cancers can exhibit a wide range of morphological phenotypes and specific histopathological types that have particular prognostic and clinical characteristics. For example, four types of breast cancer can be classified based on the presence or absence of human epidermal growth factor receptor 2 (HER2), estrogen receptors (ER), and progesterone receptors (PR) in the breast cancer. More specifically, subtypes have been identified and referred to, amongst other classifications, as follows: the subtype luminal A is HER2 negative, ER positive, and either PR positive or negative; the subtype luminal B is HER2 positive, ER negative, and either PR positive or negative; the subtype triple-negative, which is also referred to as TNBC, is HER2 negative, ER negative, and PR negative; and the subtype HER2 type is HER2 positive, ER negative, and PR negative. The majority of TNBCs are basal-like and have a poor prognosis (Penault-LLorca, F. et al., *Ann Oncol.*, 23 Suppl 6: vi19-22 (2012)).

The type of breast cancer can influence patient prognosis and treatment. For example, TNBCs are more aggressive than luminal A, luminal B, or HER2 type tumors. Unlike the other types, TNBC's growth is not driven by estrogen or progesterone, or by growth signals coming from the HER2 protein and does not respond to hormonal therapy, such as tamoxifen or aromatase inhibitors, or therapies that target HER2 receptors, such as Herceptin, and therefore, treatment options are limited for TNBC treatment. A large number of patients with TNBC treated with chemotherapy and surgery are not cured of their disease, and approximately 30% to 40% of these patients will have a recurrence of disease within 3 to 10 years of treatment with neoadjuvant therapy and surgery. Most patients with recurrent disease will die from their breast cancer. Therefore, identification and pursuit of new therapeutic advances is critical.

The invention will best be understood by reference to the following detailed description of the aspects and embodiments of the invention, taken in conjunction with the accompanying drawings and figures. The discussion below is descriptive, illustrative and exemplary and is not to be taken as limiting the scope defined by any appended claims.

As used in the specification and appended claims, unless specified to the contrary, the following terms have the meaning indicated.

As used herein and in the appended claims, the singular forms "a," "and," and "the" include plural referents unless the context clearly dictates otherwise. Thus, for example, reference to "a compound" includes a plurality of such compounds, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Hydrazino" refers to the =N—NH$_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_{15}$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_{15}$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) t-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—SR$^a$, —R$^b$—OC(O)—R$^a$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

"Heterocyclyl" refers to a 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-SR^a$, $-R^b-OC(O)-R^a$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) t-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-SR^a$, $-R^b-OC(O)-R^a$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. When the compounds described herein contain olefinic double bonds or other centers of geometric asymmetry, and unless specified otherwise, it is intended that the compounds include both E (or trans) and Z (cis) geometric isomers. Likewise, all possible isomers, as well as their racemic and optically pure forms, and all tautomeric forms are also intended to be included.

A "stereoisomer" refers to a compound made up of the same atoms bonded by the same bonds but having different three-dimensional structures, which are not interchangeable. It is therefore contemplated that various stereoisomers and mixtures thereof and includes "enantiomers," which refers to two stereoisomers whose molecules are nonsuperimposeable mirror images of one another.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In solutions where tautomerization is possible, a chemical equilibrium of the tautomers will exist. The exact ratio of the tautomers depends on several factors, including temperature, solvent, and pH. Some examples of tautomeric pairs include:

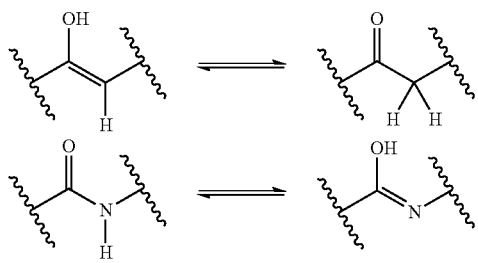

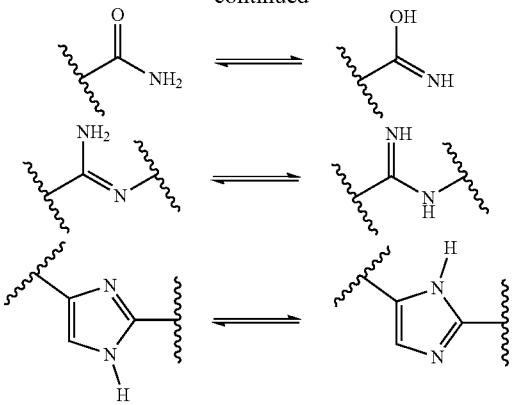

"Optional" or "optionally" means that a subsequently described event or circumstance may or may not occur and that the description includes instances when the event or circumstance occurs and instances in which it does not.

"Pharmaceutically acceptable salt" includes both acid and base addition salts. A pharmaceutically acceptable salt of any one of the alkoxyphenyl-linked amine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication, reduction, or amelioration of the underlying disorder being treated. Also, a therapeutic benefit is achieved with the eradication, reduction, or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Chlorotoxin Variants and Conjugates

The present disclosure provides methods for administering compounds that selectively bind to certain types of breast cancer cells and tissues. For example, the present disclosure provides a method for administering compounds that selectively bind to TNBC cells and tissues. As another example, the present disclosure provides a method for administering compounds that selectively bind to IDC breast cancer cells and tissues. As yet another example, the present disclosure provides a method for administering compounds that selectively bind to invasive ductal carcinoma (IDC), ductal carcinoma in situ (DCIS) breast cancer, invasive lobular carcinoma breast cancer, lobular carcinoma in situ (LCIS) cells and tissues. In various aspects, these compounds can comprise a peptide portion and a detectable agent conjugated together.

In various aspects of the compounds used in the present disclosure, the peptide portions of the compounds described herein have certain features in common with the native chlorotoxin (CTX) peptide. The native chlorotoxin peptide was originally isolated from the scorpion *Leiurus quinquestriatus*. Chlorotoxin is a 36 amino acid peptide that selectively binds to cancerous cells. The peptide portions of the present compounds have advantageously retained at least some of the cancer-cell binding activity of chlorotoxin. The cancer-cell binding activity of chlorotoxin provides certain advantages for the detection and treatment of cancer because it facilitates the selective localization of detectable agents and therapeutic agents to the breast cancer cells for the detection and treatment of breast cancer. In certain aspects, peptides used in the present disclosure are conjugated to moieties, such as detectable labels (e.g., dyes or radiolabels) that are detected (e.g., visualized) in a subject. In some aspects, the chlorotoxin and/or chlorotoxin variants are conjugated to detectable labels to enable tracking of the bio-distribution of a conjugated peptide. The fluorescent moiety can be covalently coupled to the chlorotoxin and/or chlorotoxin variants to allow for the visualization of the conjugate by fluorescence imaging, either directly or through a linker as described herein and known to one of ordinary skill in the art.

In some aspects, the fluorescent label used has emission characteristics that are desired for a particular application. For example, the fluorescent label is a fluorescent dye that has an emission wavelength maximum from 500 nm to 1100 nm, from 600 nm to 1000 nm, from 800 nm to 1000 nm, from 600 to 800 nm, from 800 nm to 900 nm, from 650 nm to 850 nm, from 650 nm to 800 nm, from 700 nm to 800 nm, from 800 nm to 880 nm, from 810 nm to 875 nm, from 825 nm to 875 nm, or from 790 nm to 840 nm, or from 800 nm to 830 nm. One of ordinary skill in the art will appreciate the various dyes that are used as detectable labels and that have the emission characteristics herein. In addition, excitation spectra can be used to optimize imaging of visualization of the conjugate. The absorption spectrum of a fluorophore can determine the wavelengths of light energy that excites the molecule to produce its fluorescence. One of ordinary skill in the art will appreciate that the range of illumination wavelengths used to excite a molecule can include light energies over a broad range of wavelengths or over a narrow range of wavelengths within the absorption spectra of the fluorophore molecule. The emission spectrum is the spectrum of light wavelengths that are given off (emitted) from the fluorophore molecule after excitation. With respect to the excitation light, depending on the environment that the fluorophore molecule is in (e.g., surgical bed, tumor tissue, solution, and the like), the fluorophore molecule has an optimal excitation spectrum at around 785 nm (e.g., from 770 nm to 795 nm), for example, from 770 nm to 800 nm, from 775 nm to 795 nm, from 780 nm to 790 nm, from 775 nm to 780 nm, from 780 nm to 785 nm, from 780 nm to 795 nm, from 785 nm to 790 nm, from 790 nm to 795 nm, from 795 nm to 800 nm, from 800 nm to 805 nm, or from 805 nm to 810 nm. In addition the fluorophore is a fluorescent dye that has an optimal excitation spectrum at 750 nm, 755 nm, 760 nm, 765 nm, 770 nm, 775 nm, 780 nm, 785 nm, 790 nm, 795 nm, 800 nm, 805 nm, or 810 nm, or any of the foregoing+/−3 nm, +/−2 nm, or +/−1 nm. In some embodiments, depending on the environment that the fluorophore molecule is in (e.g., surgical bed, tumor tissue, solution, and the like), the fluorophore molecule has an optimal excitation spectrum) from 600 nm to 900 nm. Some other exemplary dyes used in the present disclosure can include near-infrared dyes, such as, but not limited to, DyLight-680, DyLight-750, VivoTag-750, DyLight-800, IRDye-800, VivoTag-680, Cy5.5, or indocyanine green (ICG). In some aspects, near infrared dyes often include cyanine dyes. Additional non-limiting examples of fluorescent dyes for use as a conjugating molecule in the present disclosure can include acradine orange or yellow, Alexa Fluors and any derivative thereof, 7-actinomycin D, 8-anilinonaphthalene-1-sulfonic acid, ATTO dye and any derivative thereof, auramine-rhodamine stain and any derivative thereof, bensantrhone, bimane, 9-10-bis(phenylethynyl)anthracene, 5,12-bis(phenylethynyl)naththacene, bisbenzimide, brainbow, calcein, carbodyfluorescein and any derivative thereof, 1-chloro-9,10-bis(phenylethynyl)anthracene and any derivative thereof, DAPI, DiOC6, DyLight Fluors and any derivative thereof, epicocconone, ethidium bromide, FlAsH-EDT2, Fluo dye and any derivative thereof, FluoProbe and any derivative thereof, Fluorescein and any derivative thereof, Fura and any derivative thereof, GelGreen and any derivative thereof, GelRed and any derivative thereof, fluorescent proteins and any derivative thereof, m isoform proteins and any derivative thereof such as for example mCherry, hetamethine dye and any derivative thereof, hoeschst stain, iminocoumarin, indian yellow, indo-1 and any derivative thereof, laurdan, lucifer yellow and any derivative thereof, luciferin and any derivative thereof, luciferase and any derivative thereof, mercocyanine and any derivative thereof, nile dyes and any derivative thereof, perylene, phloxine, phyco dye and any derivative thereof, propium iodide, pyranine, rhodamine and any derivative thereof, ribogreen, RoGFP, rubrene, stilbene and any derivative thereof, sulforhodamine and any derivative thereof, SYBR and any derivative thereof, synaptopHluorin, tetraphenyl butadiene, tetrasodium tris, Texas Red, Titan Yellow, TSQ, umbelliferone, violanthrone, yellow fluorescent protein, YOYO-1 and ZW800. Other suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514, etc.), Texas Red, Texas Red-X, SPECTRUM RED, SPECTRUM GREEN, cyanine dyes (e.g., CY-3, Cy-5, CY-3.5, CY-5.5, etc.), ALEXA FLUOR dyes (e.g., ALEXA FLUOR 350, ALEXA FLUOR 488, ALEXA FLUOR 532, ALEXA FLUOR 546, ALEXA FLUOR 568, ALEXA FLUOR 594, ALEXA FLUOR 633, ALEXA FLUOR 660, ALEXA FLUOR 680, etc.), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665, etc.), IRDyes (e.g., IRD40, IRD 700, IRD 800, etc.), and the like. In some aspects, conjugates of the present disclosure comprise other dyes, including but not limited to those provided below in TABLE 1. Regarding TABLE 1, the peak absorption and emission values for a given fluorophore can vary depending on the environment (e.g. solution, tissue, etc.) that the fluorophore is present in as well as the concentration of fluorophore or fluorophore conjugate utilized.

TABLE 1

Exemplary Fluorescent Reporter Molecules With Peak Absorbance (Abs.) and Emission (Em.) Wavelengths Specified (nm)

| Dye | Peak Abs. | Peak Em. |
|---|---|---|
| Methoxycoumarin | 360 | 410 |
| Fluospheres Blue | 356 | 412 |
| Cascade Blue | 377 | 420 |
| PBFI | 360 | 420 |
| DyeLight 405 | 400 | 420 |
| Cascade Blue | 400 | 420 |
| Alexa Fluor 405 | 401 | 421 |
| Alexa Fluor 405 | 401 | 421 |
| LysoTracker Blue | 373 | 422 |
| LysoSensor Blue | 374 | 424 |
| AMCA | 345 | 425 |
| True Blue | 365 | 425 |
| 7-amino-4-methylcoumarin (AMC) | 351 | 430 |
| Phorwite AR | 360 | 430 |
| DyLight 350 | 353 | 432 |
| Uvitex SFC | 365 | 435 |
| 4-methylumbelliferone | 360 | 440 |
| CellTrace Calcein Blue | 373 | 440 |
| Calcofluor White | 350 | 440 |
| Fast Blue | 360 | 440 |
| LysoSensor Yellow/Blue (pH 8.0) | 329 | 440 |
| LysoSensor Yellow/Blue (pH 8.0) | 329 | 440 |
| LysoSensor Yellow/Blue (pH 8.0) | 329 | 440 |
| LysoSensor Yellow/Blue (pH 8.0) | 329 | 440 |
| Alexa Fluor 350 | 346 | 442 |
| AMCA-X | 353 | 442 |
| LIVE/DEAD Fixable Blue Dead Cell Stain | 344 | 442 |
| Y66H | 360 | 442 |
| ABQ | 344 | 445 |
| BFP | 382 | 448 |
| BFP | 382 | 448 |
| 7-hydroxy-4-methylcoumarin | 360 | 449 |
| SpectrumBlue | 405 | 449 |
| DiFMU (pH 9.0) | 357 | 450 |
| sgBFP (Super Glow BFP) | 387 | 450 |
| SpectrumBlue | 400 | 450 |
| CellTrace Calcein Violet | 401 | 451 |
| DAPI | 345 | 455 |
| NucBlue Fixed Cell Stain | 345 | 455 |
| Pacific Blue | 405 | 455 |
| Pacific Blue | 410 | 455 |
| PO-PRO-1 | 435 | 455 |
| PO-PRO-1 | 435 | 455 |
| POPO-1 | 434 | 456 |
| POPO-1 | 434 | 456 |
| TagBFP | 402 | 457 |

TABLE 1-continued

Exemplary Fluorescent Reporter Molecules With Peak Absorbance (Abs.) and Emission (Em.) Wavelengths Specified (nm)

| Dye | Peak Abs. | Peak Em. |
|---|---|---|
| Marina Blue | 365 | 460 |
| SITS | 365 | 460 |
| Thioflavin TCN | 350 | 460 |
| Monochlorobimane(mBCI) | 380 | 461 |
| Quinine Sulfate | 349 | 461 |
| Acridine | 362 | 462 |
| CellLights CFP | 434 | 477 |
| ECFP | 434 | 477 |
| CFP | 434 | 477 |
| 1,8-ANS | 372 | 480 |
| SYTOX Blue | 444 | 480 |
| SYTOX Blue | 444 | 480 |
| Hoechst 33342 | 347 | 483 |
| NucBlue Live Cell Stain | 347 | 483 |
| Thiolyte | 378 | 483 |
| SYTO 45 | 452 | 484 |
| SYTO 45 | 452 | 484 |
| SYTO 45 | 452 | 484 |
| SYTO 45 | 452 | 484 |
| SYTO 45 | 452 | 484 |
| Hoechst 33258 | 345 | 487 |
| AmCyan | 548 | 489 |
| Auramine O | 445 | 500 |
| SYTO 9 | 482 | 500 |
| SYTO 9 | 482 | 500 |
| SYTO 9 | 482 | 500 |
| SYTO 9 | 482 | 500 |
| SYTO 9 | 482 | 500 |
| DiO | 484 | 501 |
| DiO | 484 | 501 |
| DiO | 484 | 501 |
| LysoSensor Green | 448 | 503 |
| LysoSensor Green | 448 | 503 |
| LysoSensor Green | 448 | 503 |
| LysoSensor Green | 448 | 503 |
| LysoSensor Green | 448 | 503 |
| SYTO 13 | 487 | 505 |
| LysoSensor Green (pH 5) | 442 | 505 |
| SYTO 13 | 487 | 505 |
| SYTO 13 | 487 | 505 |
| SYTO 13 | 487 | 505 |
| SYTO 13 | 487 | 505 |
| DiO (Vybrant DiO) | 489 | 506 |
| HCS LipidTox Green | 498 | 506 |
| LIVE/DEAD Fixable Green | 498 | 506 |
| LIVE/DEAD Fixable Green | 498 | 506 |
| ATTO 465 | 453 | 507 |
| CellLights GFP | 488 | 507 |
| CellEvent Caspase-3/7 Green | 488 | 507 |
| Diversa Green-FP | 484 | 507 |
| GFP (EGFP) | 488 | 507 |
| S65C | 479 | 507 |
| YO-PRO-1 | 491 | 507 |
| GFP | 488 | 507 |
| YO-PRO-1 | 491 | 507 |
| GFP | 488 | 507 |
| YO-PRO-1 | 491 | 507 |
| GFP | 488 | 507 |
| YO-PRO-1 | 491 | 507 |
| Premo FUCCI Cell Cycle Sensor (S/G2/M phases) | 474 | 509 |
| sgGFP (Super Glow GFP) | 474 | 509 |
| wtGFP (wild type GFP, non-UV excitation) | 475 | 509 |
| YOYO-1 | 491 | 509 |
| YOYO-1 | 491 | 509 |
| YOYO-1 | 491 | 509 |
| YOYO-1 | 491 | 509 |
| YOYO-1 | 491 | 509 |
| HPTS (Solvent Green 7) | 455 | 510 |
| Nitrobenzoxadiazole | 465 | 510 |
| S65L | 484 | 510 |
| LysoTracker Green | 504 | 511 |
| S65T | 488 | 511 |
| LysoTracker Green | 504 | 511 |
| LysoTracker Green | 504 | 511 |
| MitoTracker Green FM | 490 | 512 |
| MitoTracker Green FM | 490 | 512 |
| MitoTracker Green FM | 490 | 512 |
| MitoTracker Green FM | 490 | 512 |
| FluoSpheres Yellow-Green | 501 | 513 |
| Evans Blue | 460 | 515 |
| Evans Blue | 460 | 515 |
| rsGFP (red shifted GFP, S65 T) | 498 | 516 |
| CellTracker Violet BMQC | 415 | 516 |
| HCS CellMask Green | 493 | 516 |
| CellTracker Violet BMQC | 415 | 516 |
| CellTracker Violet BMQC | 415 | 516 |
| CellTracker Violet BMQC | 415 | 516 |
| CellTracker Violet BMQC | 415 | 516 |
| HCS CellMask Green | 493 | 516 |
| 5-carboxyfluorescein(5-FAM) | 492 | 518 |
| ActinGreen (Alexa Fluor 488 phalloidin) | 496 | 518 |
| Alexa Fluor 488 | 496 | 518 |
| Click-iT EdU Alexa Fluor 488 | 496 | 518 |
| DyLight + C110 488 | 493 | 518 |
| Fluoro-Emerald | 494 | 518 |
| Aiexa Fluor 488 | 496 | 518 |
| Carboxyfluorescein (5-FAM) | 492 | 518 |
| Aiexa Fluor 488 | 496 | 518 |
| Carboxyfluorescein (5-FAM) | 492 | 518 |
| CellRox Green | 485 | 520 |
| FITC (Fluorescein) | 492 | 520 |
| Fluor-X | 494 | 520 |
| Rhodamine 110 | 496 | 520 |
| SYTO 16 | 490 | 520 |
| FITC | 492 | 520 |
| Rhodamine 110 | 496 | 520 |
| SYTO 16 | 490 | 520 |
| FITC | 492 | 520 |
| Rhodamine 110 | 496 | 520 |
| SYTO 16 | 490 | 520 |
| SYTO 16 | 490 | 520 |
| FITC | 492 | 520 |
| Rhodamine 110 | 496 | 520 |
| SYTO 16 | 490 | 520 |
| SYBR Green I | 497 | 521 |
| SYBR Green I | 497 | 521 |
| SYBR Green I | 497 | 521 |
| SYBR Green I | 497 | 521 |
| SYBR Green I | 497 | 521 |
| Quant-iT PicoGreen | 502 | 522 |
| Spectru mgreen | 498 | 522 |
| NucGreen Dead Cell Stain | 504 | 523 |
| Rhodamine Green | 497 | 523 |
| Rhodol Green | 496 | 523 |
| SYTOX Green | 504 | 523 |
| Rhodamine Green | 497 | 523 |
| Rhodamine Green | 497 | 523 |
| Rhodamine Green | 497 | 523 |
| Neurotrace 500/525 Green | 497 | 524 |
| Oregon Green 488 | 498 | 524 |
| SYBR Safe | 507 | 524 |
| NeuroTrace 500/525 Nissl stain | 497 | 524 |
| Oregon Green 488 | 498 | 524 |
| NeuroTrace 500/525 Nissl stain | 497 | 524 |
| Oregon Green 488 | 498 | 524 |
| NeuroTrace 500/525 Nissl stain | 497 | 524 |
| NeuroTrace 500/525 Nissl stain | 497 | 524 |
| Oregon Green 488 | 498 | 524 |
| Dansyl | 335 | 525 |
| Fluoro-Jade B | 480 | 525 |
| Qdot 525 | UV | 525 |
| SYTO 11 | 506 | 525 |
| Qdot 525 | UV | 525 |
| Qdot 525 | UV | 525 |
| Acridine Orange + DNA | 500 | 526 |
| LIVE/DEAD Fixable Green | 498 | 526 |
| Surf Green EX | 469 | 526 |
| Acridine Orange + DNA | 500 | 526 |

TABLE 1-continued

Exemplary Fluorescent Reporter Molecules With Peak Absorbance (Abs.) and Emission (Em.) Wavelengths Specified (nm)

| Dye | Peak Abs. | Peak Em. |
|---|---|---|
| Acridine Orange + DNA | 500 | 526 |
| Acridine Orange + DNA | 500 | 526 |
| Acridine Orange (+DNA) | 500 | 526 |
| ThiolTracker Violet | 405 | 526 |
| ThiolTracker Violet | 405 | 526 |
| ThiolTracker Violet | 405 | 526 |
| ThiolTracker Violet | 405 | 526 |
| Acridine Orange (+DNA) | 500 | 526 |
| ThiolTracker Violet | 405 | 526 |
| SYTO RNASelect | 503 | 527 |
| EYFP | 514 | 527 |
| SYTO RNASelect | 503 | 527 |
| SYTO RNASelect | 503 | 527 |
| SYTO RNASelect | 503 | 527 |
| SYTO RNASelect | 503 | 527 |
| Rhodamine 123 | 507 | 529 |
| YFP | 512 | 529 |
| F2N12S | 405 | 530, 585 |
| F2N12S | 405 | 530, 585 |
| F2N12S | 405 | 530, 585 |
| F2N12S | 405 | 530, 585 |
| F2N12S | 405 | 530, 585 |
| F2N12S | 405 | 530, 585 |
| F2N12S | 405 | 530, 585 |
| Magnesium Green | 506 | 530 |
| NBD Amine | 450 | 530 |
| TO-PRO-1 | 515 | 530 |
| TOTO-1 | 513 | 531 |
| Oregon Green 514 | 512 | 532 |
| Sodium Green | 506 | 532 |
| Vybrant DyeCycle Green | 505 | 532 |
| pHrodo Green | 509 | 533 |
| NBD-X | 467 | 538 |
| NBD-X | 467 | 538 |
| NBD-X | 467 | 538 |
| NBD-X | 467 | 538 |
| NBD-X | 467 | 538 |
| NBD-X | 467 | 538 |
| NBD-X | 467 | 538 |
| SYBR Gold | 495 | 539 |
| SYBR Gold | 495 | 539 |
| SYBR Gold | 495 | 539 |
| SYBR Gold | 495 | 539 |
| SYBR Gold | 495 | 539 |
| Alexa Fluor 430 | 432 | 540 |
| Auramine | 460 | 540 |
| Aurophosphine | 470 | 540 |
| BCECF | 499 | 540 |
| BODIPY 492/515 | 490 | 540 |
| BODIPY 505/515 | 502 | 540 |
| BODIPY FL | 502 | 540 |
| BTC | 464 | 540 |
| Calcein | 494 | 540 |
| Calcium Green-1 | 506 | 540 |
| Catskill Green 540 | 482 | 540 |
| CellTracker Green | 490 | 540 |
| CFDA | 494 | 540 |
| CFP | 434 | 540 |
| Cy2 | 492 | 540 |
| CyQUANT Direct (CyQUANT GR) | 500 | 540 |
| DAF-FM | 493 | 540 |
| Emerald Green | 490 | 540 |
| Fluo-3 | 506 | 540 |
| Fluo-4 | 494 | 540 |
| H2DCFDA (H2-DCF, DCFR) | 504 | 540 |
| Alexa Fluor 430 | 434 | 540 |
| Alexa Fluor 430 | 432 | 540 |
| BCECF (pH 5.2) | 499 | 540 |
| Calcein | 494 | 540 |
| CellTracker Green CMFDA | 490 | 540 |
| CFP | 434 | 540 |
| Cy2 | 492 | 540 |
| CyQUANT Direct | 500 | 540 |
| DAF-FM | 493 | 540 |
| Fluo-4 | 494 | 540 |
| Alexa Fluor 430 | 432 | 540 |
| BCECF (pH 5.2) | 499 | 540 |
| Calcein | 494 | 540 |
| CellTracker Green CMFDA | 490 | 540 |
| CFP | 434 | 540 |
| Cy2 | 492 | 540 |
| CyQUANT Direct | 500 | 540 |
| Alexa Fluor 430 | 432 | 540 |
| BCECF (pH 5.2) | 499 | 540 |
| CFP | 434 | 540 |
| Cy2 | 492 | 540 |
| Alexa Fluor 430 | 432 | 540 |
| BCECF (pH 5.2) | 499 | 540 |
| Alexa Fluor 430 | 432 | 540 |
| BCECF (pH 5.2) | 499 | 540 |
| Alexa Fluor 430 | 432 | 540 |
| BCECF (pH 5.2) | 499 | 540 |
| Calcein | 494 | 540 |
| CellTracker Green CMFDA | 490 | 540 |
| CFP | 434 | 540 |
| Cy2 | 492 | 540 |
| CyQUANT Direct | 500 | 540 |
| DAF-FM | 493 | 540 |
| Fluo-4 | 494 | 540 |
| TET | 520 | 541 |
| TET | 521 | 542 |
| Lucifer Yellow | 423 | 543 |
| Qdot 545 | UV | 543 |
| Lucifer Yellow | 423 | 543 |
| Lucifer Yellow | 423 | 543 |
| Lucifer Yellow | 423 | 543 |
| Lucifer Yellow | 423 | 543 |
| Lucifer Yellow | 423 | 543 |
| Lucifer Yellow | 423 | 543 |
| Lucifer Yellow | 423 | 543 |
| Lucifer yellow | 428 | 544 |
| Lucifer Yellow | 428 | 544 |
| Lucifer yellow | 428 | 544 |
| Eosin | 524 | 545 |
| JOJO-1 | 529 | 545 |
| Qdot 545 | UV | 545 |
| Qdot 545 | UV | 545 |
| Auramine O | 460 | 550 |
| Pacific Orange | 440 | 551 |
| Pacific Orange | 440 | 551 |
| Pacific Orange | 440 | 551 |
| Pacific Orange | 440 | 551 |
| Pacific Orange | 440 | 551 |
| Pacific Orange | 440 | 551 |
| mBanana | 540 | 553 |
| ER-Tracker Blue-White DPX | 371 | 554 |
| Alexa Fluor 532 | 532 | 554 |
| FocalCheck Double Orange | 540 | 555 |
| HEX | 533 | 558 |
| Fluospheres Orange | 539 | 560 |
| mHoneydew | 478 | 561 |
| Vybrant DyeCycle Orange | 518 | 562 |
| ActinRed 555 (rhodamin pphalloidin) | 540 | 565 |
| Alexa Fluor 555 | 555 | 565 |
| CellRox Orange | 545 | 565 |
| Qdot 565 | UV | 565 |
| Qdot 565 | UV | 565 |
| DiI (CellTracker DiI) | 551 | 568 |
| mOrange | 548 | 568 |
| OFP | 546 | 568 |
| Bodipy TMR | 544 | 569 |

TABLE 1-continued

Exemplary Fluorescent Reporter Molecules With Peak Absorbance (Abs.) and Emission (Em.) Wavelengths Specified (nm)

| Dye | Peak Abs. | Peak Em. |
|---|---|---|
| Cy3 | 552 | 570 |
| PO-PRO-3 | 539 | 570 |
| SYTOX Orange | 567 | 570 |
| CellMask Orange | 556 | 571 |
| Alexa Fluor 546 | 561 | 572 |
| POPO-3 | 532 | 573 |
| TurboRFP | 553 | 574 |
| Calcium Orange | 549 | 575 |
| CellTracker Orange | 547 | 575 |
| LIVE/DEAD Fixable Yellow | 405 | 575 |
| LIVE/DEAD Fixable Yellow | 405 | 575 |
| LIVE/DEAD Fixable Yellow | 405 | 575 |
| LIVE/DEAD Fixable Yellow | 405 | 575 |
| LIVE/DEAD Fixable Yellow | 405 | 575 |
| LIVE/DEAD Fixable Yellow | 405 | 575 |
| DyLight 594 | 562 | 576 |
| MitoTracker Orange CMTMRos(MitoTracker Orange CM-H2TMRos) | 551 | 576 |
| Phycoerythrin (PE, R-phycoerythrin) | 567 | 576 |
| Rhod-2 | 551 | 576 |
| Rhodamine Phalloidin | 557 | 576 |
| X-Rhod-1 | 570 | 576 |
| DsRed-Express | 557 | 579 |
| Rhodamine Red | 560 | 580 |
| TAMRA | 565 | 580 |
| Tetramethylrhodamine (TRITC) | 555 | 580 |
| dTomato | 554 | 581 |
| DsRed2 | 563 | 582 |
| Amplex Ultra Red | 567 | 582 |
| Amplex Red | 571 | 583 |
| Amplex UltraRed | 568 | 583 |
| Amplex Red | 570 | 583 |
| Premo FUCCI Cell Cycle Sensor (G1 phase) | 555 | 584 |
| TagRFP | 555 | 584 |
| CellLights RFP | 552 | 585 |
| mTangerine | 568 | 585 |
| Resorufin | 570 | 585 |
| RFP | 552 | 585 |
| Qdot 585 | UV | 585 |
| Qdot 585 | UV | 585 |
| DsRed Monomer | 556 | 586 |
| pHrodo Red | 559 | 586 |
| Carboxy SNARF-1 | 548 | 587 |
| pHrodo Red | 559 | 587 |
| SpectrumOrange | 559 | 588 |
| DsRed2 | 563 | 588 |
| DiA | 456 | 590 |
| DiA | 456 | 590 |
| DiA | 456 | 590 |
| DiA | 456 | 590 |
| DiA | 456 | 590 |
| DiA | 456 | 590 |
| DiA | 456 | 590 |
| rhodamine Red-X | 572 | 591 |
| CellTrace calcein red-orange | 575 | 592 |
| LysoTracker Red | 573 | 592 |
| Sulforhodamine 101 | 578 | 593 |
| sulforhodamine 101 | 577 | 593 |
| ROX (6-ROX) | 568 | 595 |
| 2-dodecylresorufin | 582 | 595 |
| Cy3.5 | 579 | 597 |
| Cy 3.5 | 581 | 597 |
| MitoTracker Red CMXRos | 578 | 597 |
| BOBO-3 | 570 | 602 |
| Ethidium Bromide | 521 | 602 |
| X-rhod-1 | 579 | 602 |
| BOBO-1 | 570 | 602 |
| BOBO-1 | 570 | 602 |
| BOBO-1 | 570 | 602 |
| 5-ROX | 577 | 603 |
| Alexa Fluor 568 | 578 | 603 |
| Qdot 605 | UV | 605 |
| Qdot 605 | UV | 605 |
| BOBO-3 | 571 | 606 |
| Calcium Crimson | 589 | 608 |
| Fluospheres Red microspheres | 577 | 608 |
| ReAsH (TC-ReAsH) | 593 | 608 |
| CellTracker Red | 585 | 612 |
| LIVE/DEAD Fixable Red | 593 | 613 |
| CellTracker Red CMTPX | 584 | 613 |
| LIVE/DEAD Fixable Red Dead Cell stain | 595 | 613 |
| DiA (FAST DiA) | 491 | 613 |
| DiA | 491 | 613 |
| HCS CellMask Red stain | 587 | 614 |
| HCS LipidTox Red | 582 | 615 |
| HCS LipidTOX Red | 582 | 615 |
| mCherry | 587 | 615 |
| Texas Red | 592 | 615 |
| Ethidium Homodimer-1 (EthD-1) | 530 | 618 |
| Propidium Iodide (PI) | 530 | 618 |
| Alexa Fluor 594 | 590 | 618 |
| Click-iT Alexa Fluor 594 | 590 | 618 |
| DyLight 594 | 593 | 618 |
| SYPRO Ruby | 450 | 618 |
| SYPRO Ruby | 450 | 618 |
| SYPRO Ruby | 450 | 618 |
| SYPRO Ruby | 450 | 618 |
| SYPRO Ruby | 450 | 618 |
| SYPRO Ruby | 450 | 618 |
| Bodipy TR-X | 588 | 621 |
| CellTrace BODIPY TR methyl esther | 597 | 625 |
| mRaspberry | 598 | 625 |
| Qdot 625 | UV | 625 |
| Qdot 625 | UV | 625 |
| FM 1-43 | 510 | 626 |
| FM 1-43 | 510 | 626 |
| FM 1-43 | 510 | 626 |
| FM 1-43 | 510 | 626 |
| FM 1-43 | 510 | 626 |
| FM 1-43 | 510 | 626 |
| FM 1-43 | 510 | 626 |
| FM 1-43 | 510 | 626 |
| YO-PRO-3 | 612 | 628 |
| Alexa Fluor 610 | 610 | 629 |
| Magic Red | 570 | 630 |
| CTC Formazan | 450 | 630 |
| CTC Formazan | 450 | 630 |
| YOYO-3 | 612 | 631 |
| Katushka (Turbo FP635) | 588 | 635 |
| mKate | 588 | 635 |
| SYTO 17 | 620 | 635 |
| Di-8 ANEPPS | 468 | 635 |
| Di-8 ANEPPS | 468 | 635 |
| Di-8-ANEPPS | 465 | 635 |
| Di-8-ANEPPS | 465 | 635 |
| Di-8-ANEPPS | 465 | 635 |
| Di-8-ANEPPS | 465 | 635 |
| Di-8-ANEPPS | 465 | 635 |
| Di-8-ANEPPS | 465 | 635 |
| Di-8-ANEPPS | 465 | 635 |
| Nile Red | 551 | 636 |
| Nile red (triglyceride) | 552 | 636 |
| Nile red (triglyceride) | 552 | 636 |
| Nile red (triglyceride) | 552 | 636 |
| Fura Red (high Ca2+) | 436 | 637 |
| Nile Red phospholipid | 551 | 638 |
| SYTO 17 | 619 | 638 |
| Bodipy 630/650-X | 625 | 641 |
| BODIPY 630/650X | 626 | 641 |
| 7-AAD | 549 | 644 |
| HCS NuclearMask Red | 624 | 644 |
| HCS NuclearMask Red | 622 | 644 |
| SYTO 59 | 621 | 644 |
| SYTO 59 | 622 | 645 |
| Fluospheres Crimson microspheres | 620 | 646 |
| FluoSpheres crimson microspheres | 621 | 646 |
| SYTOX AADvanced dead cell stain | 546 | 647 |

TABLE 1-continued

Exemplary Fluorescent Reporter Molecules With Peak Absorbance
(Abs.) and Emission (Em.) Wavelengths Specified (nm)

| Dye | Peak Abs. | Peak Em. |
|---|---|---|
| Alexa Fluor 635 | 634 | 647 |
| HcRed | 594 | 649 |
| mPlum | 590 | 649 |
| SYTO 61 | 619 | 649 |
| Alexa Fluor 633 | 631 | 650 |
| Acridine Orange + RNA | 460 | 650 |
| Acridine Orange + RNA | 460 | 650 |
| Acridine Orange (+RNA) | 460 | 650 |
| Acridine Orange (+RNA) | 460 | 650 |
| HCS LipidTOX Deep Red | 634 | 652 |
| Fura Red (+Ca2+) | 436 | 655 |
| Fura Red (+Ca2+) | 436 | 655 |
| Fura Red (+Ca2+) | 436 | 655 |
| Fura Red (+Ca2+) | 436 | 655 |
| Qdot 655 | UV | 655 |
| Fura Red (+Ca2+) | 436 | 655 |
| Fura Red (+Ca2+) | 436 | 655 |
| Qdot 655 | UV | 655 |
| FxCycle Far Red | 641 | 657 |
| TO-PRO-3 | 642 | 657 |
| DDAO | 648 | 658 |
| DyLight 633 | 638 | 658 |
| SYTOX Red | 640 | 658 |
| ATTO 635 | 635 | 658 |
| APC (Allophycocyanin) | 651 | 660 |
| MitoTracker Deep Red FM | 641 | 661 |
| NucRed Dead 647 | 642 | 661 |
| TOTO-3 | 642 | 661 |
| BODIPY 650/665 | 647 | 665 |
| CellRox Deep Red | 640 | 665 |
| LIVE/DEAD Fixable Far Red | 650 | 665 |
| Cy5 | 648 | 666 |
| Lysotracker Deep Red | 647 | 668 |
| Alexa Fluor 647 | 650 | 670 |
| Click-iT Alexa Fluor 647 | 650 | 670 |
| DiD (Vybrant DiD) | 645 | 670 |
| HCS CellMask Deep Red stain | 649 | 670 |
| ATTO 647 | 644 | 670 |
| Fura Red (−Ca2+) | 473 | 670 |
| Fura Red (−Ca2+) | 473 | 670 |
| Fura Red (−Ca2+) | 473 | 670 |
| Fura Red (−Ca2+) | 473 | 670 |
| Fura Red (−Ca2+) | 473 | 670 |
| DyLight 649 | 654 | 673 |
| Carboxynaphthofluorescein | 600 | 674 |
| PerCP | 488 | 675 |
| CellMask Deep Red plasma membrane stain | 658 | 676 |
| DRAQ5 | 650 | 680 |
| SYTO 60 | 649 | 681 |
| SYTO 62 | 650 | 681 |
| SYTO 60 | 650 | 681 |
| FluoSpheres dark red microspheres | 657 | 683 |
| ATTO 655 | 663 | 683 |
| FluoSpheres Dark Red fluorescent microspheres | 656 | 683 |
| NucRed Live 647 | 638 | 686 |
| Vybrant DyeCycle Ruby | 638 | 686 |
| HCS NuclearMask Deep Red | 635 | 687 |
| Cy5.5 | 672 | 690 |
| Alexa Fluor 660 | 663 | 691 |
| Alexa Fluor 660 | 663 | 691 |
| Cy5.5 | 678 | 696 |
| DY-675 | 675 | 699 |
| IRDye 700 Phosphoramidite | 691 | 699 |
| ATTO 680 | 680 | 700 |
| Alexa Fluor 680 | 679 | 702 |
| HiLyte Fluor 680 | 688 | 702 |
| Qdot 705 Nanocrystals | 300 | 702 |
| Alexa Fluor 680 | 679 | 704 |
| DyLight 680 | 676 | 705 |
| Qdot 705 | UV | 705 |
| Qdot 705 | UV | 705 |
| Quasa 705 | 688 | 706 |
| IRDye 680 NHS Ester | 683 | 710 |
| RH 795 | 530 | 712 |
| RH 795 | 530 | 712 |
| RH 795 | 530 | 712 |
| RH 795 | 530 | 712 |
| RH 795 | 530 | 712 |
| Alexa Fluor 700 | 696 | 719 |
| ATTO 700 | 699 | 719 |
| FM 4-64 | 558 | 734 |
| FM 4-64 | 558 | 734 |
| FM 4-64 | 558 | 734 |
| FM 4-64 | 558 | 734 |
| Cy7 | 745 | 766 |
| LIVE/DEAD Fixable near-IR | 750 | 775 |
| CellVue NIR780 | 743 | 776 |
| DyLight 750 | 752 | 778 |
| IRDye 800CW | 774 | 789 |
| XenoLight CF770 | 770 | 797 |
| Qdot 800 | UV | 800 |
| Qdot 800 | UV | 800 |
| Indocyanine Green | 768 | 807 |

In some other aspects, the conjugate compounds used include a chemiluminescent compound, colloidal metal, luminescent compound, phosphoresecent compound, enzyme, radioisotope, or paramagnetic labels.

In certain aspects, the conjugates used in the present disclosure can be conjugated to radioactive isotopes instead of or in addition to other types of detectable agents. Certain isotopes suitable for use in the present compounds can include, but are not limited to, iodine-131, iodine-125, bismuth-212, bismuth-213, lutetium-177, rhenium-186, rhenium-188, yttrium-90, astatine-211, phosphorus-32 and/or samarium-153. In some aspects, the conjugates of the present disclosure contain one or more atoms having an atomic mass or mass number different from the atomic mass or mass number usually found in nature, including but not limited to hydrogen, carbon, fluorine, phosphorous, copper, gallium, yttrium, technetium, indium, iodine, rhenium, thallium, bismuth, astatine, samarium, and lutetium (for example, $^3$H, $^3$H, $^{13}$C, $^{14}$C, $^{18}$F, $^{32}$P, $^{35}$S, $^{64}$Cu, $^{67}$Ga, $^{90}$Y, $^{99M}$Tc, $^{111}$In, $^{125}$I, $^{123}$I, $^{131}$I, $^{135}$I, $^{186}$Re, $^{187}$Re, $^{201}$Tl, $^{212}$Bi, $^{211}$At, $^{153}$Sm and/or $^{177}$Lu). In other aspects, the conjugates of the present disclosure are labeled with a paramagnetic metal ion that is a good contrast enhancer in Magnetic Resonance Imaging (MRI). Examples of such paramagnetic metal ions include, but are not limited to, gadolinium III ($Gd^{3+}$), chromium 111 ($Cr^{3+}$), dysprosium III ($Dy^{3+}$), iron 111 ($Fe^{3+}$), manganese II ($Mn^{2+}$), and ytterbium III ($Yb^{3+}$). In certain embodiments, the labeling moiety comprises gadolinium III ($Gd^{3+}$).

In some aspects, the conjugates used in the present disclosure can be conjugated to biotin. In addition of extension of half-life, biotin can also act as an affinity handle for retrieval of the peptides from tissues or other locations. In one aspect, the conjugates are conjugated, e.g., to a biotinidase resistant biotin with a PEG linker (e.g., NHS-dPEG4-Biotinidase resistant biotin). In some aspects, fluorescent biotin conjugates that can act both as a detectable label and an affinity handle are used. Non-limiting examples of commercially available fluorescent biotin conjugates can include Atto 425-Biotin, Atto 488-Biotin, Atto 520-Biotin, Atto-550 Biotin, Atto 565-Biotin, Atto 590-Biotin, Atto 610-Biotin, Atto 620-Biotin, Atto 655-Biotin, Atto 680-Biotin, Atto 700-Biotin, Atto 725-Biotin, Atto 740-Biotin, fluorescein biotin, biotin-4-fluorescein, biotin-(5-fluorescein) conjugate, and biotin-B-phycoerythrin, alexa fluor 488 biocytin, alexa flour 546, alexa fluor 549, lucifer yellow cadaverine biotin-X, Lucifer yellow biocytin, Oregon green 488 biocytin, biotin-rhodamine, and tetramethylrhodamine biocytin.

In certain embodiments, the chlorotoxin and chlorotoxin variants can be conjugated to moieties, such as detectable labels (e.g., dyes) that can be detected (e.g., visualized) in a subject. In some embodiments, the chlorotoxin and/or chlorotoxin variants can be conjugated to detectable labels to enable tracking of the bio-distribution of a conjugated peptide. The detectable labels can include fluorescent dyes. Non-limiting examples of fluorescent dyes that can be used as a conjugating molecule in the present disclosure include rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, and thiorhodamine, cyanine, indocarbocyanine, oxacarbocyanine, thiacarbocyanine, merocyanine, a cyanine dye (e.g., cyanine 2, cyanine 3, cyanine 3.5, cyanine 5, cyanine 5.5, cyanine 7), oxadiazole derivatives, pyridyloxazole, nitrobenzoxadiazole, benzoxadiazole, pyrene derivatives, cascade blue, oxazine derivatives, Nile red, Nile blue, cresyl violet, oxazine 170, acridine derivatives, proflavin, acridine orange, acridine yellow, arylmethine derivatives, auramine, xanthene dyes, sulfonated xanthenes dyes, Alexa Fluors (e.g., Alexa Fluor 594, Alexa Fluor 633, Alexa Fluor 647, Alexa Fluor 700), crystal violet, malachite green, tetrapyrrole derivatives, porphyrin, phtalocyanine, and bilirubin. Some other example dyes include near-infrared dyes, such as, but not limited to, Cy5.5, indocyanine green (ICG), DyLight 750 or IRdye 800. In some embodiments, near infrared dyes can include cyanine dyes.

In other embodiments, chemotherapuetics, anti-cancer drugs, and anti-cancer agents, include, but are not limited to: radioisotopes, toxins, enzymes, sensitizing drugs, nucleic acids, including interfering RNAs, antibodies, anti-angiogenic agents, cisplatin, anti-metabolites, mitotic inhibitors, growth factor inhibitors, paclitaxel, temozolomide, topotecan, fluorouracil, vincristine, vinblastine, procarbazine, decarbazine, altretamine, methotrexate, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomycin, tamoxifen, flutamide, leuprolide, goserelin, aminogluthimide, anastrozole, amsacrine, asparaginase, mitoxantrone, mitotane and amifostine, and their equivalents, as well as photo-ablation.

As used herein, the terms "about" and "approximately," in reference to a number, is used herein to include numbers that fall within a range of 10%, 5%, or 1% in either direction (greater than or less than) the number unless otherwise stated or otherwise evident from the context (except where such number would exceed 100% of a possible value).

Suitable diagnostic agents can include agents that provide for the detection by fluorescence methods as well as methods other than fluorescence imaging. Other suitable diagnostic agents can include radiolabels (e.g., radio isotopically labeled compounds) such as $^{125}I$, $^{14}C$, and $^{31}P$, among others; and magnetic resonance imaging agents.

Suitable targeting agents can include antibodies, polypeptides, polysaccharides, nucleic acids, fatty acids, lipids, glycolipids, sterols, vitamins, cofactors, hormones, neurotransmitters, and metabolites.

In another aspect of the invention, compositions used can include the modified chlorotoxin peptide conjugates as provided. In yet another aspect of the invention, compositions used can include chlorotoxin variants or cholorotoxin peptide variants as discussed herein. The composition used can include a pharmaceutically acceptable carrier or diluent for delivery of the modified chlorotoxin peptide conjugate. Suitable pharmaceutically acceptable carriers or diluents can include saline or dextrose for injection.

In various aspects, the presently described compounds used can further comprise a detectable label, which can be used for the detection of the peptide-label conjugate and the cancerous cells to which they are bound.

In various aspects, compounds used in the present disclosure can have the structure of Formula (I), or a pharmaceutically acceptable salt thereof:

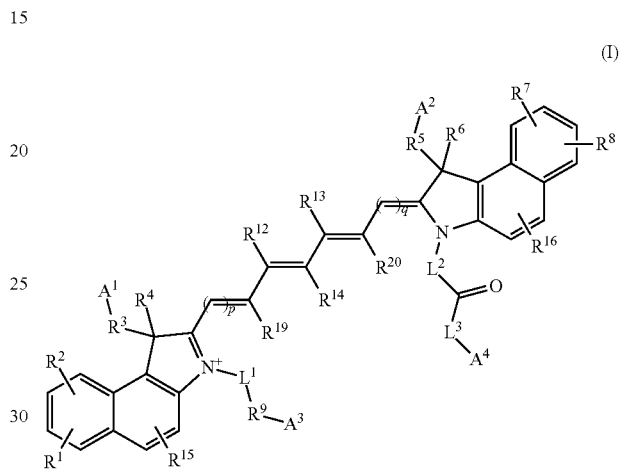

(I)

wherein:

$R^1$, $R^2$, $R^3$, $R^4$, $R^5$, $R^6$, $R^7$, $R^8$, $R^{15}$, and $R^{16}$ are each independently selected from hydrogen, $C_1$-$C_6$ alkyl, $C_1$-$C_6$ alkylene-COOH, sulfonate, —COOH, —$SO_2$—$NH_2$, $C_1$-$C_6$ alkoxy, $C_1$-$C_{10}$ alkylene-(C(=O))$_x$—, $C_1$-$C_{10}$ alkylene-(C(=O))$_x$—O—, or $C_1$-$C_{10}$ alkylene-(C(=O))$_x$—$NR^{10}$—;

$R^9$ is hydrogen, sulfonate, —COOH, $C_1$-$C_{10}$ alkylene-(C(=O))$_x$—, $C_1$-$C_{10}$ alkylene-(C(=O))$_x$—O—, or $C_1$-$C_{10}$ alkylene-(C(=O))$_x$—$NR^{10}$—;

$L^1$ is $C_3$-$C_6$ alkylene;

$L^2$ is $C_1$-$C_{10}$ alkylene;

$L^3$ is a bond, —O—, —$NR^{10}$—, —$NR^{10}$—$C_1$-$C_6$ alkylene-, —O—$NR^{11}$—, —$NR^{10}$—$C_1$-$C_6$ alkylene-(O—$C_1$-$C_6$ alkylene)$_n$-, —$NR^{10}$-$L^4$-, —$NR^{10}$—$C_1$-$C_6$ alkylene-$NR^{11}$—(C(=O)—$C_1$-$C_6$ alkylene-O—)$_m$—, or —$NR^{10}$—$C_1$-$C_6$ alkylene-$NR^{10}$—$C_1$-$C_6$ alkylene-$NR^{10}$—$C_1$-$C_6$ alkylene-;

$L^4$ is a bond, -heterocyclyl-, or -heterocyclyl-$C_1$-$C_6$ alkylene-;

$R^{10}$ is hydrogen or $C_1$-$C_6$ alkyl;

$R^{11}$ is hydrogen or $C_1$-$C_6$ alkyl;

$R^{12}$ and $R^{13}$ are each independently selected from hydrogen, $C_1$-$C_6$ alkyl, or $R^{12}$ and $R^{13}$ are joined together along with the other atoms to which they are attached to form a 5-membered or 6-membered carbocyclic or heterocyclic ring;

$R^{14}$ is hydrogen or $C_1$-$C_6$ alkylene, -($L^5$)-aryl, -($L^5$)-aryl-$A^5$, -($L^5$)-heteroaryl, -($L^5$)-heteroaryl-$A^5$, —$NR^{17}R^{18}$, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;

$L^5$ is a bond, $C_1$-$C_{10}$ alkylene, —O—, or —$NR^{10}$—;

$R^{17}$ and $R^{18}$ are each independently hydrogen or aryl;

$R^{19}$ and $R^{20}$ are each independently selected from hydrogen, $C_1$-$C_6$ alkyl, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;

n is 0, 1, 2, or 3;
m is 0, 1, 2, or 3;
p is 0, 1, 2, or 3;
q is 0, 1, 2, or 3;
x is 0 or 1; and one of $A^1$, $A^2$, $A^3$, $A^4$, or $A^5$ is a polypeptide having at least 85% sequence identity with MCMPCFTTDHQMARRCDDCCGGR-GRGKCYGPQCLCR (SEQ ID NO: 9) or a fragment thereof and the others of $A^1$, $A^2$, $A^3$, $A^4$, or $A^5$ are each independently absent, hydrogen, —COOH, or sulfonate.

In various aspects, the presently described compounds used can further comprise a detectable label, which can be used for the detection of the peptide-label conjugate and the cancerous cells to which they are bound.

In various aspects, compounds used in the present disclosure have the structure of Formula (II), or a pharmaceutically acceptable salt thereof:

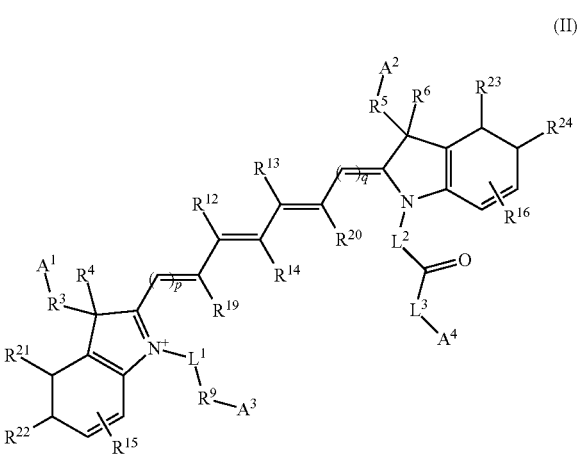

(II)

wherein:

$R^3$, $R^4$, $R^5$, $R^6$, $R^{15}$, and $R^{16}$ are each independently selected from hydrogen, $C_1$-$C_6$ alkyl, $C_1$-$C_6$ alkylene-COOH, sulfonate, —COOH, —$SO_2$—$NH_2$, $C_1$-$C_6$ alkoxy, $C_1$-$C_{10}$ alkylene-(C(=O))$_x$—, $C_1$-$C_{10}$ alkylene-(C(=O))$_x$—O—, or $C_1$-$C_{10}$ alkylene-(C(=O))$_x$—$NR^{10}$—;

$R^9$ is hydrogen, sulfonate, —COOH, $C_1$-$C_{10}$ alkylene-(C(=O))$_x$—, $C_1$-$C_{10}$ alkylene-(C(=O))$_x$—O—, or $C_1$-$C_{10}$ alkylene-(C(=O))$_x$—$NR^{10}$—;

$L^1$ is $C_3$-$C_6$ alkylene;

$L^2$ is $C_1$-$C_{10}$ alkylene;

$L^3$ is a bond, —O—, —$NR^{10}$—, —$NR^{10}$—$C_1$-$C_6$ alkylene-, —O—$NR^{11}$—, —$NR^{10}$—$C_1$-$C_6$ alkylene-(O—$C_1$-$C_6$ alkylene)$_n$-, —$NR^{10}$-$L^4$-, —$NR^{10}$—$C_1$-$C_6$ alkylene-$NR^{11}$—(C(=O)—$C_1$-$C_6$ alkylene-O—)$_m$—, or —$NR^{10}$—$C_1$-$C_6$ alkylene-$NR^{10}$—$C_1$-$C_6$ alkylene-$NR^{10}$—$C_1$-$C_6$ alkylene-;

$L^4$ is a bond, -heterocyclyl-, or -heterocyclyl-$C_1$-$C_6$ alkylene-;

$R^{10}$ is hydrogen or $C_1$-$C_6$ alkyl;

$R^{11}$ is hydrogen or $C_1$-$C_6$ alkyl;

$R^{12}$ and $R^{13}$ are each independently selected from hydrogen, $C_1$-$C_6$ alkyl, or $R^{12}$ and $R^{13}$ are joined together along with the other atoms to which they are attached to form a 5-membered or 6-membered carbocyclic or heterocyclic ring;

$R^{14}$ is hydrogen or $C_1$-$C_6$ alkylene, -($L^5$)-aryl, -($L^5$)-aryl-$A^5$, -($L^5$)-heteroaryl, -($L^5$)-heteroaryl-$A^5$, —$NR^{17}R^{18}$, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;

$L^5$ is a bond, $C_1$-$C_{10}$ alkylene, —O—, or —$NR^{10}$—;

$R^{17}$ and $R^{18}$ are each independently hydrogen or aryl;

$R^{19}$ and $R^{20}$ are each independently selected from hydrogen, $C_1$-$C_6$ alkyl, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;

$R^{21}$ and $R^{22}$ are each independently selected from hydrogen, $C_1$-$C_6$ alkyl, sulfonate, or $R^{21}$ and $R^{22}$ are joined together along with the other atoms to which they are attached to form a 5-membered or 6-membered aryl;

$R^{23}$ and $R^{24}$ are each independently selected from hydrogen, $C_1$-$C_6$ alkyl, sulfonate, or $R^{23}$ and $R^{24}$ are joined together along with the other atoms to which they are attached to form a 5-membered or 6-membered aryl;

n is 0, 1, 2, or 3;
m is 0, 1, 2, or 3;
p is 0, 1, 2, or 3;
q is 0, 1, 2, or 3;
x is 0 or 1; and one of $A^1$, $A^2$, $A^3$, $A^4$, or $A^5$ is a polypeptide having at least 85% sequence identity with MCMPCFTTDHQMARRCDDCCGGR-GRGKCYGPQCLCR (SEQ ID NO: 9) or a fragment thereof and the others of $A^1$, $A^2$, $A^3$, $A^4$, or $A^5$ are each independently absent, hydrogen, —COOH, or sulfonate.

In some aspects, the compounds used in the present disclosure have a structure of Formula (III), or a pharmaceutically acceptable salt thereof:

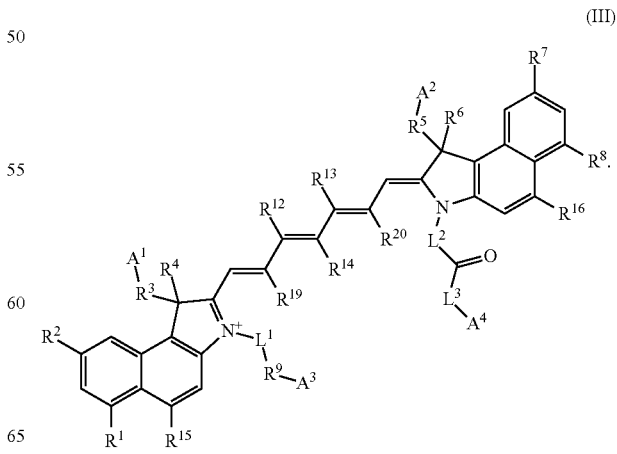

(III)

In certain aspects, the present compounds have a structure of Formula (IV), or a pharmaceutically acceptable salt thereof:

(IV)

wherein:
$R^1$, $R^2$, $R^3$, $R^4$, $R^5$, $R^6$, $R^7$, $R^8$, $R^{15}$, and $R^{16}$ are each independently selected from hydrogen, $C_1$-$C_6$ alkyl, C—C alkylene-COOH, sulfonate, $C_1$-$C_6$ alkylene-sulfonate, —COOH, —SO$_2$—NH$_2$, or $C_1$-$C_6$ alkoxy;

$R^9$ is hydrogen, sulfonate, amine or —COOH;

$L^1$ is $C_3$-$C_6$ alkylene;

$L^2$ is $C_1$-$C_{10}$ alkylene;

$L^3$ is a bond, —O—, —NR$^{10}$—, —NR$^{10}$—$C_1$-$C_6$ alkylene-, —O—NR$^{10}$—, —NR$^{10}$—$C_1$-$C_6$ alkylene-(O—$C_1$-$C_6$ alkylene)$_n$-, —NR$^{10}$-L$^4$-, —NR$^{10}$—$C_1$-$C_6$ alkylene-NR$^{10}$—(C(=O)—$C_1$-$C_6$ alkylene-O—)$_m$—, or —NR$^{10}$—$C_1$-$C_6$ alkylene-NR$^{10}$—$C_1$-$C_6$ alkylene-NR$^{10}$—$C_1$-$C_6$ alkylene-;

$L^4$ is a bond, -heterocyclyl-, or -heterocyclyl-$C_1$-$C_6$ alkylene-;

$R^{10}$ is hydrogen or $C_1$-$C_6$ alkyl;

$R^{11}$ is hydrogen or $C_1$-$C_6$ alkyl;

$R^{12}$ and $R^{13}$ are independently selected from hydrogen, $C_1$-$C_6$ alkyl, or $R^{12}$ and $R^{13}$ are joined together along with the other atoms to which they are attached to form a 5-membered or 6-membered carbocyclic or heterocyclic ring;

$R^{14}$ is hydrogen or $C_1$-$C_6$ alkylene, -(L$^5$)-aryl, -(L$^5$)-aryl-R$^{21}$, -(L$^5$)-heteroaryl, -(L$^5$)-heteroaryl-R$^{21}$, —NR$^{17}$R$^{18}$, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;

$L^5$ is a bond, $C_1$-$C_{10}$ alkylene, —O—, —NR$^{10}$—;

$R^{17}$ and $R^{18}$ are each independently hydrogen or aryl;

$R^{19}$ and $R^{20}$ are independently selected from hydrogen, $C_1$-$C_6$ alkyl, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;

$R^{21}$ is hydrogen, sulfonate, or —COOH;

n is 0, 1, 2, or 3;

m is 0, 1, 2, or 3;

p is 0, 1, 2, or 3;

q is 0, 1, 2, or 3; and $A^4$ is a polypeptide having at least 80% sequence identity with MCMPCFTTDHQMARRCDDCCGGR-GRGKCYGPQCLCR (SEQ ID NO: 9) or a fragment thereof.

In other aspects, compounds used in the present disclosure have a structure of Formula (V), or a pharmaceutically acceptable salt thereof:

(V)

wherein:
$R^1$, $R^2$, $R^4$, $R^5$, $R^6$, $R^7$, $R^8$, $R^{15}$, and $R^{16}$ are each independently selected from hydrogen, $C_1$-$C_6$ alkyl, $C_1$-$C_6$ alkylene-COOH, sulfonate, —COOH, —SO$_2$—NH$_2$, or $C_1$-$C_6$ alkoxy;

$R^3$ is selected from $C_1$-$C_{10}$ alkylene-(C(=O))$_x$—, $C_1$-$C_{10}$ alkylene-(C(=O)), —O—, or $C_1$-$C_{10}$ alkylene-(C(=O))$_x$—NR$^{10}$—;

$R^9$ is hydrogen, sulfonate, or —COOH, or $C_1$-$C_{10}$ alkyl;

$L^1$ is $C_3$-$C_6$ alkylene;

$L^2$ is $C_1$-$C_{10}$ alkylene;

$L^3$ is hydrogen, sulfonate, —COOH, $C_1$-$C_{10}$ alkyl;

$L^4$ is a bond, -heterocyclyl-, or -heterocyclyl-$C_1$-$C_6$ alkylene-;

$R^{10}$ is hydrogen or $C_1$-$C_6$ alkyl;

$R^{11}$ is hydrogen or $C_1$-$C_6$ alkyl;

$R^{12}$ and $R^{13}$ are independently selected from hydrogen, $C_1$-$C_6$ alkyl, or $R^{12}$ and $R^{13}$ are joined together along with the other atoms to which they are attached to form a 5-membered or 6-membered carbocyclic or heterocyclic ring;

$R^{14}$ is hydrogen or $C_1$-$C_6$ alkylene, -(L$^5$)-aryl, -(L$^5$)-heteroaryl, —NR$^{17}$R$^{18}$, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;

$L^5$ is a bond, $C_1$-$C_{10}$ alkylene, —O—, —NR$^{10}$—;

$R^{17}$ and $R^{18}$ are each independently hydrogen or aryl;

$R^{19}$ and $R^{20}$ are independently selected from hydrogen, $C_1$-$C_6$ alkyl, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;

n is 0, 1, 2, or 3;
m is 0, 1, 2, or 3;
p is 0, 1, 2, or 3;
q is 0, 1, 2, or 3;
x is 0 or 1; and $A^1$ is a polypeptide having at least 85% sequence identity with MCMPCFTTDHQMARRCDDCCGGR-GRGKCYGPQCLCR (SEQ ID NO: 9) or a fragment thereof.

In other aspects, compounds used in the present disclosure have a structure of Formula (VI), or a pharmaceutically acceptable salt thereof:

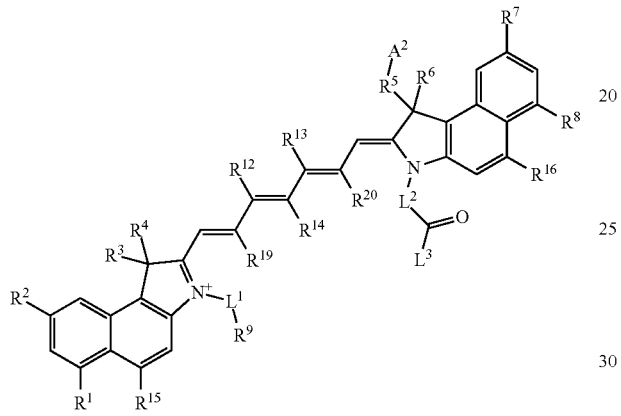

(VI)

wherein:
$R^1$, $R^2$, $R^3$, $R^4$, $R^6$, $R^7$, $R^8$, $R^{15}$, and $R^{16}$ are each independently selected from hydrogen, $C_1$-$C_6$ alkyl, $C_1$-$C_6$ alkylene-COOH, sulfonate, —COOH, —$SO_2$—$NH_2$, or $C_1$-$C_6$ alkoxy;
$R^5$ is selected from $C_1$-$C_{10}$ alkylene-(C(=O))$_x$—, $C_1$-$C_{10}$ alkylene-(C(=O))$_x$—O—, or $C_1$-$C_{10}$ alkylene-(C(=O))$_x$—$NR^{10}$—;
$R^9$ is hydrogen, sulfonate, or —COOH, or $C_1$-$C_{10}$ alkyl;
$L^1$ is $C_3$-$C_6$ alkylene;
$L^2$ is $C_1$-$C_{10}$ alkylene;
$L^3$ is hydrogen, sulfonate, —COOH, or $C_1$-$C_{10}$ alkyl;
$L^4$ is a bond, -heterocyclyl-, or -heterocyclyl-$C_1$-$C_6$ alkylene-;
$R^{10}$ is hydrogen or $C_1$-$C_6$ alkyl;
$R^{11}$ is hydrogen or $C_1$-$C_6$ alkyl;
$R^{12}$ and $R^{13}$ are independently selected from hydrogen, $C_1$-$C_6$ alkyl, or $R^{12}$ and $R^{13}$ are joined together along with the other atoms to which they are attached to form a 5-membered or 6-membered carbocyclic or heterocyclic ring;
$R^{14}$ is hydrogen or $C_1$-$C_6$ alkylene, -($L^5$)-aryl, -($L^5$)-heteroaryl, —$NR^{17}R^{18}$, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;
$L^5$ is a bond, $C_1$-$C_{10}$ alkylene, —O—, —$NR^{10}$—;
$R^{17}$ and $R^{18}$ are each independently hydrogen or aryl;
$R^{19}$ and $R^{20}$ are independently selected from hydrogen, $C_1$-$C_6$ alkyl, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;
n is 0, 1, 2, or 3;
m is 0, 1, 2, or 3;
p is 0, 1, 2, or 3;
q is 0, 1, 2, or 3;
x is 0 or 1; and $A^2$ is a polypeptide having at least 85% sequence identity with MCMPCFTTDHQMARRCDDCCGGR-GRGKCYGPQCLCR (SEQ ID NO: 9) or a fragment thereof.

In some aspects, compounds used in the present disclosure have a structure of Formula (VII), or a pharmaceutically acceptable salt thereof:

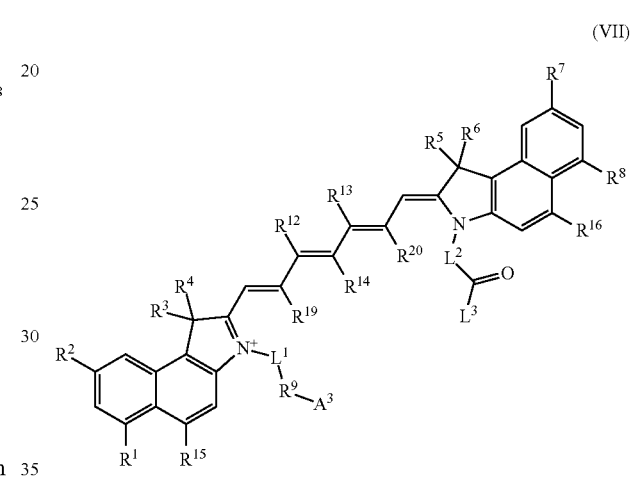

(VII)

wherein:
$R^1$, $R^2$, $R^3$, $R^4$, $R^5$, $R^6$, $R^7$, $R^8$, $R^{15}$, and $R^{16}$ are each independently selected from hydrogen, $C_1$-$C_6$ alkyl, $C_1$-$C_6$ alkylene-COOH, sulfonate, —COOH, —$SO_2$—$NH_2$, or $C_1$-$C_6$ alkoxy;
$R^9$ is selected from $C_1$-$C_{10}$ alkylene-(C(=O))$_x$—, $C_1$-$C_{10}$ alkylene-(C(=O))$_x$—O—, or $C_1$-$C_{10}$ alkylene-(C(=O))$_x$—$NR^{10}$—;
$L^1$ is $C_3$-$C_6$ alkylene;
$L^2$ is $C_1$-$C_{10}$ alkylene;
$L^3$ is hydrogen, sulfonate, —COOH, or $C_1$-$C_{10}$ alkyl;
$L^4$ is a bond, -heterocyclyl-, or -heterocyclyl-$C_1$-$C_6$ alkylene-;
$R^{10}$ is hydrogen or $C_1$-$C_6$ alkyl;
$R^{11}$ is hydrogen or $C_1$-$C_6$ alkyl;
$R^{12}$ and $R^{13}$ are independently selected from hydrogen, $C_1$-$C_6$ alkyl, or $R^{12}$ and $R^{13}$ are joined together along with the other atoms to which they are attached to form a 5-membered or 6-membered carbocyclic or heterocyclic ring;
$R^{14}$ is hydrogen or $C_1$-$C_6$ alkylene, -($L^5$)-aryl, -($L^5$)-heteroaryl, —$NR^{17}R^{18}$, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;
$R^{17}$ and $R^{18}$ are each independently hydrogen or aryl;
$R^{19}$ and $R^{20}$ are independently selected from hydrogen, $C_1$-$C_6$ alkyl, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;

n is 0, 1, 2, or 3;
m is 0, 1, 2, or 3;
p is 0, 1, 2, or 3;
q is 0, 1, 2, or 3;
x is 0 or 1;
$L^5$ is a bond, $C_1$-$C_{10}$ alkylene, —O—, —$NR^{10}$—; $A^3$ is a polypeptide having at least 85% sequence identity with MCMPCFTTDHQMARRCDDCCGGR-GRGKCYGPQCLCR (SEQ ID NO: 9) or a fragment thereof.

In additional aspects, compounds used in the present disclosure have a structure Formula (VIII), or a pharmaceutically acceptable salt thereof:

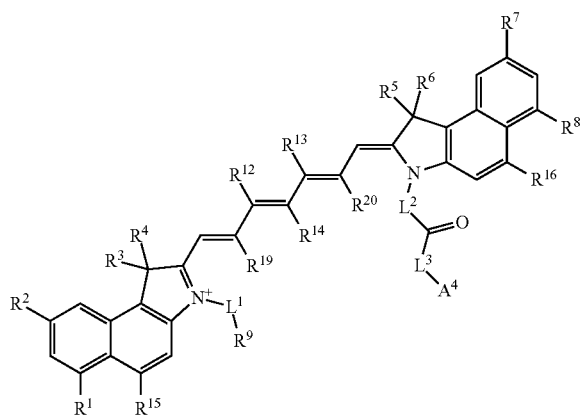

(VIII)

wherein:
$R^1$, $R^2$, $R^3$, $R^4$, $R^5$, $R^6$, $R^7$, $R^8$, $R^{15}$, and $R^{16}$ are each independently selected from hydrogen, $C_1$-$C_6$ alkyl, $C_1$-$C_6$ alkylene-COOH, sulfonate, —COOH, —$SO_2$—$NH_2$, or $C_1$-$C_6$ alkoxy;
$R^9$ is hydrogen, sulfonate, or —COOH;
$L^1$ is $C_3$-$C_6$ alkylene;
$L^2$ is $C_1$-$C_{10}$ alkylene;
$L^3$ is a bond, —O—, —$NR^{10}$—, —$NR^{10}$—$C_1$-$C_6$ alkylene-, —O—$NR^{11}$—, —$NR^{10}$—$C_1$-$C_6$ alkylene-(O—$C_1$-$C_6$ alkylene)$_n$-, —$NR^{10}$-$L^4$-, —$NR^{10}$—$C_1$-$C_6$ alkylene-$NR^{11}$—(C(=O)—$C_1$-$C_6$ alkylene-O—)$_m$—, or —$NR^{10}$—$C_1$-$C_6$ alkylene-$NR^{10}$—$C_1$-$C_6$ alkylene-$NR^{10}$—$C_1$-$C_6$ alkylene-;
$L^4$ is a bond, -heterocyclyl-, or -heterocyclyl-$C_1$-$C_6$ alkylene-;
$R^{10}$ is hydrogen or $C_1$-$C_6$ alkyl;
$R^{11}$ is hydrogen or $C_1$-$C_6$ alkyl;
$R^{12}$ and $R^{13}$ are independently selected from hydrogen, $C_1$-$C_6$ alkyl, or $R^{12}$ and $R^{13}$ are joined together along with the other atoms to which they are attached to form a 5-membered or 6-membered carbocyclic or heterocyclic ring;
$R^{14}$ is -($L^5$)-aryl-$A^5$, or -($L^5$)-heteroaryl-$A^5$;
$L^5$ is a bond, $C_1$-$C_{10}$ alkylene, —O—, —$NR^{10}$—;
$R^{17}$ and $R^{18}$ are each independently hydrogen or aryl;
$R^{19}$ and $R^{20}$ are independently selected from hydrogen, $C_1$-$C_6$ alkyl, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;

n is 0, 1, 2, or 3;
m is 0, 1, 2, or 3;
p is 0, 1, 2, or 3;
q is 0, 1, 2, or 3;
x is 0 or 1;
$A^4$ is hydrogen, —COOH, or sulfonate; and
$A^5$ is a polypeptide having at least 85% sequence identity with MCMPCFTTDHQMARRCDDCCGGR-GRGKCYGPQCLCR (SEQ ID NO: 9) or a fragment thereof.

In certain aspects, $A^1$, $A^2$, and $A^3$ are absent. In some aspects, $A^5$ is hydrogen. In certain aspects, $R^3$, $R^4$, $R^5$, and $R^6$ are each independently $C_1$-$C_6$ alkyl. In some aspects, $R^3$, $R^4$, $R^5$, and $R^6$ are each independently methyl. In certain aspects, $R^1$, $R^2$, $R^7$, $R^8$, $R^{15}$, and $R^{16}$ are each independently selected from hydrogen or sulfonate. In further aspects, $R^1$, $R^2$, $R^7$, $R^8$, $R^{15}$, and $R^{16}$ are each independently hydrogen. In some aspects, $R^{12}$, $R^{13}$, $R^{14}$, $R^{19}$, $R^{20}$ are each independently hydrogen.

In certain aspects, $R^{12}$ and $R^{13}$ join together along with the atoms to which they are attached to form a six-membered carbocyclic ring. In other aspects, $R^{12}$ and $R^{13}$ join together along with the atoms to which they are attached to form a five-membered carbocyclic ring. In certain aspects, $R^{14}$ and $R^{19}$ join together along with the atoms to which they are attached to form a six-membered carbocyclic ring. In some aspects, $R^{14}$ and $R^{20}$ join together along with the atoms to which they are attached to form a six-membered carbocyclic ring. In certain aspects, $L^1$ is $C_3$-$C_6$ alkylene. In other aspects, $L^1$ is $C_3$-$C_5$ alkylene. In still other aspects, $L^1$ is propylene. In still other aspects, $L^1$ is butylene. In other aspects, $L^1$ is pentylene. In some aspects, $L^2$ is $C_3$-$C_6$ alkylene. In other aspects, $L^2$ is propylene. In still other aspects, $L^2$ is butylene. In other aspects, $L^2$ is pentylene. In some aspects, $R^9$ is sulfonate. In other aspects, $R^9$ is hydrogen. In some aspects, $R^{14}$ is hydrogen. In other aspects, $R^{14}$ is -($L^5$)-aryl. In still other aspects, $R^{14}$ is -($L^5$)-aryl-$A^5$.

In some aspects, $R^1$ is hydrogen. In certain aspects, $R^2$ is hydrogen. In some aspects, $R^3$ is methyl. In certain aspects, $R^4$ is methyl. In some aspects, $R^5$ is methyl. In certain aspects $R^6$ is methyl. In some aspects, $R^7$ is hydrogen. In certain aspects, $R^8$ is hydrogen. In some aspects, $R^{12}$ is hydrogen. In certain aspects, $R^{13}$ is hydrogen. In some aspects, $R^{14}$ is hydrogen. In certain aspects, $R^{19}$ is hydrogen. In some aspects, $R^{20}$ is hydrogen. In certain aspects, $R^{10}$ is hydrogen. In some aspects, $R^{11}$ is hydrogen.

In some aspects, $R^{17}$ and $R^{18}$ are independently phenyl. In some aspects, $L^1$ is buytlene. In some aspects, $L^2$ is pentylene. In some aspects, $L^3$ is selected from a bond, —O—, —$NR^{10}$—, —$NR^{10}$—$C_1$-$C_6$ alkylene-, —O—$NR^{10}$—, or —$NR^{10}$-$L^4$-. In further aspects, $L^3$ is a bond.

In some aspects, $L^4$ is -heterocyclyl- or -heterocyclyl-$C_1$-$C_6$ alkylene-. In further aspects, $L^4$ is -piperizinyl-($C_1$-$C_6$ alkylene)-. In still further aspects, $L^4$ is

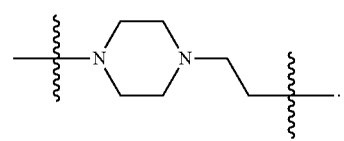

In some aspects, p is 1. In certain aspects, q is 1.
In some aspects, the compound used has the structure of any one of Formulas (IX), (X), (XI), (XII), (XIII), (XIV), (XV), or (XVI):
(IX)
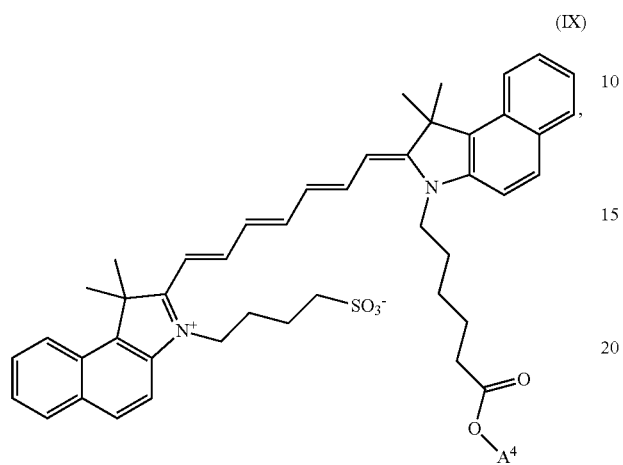
(X)
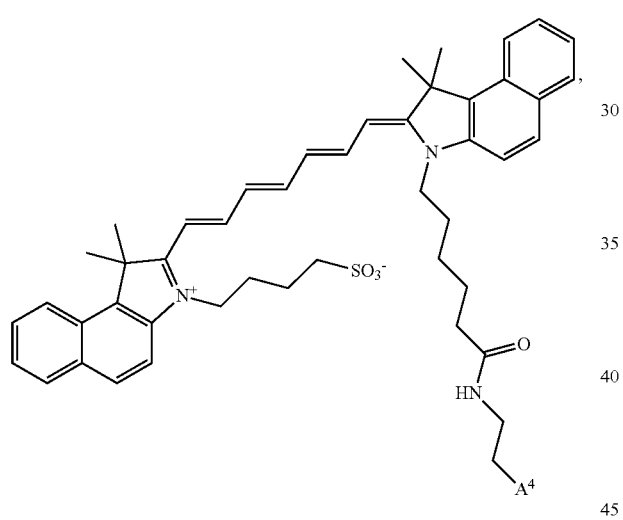
(XI)
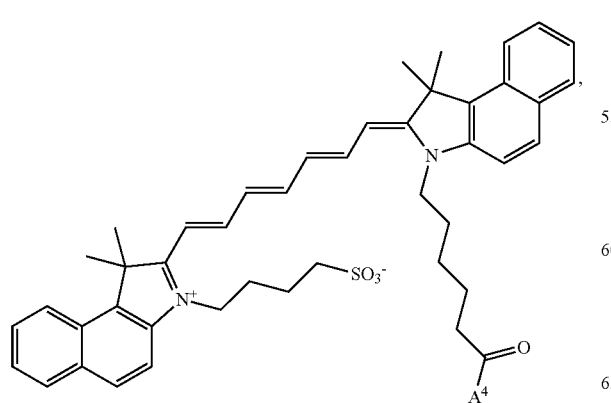
(XII)
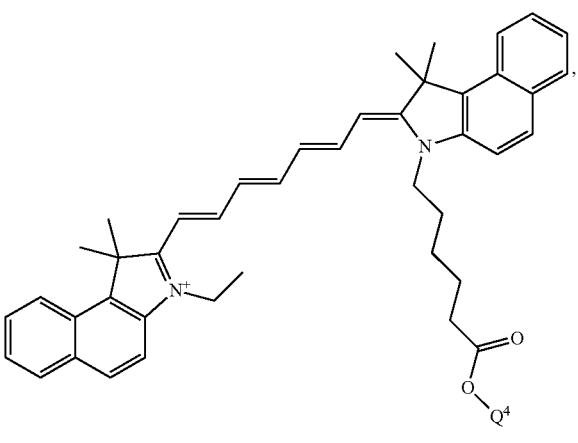
(XIII)
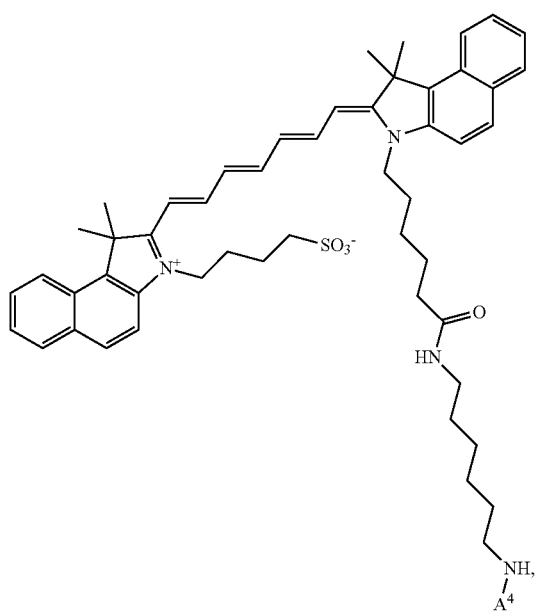
(XIV)
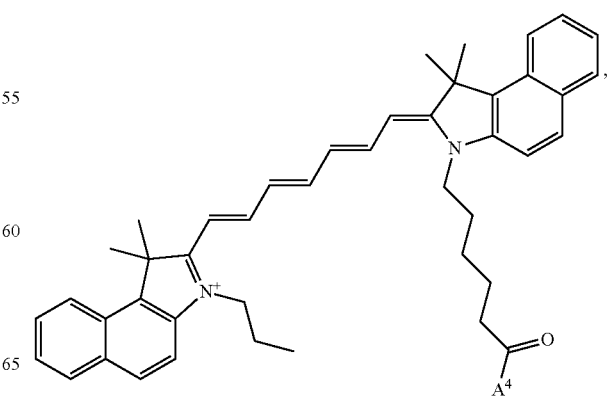

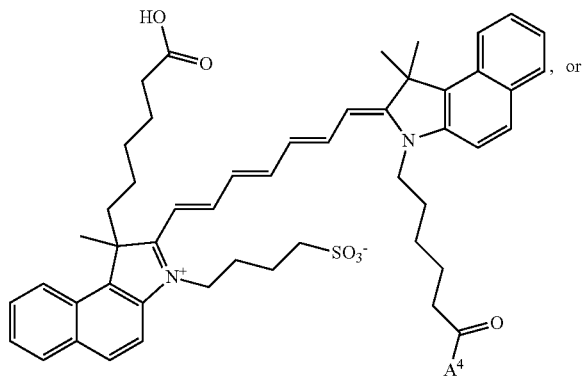

(XV)

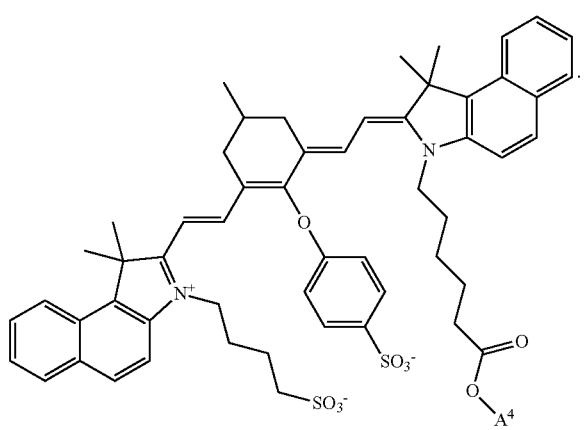

(XVI)

In some aspects, the compound has the structures of any one of Formulas (IX), (X), (XI), (XII), (XIII), (XIV), (XV), or (XVI), wherein $A^4$ is a polypeptide.

In some aspects, one of $A^1$, $A^2$, $A^3$, $A^4$, or $A^5$ is a polypeptide having at least 87% sequence identity with MCMPCFTTDHQMARRCDDCCGGR-GRGKCYGPQCLCR (SEQ ID NO: 9) or a fragment thereof. In further aspects, one of $A^1$, $A^2$, $A^3$, $A^4$, or $A^5$ is a polypeptide having at least 90% sequence identity with MCMPCFTTDHQMARRCDDCCGGR-GRGKCYGPQCLCR (SEQ ID NO: 9) or a fragment thereof. In still further aspects, one of $A^1$, $A^2$, $A^3$, $A^4$, or $A^5$ is a polypeptide having at least 92% sequence identity with MCMPCFTTDHQMARRCDDCCGGR-GRGKCYGPQCLCR (SEQ ID NO: 9) or a fragment thereof. In still further aspects, one of $A^1$, $A^2$, $A^3$, $A^4$, or $A^5$ is a polypeptide having at least 95% sequence identity with MCMPCFTTDHQMARRCDDCCGGR-GRGKCYGPQCLCR (SEQ ID NO: 9) or a fragment thereof. In still further aspects, one of $A^1$, $A^2$, $A^3$, $A^4$, or $A^5$ is a polypeptide having at least 97% sequence identity with MCMPCFTTDHQMARRCDDCCGGR-GRGKCYGPQCLCR (SEQ ID NO: 9) or a fragment thereof. In still further aspects, one of $A^1$, $A^2$, $A^3$, $A^4$, or $A^5$ is a polypeptide having 100% sequence identity with MCMPCFTTDHQMARRCDDCCGGR-GRGKCYGPQCLCR (SEQ ID NO: 9) or a fragment thereof. In still further aspects, one of $A^1$, $A^2$, $A^3$, $A^4$, or $A^5$ is a polypeptide having the sequence MCMPCFTTDHQMARRCDDCCGGR-GRGKCYGPQCLCR (SEQ ID NO: 9) or a fragment thereof.

In some aspects, the fragment of $A^1$, $A^2$, $A^3$, $A^4$, or $A^5$ has a length of at least 25 amino acid residues. In further aspects, the fragment of $A^1$, $A^2$, $A^3$, $A^4$, or $A^5$ has a length of at least 27 amino acid residues. In still further aspects, the fragment of $A^1$, $A^2$, $A^3$, $A^4$, or $A^5$ has a length of at least 29 amino acid residues. In still further aspects, the fragment of $A^1$, $A^2$, $A^3$, $A^4$, or $A^5$ has a length of at least 31 amino acid residues. In still further aspects, the fragment of $A^1$, $A^2$, $A^3$, $A^4$, or $A^5$ has a length of at least 33 amino acid residues.

In some aspects, one of $A^1$, $A^2$, $A^3$, $A^4$, or $A^5$ is a polypeptide having at least 85% sequence identity with MCMPCFTTDHQMARRCDDCCGGR-GRGKCYGPQCLCR (SEQ ID NO: 9) or a fragment thereof having the tumor cell binding affinity of native chlorotoxin. In certain aspects, one of $A^1$, $A^2$, $A^3$, $A^4$, or $A^5$ is a polypeptide having at least 85% sequence identity with MCMPCFTTDHQMARRCDDCCGGR-GRGKCYGPQCLCR (SEQ ID NO: 9) or a fragment thereof having about the same the tumor cell binding affinity of native chlorotoxin. In some aspects, one of $A^1$, $A^2$, $A^3$, $A^4$, or $A^5$ is a polypeptide having at least 85% sequence identity with MCMPCFTTDHQMARRCDDCCGGR-GRGKCYGPQCLCR (SEQ ID NO: 9) or a fragment thereof having the tumor cell binding affinity of native chlorotoxin wherein one of $A^1$, $A^2$, $A^3$, $A^4$, or $A^5$ has a sequence selected from SEQ ID NO: 1-SEQ ID NO: 485.

In some aspect, the polypeptide contains no lysine residues. In some aspects, the polypeptide used comprises at least one lysine amino acid residue. In certain aspects, the polypeptide comprises a single lysine amino acid residue. In some aspects, the polypeptide comprises one, two, or three lysine amino acid residues. In some aspects, the polypeptide comprises a lysine residue at the position corresponding to K-27 of native chlorotoxin. In some aspects, the polypeptide comprises a lysine residue at the position corresponding to K-23 of native chlorotoxin. In some aspects, the polypeptide comprises a lysine residue at the position corresponding to K-15 of native chlorotoxin.

In some aspects, one or more of the amino acids of the polypeptide used is substituted with a non-naturally occurring amino acid residue. In further aspects the non-naturally occurring amino acid residue is a citrulline amino acid residue. In still further aspects, $L^3$ is attached to $A^4$ at a citrulline amino acid residue of the polypeptide.

In some aspects, $L^3$ is attached to $A^4$ at a lysine amino acid residue of the polypeptide. In certain aspects, $L^3$ is attached to $A^4$ at the N-terminus of the polypeptide. In some aspects, $L^3$ is attached to $A^4$ at the C-terminus of the polypeptide. In some aspects, the $R^3$ is attached to $A^1$ at a lysine amino acid residue of the peptide, a citrulline amino acid residue of the polypeptide, the N-terminus of the polypeptide, or the C-terminus of the polypeptide. In some aspects, the $R^5$ is attached to $A^2$ at a lysine amino acid residue of the polypeptide, a citrulline amino acid residue of the polypeptide, the N-terminus of the polypeptide, or the C-terminus of the polypeptide. In some aspects, the $R^9$ is attached to $A^3$ at a lysine amino acid residue of the polypeptide, a citrulline amino acid residue of the polypeptide, the N-terminus of the polypeptide, or the C-terminus of the polypeptide. In some aspects, the aryl is attached to $A^5$ at a lysine amino acid residue of the polypeptide, a citrulline amino acid residue of the polypeptide, the N-terminus of the polypeptide, or the C-terminus of the polypeptide.

In some aspects, the compound used has the structure of any one of compounds 1 to 60 as found in TABLE 2, in which A is a peptide portion and can comprise any of the peptides described herein, such as any one of SEQ ID NO: 1-SEQ ID NO: 485. In other aspects, the compound used has the structure of any one of compounds 1 to 60 as found in TABLE 2, in which A is a peptide fragment and can comprise a fragment of any of the peptides described herein, such as any one of SEQ ID NO: 1-SEQ ID NO: 485. In some embodiments, the fragment of the polypeptide has a length of at least 25 residues.

In some aspects, the compound used is conjugated to polyethylene glycol (PEG), hydroxyethyl starch, polyvinyl alcohol, a water soluble polymer, a zwitterionic water soluble polymer, a water soluble poly(amino acid), an albumin derivative, or a fatty acid.

In some aspects, the polypeptide used has an isoelectric point of from 5.5 to 9.5. In some aspects, the polypeptide has an isoelectric point of from 7.5 to 9.0. In some aspects, the polypeptide has an isoelectric point of from 8.0 to 9.0. In some aspects, the polypeptide has an isoelectric point of from 8.5 to 9.0. In some aspects, the polypeptide is basic and has an isoelectric point of greater than 7.5. In some aspects, the polypeptide has an isoelectric point of about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In other aspects, the polypeptide comprises an isoelectric point of at least 5.5, at least 6.0, at least 6.5, at least 7.0, at least 7.5, at least 8.0, at least 8.5, at least 9.0, or at least 9.5.

In some aspects, the polypeptide used comprises at least eight cysteine amino acid residues. In some aspects, the polypeptide comprises eight cysteine amino acid residues. In some aspects, the polypeptide comprises four disulfide bonds. In some aspects, the polypeptide comprises from six to seven cysteine amino acid residues. In some aspects, the polypeptide comprises three disulfide bonds. In some aspects, the polypeptide comprises at least 1 disulfide bond, at least 2 disulfide bonds, at least 3 disulfide bonds, at least 4 disulfide bonds, at least 5 disulfide bonds, or at least 6 disulfide bonds. In some aspects, the spacing between the cysteine amino acid residues in the polypeptide is about the same as in native chlorotoxin. In some aspects, the distribution of charge on the surface of the polypeptide is about the same as in native chlorotoxin.

In some aspects, the N-terminus of the polypeptide is blocked by acetylation or cyclization.

In some aspects, one or more of the methionine amino acid residues used is replaced with an amino acid residue selected from isoleucine, threonine, valine, leucine, serine, glycine, alanine, or a combination thereof. In other aspects, one, two, or three methionine residues of the polypeptide are replaced with other amino acids.

In some aspects, each amino acid of the polypeptide is independently selected as an L- or D-enantiomer.

In some aspects, the compound used is capable of passing across the blood brain barrier. In some aspects, the compound used further comprises a therapeutic agent. In some aspects, the polypeptide is conjugated to the therapeutic agent. In some aspects, the compound used further comprises a therapeutic agent attached to A. In further aspects, the therapeutic agent is a cytotoxic agent. In still other aspects, the therapeutic agent comprises a radioisotype, toxin, enzyme, sensitizing drug, radiosensitizer, nucleic acid, interfering RNA, antibody, antibody fragment, aptamer, anti-angiogenic agent, cisplatin, carboplatin, oxaliplatin, anti-metabolite, mitotic inhibitor, growth factor inhibitor, cytotoxin, microtubule disrupting agent, DNA modifying agent, maytansine derivative, auristatin derivative, dolostatin derivative, monomethyl auristatin E, monomethyl auristatin F, DM1, calicheamicin, duocarmycin derivative, campthotecin, pyrrolobenzodiazepine, paclitaxel, cyclophosphamide, chlorambucil, melphlan, bufulfan, carmustine, ifosfamide, temozolomide, topotecan, fluorouracil, vincristine, vinblastine, procarbazine, dacarbazine, altretamine, methotrexate, pemetrexed, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomycin, tamoxifen, flutamide, leuprolide, goserelin, aminogluthimide, anastrozole, amsacrine, asparaginase, mitoxantrone, mitotane, amifostine, lenalidomide, imatinib, abiraterone, erlotinib, enzalutimide, everolimus palbociclib, pomalidomide, sutininib, sorafenib, imatinib, gefitinib, afatinib, axitinib, crizotinib, vismoegib, dabrefenib, vemurafenib, or a combination thereof.

In some aspects, the compound of the composition used is any suitable compound described herein. In other aspects, the compound of the composition further comprises an agent. In some aspects, the compound comprises a detectable agent. In one embodiment, the polypeptide is conjugated to an agent. In another embodiment, the polypeptide is conjugated to a detectable agent. In some embodiments, a detectable agent is a detectable label. In some embodiments, a detectable agent comprises a dye, a fluorophore, a fluorescent biotin compound, a luminescent compound, a chemiluminescent compound, a radioisotope, a paramagnetic metal ion, or a combination thereof. In some embodiments, the polypeptide comprises a single lysine residue and the agent is conjugated to the polypeptide at the single lysine residue. In some embodiments, the polypeptide comprises no lysine residues and the agent is conjugated to the polypeptide at the N-terminus of the polypeptide.

Certain exemplary compounds falling within the scope of these genuses are provided below in TABLE 2 and further described herein, including both the peptide portion (indicated by A) and the detectable label portion.

TABLE 2
Compounds According to the Present Disclosure
| No. | Structure |
|---|---|
| 1 | 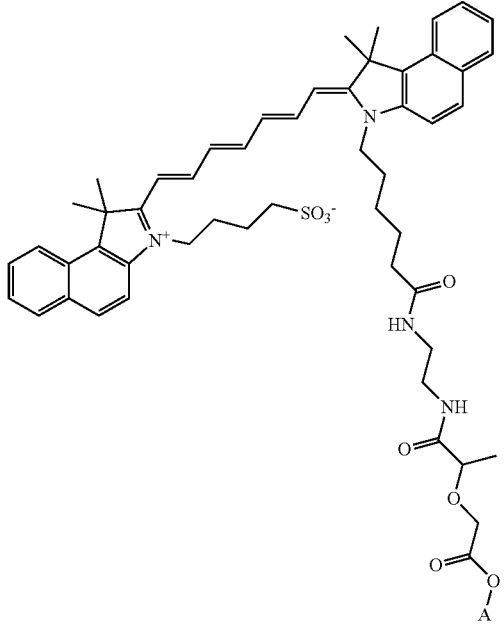 |
| 2 | 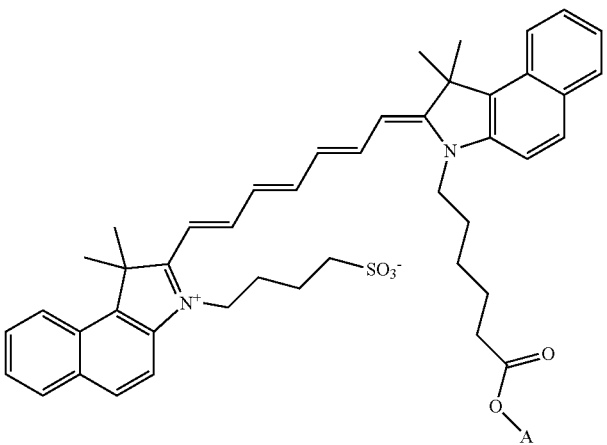 |

TABLE 2-continued
Compounds According to the Present Disclosure
| No. | Structure |
|---|---|
| 3 | 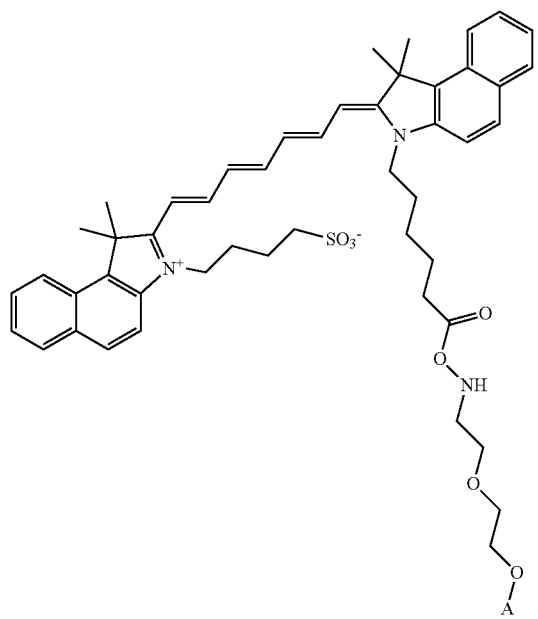 |
| 4 | 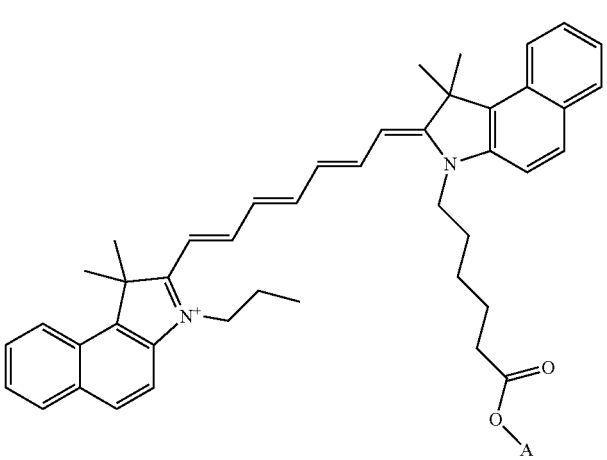 |
| 5 | 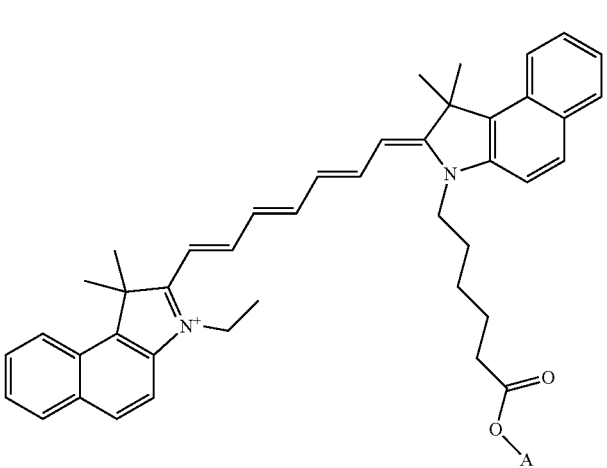 |

TABLE 2-continued

Compounds According to the Present Disclosure

| No. | Structure |
|---|---|
| 6 | *(chemical structure)* |
| 7 | *(chemical structure)* |
| 8 | *(chemical structure)* |

TABLE 2-continued

Compounds According to the Present Disclosure

| No. | Structure |
|---|---|
| 9 | 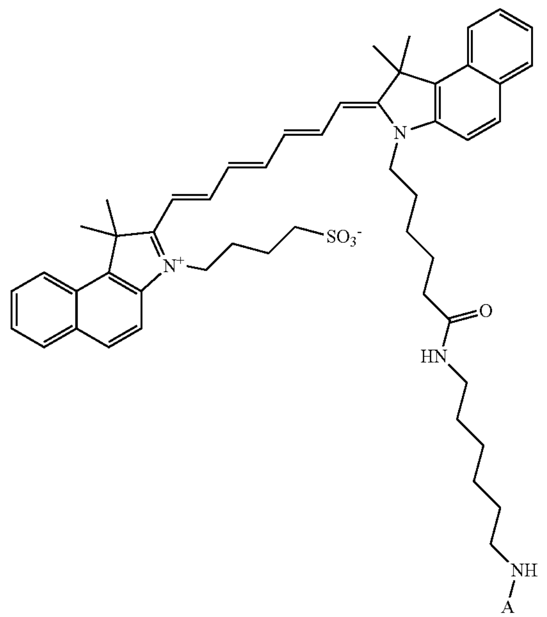 |
| 10 | 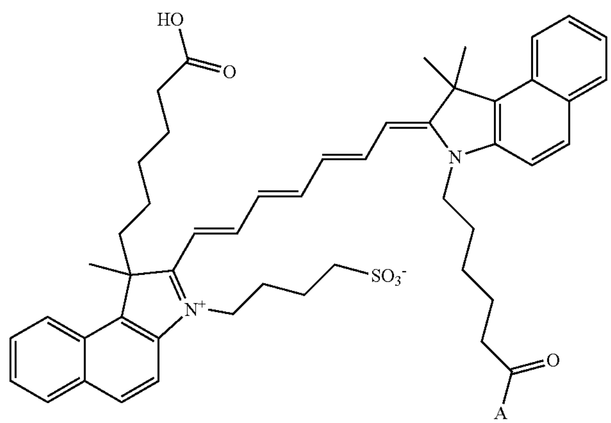 |
| 11 | 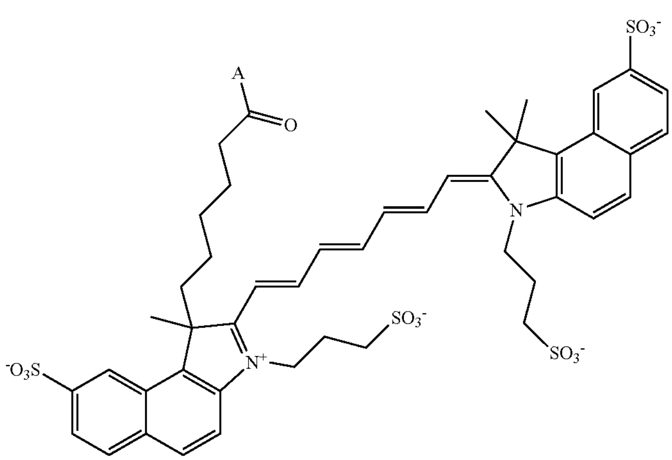 |

TABLE 2-continued
Compounds According to the Present Disclosure
| No. | Structure |
|---|---|
| 12 | 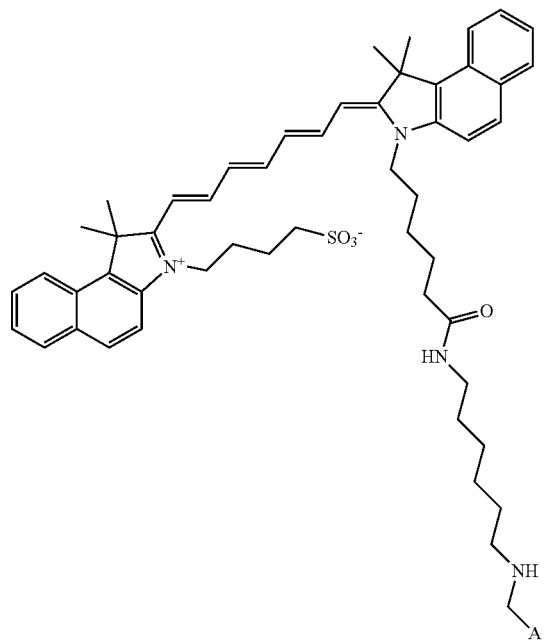 |
| 13 | 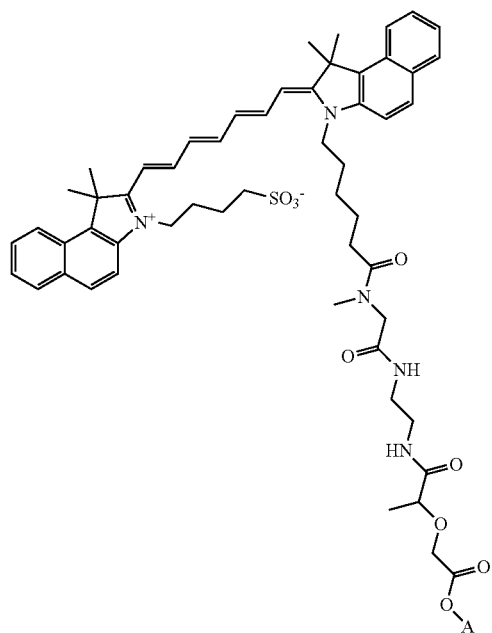 |

TABLE 2-continued

Compounds According to the Present Disclosure

| No. | Structure |
|---|---|
| 14 | 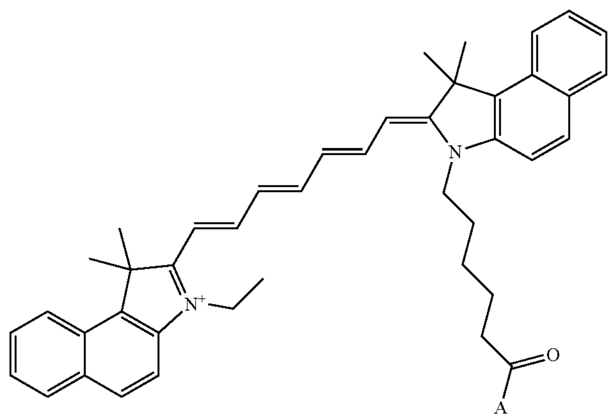 |
| 15 | 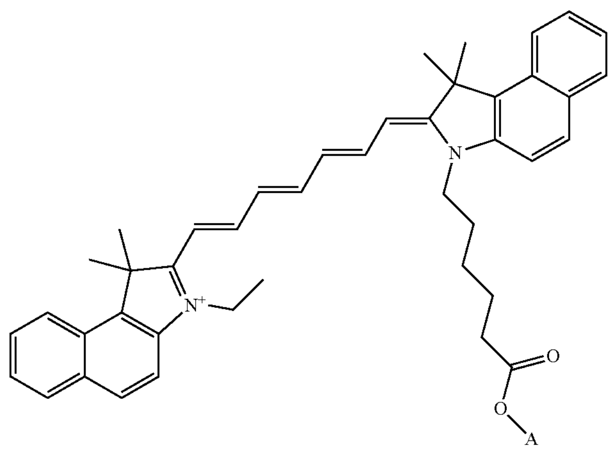 |
| 16 | 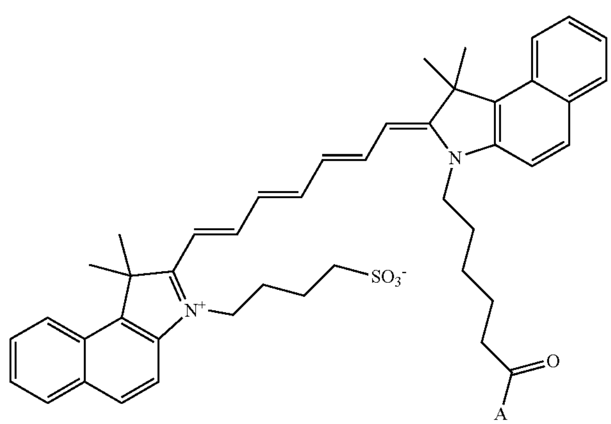 |

TABLE 2-continued

Compounds According to the Present Disclosure

| No. | Structure |
|-----|-----------|
| 17  | 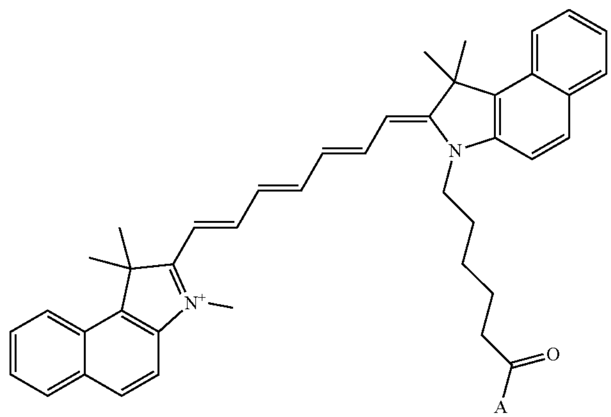          |
| 18  | 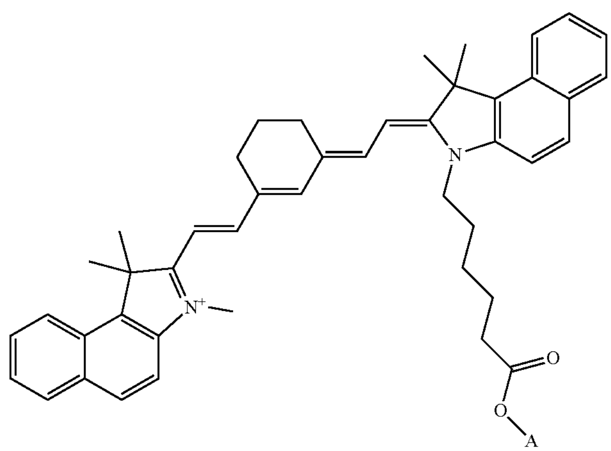          |
| 19  | 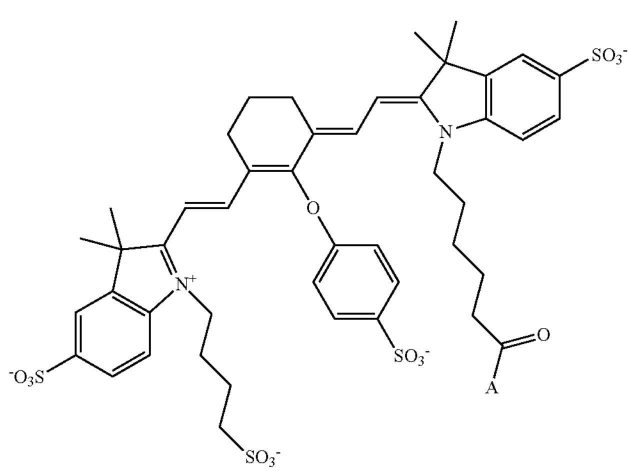          |

TABLE 2-continued

Compounds According to the Present Disclosure

| No. | Structure |
|---|---|
| 20 | 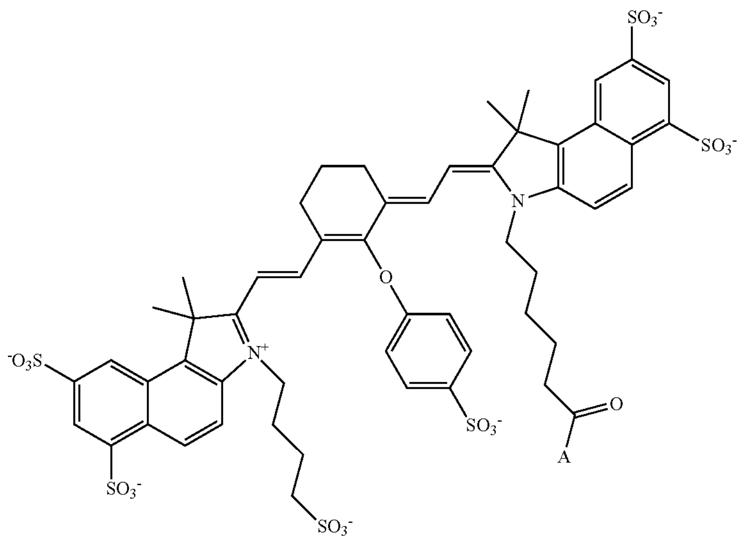 |
| 21 | 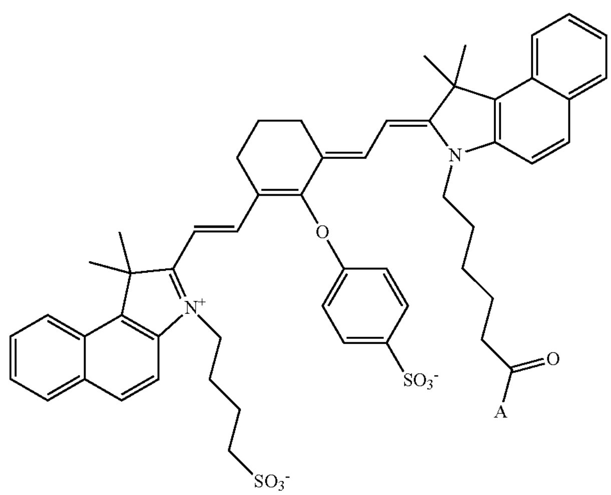 |
| 22 | 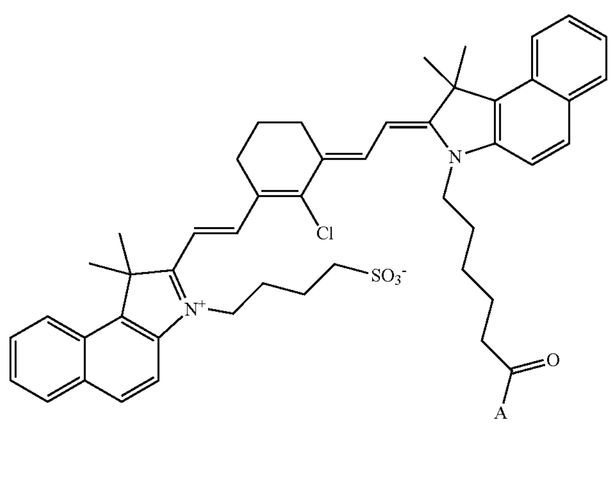 |

TABLE 2-continued

Compounds According to the Present Disclosure

| No. | Structure |
|---|---|
| 23 | 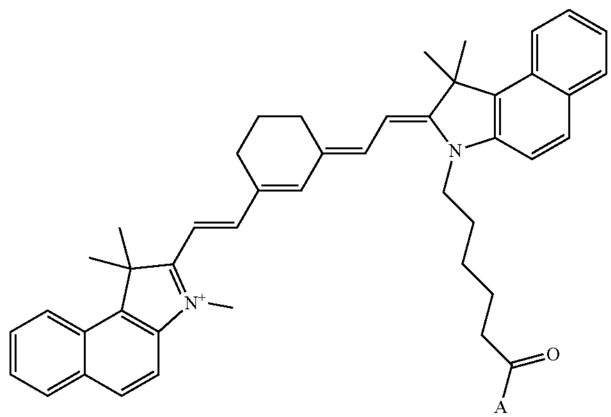 |
| 24 | 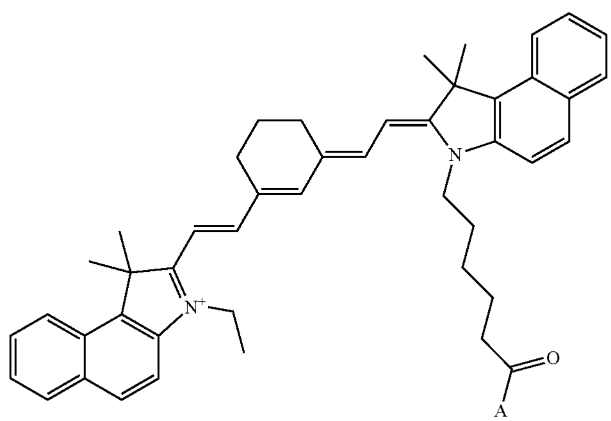 |
| 25 | 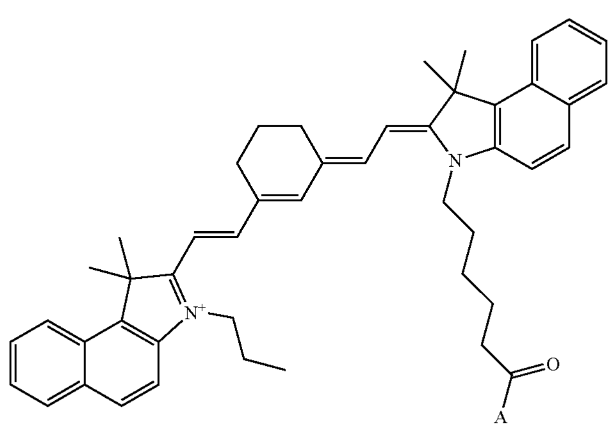 |

TABLE 2-continued
Compounds According to the Present Disclosure
| No. | Structure |
|---|---|
| 26 | 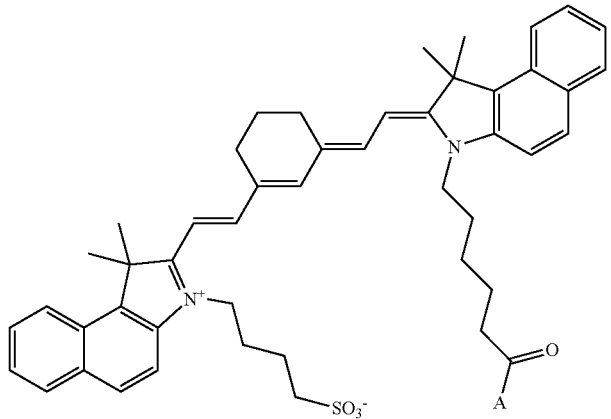 |
| 27 | 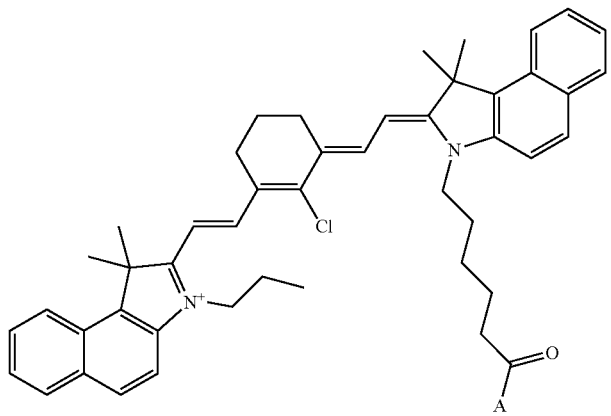 |
| 28 | 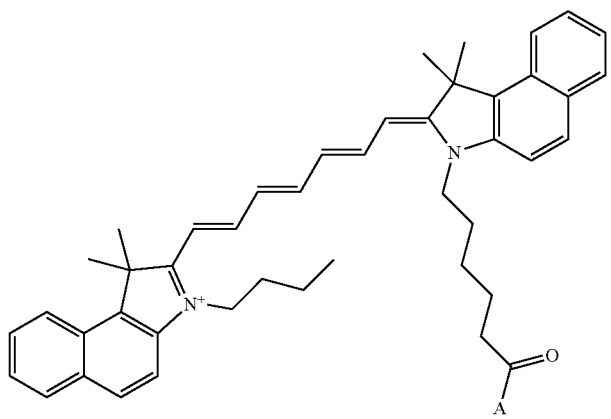 |

TABLE 2-continued

Compounds According to the Present Disclosure

| No. | Structure |
|---|---|
| 29 | 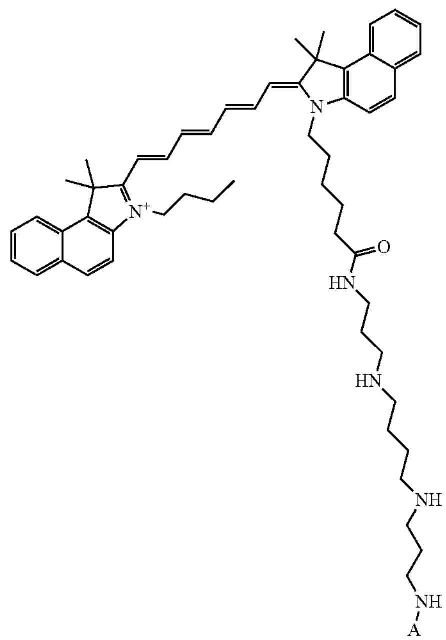 |
| 30 | 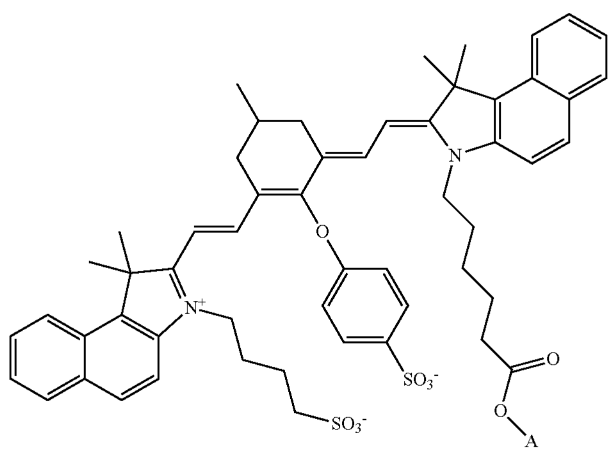 |
| 31 | 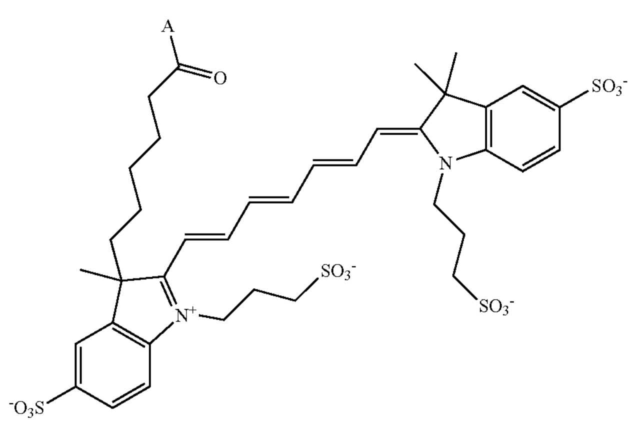 |

TABLE 2-continued
Compounds According to the Present Disclosure
| No. | Structure |
|---|---|
| 32 | 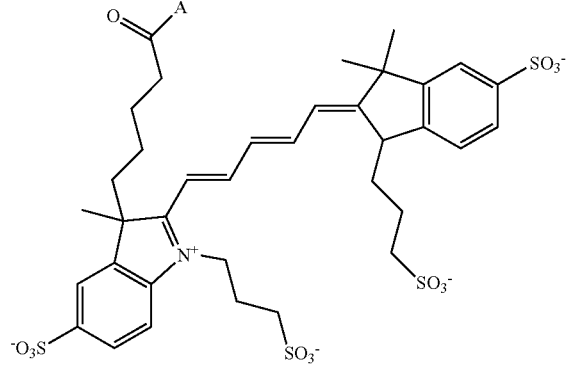 |
| 33 | 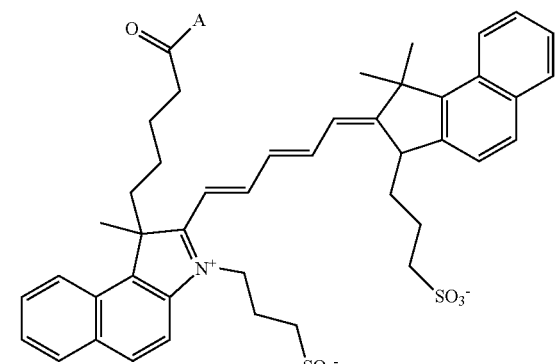 |
| 34 | 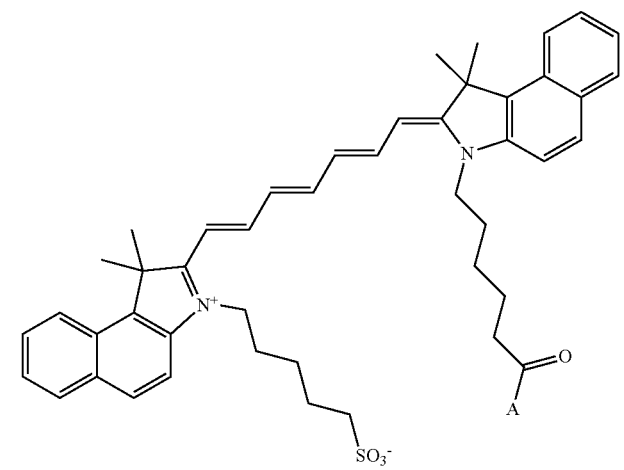 |

TABLE 2-continued
Compounds According to the Present Disclosure
| No. | Structure |
|---|---|
| 35 | 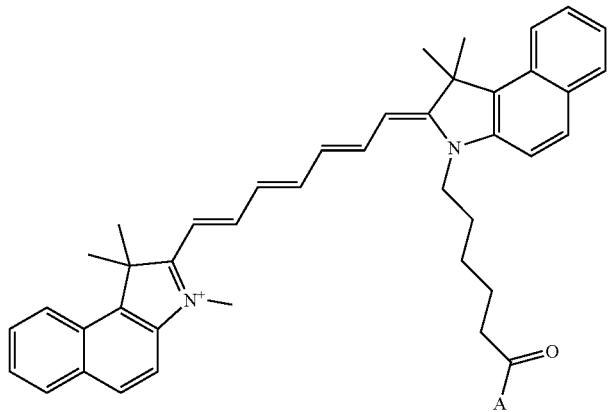 |
| 36 | 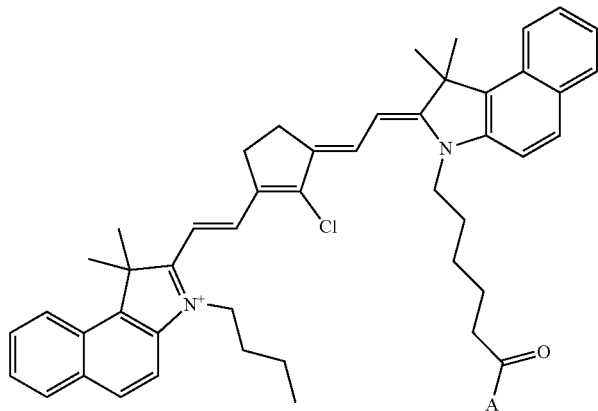 |
| 37 | 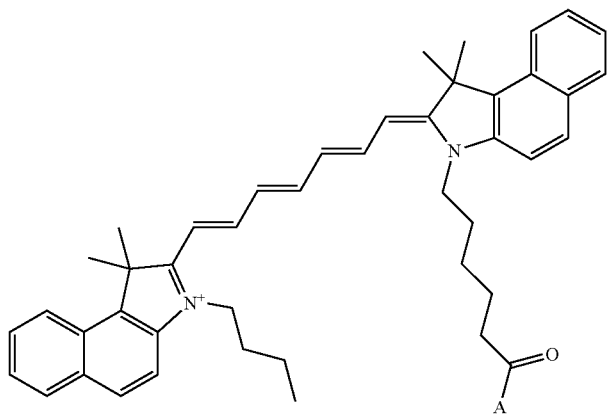 |

TABLE 2-continued

Compounds According to the Present Disclosure

| No. | Structure |
|---|---|
| 38 | 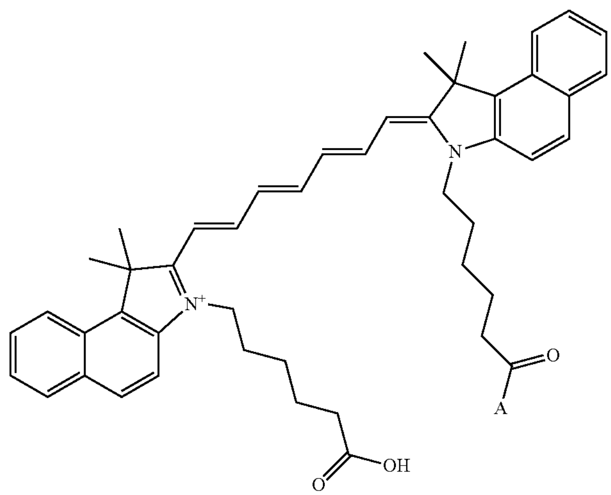 |
| 39 | 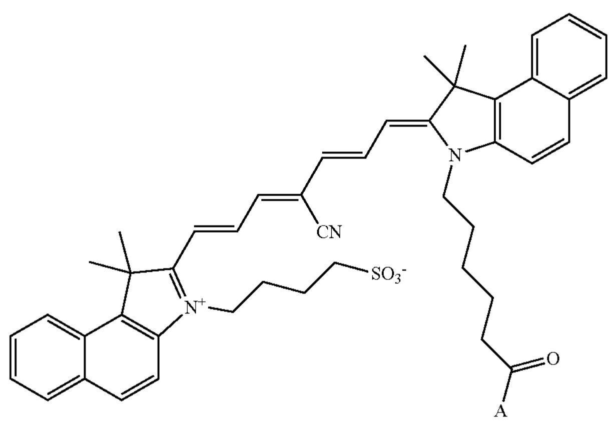 |
| 40 | 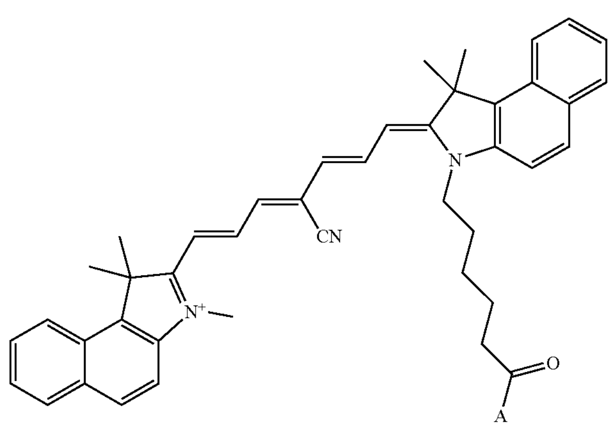 |

TABLE 2-continued

Compounds According to the Present Disclosure

| No. | Structure |
|-----|-----------|
| 41  | 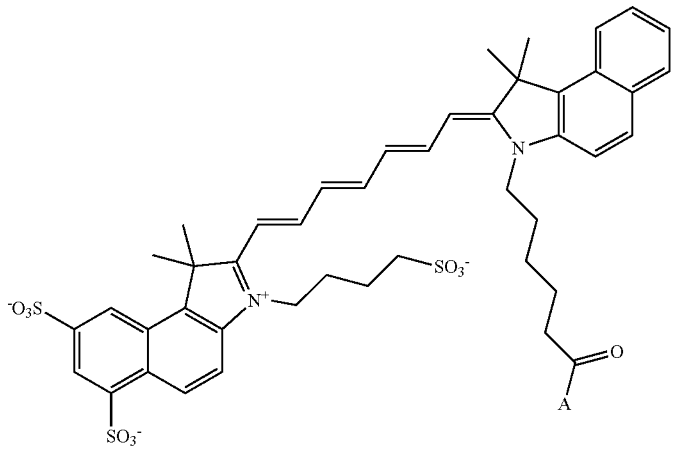          |
| 42  | 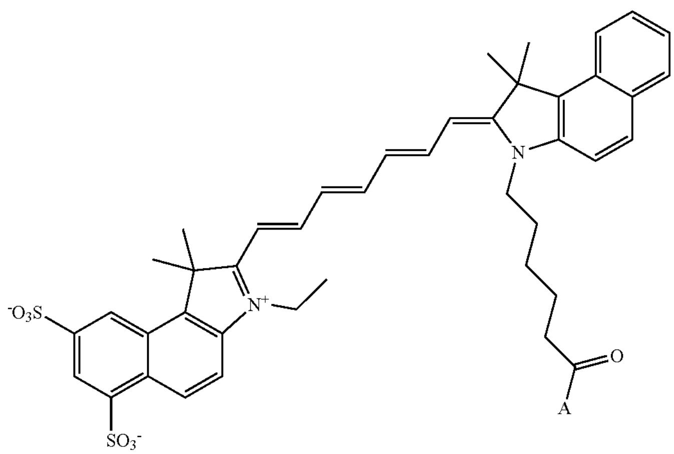          |
| 43  | 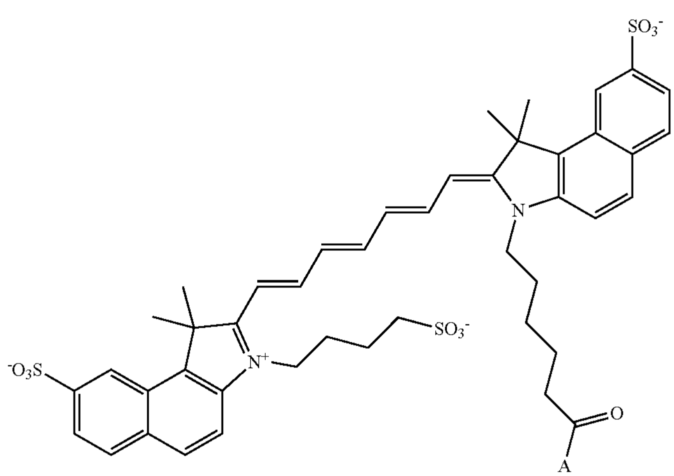          |

TABLE 2-continued
Compounds According to the Present Disclosure
| No. | Structure |
|---|---|
| 44 | 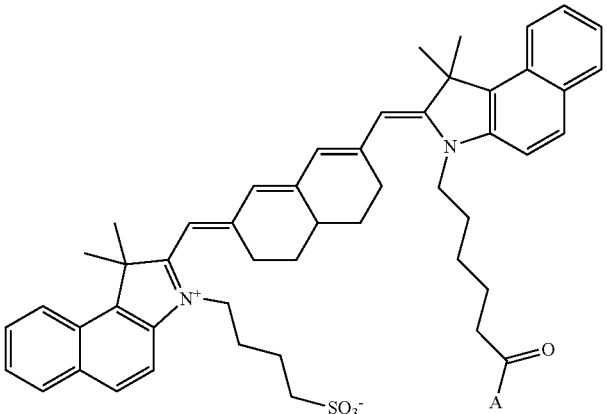 |
| 45 | 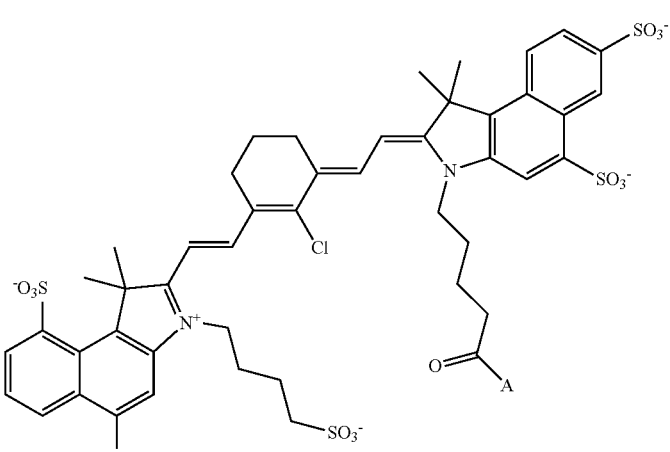 |
| 46 | 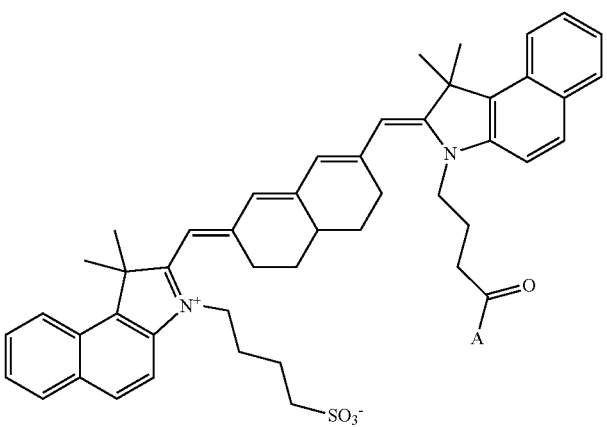 |

TABLE 2-continued
Compounds According to the Present Disclosure
| No. | Structure |
|---|---|
| 47 | 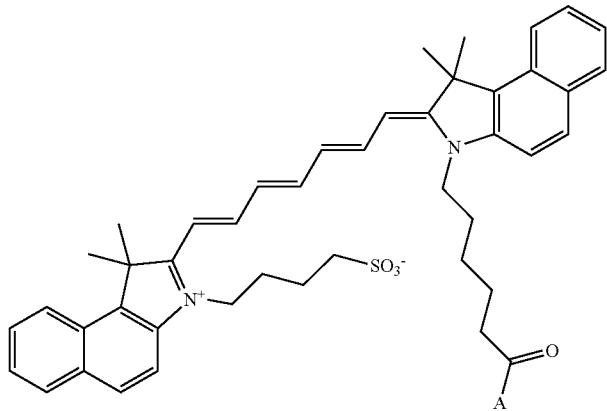 |
| 48 | 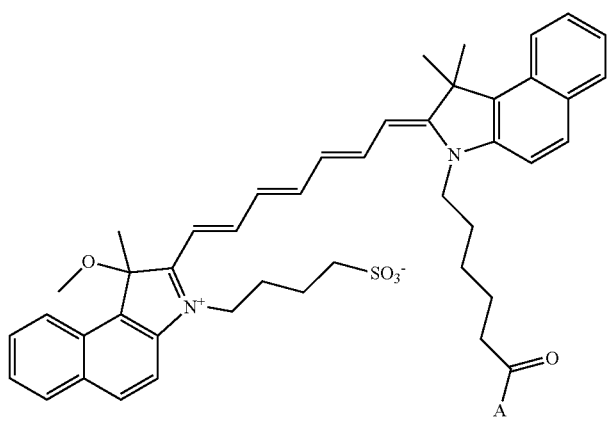 |
| 49 | 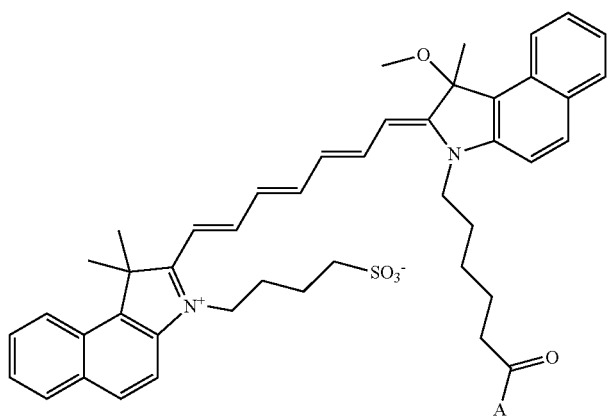 |

TABLE 2-continued
Compounds According to the Present Disclosure
| No. | Structure |
|---|---|
| 50 | 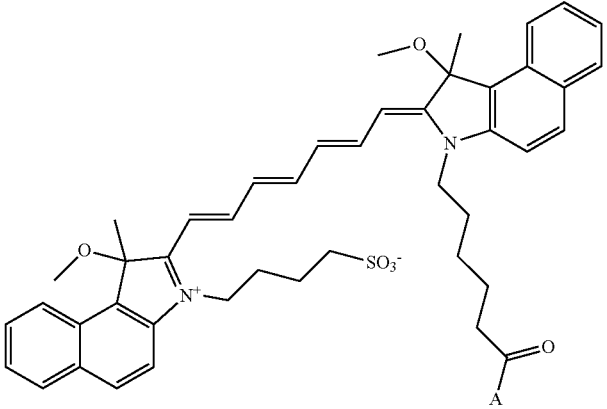 |
| 51 | 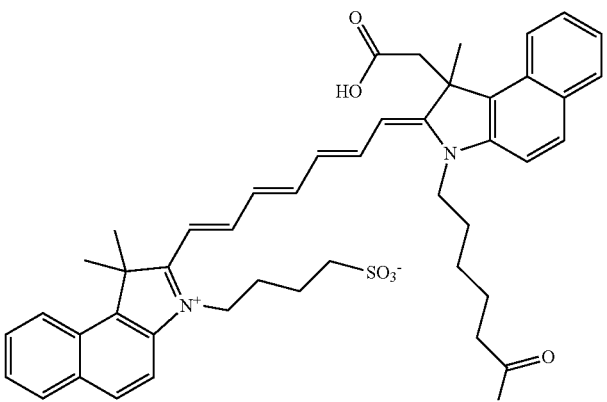 |
| 52 | 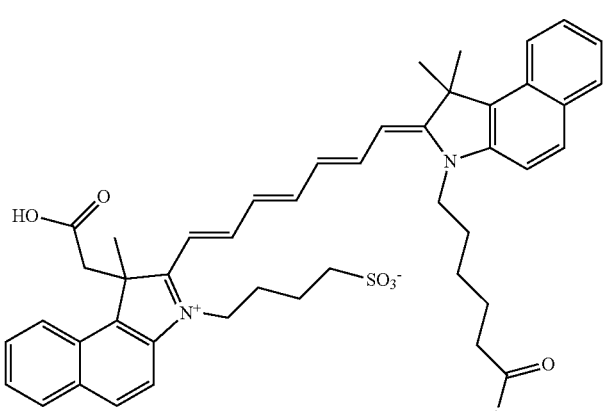 |

TABLE 2-continued
Compounds According to the Present Disclosure
| No. | Structure |
|---|---|
| 53 | 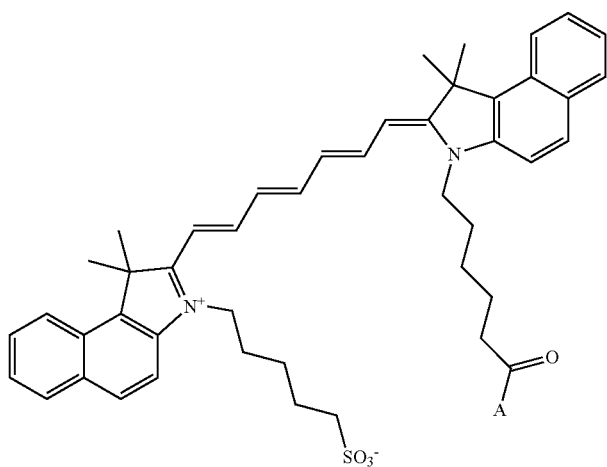 |
| 54 | 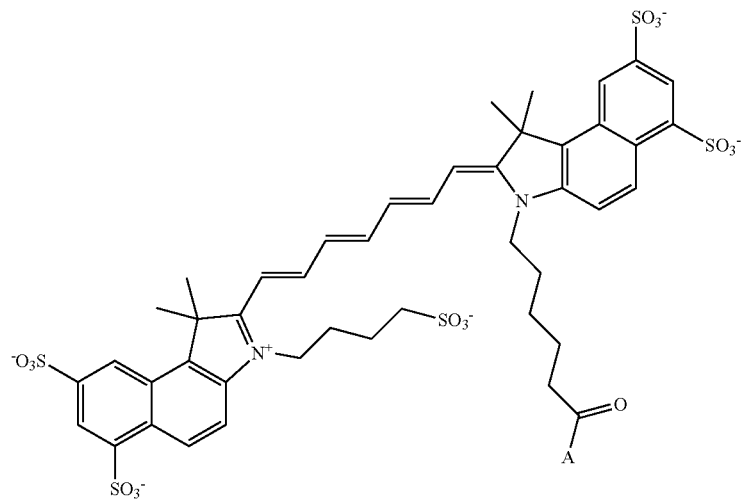 |
| 55 | 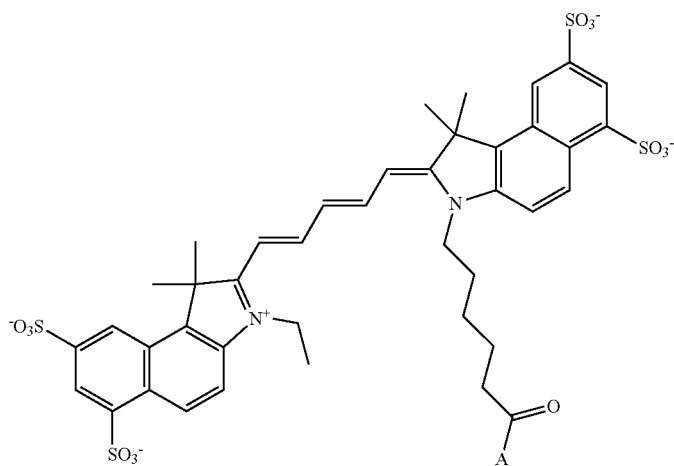 |

TABLE 2-continued

Compounds According to the Present Disclosure

| No. | Structure |
|---|---|
| 56 | 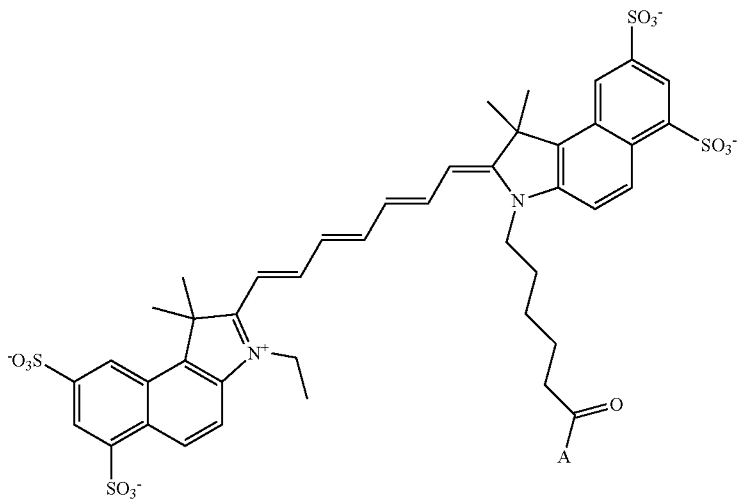 |
| 57 | 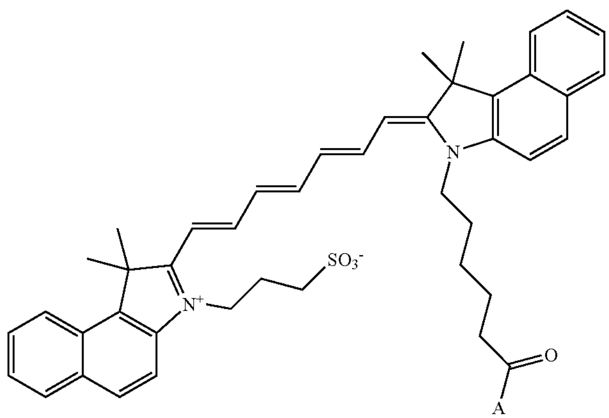 |
| 58 | 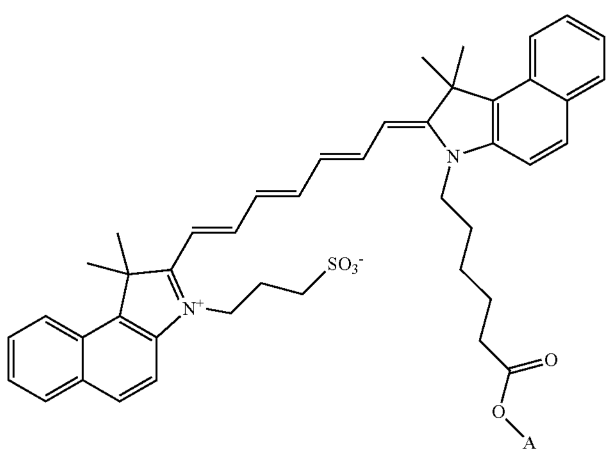 |

TABLE 2-continued

Compounds According to the Present Disclosure

| No. | Structure |
|---|---|
| 59 | 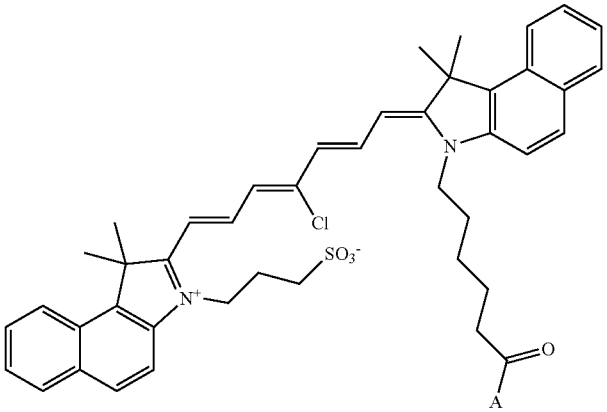 |
| 60 | 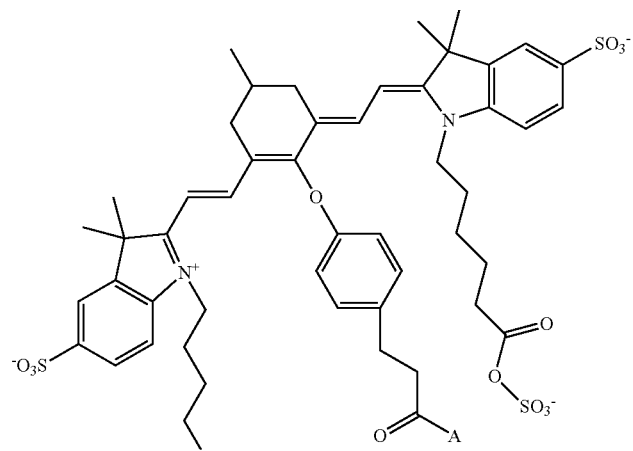 |

The peptide portion A in compounds 1-60 can comprise any of the peptides described herein, such as any one of SEQ ID NO: 1-SEQ ID NO: 485. In some embodiments, the peptide portion A is SEQ ID NO: 5 attached at K-27 to any one of compounds 1-60. In some embodiments, the peptide portion A is SEQ ID NO: 6 attached at K-27 to any one of compounds 1-60. In some embodiments, the peptide portion A is SEQ ID NO: 8 attached at K-27 to any one of compounds 1-60. In some embodiments, the peptide portion A is SEQ ID NO: 9 attached at K-27 to any one of compounds 1-60. In some embodiments, the peptide portion A is SEQ ID NO: 11 attached at K-23 to any one of compounds 1-60. In some embodiments, the peptide portion A is SEQ ID NO: 12 attached at K-23 to any one of compounds 1-60. In some embodiments, the peptide portion A is SEQ ID NO: 13 attached at K-15 to any one of compounds 1-60. In some embodiments, the peptide portion A is SEQ ID NO: 16 attached at K-15 to any one of compounds 1-60. In some embodiments, the peptide portion A is SEQ ID NO: 20 attached at K-23 to any one of compounds 1-60. In some embodiments, the peptide portion A is SEQ ID NO: 21 attached at K-23 to any one of compounds 1-60. In some embodiments, the peptide portion A is SEQ ID NO. 22 attached at K-15 to any one of compounds 1-60. In some embodiments, the peptide portion A is SEQ ID NO: 25 attached at K-15 to any one of compounds 1-60.

TABLE 3 below sets forth certain polypeptide sequences for use with the present disclosure. Citrulline is designated as "Cit" in the sequences.

TABLE 3

Exemplary Peptide Sequence Suitable for Use in the Compounds of the Present Disclosure. Cit = Citrulline.

| SEQ ID NO | Polypeptide Sequence |
|---|---|
| 1 | MCMPCFTTDHQMARKCDDCCGGKGRGKCYGPQCLCR |
| 2 | MCMPCFTTDHQMARACDDCCGGKGRGKCYGPQCLCR |

TABLE 3-continued

Exemplary Peptide Sequence Suitable for Use in the Compounds of the Present Disclosure. Cit = Citrulline.

| SEQ ID NO | Polypeptide Sequence |
|---|---|
| 3 | MCMPCFTTDHQMARRCDDCCGGKGRGKCYGPQCLCR |
| 4 | MCMPCFTTDHQMARKCDDCCGGAGRGKCYGPQCLCR |
| 5 | MCMPCFTTDHQMARACDDCCGGAGRGKCYGPQCLCR |
| 6 | MCMPCFTTDHQMARRCDDCCGGAGRGKCYGPQCLCR |
| 7 | MCMPCFTTDHQMARKCDDCCGGRGRGKCYGPQCLCR |
| 8 | MCMPCFTTDHQMARACDDCCGGRGRGKCYGPQCLCR |
| 9 | MCMPCFTTDHQMARRCDDCCGGRGRGKCYGPQCLCR |
| 10 | MCMPCFTTDHQMARKCDDCCGGKGRGACYGPQCLCR |
| 11 | MCMPCFTTDHQMARACDDCCGGKGRGACYGPQCLCR |
| 12 | MCMPCFTTDHQMARRCDDCCGGKGRGACYGPQCLCR |
| 13 | MCMPCFTTDHQMARKCDDCCGGAGRGACYGPQCLCR |
| 14 | MCMPCFTTDHQMARACDDCCGGAGRGACYGPQCLCR |
| 15 | MCMPCFTTDHQMARRCDDCCGGAGRGACYGPQCLCR |
| 16 | MCMPCFTTDHQMARKCDDCCGGRGRGACYGPQCLCR |
| 17 | MCMPCFTTDHQMARACDDCCGGRGRGACYGPQCLCR |
| 18 | MCMPCFTTDHQMARRCDDCCGGRGRGACYGPQCLCR |
| 19 | MCMPCFTTDHQMARKCDDCCGGKGRGRCYGPQCLCR |
| 20 | MCMPCFTTDHQMARACDDCCGGKGRGRCYGPQCLCR |
| 21 | MCMPCFTTDHQMARRCDDCCGGKGRGRCYGPQCLCR |
| 22 | MCMPCFTTDHQMARKCDDCCGGAGRGRCYGPQCLCR |
| 23 | MCMPCFTTDHQMARACDDCCGGAGRGRCYGPQCLCR |
| 24 | MCMPCFTTDHQMARRCDDCCGGAGRGRCYGPQCLCR |
| 25 | MCMPCFTTDHQMARKCDDCCGGRGRGRCYGPQCLCR |
| 26 | MCMPCFTTDHQMARACDDCCGGRGRGRCYGPQCLCR |
| 27 | MCMPCFTTDHQMARRCDDCCGGRGRGRCYGPQCLCR |
| 28 | MCMPCFTTDHQMARRCDDCCGGRGRGRCYGPQCLCR |
| 29 | KCMPCFTTDHQMARRCDDCCGGRGRGRCYGPQCLCR |
| 30 | ACAPCFTTDHQAARRCDDCCGGRGRGRCYGPQCLCR |
| 31 | KCAPCFTTDHQAARRCDDCCGGRGRGRCYGPQCLCR |
| 32 | MCMPCFTTDHQMAR(Cit)CDDCCGG(Cit)GRGKCYGPQCLCR |
| 33 | MCMPCFTTDHQMAR(Cit)CDDCCGG(Cit)GRG(Cit)CYGPQCLCR |
| 34 | KCMPCFTTDHQMAR(Cit)CDDCCGG(Cit)GRG(Cit)CYGPQCLCR |
| 35 | ACAPCFTTDHQAAR(Cit)CDDCCGG(Cit)GRGKCYGPQCLCR |
| 36 | ACAPCFTTDHQAAR(Cit)CDDCCGG(Cit)GRG(Cit)CYGPQCLCR |
| 37 | KCAPCFTTDHQAAR(Cit)CDDCCGG(Cit)GRG(Cit)CYGPQCLCR |
| 38 | MCMPCFTTDHQMARKCDDCCGGKGRGKCYGPQCLCRGAGAAGG |
| 39 | MCMPCFTTDHQMARACDDCCGGKGRGKCYGPQCLCRGAGAAGG |
| 40 | MCMPCFTTDHQMARRCDDCCGGKGRGKCYGPQCLCRGAGAAGG |

TABLE 3-continued

Exemplary Peptide Sequence Suitable for Use in the Compounds of the Present Disclosure. Cit = Citrulline.

| SEQ ID NO | Polypeptide Sequence |
|---|---|
| 41 | MCMPCFTTDHQMARKCDDCCGGAGRGKCYGPQCLCRGAGAAGG |
| 42 | MCMPCFTTDHQMARACDDCCGGAGRGKCYGPQCLCRGAGAAGG |
| 43 | MCMPCFTTDHQMARRCDDCCGGAGRGKCYGPQCLCRGAGAAGG |
| 44 | MCMPCFTTDHQMARKCDDCCGGRGRGKCYGPQCLCRGAGAAGG |
| 45 | MCMPCFTTDHQMARACDDCCGGRGRGKCYGPQCLCRGAGAAGG |
| 46 | MCMPCFTTDHQMARRCDDCCGGRGRGKCYGPQCLCRGAGAAGG |
| 47 | MCMPCFTTDHQMARKCDDCCGGKGRGACYGPQCLCRGAGAAGG |
| 48 | MCMPCFTTDHQMARACDDCCGGKGRGACYGPQCLCRGAGAAGG |
| 49 | MCMPCFTTDHQMARRCDDCCGGKGRGACYGPQCLCRGAGAAGG |
| 50 | MCMPCFTTDHQMARKCDDCCGGAGRGACYGPQCLCRGAGAAGG |
| 51 | MCMPCFTTDHQMARACDDCCGGAGRGACYGPQCLCRGAGAAGG |
| 52 | MCMPCFTTDHQMARRCDDCCGGAGRGACYGPQCLCRGAGAAGG |
| 53 | MCMPCFTTDHQMARKCDDCCGGRGRGACYGPQCLCRGAGAAGG |
| 54 | MCMPCFTTDHQMARACDDCCGGRGRGACYGPQCLCRGAGAAGG |
| 55 | MCMPCFTTDHQMARRCDDCCGGRGRGACYGPQCLCRGAGAAGG |
| 56 | MCMPCFTTDHQMARKCDDCCGGKGRGRCYGPQCLCRGAGAAGG |
| 57 | MCMPCFTTDHQMARACDDCCGGKGRGRCYGPQCLCRGAGAAGG |
| 58 | MCMPCFTTDHQMARRCDDCCGGKGRGRCYGPQCLCRGAGAAGG |
| 59 | MCMPCFTTDHQMARKCDDCCGGAGRGRCYGPQCLCRGAGAAGG |
| 60 | MCMPCFTTDHQMARACDDCCGGAGRGRCYGPQCLCRGAGAAGG |
| 61 | MCMPCFTTDHQMARRCDDCCGGAGRGRCYGPQCLCRGAGAAGG |
| 62 | MCMPCFTTDHQMARKCDDCCGGRGRGRCYGPQCLCRGAGAAGG |
| 63 | MCMPCFTTDHQMARACDDCCGGRGRGRCYGPQCLCRGAGAAGG |
| 64 | MCMPCFTTDHQMARRCDDCCGGRGRGRCYGPQCLCRGAGAAGG |
| 65 | MCMPCFTTDHQMARRCDDCCGGRGRGRCYGPQCLCRGAGAAGG |
| 66 | KCMPCFTTDHQMARRCDDCCGGRGRGRCYGPQCLCRGAGAAGG |
| 67 | ACAPCFTTDHQAARRCDDCCGGRGRGRCYGPQCLCRGAGAAGG |
| 68 | KCAPCFTTDHQAARRCDDCCGGRGRGRCYGPQCLCRGAGAAGG |
| 69 | MCMPCFTTDHQMAR(Cit)CDDCCGG(Cit)GRGKCYGPQCLCRGAGAAGG |
| 70 | MCMPCFTTDHQMAR(Cit)CDDCCGG(Cit)GRG((Cit)CYGPQCLCRGAGAAGG |
| 71 | KCMPCFTTDHQMAR(Cit)CDDCCGG(Cit)GRG(Cit)CYGPQCLCRGAGAAGG |
| 72 | ACAPCFTTDHQAAR(Cit)CDDCCGG(Cit)GRGKCYGPQCLCRGAGAAGG |
| 73 | ACAPCFTTDHQAAR(Cit)CDDCCGG(Cit)GRG(Cit)CYGPQCLCRGAGAAGG |
| 74 | KCAPCFTTDHQAAR(Cit)CDDCCGG(Cit)GRG(Cit)CYGPQCLCRGAGAAGG |
| 75 | MCMPCFTTDHQMVRKCDDCCGGKGRGKCYGPQCLCR |
| 76 | MCMPCFTTDHQMVRVCDDCCGGKGRGKCYGPQCLCR |
| 77 | MCMPCFTTDHQMVRRCDDCCGGKGRGKCYGPQCLCR |

TABLE 3-continued

Exemplary Peptide Sequence Suitable for Use in the Compounds of the Present Disclosure. Cit = Citrulline.

| SEQ ID NO | Polypeptide Sequence |
|---|---|
| 78 | MCMPCFTTDHQMVRKCDDCCGGVGRGKCYGPQCLCR |
| 79 | MCMPCFTTDHQMVRVCDDCCGGVGRGKCYGPQCLCR |
| 80 | MCMPCFTTDHQMVRRCDDCCGGVGRGKCYGPQCLCR |
| 81 | MCMPCFTTDHQMVRKCDDCCGGRGRGKCYGPQCLCR |
| 82 | MCMPCFTTDHQMVRVCDDCCGGRGRGKCYGPQCLCR |
| 83 | MCMPCFTTDHQMVRRCDDCCGGRGRGKCYGPQCLCR |
| 84 | MCMPCFTTDHQMVRKCDDCCGGKGRGVCYGPQCLCR |
| 85 | MCMPCFTTDHQMVRVCDDCCGGKGRGVCYGPQCLCR |
| 86 | MCMPCFTTDHQMVRRCDDCCGGKGRGVCYGPQCLCR |
| 87 | MCMPCFTTDHQMVRKCDDCCGGVGRGVCYGPQCLCR |
| 88 | MCMPCFTTDHQMVRVCDDCCGGVGRGVCYGPQCLCR |
| 89 | MCMPCFTTDHQMVRRCDDCCGGVGRGVCYGPQCLCR |
| 90 | MCMPCFTTDHQMVRKCDDCCGGRGRGVCYGPQCLCR |
| 91 | MCMPCFTTDHQMVRVCDDCCGGRGRGVCYGPQCLCR |
| 92 | MCMPCFTTDHQMVRRCDDCCGGRGRGVCYGPQCLCR |
| 93 | MCMPCFTTDHQMVRKCDDCCGGKGRGRCYGPQCLCR |
| 94 | MCMPCFTTDHQMVRVCDDCCGGKGRGRCYGPQCLCR |
| 95 | MCMPCFTTDHQMVRRCDDCCGGKGRGRCYGPQCLCR |
| 96 | MCMPCFTTDHQMVRKCDDCCGGVGRGRCYGPQCLCR |
| 97 | MCMPCFTTDHQMVRVCDDCCGGVGRGRCYGPQCLCR |
| 98 | MCMPCFTTDHQMVRRCDDCCGGVGRGRCYGPQCLCR |
| 99 | MCMPCFTTDHQMVRKCDDCCGGRGRGRCYGPQCLCR |
| 100 | MCMPCFTTDHQMVRVCDDCCGGRGRGRCYGPQCLCR |
| 101 | MCMPCFTTDHQMVRRCDDCCGGRGRGRCYGPQCLCR |
| 102 | MCMPCFTTDHQMVRRCDDCCGGRGRGRCYGPQCLCR |
| 103 | KCMPCFTTDHQMVRRCDDCCGGRGRGRCYGPQCLCR |
| 104 | VCVPCFTTDHQVVRRCDDCCGGRGRGRCYGPQCLCR |
| 105 | KCVPCFTTDHQVVRRCDDCCGGRGRGRCYGPQCLCR |
| 106 | MCMPCFTTDHQMVR(Cit)CDDCCGG(Cit)GRGKCYGPQCLCR |
| 107 | MCMPCFTTDHQMVR(Cit)CDDCCGG(Cit)GRG(Cit)CYGPQCLCR |
| 108 | KCMPCFTTDHQMVR(Cit)CDDCCGG(Cit)GRG(Cit)CYGPQCLCR |
| 109 | VCVPCFTTDHQVVR(Cit)CDDCCGG(Cit)GRGKCYGPQCLCR |
| 110 | VCVPCFTTDHQVVR(Cit)CDDCCGG(Cit)GRG(Cit)CYGPQCLCR |
| 111 | KCVPCFTTDHQVVR(Cit)CDDCCGG(Cit)GRG(Cit)CYGPQCLCR |
| 112 | MCMPCFTTDHQMVRKCDDCCGGKGRGKCYGPQCLCRGAGAAGG |
| 113 | MCMPCFTTDHQMVRVCDDCCGGKGRGKCYGPQCLCRGAGAAGG |
| 114 | MCMPCFTTDHQMVRRCDDCCGGKGRGKCYGPQCLCRGAGAAGG |

TABLE 3-continued

Exemplary Peptide Sequence Suitable for Use in the Compounds of the Present Disclosure. Cit = Citrulline.

| SEQ ID NO | Polypeptide Sequence |
|---|---|
| 115 | MCMPCFTTDHQMVRKCDDCCGGVGRGKCYGPQCLCRGAGAAGG |
| 116 | MCMPCFTTDHQMVRVCDDCCGGVGRGKCYGPQCLCRGAGAAGG |
| 117 | MCMPCFTTDHQMVRRCDDCCGGVGRGKCYGPQCLCRGAGAAGG |
| 118 | MCMPCFTTDHQMVRKCDDCCGGRGRGKCYGPQCLCRGAGAAGG |
| 119 | MCMPCFTTDHQMVRVCDDCCGGRGRGKCYGPQCLCRGAGAAGG |
| 120 | MCMPCFTTDHQMVRRCDDCCGGRGRGKCYGPQCLCRGAGAAGG |
| 121 | MCMPCFTTDHQMVRKCDDCCGGKGRGVCYGPQCLCRGAGAAGG |
| 122 | MCMPCFTTDHQMVRVCDDCCGGKGRGVCYGPQCLCRGAGAAGG |
| 123 | MCMPCFTTDHQMVRRCDDCCGGKGRGVCYGPQCLCRGAGAAGG |
| 124 | MCMPCFTTDHQMVRKCDDCCGGVGRGVCYGPQCLCRGAGAAGG |
| 125 | MCMPCFTTDHQMVRVCDDCCGGVGRGVCYGPQCLCRGAGAAGG |
| 126 | MCMPCFTTDHQMVRRCDDCCGGVGRGVCYGPQCLCRGAGAAGG |
| 127 | MCMPCFTTDHQMVRKCDDCCGGRGRGVCYGPQCLCRGAGAAGG |
| 128 | MCMPCFTTDHQMVRVCDDCCGGRGRGVCYGPQCLCRGAGAAGG |
| 129 | MCMPCFTTDHQMVRRCDDCCGGRGRGVCYGPQCLCRGAGAAGG |
| 130 | MCMPCFTTDHQMVRKCDDCCGGKGRGRCYGPQCLCRGAGAAGG |
| 131 | MCMPCFTTDHQMVRVCDDCCGGKGRGRCYGPQCLCRGAGAAGG |
| 132 | MCMPCFTTDHQMVRRCDDCCGGKGRGRCYGPQCLCRGAGAAGG |
| 133 | MCMPCFTTDHQMVRKCDDCCGGVGRGRCYGPQCLCRGAGAAGG |
| 134 | MCMPCFTTDHQMVRVCDDCCGGVGRGRCYGPQCLCRGAGAAGG |
| 135 | MCMPCFTTDHQMVRRCDDCCGGVGRGRCYGPQCLCRGAGAAGG |
| 136 | MCMPCFTTDHQMVRKCDDCCGGRGRGRCYGPQCLCRGAGAAGG |
| 137 | MCMPCFTTDHQMVRVCDDCCGGRGRGRCYGPQCLCRGAGAAGG |
| 138 | MCMPCFTTDHQMVRRCDDCCGGRGRGRCYGPQCLCRGAGAAGG |
| 139 | MCMPCFTTDHQMVRRCDDCCGGRGRGRCYGPQCLCRGAGAAGG |
| 140 | KCMPCFTTDHQMVRRCDDCCGGRGRGRCYGPQCLCRGAGAAGG |
| 141 | VCVPCFTTDHQVVRRCDDCCGGRGRGRCYGPQCLCRGAGAAGG |
| 142 | KCVPCFTTDHQVVRRCDDCCGGRGRGRCYGPQCLCRGAGAAGG |
| 143 | MCMPCFTTDHQMVR(Cit)CDDCCGG(Cit)GRGKCYGPQCLCRGAGAAGG |
| 144 | MCMPCFTTDHQMVR(Cit)CDDCCGG(Cit)GRG(Cit)CYGPQCLCRGAGAAGG |
| 145 | KCMPCFTTDHQMVR(Cit)CDDCCGG(Cit)GRG(Cit)CYGPQCLCRGAGAAGG |
| 146 | VCVPCFTTDHQVVR(Cit)CDDCCGG(Cit)GRGKCYGPQCLCRGAGAAGG |
| 147 | VCVPCFTTDHQVVR(Cit)CDDCCGG(Cit)GRG(Cit)CYGPQCLCRGAGAAGG |
| 148 | KCVPCFTTDHQVVR(Cit)CDDCCGG(Cit)GRG(Cit)CYGPQCLCRGAGAAGG |
| 149 | MCMPCFTTDHQMLRKCDDCCGGKGRGKCYGPQCLCR |
| 150 | MCMPCFTTDHQMLRLCDDCCGGKGRGKCYGPQCLCR |
| 151 | MCMPCFTTDHQMLRRCDDCCGGKGRGKCYGPQCLCR |
| 152 | MCMPCFTTDHQMLRKCDDCCGGLGRGKCYGPQCLCR |

TABLE 3-continued

Exemplary Peptide Sequence Suitable for Use in the Compounds of the Present Disclosure. Cit = Citrulline.

| SEQ ID NO | Polypeptide Sequence |
|---|---|
| 153 | MCMPCFTTDHQMLRLCDDCCGGLGRGKCYGPQCLCR |
| 154 | MCMPCFTTDHQMLRRCDDCCGGLGRGKCYGPQCLCR |
| 155 | MCMPCFTTDHQMLRKCDDCCGGRGRGKCYGPQCLCR |
| 156 | MCMPCFTTDHQMLRLCDDCCGGRGRGKCYGPQCLCR |
| 157 | MCMPCFTTDHQMLRRCDDCCGGRGRGKCYGPQCLCR |
| 158 | MCMPCFTTDHQMLRKCDDCCGGKGRGLCYGPQCLCR |
| 159 | MCMPCFTTDHQMLRLCDDCCGGKGRGLCYGPQCLCR |
| 160 | MCMPCFTTDHQMLRRCDDCCGGKGRGLCYGPQCLCR |
| 161 | MCMPCFTTDHQMLRKCDDCCGGLGRGLCYGPQCLCR |
| 162 | MCMPCFTTDHQMLRLCDDCCGGLGRGLCYGPQCLCR |
| 163 | MCMPCFTTDHQMLRRCDDCCGGLGRGLCYGPQCLCR |
| 164 | MCMPCFTTDHQMLRKCDDCCGGRGRGLCYGPQCLCR |
| 165 | MCMPCFTTDHQMLRLCDDCCGGRGRGLCYGPQCLCR |
| 166 | MCMPCFTTDHQMLRRCDDCCGGRGRGLCYGPQCLCR |
| 167 | MCMPCFTTDHQMLRKCDDCCGGKGRGRCYGPQCLCR |
| 168 | MCMPCFTTDHQMLRLCDDCCGGKGRGRCYGPQCLCR |
| 169 | MCMPCFTTDHQMLRRCDDCCGGKGRGRCYGPQCLCR |
| 170 | MCMPCFTTDHQMLRKCDDCCGGLGRGRCYGPQCLCR |
| 171 | MCMPCFTTDHQMLRLCDDCCGGLGRGRCYGPQCLCR |
| 172 | MCMPCFTTDHQMLRRCDDCCGGLGRGRCYGPQCLCR |
| 173 | MCMPCFTTDHQMLRKCDDCCGGRGRGRCYGPQCLCR |
| 174 | MCMPCFTTDHQMLRLCDDCCGGRGRGRCYGPQCLCR |
| 175 | MCMPCFTTDHQMLRRCDDCCGGRGRGRCYGPQCLCR |
| 176 | MCMPCFTTDHQMLRRCDDCCGGRGRGRCYGPQCLCR |
| 177 | KCMPCFTTDHQMLRRCDDCCGGRGRGRCYGPQCLCR |
| 178 | LCLPCFTTDHQLLRRCDDCCGGRGRGRCYGPQCLCR |
| 179 | KCLPCFTTDHQLLRRCDDCCGGRGRGRCYGPQCLCR |
| 180 | MCMPCFTTDHQMLR(Cit)CDDCCGG(Cit)GRGKCYGPQCLCR |
| 181 | MCMPCFTTDHQMLR(Cit)CDDCCGG(Cit)GRG(Cit)CYGPQCLCR |
| 182 | KCMPCFTTDHQMLR(Cit)CDDCCGG(Cit)GRG(Cit)CYGPQCLCR |
| 183 | LCLPCFTTDHQLLR(Cit)CDDCCGG(Cit)GRGKCYGPQCLCR |
| 184 | LCLPCFTTDHQLLR(Cit)CDDCCGG(Cit)GRG(Cit)CYGPQCLCR |
| 185 | KCLPCFTTDHQLLR(Cit)CDDCCGG(Cit)GRG(Cit)CYGPQCLCR |
| 186 | MCMPCFTTDHQMLRKCDDCCGGKGRGKCYGPQCLCRGAGAAGG |
| 187 | MCMPCFTTDHQMLRLCDDCCGGKGRGKCYGPQCLCRGAGAAGG |
| 188 | MCMPCFTTDHQMLRRCDDCCGGKGRGKCYGPQCLCRGAGAAGG |
| 189 | MCMPCFTTDHQMLRKCDDCCGGLGRGKCYGPQCLCRGAGAAGG |

TABLE 3-continued

Exemplary Peptide Sequence Suitable for Use in the Compounds of the Present Disclosure. Cit = Citrulline.

| SEQ ID NO | Polypeptide Sequence |
|---|---|
| 190 | MCMPCFTTDHQMLRLCDDCCGGLGRGKCYGPQCLCRGAGAAGG |
| 191 | MCMPCFTTDHQMLRRCDDCCGGLGRGKCYGPQCLCRGAGAAGG |
| 192 | MCMPCFTTDHQMLRKCDDCCGGRGRGKCYGPQCLCRGAGAAGG |
| 193 | MCMPCFTTDHQMLRLCDDCCGGRGRGKCYGPQCLCRGAGAAGG |
| 194 | MCMPCFTTDHQMLRRCDDCCGGRGRGKCYGPQCLCRGAGAAGG |
| 195 | MCMPCFTTDHQMLRKCDDCCGGKGRGLCYGPQCLCRGAGAAGG |
| 196 | MCMPCFTTDHQMLRLCDDCCGGKGRGLCYGPQCLCRGAGAAGG |
| 197 | MCMPCFTTDHQMLRRCDDCCGGKGRGLCYGPQCLCRGAGAAGG |
| 198 | MCMPCFTTDHQMLRKCDDCCGGLGRGLCYGPQCLCRGAGAAGG |
| 199 | MCMPCFTTDHQMLRLCDDCCGGLGRGLCYGPQCLCRGAGAAGG |
| 200 | MCMPCFTTDHQMLRRCDDCCGGLGRGLCYGPQCLCRGAGAAGG |
| 201 | MCMPCFTTDHQMLRKCDDCCGGRGRGLCYGPQCLCRGAGAAGG |
| 202 | MCMPCFTTDHQMLRLCDDCCGGRGRGLCYGPQCLCRGAGAAGG |
| 203 | MCMPCFTTDHQMLRRCDDCCGGRGRGLCYGPQCLCRGAGAAGG |
| 204 | MCMPCFTTDHQMLRKCDDCCGGKGRGRCYGPQCLCRGAGAAGG |
| 205 | MCMPCFTTDHQMLRLCDDCCGGKGRGRCYGPQCLCRGAGAAGG |
| 206 | MCMPCFTTDHQMLRRCDDCCGGKGRGRCYGPQCLCRGAGAAGG |
| 207 | MCMPCFTTDHQMLRKCDDCCGGLGRGRCYGPQCLCRGAGAAGG |
| 208 | MCMPCFTTDHQMLRLCDDCCGGLGRGRCYGPQCLCRGAGAAGG |
| 209 | MCMPCFTTDHQMLRRCDDCCGGLGRGRCYGPQCLCRGAGAAGG |
| 210 | MCMPCFTTDHQMLRKCDDCCGGRGRGRCYGPQCLCRGAGAAGG |
| 211 | MCMPCFTTDHQMLRLCDDCCGGRGRGRCYGPQCLCRGAGAAGG |
| 212 | MCMPCFTTDHQMLRRCDDCCGGRGRGRCYGPQCLCRGAGAAGG |
| 213 | MCMPCFTTDHQMLRRCDDCCGGRGRGRCYGPQCLCRGAGAAGG |
| 214 | KCMPCFTTDHQMLRRCDDCCGGRGRGRCYGPQCLCRGAGAAGG |
| 215 | LCLPCFTTDHQLLRRCDDCCGGRGRGRCYGPQCLCRGAGAAGG |
| 216 | KCLPCFTTDHQLLRRCDDCCGGRGRGRCYGPQCLCRGAGAAGG |
| 217 | MCMPCFTTDHQMLR(Cit)CDDCCGG(Cit)GRGKCYGPQCLCRGAGAAGG |
| 218 | MCMPCFTTDHQMLR(Cit)CDDCCGG(Cit)GRG(Cit)CYGPQCLCRGAGAAGG |
| 219 | KCMPCFTTDHQMLR(Cit)CDDCCGG(Cit)GRG(Cit)CYGPQCLCRGAGAAGG |
| 220 | LCLPCFTTDHQLLR(Cit)CDDCCGG(Cit)GRGKCYGPQCLCRGAGAAGG |
| 221 | LCLPCFTTDHQLLR(Cit)CDDCCGG(Cit)GRG(Cit)CYGPQCLCRGAGAAGG |
| 222 | KCLPCFTTDHQLLR(Cit)CDDCCGG(Cit)GRG(Cit)CYGPQCLCRGAGAAGG |
| 223 | GCGPCFTTDHQGARKCDDCCGGKGRGKCYGPQCLCR |
| 224 | GCGPCFTTDHQGARACDDCCGGKGRGKCYGPQCLCR |
| 225 | GCGPCFTTDHQGARRCDDCCGGKGRGKCYGPQCLCR |
| 226 | GCGPCFTTDHQGARKCDDCCGGAGRGKCYGPQCLCR |
| 227 | GCGPCFTTDHQGARACDDCCGGAGRGKCYGPQCLCR |

TABLE 3-continued

Exemplary Peptide Sequence Suitable for Use in the Compounds of the Present Disclosure. Cit = Citrulline.

| SEQ ID NO | Polypeptide Sequence |
|---|---|
| 228 | GCGPCFTTDHQGARRCDDCCGGAGRGKCYGPQCLCR |
| 229 | GCGPCFTTDHQGARKCDDCCGGRGRGKCYGPQCLCR |
| 230 | GCGPCFTTDHQGARACDDCCGGRGRGKCYGPQCLCR |
| 231 | GCGPCFTTDHQGARRCDDCCGGRGRGKCYGPQCLCR |
| 232 | GCGPCFTTDHQGARKCDDCCGGKGRGACYGPQCLCR |
| 233 | GCGPCFTTDHQGARACDDCCGGKGRGACYGPQCLCR |
| 234 | GCGPCFTTDHQGARRCDDCCGGKGRGACYGPQCLCR |
| 235 | GCGPCFTTDHQGARKCDDCCGGAGRGACYGPQCLCR |
| 236 | GCGPCFTTDHQGARACDDCCGGAGRGACYGPQCLCR |
| 237 | GCGPCFTTDHQGARRCDDCCGGAGRGACYGPQCLCR |
| 238 | GCGPCFTTDHQGARKCDDCCGGRGRGACYGPQCLCR |
| 239 | GCGPCFTTDHQGARACDDCCGGRGRGACYGPQCLCR |
| 240 | GCGPCFTTDHQGARRCDDCCGGRGRGACYGPQCLCR |
| 241 | GCGPCFTTDHQGARKCDDCCGGKGRGRCYGPQCLCR |
| 242 | GCGPCFTTDHQGARACDDCCGGKGRGRCYGPQCLCR |
| 243 | GCGPCFTTDHQGARRCDDCCGGKGRGRCYGPQCLCR |
| 244 | GCGPCFTTDHQGARKCDDCCGGAGRGRCYGPQCLCR |
| 245 | GCGPCFTTDHQGARACDDCCGGAGRGRCYGPQCLCR |
| 246 | GCGPCFTTDHQGARRCDDCCGGAGRGRCYGPQCLCR |
| 247 | GCGPCFTTDHQGARKCDDCCGGRGRGRCYGPQCLCR |
| 248 | GCGPCFTTDHQGARACDDCCGGRGRGRCYGPQCLCR |
| 249 | GCGPCFTTDHQGARRCDDCCGGRGRGRCYGPQCLCR |
| 250 | GCGPCFTTDHQGARRCDDCCGGRGRGRCYGPQCLCR |
| 251 | KCGPCFTTDHQGARRCDDCCGGRGRGRCYGPQCLCR |
| 252 | ACAPCFTTDHQAARRCDDCCGGRGRGRCYGPQCLCR |
| 253 | KCAPCFTTDHQAARRCDDCCGGRGRGRCYGPQCLCR |
| 254 | GCGPCFTTDHQGAR(Cit)CDDCCGG(Cit)GRGKCYGPQCLCR |
| 255 | GCGPCFTTDHQGAR(Cit)CDDCCGG(Cit)GRG(Cit)CYGPQCLCR |
| 256 | KCGPCFTTDHQGAR(Cit)CDDCCGG(Cit)GRG(Cit)CYGPQCLCR |
| 257 | ACAPCFTTDHQAAR(Cit)CDDCCGG(Cit)GRGKCYGPQCLCR |
| 258 | ACAPCFTTDHQAAR(Cit)CDDCCGG(Cit)GRG(Cit)CYGPQCLCR |
| 259 | KCAPCFTTDHQAAR(Cit)CDDCCGG(Cit)GRG(Cit)CYGPQCLCR |
| 260 | ACAPCFTTDHQAARKCDDCCGGKGRGKCYGPQCLCR |
| 261 | ACAPCFTTDHQAARACDDCCGGKGRGKCYGPQCLCR |
| 262 | ACAPCFTTDHQAARRCDDCCGGKGRGKCYGPQCLCR |
| 263 | ACAPCFTTDHQAARKCDDCCGGAGRGKCYGPQCLCR |
| 264 | ACAPCFTTDHQAARACDDCCGGAGRGKCYGPQCLCR |

TABLE 3-continued

Exemplary Peptide Sequence Suitable for Use in the Compounds of the Present Disclosure. Cit = Citrulline.

| SEQ ID NO | Polypeptide Sequence |
| --- | --- |
| 265 | ACAPCFTTDHQAARRCDDCCGGAGRGKCYGPQCLCR |
| 266 | ACAPCFTTDHQAARKCDDCCGGRGRGKCYGPQCLCR |
| 267 | ACAPCFTTDHQAARACDDCCGGRGRGKCYGPQCLCR |
| 268 | ACAPCFTTDHQAARRCDDCCGGRGRGKCYGPQCLCR |
| 269 | ACAPCFTTDHQAARKCDDCCGGKGRGACYGPQCLCR |
| 270 | ACAPCFTTDHQAARACDDCCGGKGRGACYGPQCLCR |
| 271 | ACAPCFTTDHQAARRCDDCCGGKGRGACYGPQCLCR |
| 272 | ACAPCFTTDHQAARKCDDCCGGAGRGACYGPQCLCR |
| 273 | ACAPCFTTDHQAARACDDCCGGAGRGACYGPQCLCR |
| 274 | ACAPCFTTDHQAARRCDDCGGAGRGACYGPQCLCR |
| 275 | ACAPCFTTDHQAARKCDDCCGGRGRGACYGPQCLCR |
| 276 | ACAPCFTTDHQAARACDDCCGGRGRGACYGPQCLCR |
| 277 | ACAPCFTTDHQAARRCDDCCGGRGRGACYGPQCLCR |
| 278 | ACAPCFTTDHQAARKCDDCCGGKGRGRCYGPQCLCR |
| 279 | ACAPCFTTDHQAARACDDCCGGKGRGRCYGPQCLCR |
| 280 | ACAPCFTTDHQAARRCDDCCGGKGRGRCYGPQCLCR |
| 281 | ACAPCFTTDHQAARKCDDCCGGAGRGRCYGPQCLCR |
| 282 | ACAPCFTTDHQAARACDDCCGGAGRGRCYGPQCLCR |
| 283 | ACAPCFTTDHQAARRCDDCCGGAGRGRCYGPQCLCR |
| 284 | ACAPCFTTDHQAARKCDDCCGGRGRGRCYGPQCLCR |
| 285 | ACAPCFTTDHQAARACDDCCGGRGRGRCYGPQCLCR |
| 286 | ACAPCFTTDHQAARRCDDCCGGRGRGRCYGPQCLCR |
| 287 | ACAPCFTTDHQAARRCDDCCGGRGRGRCYGPQCLCR |
| 288 | KCAPCFTTDHQAARRCDDCCGGRGRGRCYGPQCLCR |
| 289 | ACAPCFTTDHQAARRCDDCCGGRGRGRCYGPQCLCR |
| 290 | KCAPCFTTDHQAARRCDDCCGGRGRGRCYGPQCLCR |
| 291 | ACAPCFTTDHQAAR(Cit)CDDCCGG(Cit)GRGKCYGPQCLCR |
| 292 | ACAPCFTTDHQAAR(Cit)CDDCCGG(Cit)GRG(Cit)CYGPQCLCR |
| 293 | KCAPCFTTDHQAAR(Cit)CDDCCGG(Cit)GRG(Cit)CYGPQCLCR |
| 294 | ACAPCFTTDHQAAR(Cit)CDDCCGG(Cit)GRGKCYGPQCLCR |
| 295 | ACAPCFTTDHQAAR(Cit)CDDCCGG(Cit)GRG(Cit)CYGPQCLCR |
| 296 | KCAPCFTTDHQAAR(Cit)CDDCCGG(Cit)GRG(Cit)CYGPQCLCR |
| 297 | ICIPCFTTDHQIARKCDDCCGGKGRGKCYGPQCLCR |
| 298 | ICIPCFTTDHQIARACDDCCGGKGRGKCYGPQCLCR |
| 299 | ICIPCFTTDHQIARRCDDCCGGKGRGKCYGPQCLCR |
| 300 | ICIPCFTTDHQIARKCDDCCGGAGRGKCYGPQCLCR |
| 301 | ICIPCFTTDHQIARACDDCCGGAGRGKCYGPQCLCR |
| 302 | ICIPCFTTDHQIARRCDDCCGGAGRGKCYGPQCLCR |

TABLE 3-continued

Exemplary Peptide Sequence Suitable for Use in the Compounds of the Present Disclosure. Cit = Citrulline.

| SEQ ID NO | Polypeptide Sequence |
| --- | --- |
| 303 | ICIPCFTTDHQIARKCDDCCGGRGRGKCYGPQCLCR |
| 304 | ICIPCFTTDHQIARACDDCCGGRGRGKCYGPQCLCR |
| 305 | ICIPCFTTDHQIARRCDDCCGGRGRGKCYGPQCLCR |
| 306 | ICIPCFTTDHQIARKCDDCCGGKGRGACYGPQCLCR |
| 307 | ICIPCFTTDHQIARACDDCCGGKGRGACYGPQCLCR |
| 308 | ICIPCFTTDHQIARRCDDCCGGKGRGACYGPQCLCR |
| 309 | ICIPCFTTDHQIARKCDDCCGGAGRGACYGPQCLCR |
| 310 | ICIPCFTTDHQIARACDDCCGGAGRGACYGPQCLCR |
| 311 | ICIPCFTTDHQIARRCDDCCGGAGRGACYGPQCLCR |
| 312 | ICIPCFTTDHQIARKCDDCCGGRGRGACYGPQCLCR |
| 313 | ICIPCFTTDHQIARACDDCCGGRGRGACYGPQCLCR |
| 314 | ICIPCFTTDHQIARRCDDCCGGRGRGACYGPQCLCR |
| 315 | ICIPCFTTDHQIARKCDDCCGGKGRGRCYGPQCLCR |
| 316 | ICIPCFTTDHQIARACDDCCGGKGRGRCYGPQCLCR |
| 317 | ICIPCFTTDHQIARRCDDCCGGKGRGRCYGPQCLCR |
| 318 | ICIPCFTTDHQIARKCDDCCGGAGRGRCYGPQCLCR |
| 319 | ICIPCFTTDHQIARACDDCCGGAGRGRCYGPQCLCR |
| 320 | ICIPCFTTDHQIARRCDDCCGGAGRGRCYGPQCLCR |
| 321 | ICIPCFTTDHQIARKCDDCCGGRGRGRCYGPQCLCR |
| 322 | ICIPCFTTDHQIARACDDCCGGRGRGRCYGPQCLCR |
| 323 | ICIPCFTTDHQIARRCDDCCGGRGRGRCYGPQCLCR |
| 324 | ICIPCFTTDHQIARRCDDCCGGRGRGRCYGPQCLCR |
| 325 | KCIPCFTTDHQIARRCDDCCGGRGRGRCYGPQCLCR |
| 326 | ACAPCFTTDHQAARRCDDCCGGRGRGRCYGPQCLCR |
| 327 | KCAPCFTTDHQAARRCDDCCGGRGRGRCYGPQCLCR |
| 328 | ICIPCFTTDHQIAR(Cit)CDDCCGG(Cit)GRGKCYGPQCLCR |
| 329 | ICIPCFTTDHQIAR(Cit)CDDCCGG(Cit)GRG(Cit)CYGPQCLCR |
| 330 | KCIPCFTTDHQIAR(Cit)CDDCCGG(Cit)GRG(Cit)CYGPQCLCR |
| 331 | ACAPCFTTDHQAAR(Cit)CDDCCGG(Cit)GRGKCYGPQCLCR |
| 332 | ACAPCFTTDHQAAR(Cit)CDDCCGG(Cit)GRG(Cit)CYGPQCLCR |
| 333 | KCAPCFTTDHQAAR(Cit)CDDCCGG(Cit)GRG(Cit)CYGPQCLCR |
| 334 | TCTPCFTTDHQTARKCDDCCGGKGRGKCYGPQCLCR |
| 335 | TCTPCFTTDHQTARACDDCCGGKGRGKCYGPQCLCR |
| 336 | TCTPCFTTDHQTARRCDDCCGGKGRGKCYGPQCLCR |
| 337 | TCTPCFTTDHQTARKCDDCCGGAGRGKCYGPQCLCR |
| 338 | TCTPCFTTDHQTARACDDCCGGAGRGKCYGPQCLCR |
| 339 | TCTPCFTTDHQTARRCDDCCGGAGRGKCYGPQCLCR |

TABLE 3-continued

Exemplary Peptide Sequence Suitable for Use in the Compounds of the Present Disclosure. Cit = Citrulline.

| SEQ ID NO | Polypeptide Sequence |
|---|---|
| 340 | TCTPCFTTDHQTARKCDDCCGGRGRGKCYGPQCLCR |
| 341 | TCTPCFTTDHQTARACDDCCGGRGRGKCYGPQCLCR |
| 342 | TCTPCFTTDHQTARRCDDCCGGRGRGKCYGPQCLCR |
| 343 | TCTPCFTTDHQTARKCDDCCGGKGRGACYGPQCLCR |
| 344 | TCTPCFTTDHQTARACDDCCGGKGRGACYGPQCLCR |
| 345 | TCTPCFTTDHQTARRCDDCCGGKGRGACYGPQCLCR |
| 346 | TCTPCFTTDHQTARKCDDCCGGAGRGACYGPQCLCR |
| 347 | TCTPCFTTDHQTARACDDCCGGAGRGACYGPQCLCR |
| 348 | TCTPCFTTDHQTARRCDDCCGGAGRGACYGPQCLCR |
| 349 | TCTPCFTTDHQTARKCDDCCGGRGRGACYGPQCLCR |
| 350 | TCTPCFTTDHQTARACDDCCGGRGRGACYGPQCLCR |
| 351 | TCTPCFTTDHQTARRCDDCCGGRGRGACYGPQCLCR |
| 352 | TCTPCFTTDHQTARKCDDCCGGKGRGRCYGPQCLCR |
| 353 | TCTPCFTTDHQTARACDDCCGGKGRGRCYGPQCLCR |
| 354 | TCTPCFTTDHQTARRCDDCCGGKGRGRCYGPQCLCR |
| 355 | TCTPCFTTDHQTARKCDDCCGGAGRGRCYGPQCLCR |
| 356 | TCTPCFTTDHQTARACDDCCGGAGRGRCYGPQCLCR |
| 357 | TCTPCFTTDHQTARRCDDCCGGAGRGRCYGPQCLCR |
| 358 | TCTPCFTTDHQTARKCDDCCGGRGRGRCYGPQCLCR |
| 359 | TCTPCFTTDHQTARACDDCCGGRGRGRCYGPQCLCR |
| 360 | TCTPCFTTDHQTARRCDDCCGGRGRGRCYGPQCLCR |
| 361 | TCTPCFTTDHQTARRCDDCCGGRGRGRCYGPQCLCR |
| 362 | KCTPCFTTDHQTARRCDDCCGGRGRGRCYGPQCLCR |
| 363 | ACAPCFTTDHQAARRCDDCCGGRGRGRCYGPQCLCR |
| 364 | KCAPCFTTDHQAARRCDDCCGGRGRGRCYGPQCLCR |
| 365 | TCTPCFTTDHQTAR(Cit)CDDCCGG(Cit)GRGKCYGPQCLCR |
| 366 | TCTPCFTTDHQTAR(Cit)CDDCCGG(Cit)GRG(Cit)CYGPQCLCR |
| 367 | KCTPCFTTDHQTAR(Cit)CDDCCGG(Cit)GRG(Cit)CYGPQCLCR |
| 368 | ACAPCFTTDHQAAR(Cit)CDDCCGG(Cit)GRGKCYGPQCLCR |
| 369 | ACAPCFTTDHQAAR(Cit)CDDCCGG(Cit)GRG(Cit)CYGPQCLCR |
| 370 | KCAPCFTTDHQAAR(Cit)CDDCCGG(Cit)GRG(Cit)CYGPQCLCR |
| 371 | VCVPCFTTDHQVARKCDDCCGGKGRGKCYGPQCLCR |
| 372 | VCVPCFTTDHQVARACDDCCGGKGRGKCYGPQCLCR |
| 373 | VCVPCFTTDHQVARRCDDCCGGKGRGKCYGPQCLCR |
| 374 | VCVPCFTTDHQVARKCDDCCGGAGRGKCYGPQCLCR |
| 375 | VCVPCFTTDHQVARACDDCCGGAGRGKCYGPQCLCR |
| 376 | VCVPCFTTDHQVARRCDDCCGGAGRGKCYGPQCLCR |
| 377 | VCVPCFTTDHQVARKCDDCCGGRGRGKCYGPQCLCR |

TABLE 3-continued

Exemplary Peptide Sequence Suitable for Use in the Compounds of the Present Disclosure. Cit = Citrulline.

| SEQ ID NO | Polypeptide Sequence |
|---|---|
| 378 | VCVPCFTTDHQVARACDDCCGGRGRGKCYGPQCLCR |
| 379 | VCVPCFTTDHQVARRCDDCCGGRGRGKCYGPQCLCR |
| 380 | VCVPCFTTDHQVARKCDDCCGGKGRGACYGPQCLCR |
| 381 | VCVPCFTTDHQVARACDDCCGGKGRGACYGPQCLCR |
| 382 | VCVPCFTTDHQVARRCDDCCGGKGRGACYGPQCLCR |
| 383 | VCVPCFTTDHQVARKCDDCCGGAGRGACYGPQCLCR |
| 384 | VCVPCFTTDHQVARACDDCCGGAGRGACYGPQCLCR |
| 385 | VCVPCFTTDHQVARRCDDCCGGAGRGACYGPQCLCR |
| 386 | VCVPCFTTDHQVARKCDDCCGGRGRGACYGPQCLCR |
| 387 | VCVPCFTTDHQVARACDDCCGGRGRGACYGPQCLCR |
| 388 | VCVPCFTTDHQVARRCDDCCGGRGRGACYGPQCLCR |
| 389 | VCVPCFTTDHQVARKCDDCCGGKGRGRCYGPQCLCR |
| 390 | VCVPCFTTDHQVARACDDCCGGKGRGRCYGPQCLCR |
| 391 | VCVPCFTTDHQVARRCDDCCGGKGRGRCYGPQCLCR |
| 392 | VCVPCFTTDHQVARKCDDCCGGAGRGRCYGPQCLCR |
| 393 | VCVPCFTTDHQVARACDDCCGGAGRGRCYGPQCLCR |
| 394 | VCVPCFTTDHQVARRCDDCCGGAGRGRCYGPQCLCR |
| 395 | VCVPCFTTDHQVARKCDDCCGGRGRGRCYGPQCLCR |
| 396 | VCVPCFTTDHQVARACDDCCGGRGRGRCYGPQCLCR |
| 397 | VCVPCFTTDHQVARRCDDCCGGRGRGRCYGPQCLCR |
| 398 | VCVPCFTTDHQVARRCDDCCGGRGRGRCYGPQCLCR |
| 399 | KCVPCFTTDHQVARRCDDCCGGRGRGRCYGPQCLCR |
| 400 | ACAPCFTTDHQAARRCDDCCGGRGRGRCYGPQCLCR |
| 401 | KCAPCFTTDHQAARRCDDCCGGRGRGRCYGPQCLCR |
| 402 | VCVPCFTTDHQVAR(Cit)CDDCCGG(Cit)GRGKCYGPQCLCR |
| 403 | VCVPCFTTDHQVAR(Cit)CDDCCGG(Cit)GRG(Cit)CYGPQCLCR |
| 404 | KCVPCFTTDHQVAR(Cit)CDDCCGG(Cit)GRG(Cit)CYGPQCLCR |
| 405 | ACAPCFTTDHQAAR(Cit)CDDCCGG(Cit)GRGKCYGPQCLCR |
| 406 | ACAPCFTTDHQAAR(Cit)CDDCCGG(Cit)GRG(Cit)CYGPQCLCR |
| 407 | KCAPCFTTDHQAAR(Cit)CDDCCGG(Cit)GRG(Cit)CYGPQCLCR |
| 408 | LCLPCFTTDHQLARKCDDCCGGKGRGKCYGPQCLCR |
| 409 | LCLPCFTTDHQLARACDDCCGGKGRGKCYGPQCLCR |
| 410 | LCLPCFTTDHQLARRCDDCCGGKGRGKCYGPQCLCR |
| 411 | LCLPCFTTDHQLARKCDDCCGGAGRGKCYGPQCLCR |
| 412 | LCLPCFTTDHQLARACDDCCGGAGRGKCYGPQCLCR |
| 413 | LCLPCFTTDHQLARRCDDCCGGAGRGKCYGPQCLCR |
| 414 | LCLPCFTTDHQLARKCDDCCGGRGRGKCYGPQCLCR |

TABLE 3-continued

Exemplary Peptide Sequence Suitable for Use in the Compounds of the Present Disclosure. Cit = Citrulline.

| SEQ ID NO | Polypeptide Sequence |
|---|---|
| 415 | LCLPCFTTDHQLARACDDCCGGRGRGKCYGPQCLCR |
| 416 | LCLPCFTTDHQLARRCDDCCGGRGRGKCYGPQCLCR |
| 417 | LCLPCFTTDHQLARKCDDCCGGKGRGACYGPQCLCR |
| 418 | LCLPCFTTDHQLARACDDCCGGKGRGACYGPQCLCR |
| 419 | LCLPCFTTDHQLARRCDDCCGGKGRGACYGPQCLCR |
| 420 | LCLPCFTTDHQLARKCDDCCGGAGRGACYGPQCLCR |
| 421 | LCLPCFTTDHQLARACDDCCGGAGRGACYGPQCLCR |
| 422 | LCLPCFTTDHQLARRCDDCCGGAGRGACYGPQCLCR |
| 423 | LCLPCFTTDHQLARKCDDCCGGRGRGACYGPQCLCR |
| 424 | LCLPCFTTDHQLARACDDCCGGRGRGACYGPQCLCR |
| 425 | LCLPCFTTDHQLARRCDDCCGGRGRGACYGPQCLCR |
| 426 | LCLPCFTTDHQLARKCDDCCGGKGRGRCYGPQCLCR |
| 427 | LCLPCFTTDHQLARACDDCCGGKGRGRCYGPQCLCR |
| 428 | LCLPCFTTDHQLARRCDDCCGGKGRGRCYGPQCLCR |
| 429 | LCLPCFTTDHQLARKCDDCCGGAGRGRCYGPQCLCR |
| 430 | LCLPCFTTDHQLARACDDCCGGAGRGRCYGPQCLCR |
| 431 | LCLPCFTTDHQLARRCDDCCGGAGRGRCYGPQCLCR |
| 432 | LCLPCFTTDHQLARKCDDCCGGRGRGRCGPQCLCR |
| 433 | LCLPCFTTDHQLARACDDCCGGRGRGRCYGPQCLCR |
| 434 | LCLPCFTTDHQLARRCDDCCGGRGRGRCYGPQCLCR |
| 435 | LCLPCFTTDHQLARRCDDCCGGRGRGRCYGPQCLCR |
| 436 | KCLPCFTTDHQLARRCDDCCGGRGRGRCYGPQCLCR |
| 437 | ACAPCFTTDHQAARRCDDCCGGRGRGRCYGPQCLCR |
| 438 | KCAPCFTTDHQAARRCDDCCGGRGRGRCYGPQCLCR |
| 439 | LCLPCFTTDHQLAR(Cit)CDDCCGG(Cit)GRGKCYGPQCLCR |
| 440 | LCLPCFTTDHQLAR(Cit)CDDCCGG(Cit)GRG(Cit)CYGPQCLCR |
| 441 | KCLPCFTTDHQLAR(Cit)CDDCCGG(Cit)GRG(Cit)CYGPQCLCR |
| 442 | ACAPCFTTDHQAAR(Cit)CDDCCGG(Cit)GRGKCYGPQCLCR |
| 443 | ACAPCFTTDHQAAR(Cit)CDDCCGG(Cit)GRG(Cit)CYGPQCLCR |
| 444 | KCAPCFTTDHQAAR(Cit)CDDCCGG(Cit)GRG(Cit)CYGPQCLCR |
| 445 | SCSPCFTTDHQSARKCDDCCGGKGRGKCYGPQCLCR |
| 446 | SCSPCFTTDHQSARACDDCCGGKGRGKCYGPQCLCR |
| 447 | SCSPCFTTDHQSARRCDDCCGGKGRGKCYGPQCLCR |
| 448 | SCSPCFTTDHQSARKCDDCCGGAGRGKCYGPQCLCR |
| 449 | SCSPCFTTDHQSARACDDCCGGAGRGKCYGPQCLCR |
| 450 | SCSPCFTTDHQSARRCDDCCGGAGRGKCYGPQCLCR |
| 451 | SCSPCFTTDHQSARKCDDCCGGRGRGKCYGPQCLCR |
| 452 | SCSPCFTTDHQSARACDDCCGGRGRGKCYGPQCLCR |

TABLE 3-continued

Exemplary Peptide Sequence Suitable for Use in the Compounds of the Present Disclosure. Cit = Citrulline.

| SEQ ID NO | Polypeptide Sequence |
|---|---|
| 453 | SCSPCFTTDHQSARRCDDCCGGRGRGKCYGPQCLCR |
| 454 | SCSPCFTTDHQSARKCDDCCGGKGRGACYGPQCLCR |
| 455 | SCSPCFTTDHQSARACDDCCGGKGRGACYGPQCLCR |
| 456 | SCSPCFTTDHQSARRCDDCCGGKGRGACYGPQCLCR |
| 457 | SCSPCFTTDHQSARKCDDCCGGAGRGACYGPQCLCR |
| 458 | SCSPCFTTDHQSARACDDCCGGAGRGACYGPQCLCR |
| 459 | SCSPCFTTDHQSARRCDDCCGGAGRGACYGPQCLCR |
| 460 | SCSPCFTTDHQSARKCDDCCGGRGRGACYGPQCLCR |
| 461 | SCSPCFTTDHQSARACDDCCGGRGRGACYGPQCLCR |
| 462 | SCSPCFTTDHQSARRCDDCCGGRGRGACYGPQCLCR |
| 463 | SCSPCFTTDHQSARKCDDCCGGKGRGRCYGPQCLCR |
| 464 | SCSPCFTTDHQSARACDDCCGGKGRGRCYGPQCLCR |
| 465 | SCSPCFTTDHQSARRCDDCCGGKGRGRCYGPQCLCR |
| 466 | SCSPCFTTDHQSARKCDDCCGGAGRGRCYGPQCLCR |
| 467 | SCSPCFTTDHQSARACDDCCGGAGRGRCYGPQCLCR |
| 468 | SCSPCFTTDHQSARRCDDCCGGAGRGRCYGPQCLCR |
| 469 | SCSPCFTTDHQSARKCDDCCGGRGRGRCYGPQCLCR |
| 470 | SCSPCFTTDHQSARACDDCCGGRGRGRCYGPQCLCR |
| 471 | SCSPCFTTDHQSARRCDDCCGGRGRGRCYGPQCLCR |
| 472 | SCSPCFTTDHQSARRCDDCCGGRGRGRCYGPQCLCR |
| 473 | KCSPCFTTDHQSARRCDDCCGGRGRGRCYGPQCLCR |
| 474 | ACAPCFTTDHQAARRCDDCCGGRGRGRCYGPQCLCR |
| 475 | KCAPCFTTDHQAARRCDDCCGGRGRGRCYGPQCLCR |
| 476 | SCSPCFTTDHQSAR(Cit)CDDCCGG(Cit)GRGKCYGPQCLCR |
| 477 | SCSPCFTTDHQSAR(Cit)CDDCCGG(Cit)GRG(Cit)CYGPQCLCR |
| 478 | KCSPCFTTDHQSAR(Cit)CDDCCGG(Cit)GRG(Cit)CYGPQCLCR |
| 479 | ACAPCFTTDHQAAR(Cit)CDDCCGG(Cit)GRGKCYGPQCLCR |
| 480 | ACAPCFTTDHQAAR(Cit)CDDCCGG(Cit)GRG(Cit)CYGPQCLCR |
| 481 | KCAPCFTTDHQAAR(Cit)CDDCCGG(Cit)GRG(Cit)CYGPQCLCR |

Chlorotoxin conjugates used in this disclosure can comprise a chlorotoxin and a labeling agent or detectable label. In an embodiment, chlorotoxin is a variant comprising at least 60%, 65%, 70%, 75%, 80%, 83%, 85%, 86%, 89%, 90%, 92%, 93%, 94%, 95%, 96%, 97%, 98%, or 99% identical to the sequence of the native peptide of chlorotoxin or a fragment thereof.

In another embodiment, the compound comprises a polypeptide having at least at least 60%, 65%, 70%, 75%, 80%, 83%, 85%, 86%, 89%, 90%, 92%, 93%, 94%, 95%, 96%, 97%, 98%, or 99% sequence identity with any one of SEQ ID NO: 1-SEQ ID NO: 481, or any fragment thereof.

In another embodiment, the present disclosure provides a chlorotoxin having the following amino acid sequence: MCMPCFTTDHQ-MARKCDDCCGGKGRGKCYGPQCLCR (SEQ ID NO: 1) or a fragment thereof. In a further embodiment, the present disclosure provides chlorotoxin variants comprising at least 60%, 65%, 70%, 75%, 80%, 83%, 85%, 86%, 89%, 90%, 92%, 93%, 94%, 95%, 96%, 97%, 98%, or 99% identical to the following amino acid sequence: MCMPCFTTDHQ-MARKCDDCCGGKGRGKCYGPQCLCR (SEQ ID NO: 1) or a fragment thereof.

In another embodiment, the present disclosure provides a chlorotoxin having the following amino acid sequence: MCMPCFTTDHQMARRCDDCCGGR-GRGKCYGPQCLCR (SEQ ID NO: 9) or a fragment thereof. In a further embodiment, the present disclosure provides chlorotoxin variants comprising at least 60%, 65%, 70%, 75%, 80%, 83%, 85%, 86%, 89%, 90%, 92%, 93%, 94%, 95%, 96%, 97%, 98%, or 99% identical to the following amino acid sequence: MCMPCFTTDHQMARRCDDCCGGR-GRGKCYGPQCLCR (SEQ ID NO: 9) or a fragment thereof.

In a further embodiment, the present disclosure provides chlorotoxin variants comprising at least 80%, identical to the following amino acid sequence: MCMPCFTTDHQMARRCDDCCGGR-GRGKCYGPQCLCR (SEQ ID NO: 9) or a fragment thereof.

In a further embodiment, the present disclosure provides chlorotoxin variants comprising at least 83% identical to the following amino acid sequence: MCMPCFTTDHQMARRCDDCCGGR-GRGKCYGPQCLCR (SEQ ID NO: 9) or a fragment thereof.

In a still further embodiment, the present disclosure provides chlorotoxin variants comprising at least 86% identical to the following amino acid sequence: MCMPCFTTDHQMARRCDDCCGGR-GRGKCYGPQCLCR (SEQ ID NO: 9) or a fragment thereof.

In another embodiment, the present disclosure provides chlorotoxin variants comprising at least 88% identical to the following amino acid sequence: MCMPCFTTDHQMARRCDDCCGGR-GRGKCYGPQCLCR (SEQ ID NO: 9) or a fragment thereof.

In a further embodiment, the present disclosure provides chlorotoxin variants comprising at least 90% identical to the following amino acid sequence: MCMPCFTTDHQMARRCDDCCGGR-GRGKCYGPQCLCR (SEQ ID NO: 9) or a fragment thereof.

In a still further embodiment, the present disclosure provides chlorotoxin variants comprising at least 91% identical to the following amino acid sequence: MCMPCFTTDHQMARRCDDCCGGR-GRGKCYGPQCLCR (SEQ ID NO: 9) or a fragment thereof.

In a still further embodiment, the present disclosure provides chlorotoxin variants comprising at least 94% identical to the following amino acid sequence: MCMPCFTTDHQMARRCDDCCGGR-GRGKCYGPQCLCR (SEQ ID NO: 9) or a fragment thereof.

In yet another embodiment, the present disclosure provides chlorotoxin variants comprising at least 97% identical to the following amino acid sequence: MCMPCFTTDHQMARRCDDCCGGR-GRGKCYGPQCLCR (SEQ ID NO: 9) or a fragment thereof.

In another embodiment, the present disclosure provides a chlorotoxin having the following amino acid sequence: MCMPCFTTDHQMARXCDDCCGGXGRGXCYGPQCL-CR (SEQ ID NO: 482) or a fragment thereof, wherein each X can each independently be any amino acid. In another embodiment, the present disclosure provides a chlorotoxin having the following amino acid sequence: MCMPCFTTDHQMARXCDDCCGGXGRGXCYGPQCL-CR (SEQ ID NO: 483) or a fragment thereof, wherein X is selected from K, A and R.

In another embodiment, the cholorotoxin is a chlorotoxin or variant thereof having the following amino acid sequence: MCMPCFTTDHQMARXCDDCCGGXGRGXCYGPQCL-CR (SEQ ID NO: 484) or a fragment thereof, wherein each X can independently be R or A.

In another embodiment, the cholorotoxin is a chlorotoxin or variant thereof having the following amino acid sequence: MCMPCFTTDHQMARXCDDCCGGXGRGKCYGPQCL-CR (SEQ ID NO: 485) or a fragment thereof, wherein each X can independently be R or A.

In still other instances, the variant nucleic acid molecules of a peptide of any one of SEQ ID NO: 1-SEQ ID NO: 485 can be identified by either a determination of the sequence identity of the encoded peptide amino acid sequence with the amino acid sequence of any one of SEQ ID NO: 1-SEQ ID NO: 481, or by a nucleic acid hybridization assay. Such peptide variants can include nucleic acid molecules (1) that remain hybridized with a nucleic acid molecule having the nucleotide sequence of any one of SEQ ID NO: 1-SEQ ID NO: 481 (or its complement) under stringent washing conditions, in which the wash stringency is equivalent to 0.5×-2×SSC with 0.1% SDS at 55-65° C., and (2) that encode a peptide having at least 70%, at least 80%, at least 90%, at least 95% or greater than 95% sequence identity to the amino acid sequence of any one of SEQ ID NO: 1-SEQ ID NO: 481. Alternatively, peptide variants of any one of SEQ ID NO: 1-SEQ ID NO: 481 can be characterized as nucleic acid molecules (1) that remain hybridized with a nucleic acid molecule having the nucleotide sequence of any one of SEQ ID NO: 1-SEQ ID NO: 481 (or its complement) under highly stringent washing conditions, in which the wash stringency is equivalent to 0.1×-0.2×SSC with 0.1% SDS at 50-65° C., and (2) that encode a peptide having at least 70%, at least 80%, at least 90%, at least 95% or greater than 95% sequence identity to the amino acid sequence of any one of SEQ ID NO: 1-SEQ ID NO: 481.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (Id.). The sequence identity is then calculated as: ([Total number of identical matches]/[length of the longer sequence plus the number of gaps introduced into the longer sequence in order to align the two sequences])(100).

Additionally, there are many established algorithms available to align two amino acid sequences. For example, the "FASTA" similarity search algorithm of Pearson and Lipman is a suitable protein alignment method for examining the level of sequence identity or homology shared by an amino acid sequence of a peptide disclosed herein and the amino acid sequence of a peptide variant. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO: 9) and a test sequence that has either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *Siam J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

Some examples of common amino acids that are a "conservative amino acid substitution" are illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci.* USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Determination of amino acid residues that are within regions or domains that are critical to maintaining structural integrity can be determined. Within these regions one can determine specific residues that can be more or less tolerant of change and maintain the overall tertiary structure of the molecule. Methods for analyzing sequence structure include, but are not limited to, alignment of multiple sequences with high amino acid or nucleotide identity and computer analysis using available software (e.g., the Insight II® viewer and homology modeling tools; MSI, San Diego, Calif.), secondary structure propensities, binary patterns, complementary packing and buried polar interactions (Barton, G. J., *Current Opin. Struct. Biol.* 5:372-6 (1995) and Cordes, M. H. et al., *Current Opin. Struct. Biol.* 6:3-10 (1996)). In general, when designing modifications to molecules or identifying specific fragments determination of structure can typically be accompanied by evaluating activity of modified molecules.

In another embodiment, the chlorotoxin is Compound 76, which is a chlorotoxin variant comprising the sequence of MCMPCFTTDHQMARRCDDCCGGR-GRGKCYGP TABLE 4-continued Exemplary Compounds According to the Present Disclosure
A = MCMPCFTTDHQMARRCDDCCGGRGRGKCYGPQCLCR (SEQ ID NO: 9)

| No. | Structure |
|-----|-----------|
| 62 | 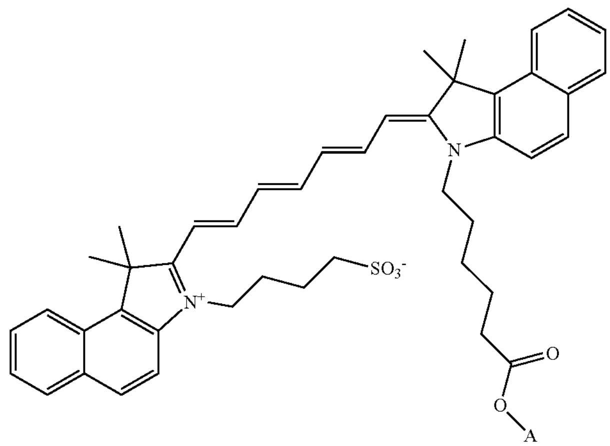 |
| 63 | 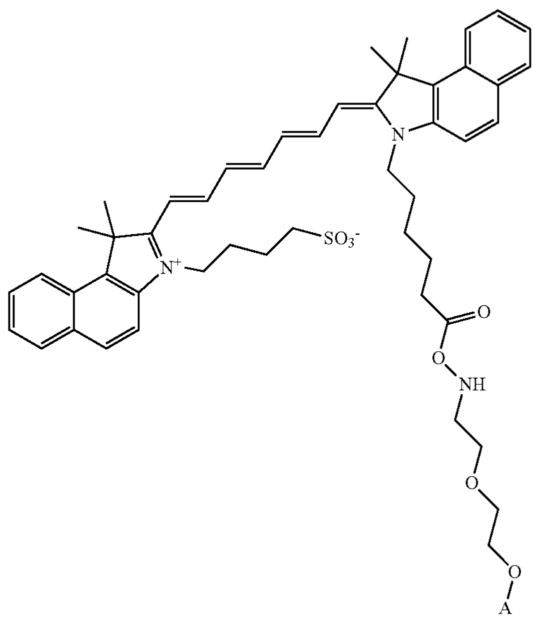 |
| 64 | 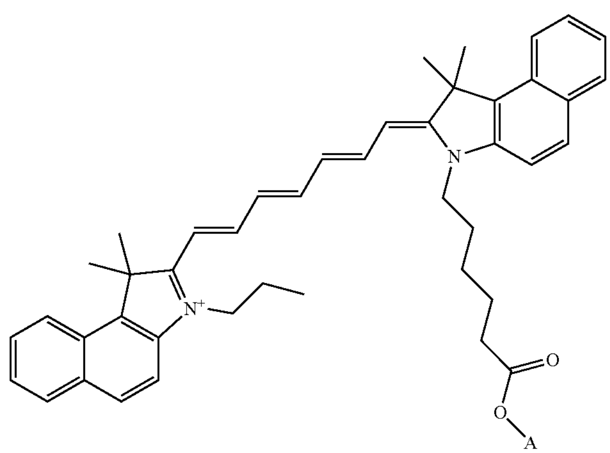 |

131
TABLE 4-continued
Exemplary Compounds According to the Present Disclosure
A = MCMPCFTTDHQMARRCDDCCGGRGRGKCYGPQCLCR (SEQ ID NO: 9)
| No. | Structure |
|---|---|
| 65 | 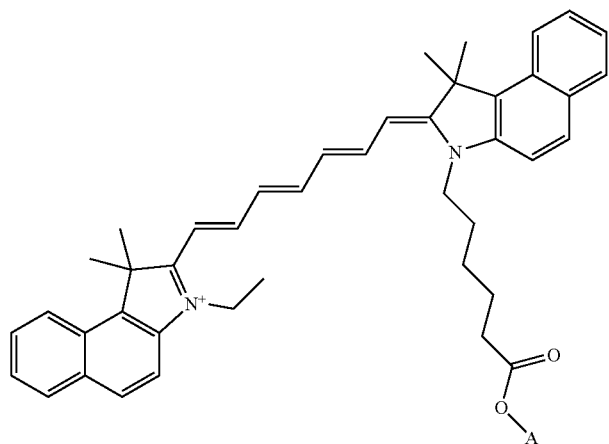 |
| 66 | 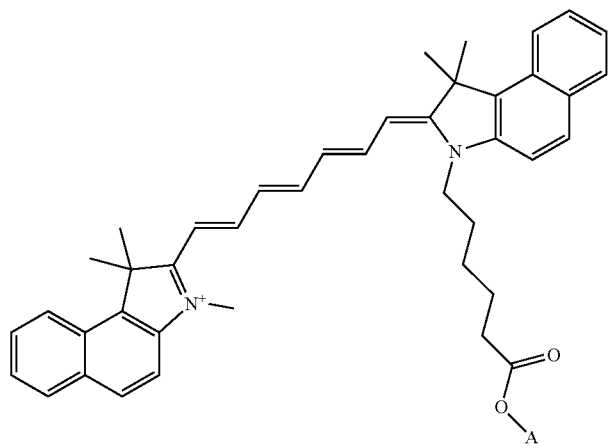 |
| 67 | 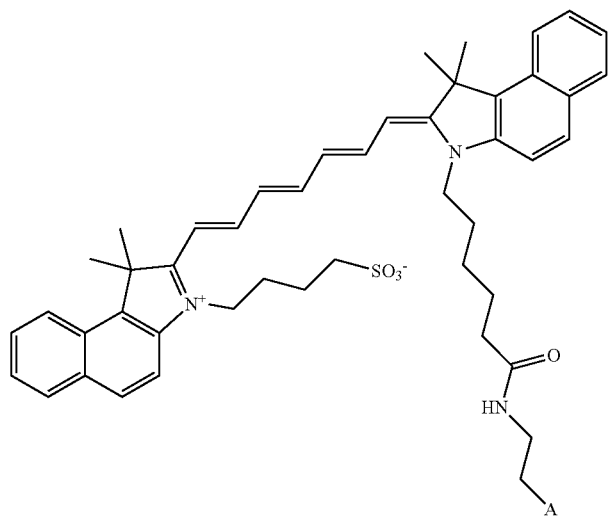 |

TABLE 4-continued
Exemplary Compounds According to the Present Disclosure
A = MCMPCFTTDHQMARRCDDCCGGRGRGKCYGPQCLCR (SEQ ID NO: 9)
| No. | Structure |
|---|---|
| 68 | 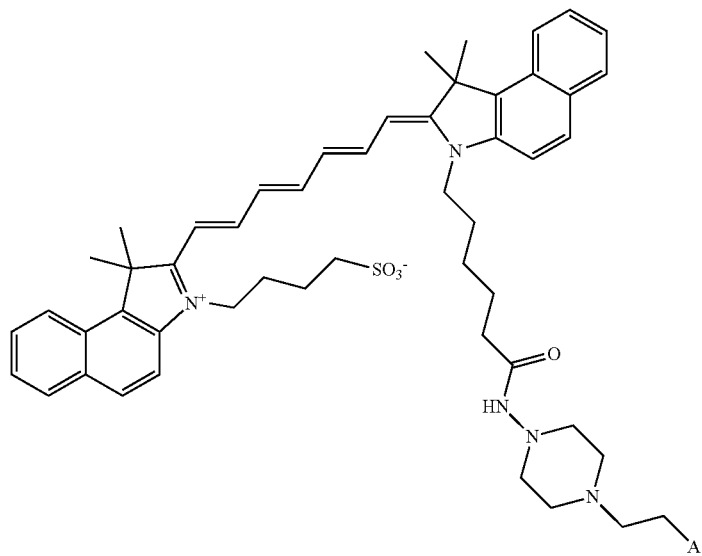 |
| 69 | 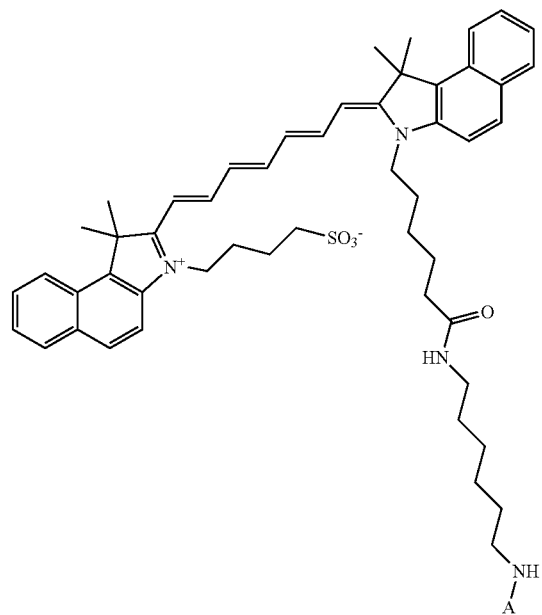 |

TABLE 4-continued

Exemplary Compounds According to the Present Disclosure
A = MCMPCFTTDHQMARRCDDCCGGRGRGKCYGPQCLCR (SEQ ID NO: 9)

| No. | Structure |
|---|---|
| 70 | 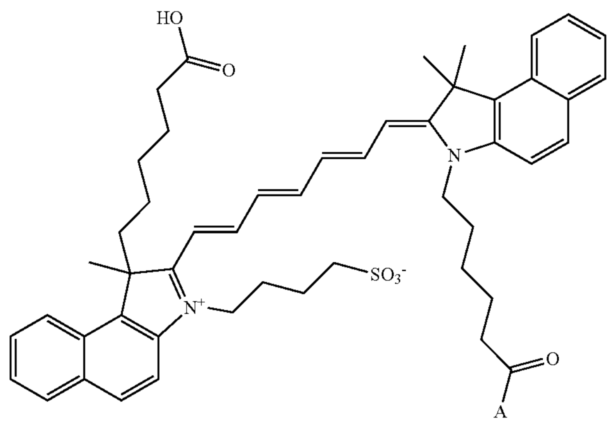 |
| 71 | 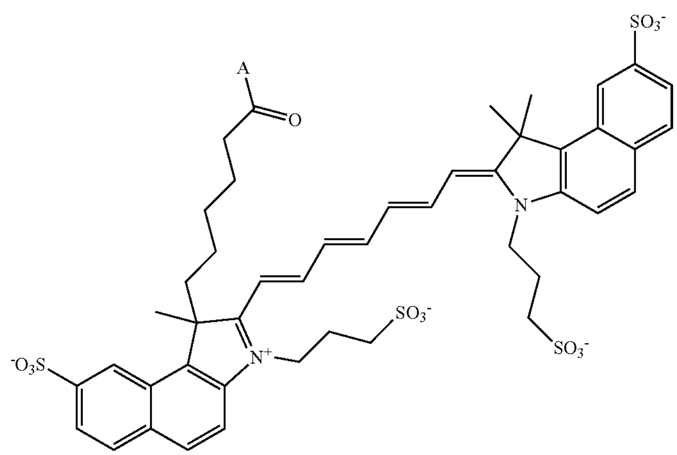 |
| 72 | 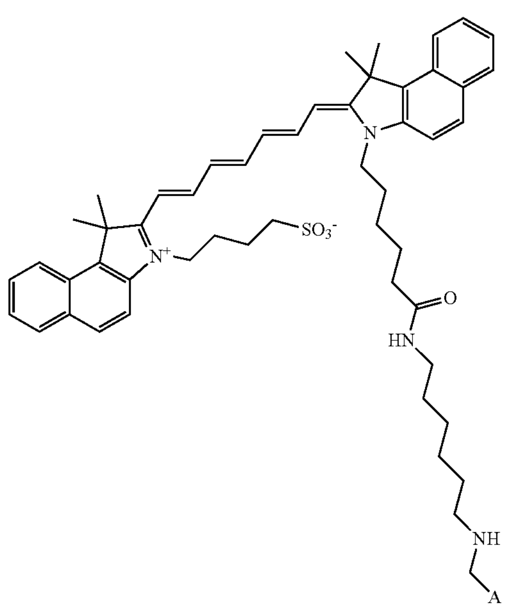 |

TABLE 4-continued
Exemplary Compounds According to the Present Disclosure
A = MCMPCFTTDHQMARRCDDCCGGRGRGKCYGPQCLCR (SEQ ID NO: 9)
| No. | Structure |
|---|---|
| 73 | 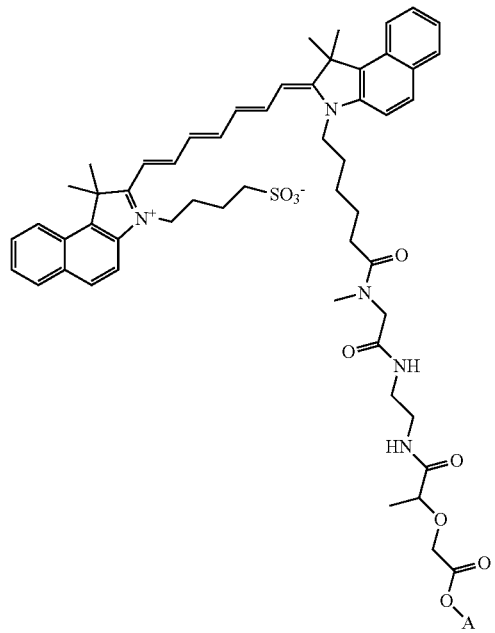 |
| 74 | 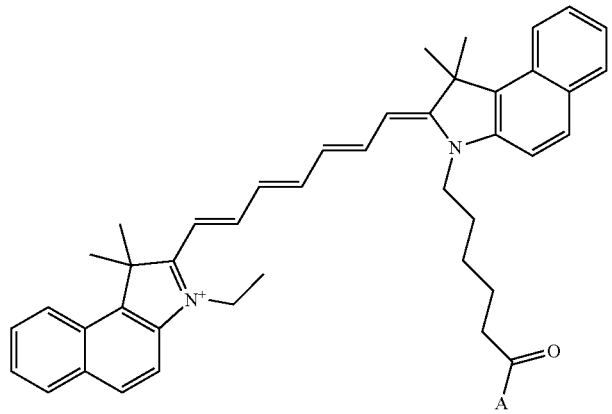 |
| 75 | 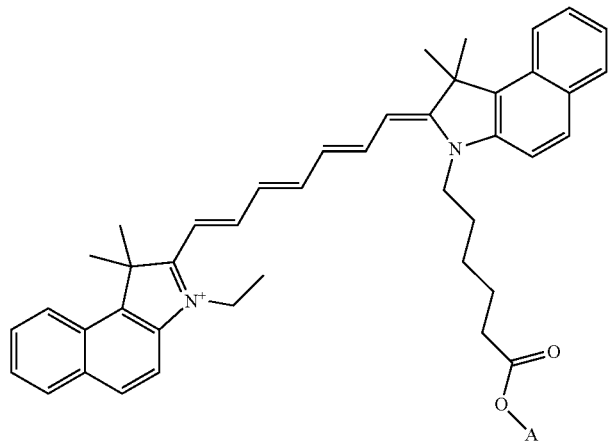 |

TABLE 4-continued
Exemplary Compounds According to the Present Disclosure
A = MCMPCFTTDHQMARRCDDCCGGRGRGKCYGPQCLCR (SEQ ID NO: 9)
| No. | Structure |
|---|---|
| 76 | 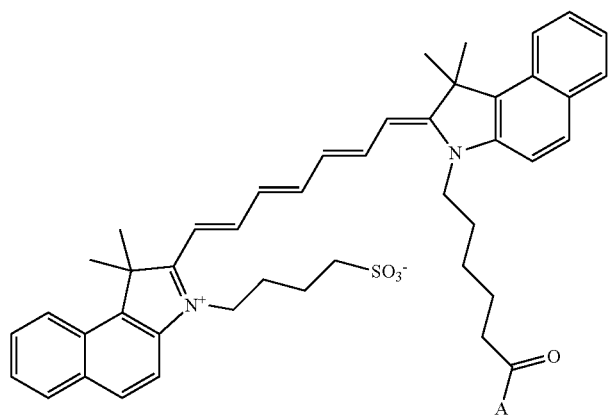 |
| 77 | 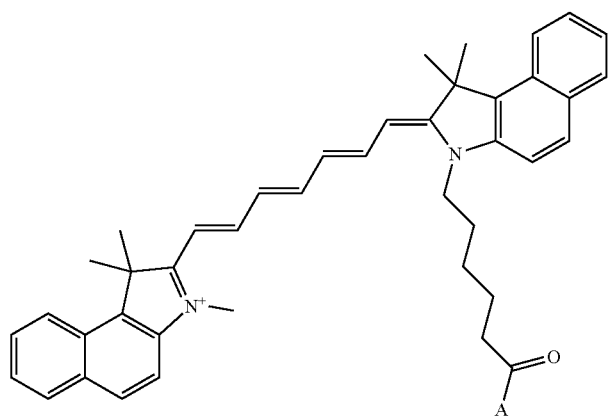 |
| 78 | 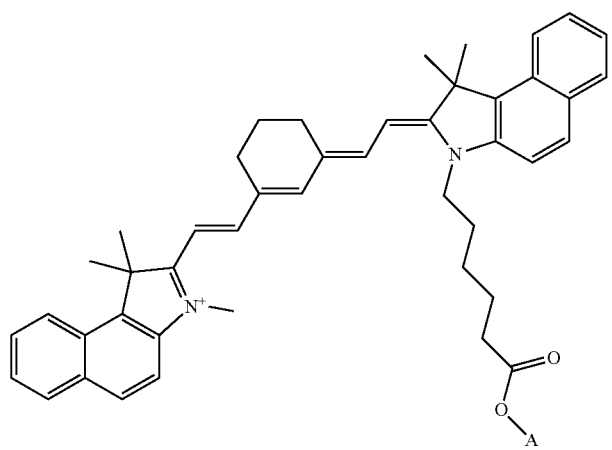 |

TABLE 4-continued

Exemplary Compounds According to the Present Disclosure
A = MCMPCFTTDHQMARRCDDCCGGRGRGKCYGPQCLCR (SEQ ID NO: 9)

| No. | Structure |
|---|---|
| 79 | 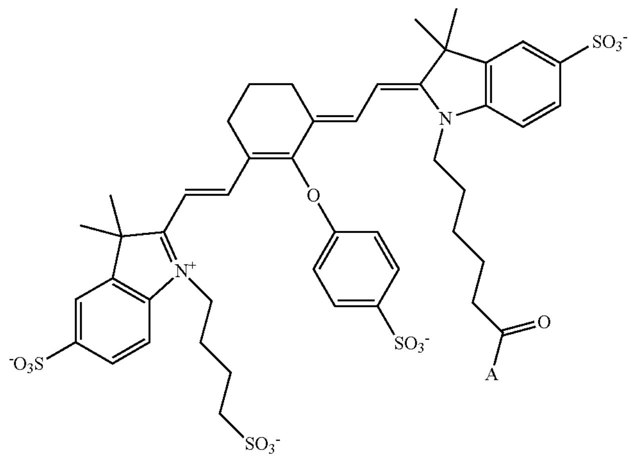 |
| 80 | 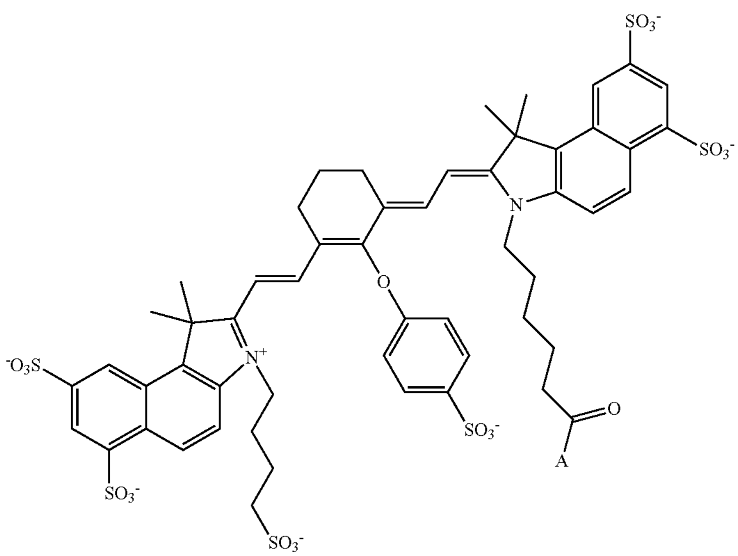 |
| 81 | 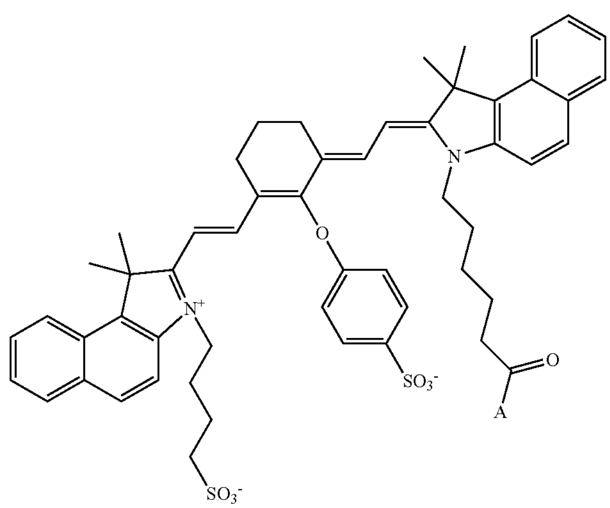 |

TABLE 4-continued
Exemplary Compounds According to the Present Disclosure
A = MCMPCFTTDHQMARRCDDCCGGRGRGKCYGPQCLCR (SEQ ID NO: 9)
| No. | Structure |
|---|---|
| 82 | 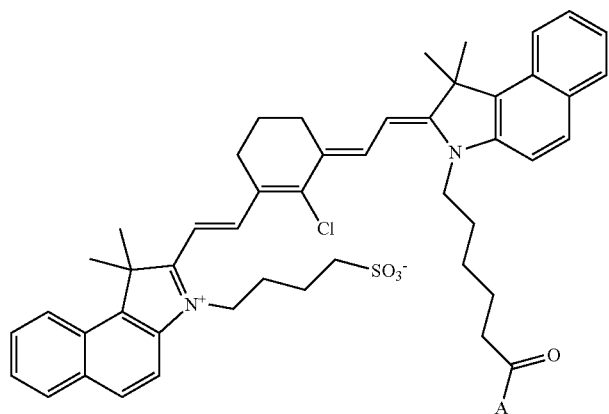 |
| 83 | 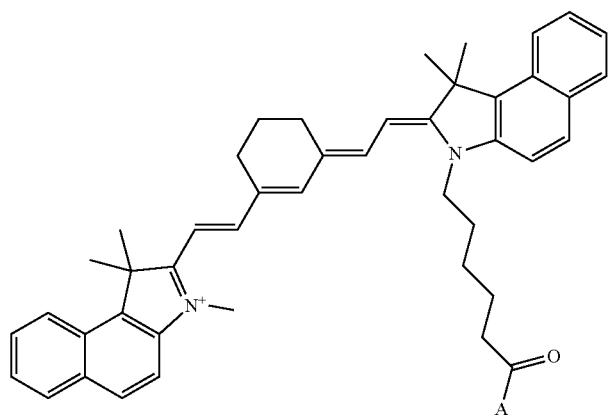 |
| 84 | 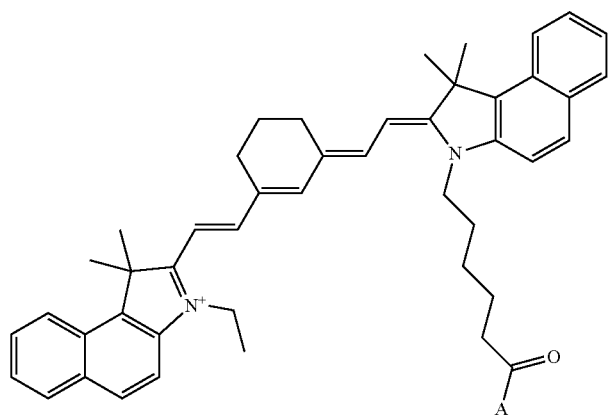 |

TABLE 4-continued
Exemplary Compounds According to the Present Disclosure
A = MCMPCFTTDHQMARRCDDCCGGRGRGKCYGPQCLCR (SEQ ID NO: 9)
| No. | Structure |
|---|---|
| 85 | 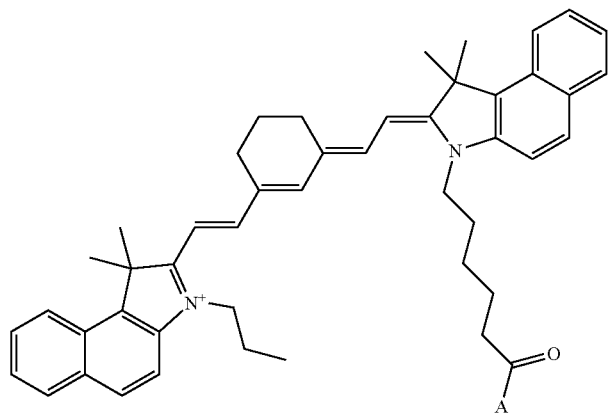 |
| 86 | 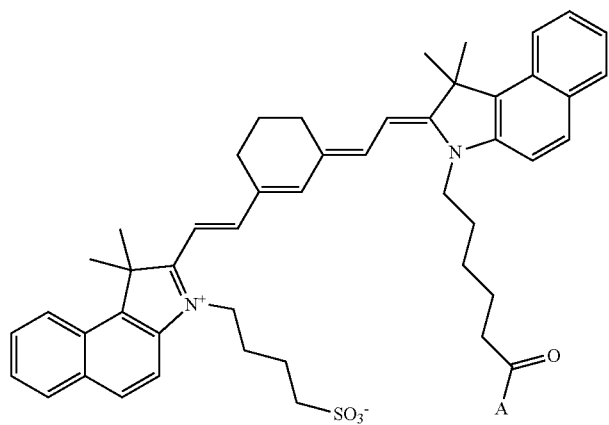 |
| 87 | 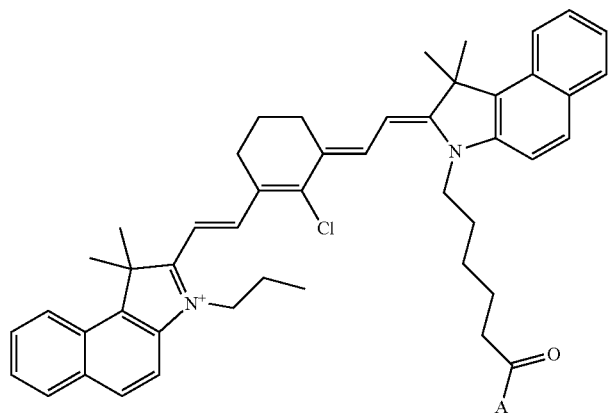 |

TABLE 4-continued

Exemplary Compounds According to the Present Disclosure
A = MCMPCFTTDHQMARRCDDCCGGRGRGKCYGPQCLCR (SEQ ID NO: 9)

| No. | Structure |
|---|---|
| 88 | 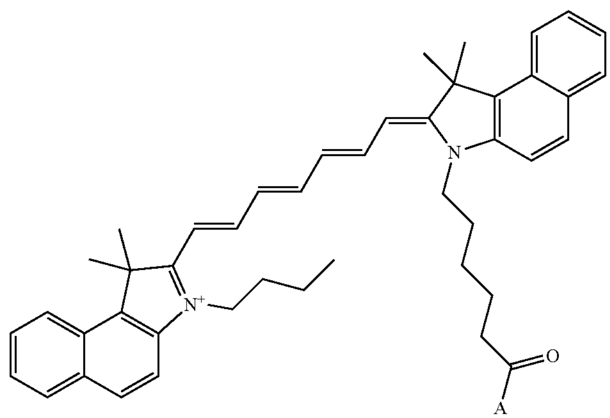 |
| 89 | 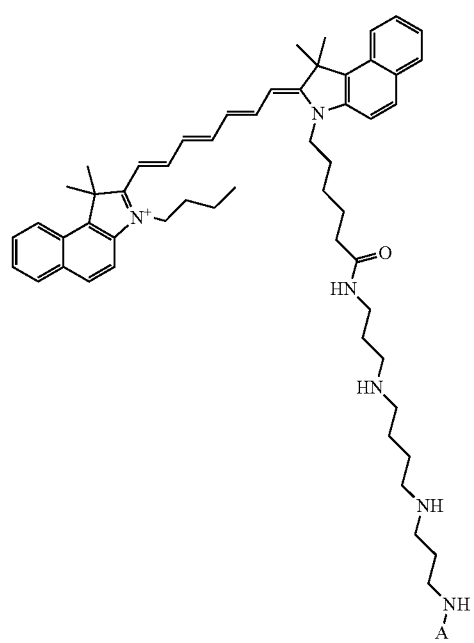 |
| 90 | 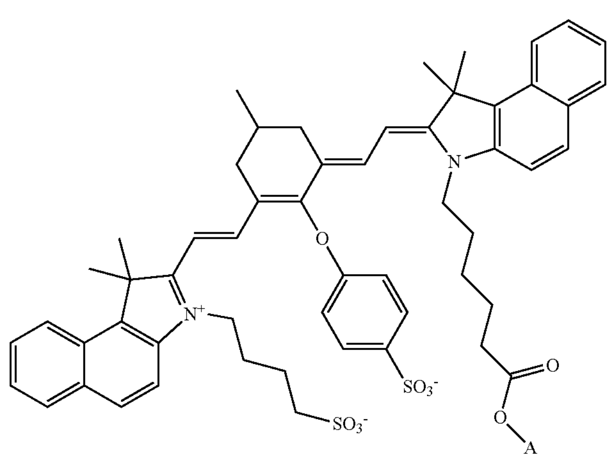 |

TABLE 4-continued
Exemplary Compounds According to the Present Disclosure
A = MCMPCFTTDHQMARRCDDCCGGRGRGKCYGPQCLCR (SEQ ID NO: 9)
| No. | Structure |
|---|---|
| 91 | 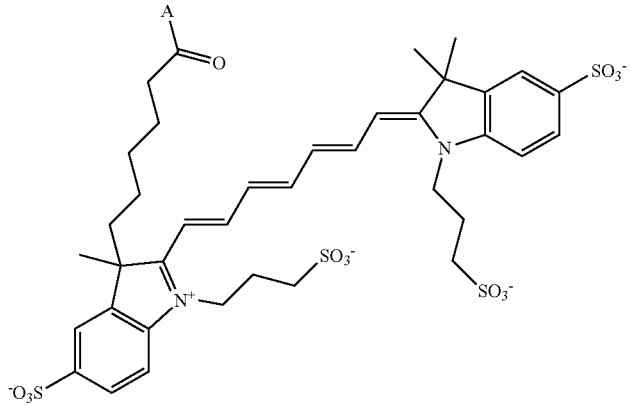 |
| 92 | 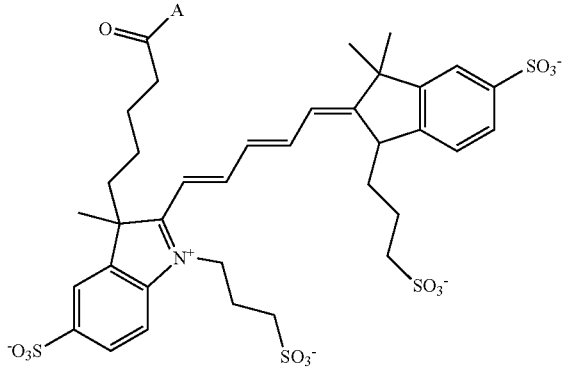 |
| 93 | 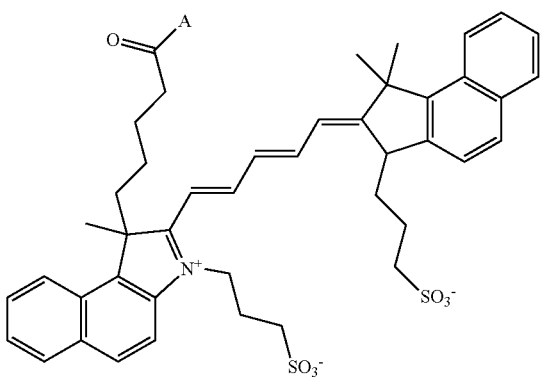 |

TABLE 4-continued
Exemplary Compounds According to the Present Disclosure
A = MCMPCFTTDHQMARRCDDCCGGRGRGKCYGPQCLCR (SEQ ID NO: 9)
| No. | Structure |
|---|---|
| 94 | 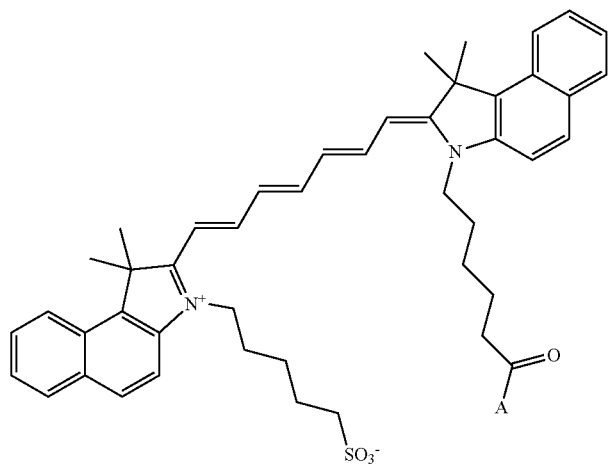 |
| 95 | 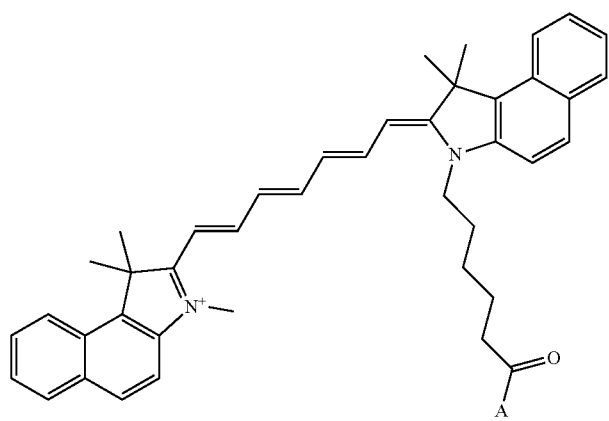 |
| 96 | 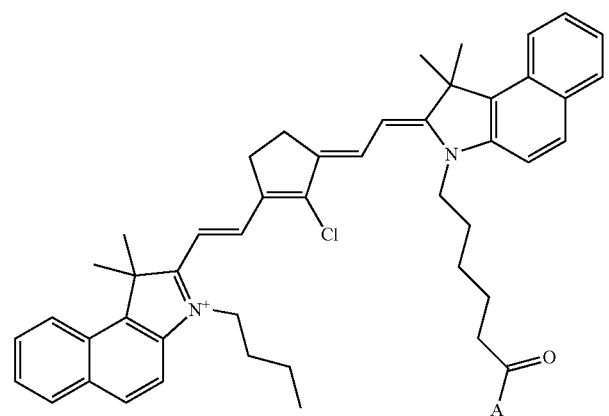 |

TABLE 4-continued
Exemplary Compounds According to the Present Disclosure
A = MCMPCFTTDHQMARRCDDCCGGRGRGKCYGPQCLCR (SEQ ID NO: 9)
| No. | Structure |
|-----|-----------|
| 97 | 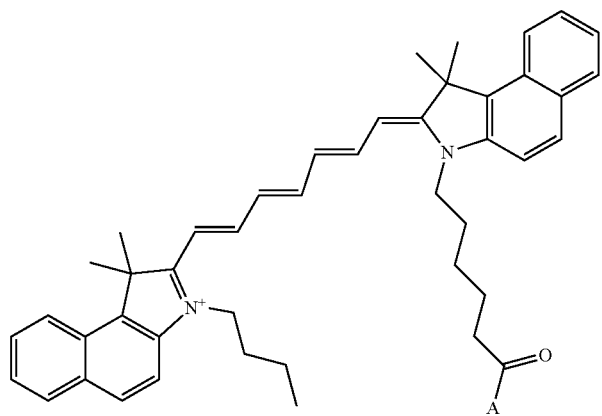 |
| 98 | 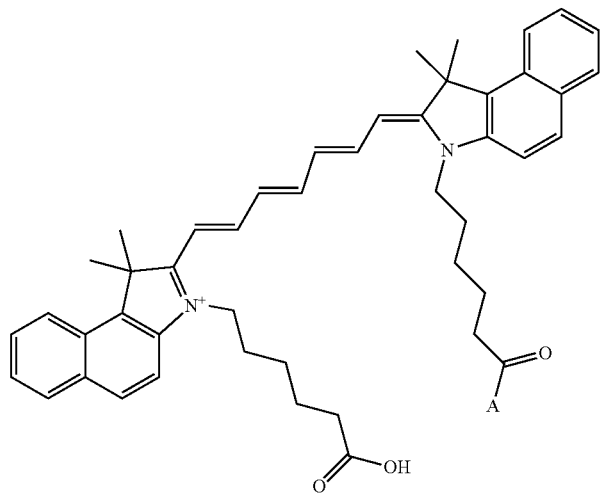 |
| 99 | 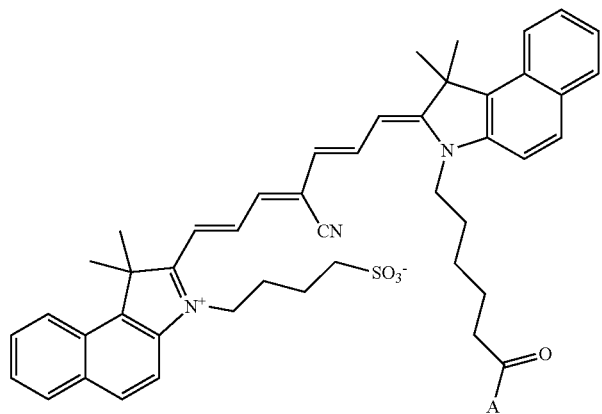 |

TABLE 4-continued

Exemplary Compounds According to the Present Disclosure
A = MCMPCFTTDHQMARRCDDCCGGRGRGKCYGPQCLCR (SEQ ID NO: 9)

| No. | Structure |
|---|---|
| 100 | 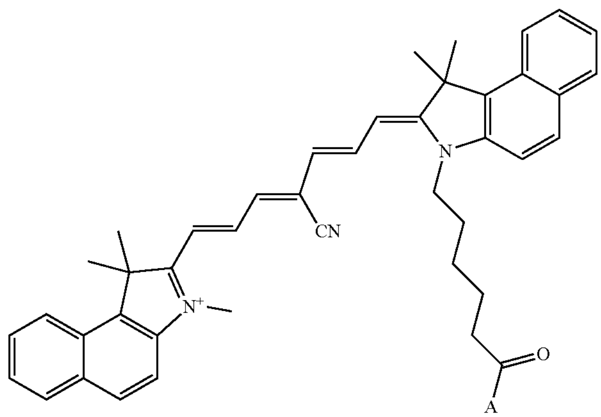 |
| 101 | 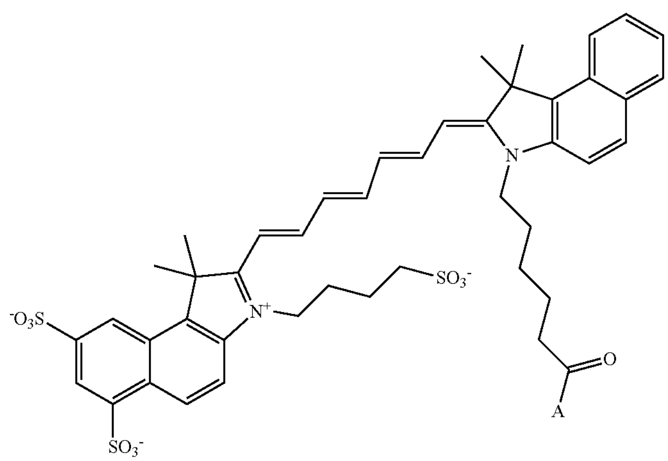 |
| 102 | 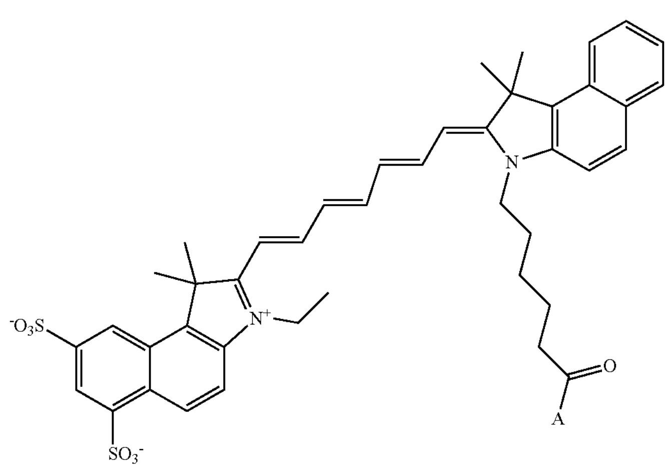 |

TABLE 4-continued

Exemplary Compounds According to the Present Disclosure
A = MCMPCFTTDHQMARRCDDCCGGRGRGKCYGPQCLCR (SEQ ID NO: 9)

| No. | Structure |
|---|---|
| 103 | 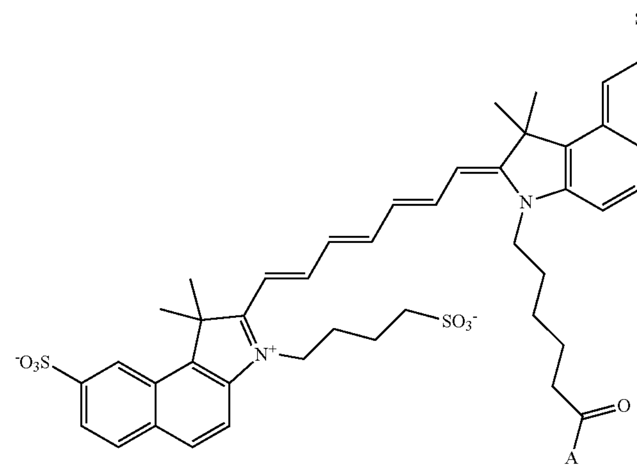 |
| 104 | 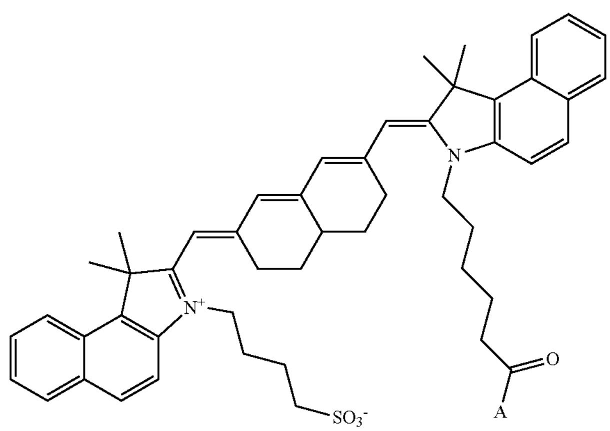 |
| 105 | 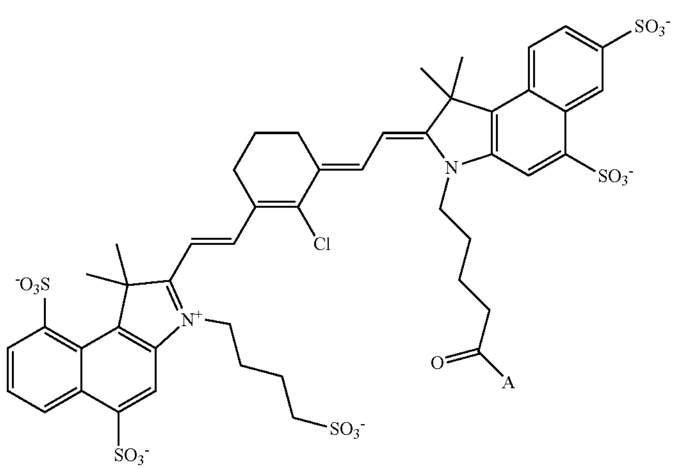 |

TABLE 4-continued
Exemplary Compounds According to the Present Disclosure
A = MCMPCFTTDHQMARRCDDCCGGRGRGKCYGPQCLCR (SEQ ID NO: 9)
| No. | Structure |
|---|---|
| 106 | 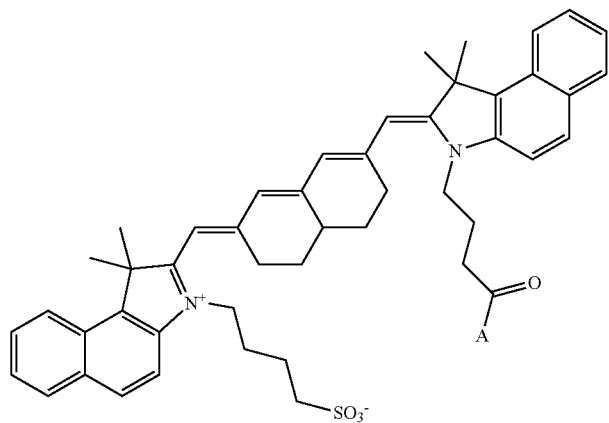 |
| 107 | 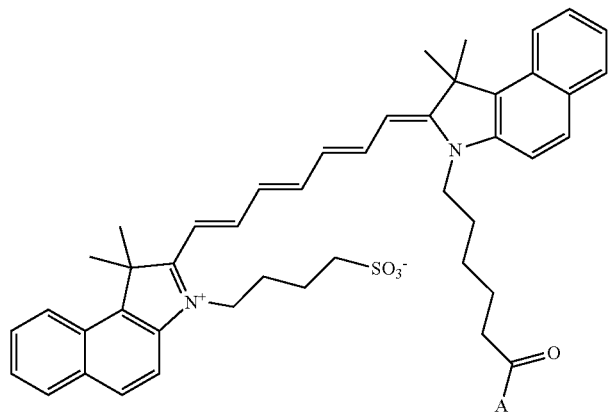 |
| 108 | 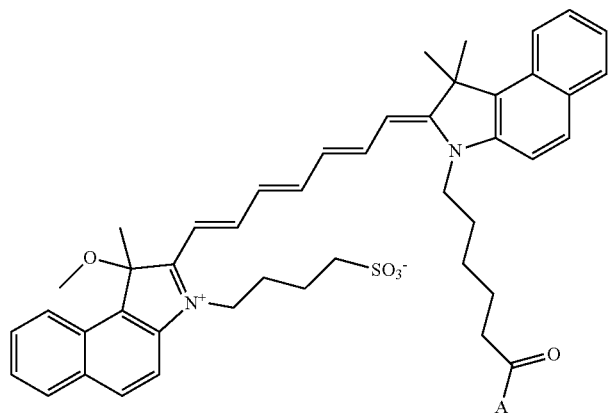 |

TABLE 4-continued

Exemplary Compounds According to the Present Disclosure
A = MCMPCFTTDHQMARRCDDCCGGRGRGKCYGPQCLCR (SEQ ID NO: 9)

| No. | Structure |
|---|---|
| 109 | 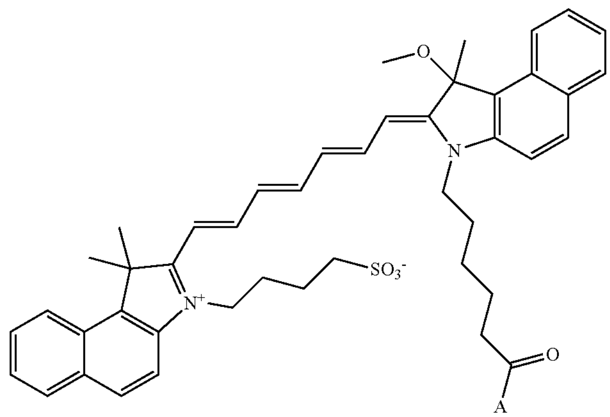 |
| 110 | 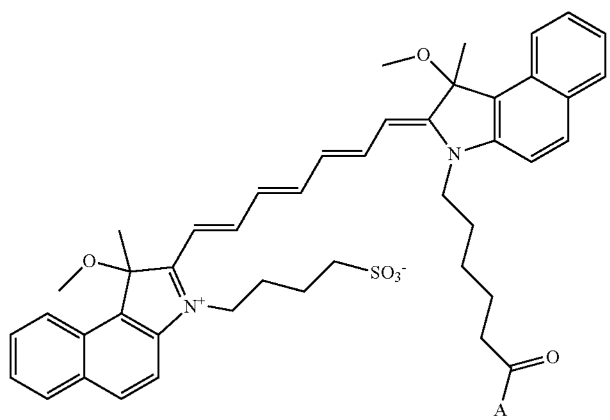 |
| 111 | 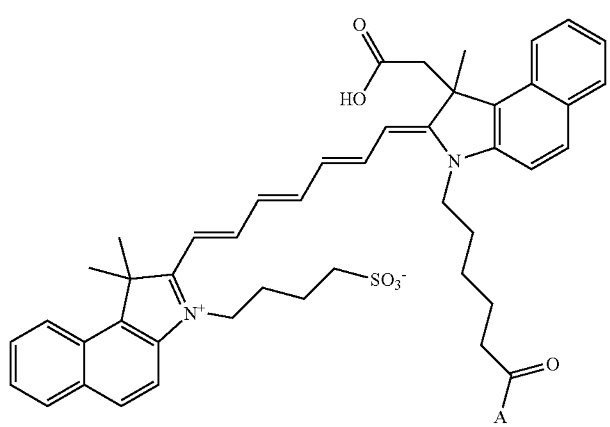 |

TABLE 4-continued

Exemplary Compounds According to the Present Disclosure
A = MCMPCFTTDHQMARRCDDCCGGRGRGKCYGPQCLCR (SEQ ID NO: 9)

| No. | Structure |
|-----|-----------|
| 112 | 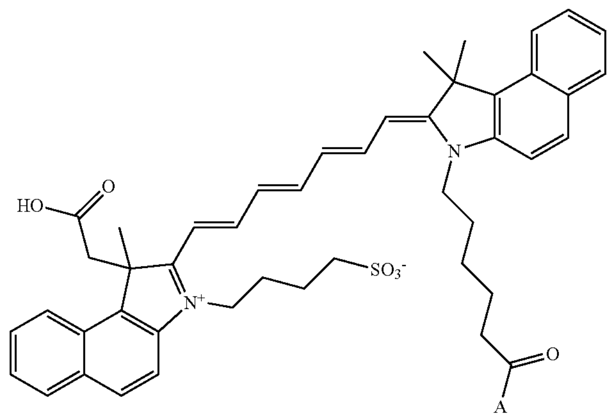 |
| 113 | 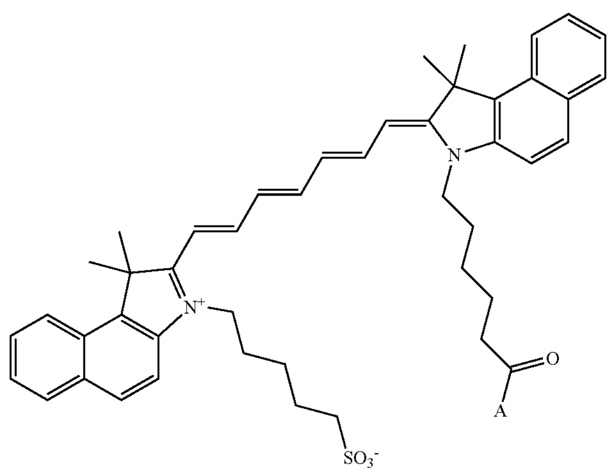 |
| 114 | 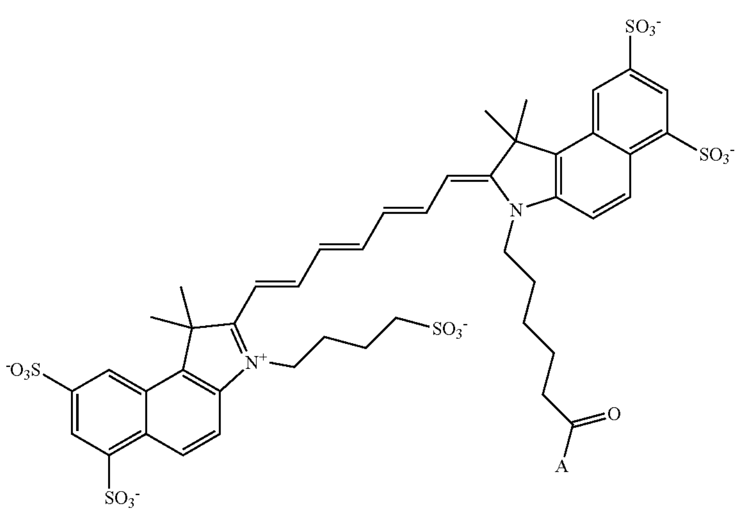 |

TABLE 4-continued
Exemplary Compounds According to the Present Disclosure
A = MCMPCFTTDHQMARRCDDCCGGRGRGKCYGPQCLCR (SEQ ID NO: 9)
| No. | Structure |
|---|---|
| 115 | 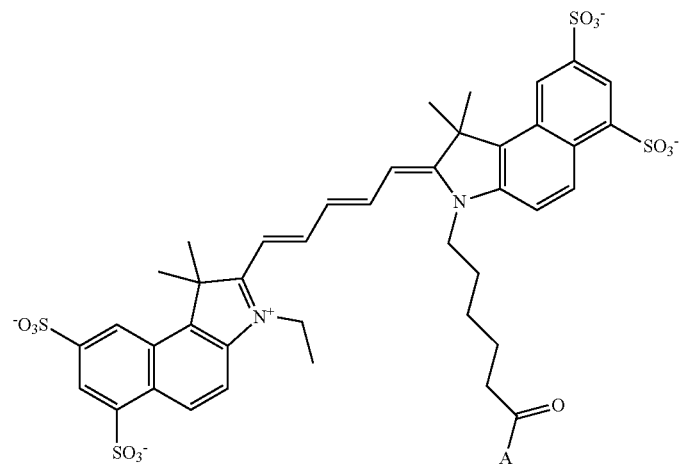 |
| 116 | 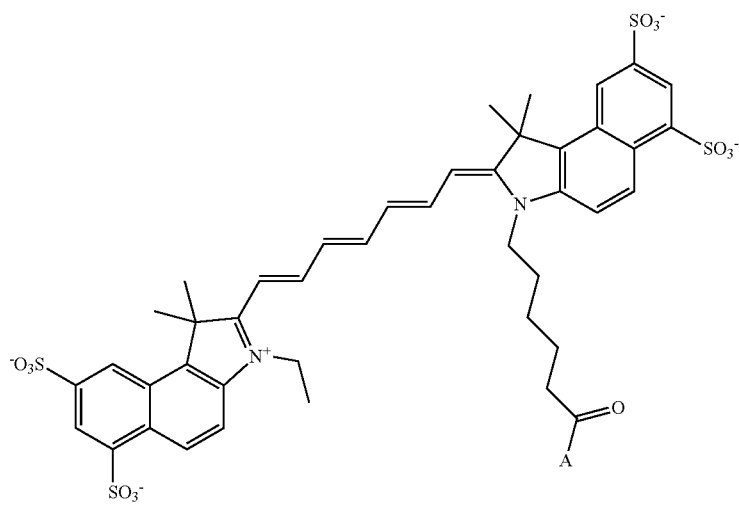 |
| 117 | 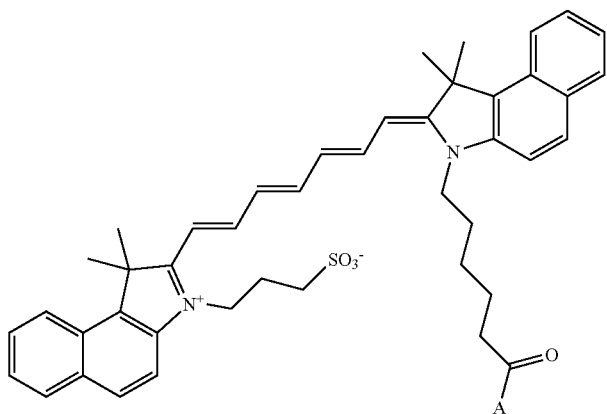 |

TABLE 4-continued

Exemplary Compounds According to the Present Disclosure
A = MCMPCFTTDHQMARRCDDCCGGRGRGKCYGPQCLCR (SEQ ID NO: 9)

| No. | Structure |
|---|---|
| 118 | 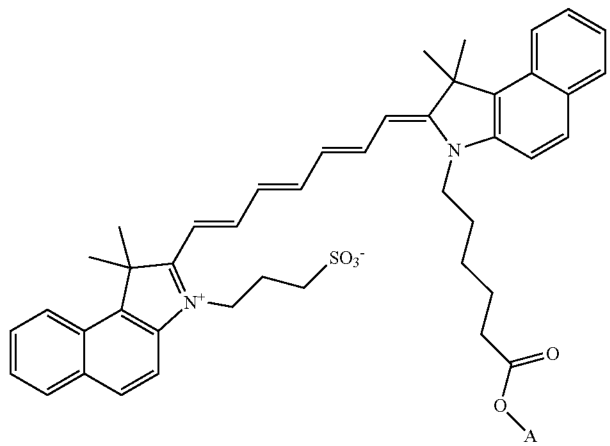 |
| 119 | 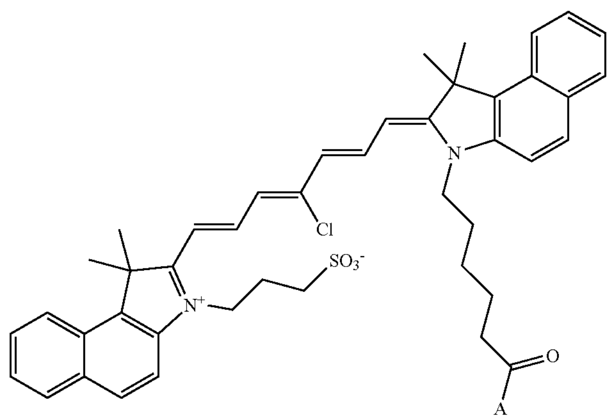 |
| 120 | 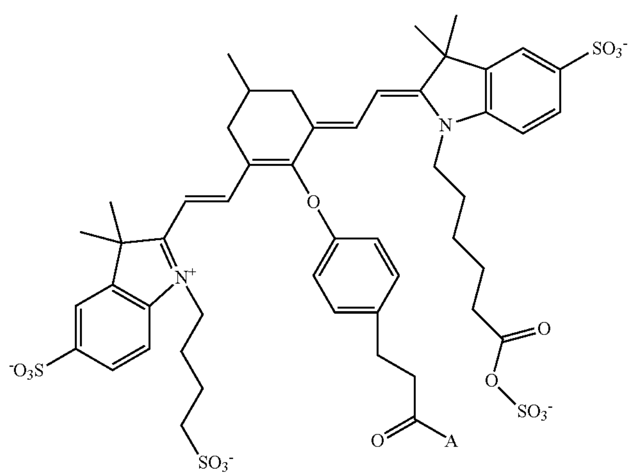 |

In some aspects, the peptide is a variant of the native peptide of chlorotoxin but retains all eight cysteine residues of the native peptide, enabling cross-linking by up to four disulfide bonds. Conservation of cysteine residues helps to preserve the secondary structure and other features of the native chlorotoxin peptide because of the disulfide bonds that form between the cysteine residues. In some aspects, the chlorotoxin peptide variant retains all eight cysteine residues of the native peptide and has at least 40%, 45%, 50%, 55%, 60%, 65%, 70%, 75%, 80%, 83%, 85%, 86%, 89%, 90%, 92%, 93%, 94%, 95%, 96%, 97%, 98%, or 99% sequence identity with the native chlorotoxin peptide.

In some aspects, the chlorotoxin peptide variant has eight cysteine residues positioned so that the distances between pairs of cysteines is the same as the distances between pairs of cysteines found in the native peptide, and the chlorotoxin peptide variant has at least 40%, 45%, 50%, 55%, 60%, 65%, 70%, 75%, 80%, 83%, 85%, 86%, 89%, 90%, 92%, 93%, 94%, 95%, 96%, 97%, 98%, or 99% sequence identity with the native chlorotoxin peptide.

In some aspects, the chlorotoxin peptide variant has eight cysteine residues positioned so that the distances between pairs of cysteines is functionally equivalent or functionally similar to the distances between pairs of cysteines found in the native peptide, and the chlorotoxin peptide variant has at least 40%, 45%, 50%, 55%, 60%, 65%, 70%, 75%, 80%, 83%, 85%, 86%, 89%, 90%, 92%, 93%, 94%, 95%, 96%, 97%, 98%, or 99% sequence identity with the native chlorotoxin peptide.

In some aspects, the chlorotoxin peptide variant has eight cysteine residues positioned so that the distances between pairs of cysteines allows for secondary structure and isoelectric point of the native chlorotoxin peptide to be preserved, and the chlorotoxin peptide variant has at least 40%, 45%, 50%, 55%, 60%, 65%, 70%, 75%, 80%, 83%, 85%, 86%, 89%, 90%, 92%, 93%, 94%, 95%, 96%, 97%, 98%, or 99% sequence identity with the native chlorotoxin peptide.

In some aspects, the chlorotoxin peptide variant has eight cysteine residues positioned so that the distances between pairs of cysteines is sufficient to allow disulfide bonds to form, and the chlorotoxin peptide variant has at least 40%, 45%, 50%, 55%, 60%, 65%, 70%, 75%, 80%, 83%, 85%, 86%, 89%, 90%, 92%, 93%, 94%, 95%, 96%, 97%, 98%, or 99% sequence identity with the native chlorotoxin peptide.

In some aspects, one or more methionines of the chlorotoxin peptide variant are replaced with other amino acids. In some aspects, one or more methionines of the chlorotoxin peptide variant are replaced with other amino acids selected from glycine, alanine, isoleucine, threonine, valine, leucine, serine or a combination thereof.

In some embodiments, the chlorotoxin can be a chlorotoxin variant. Chlorotoxin and chlorotoxin variants are further described in PCT Patent Application Publication Numbers WO2006115633 and WO2011142858, which are incorporated in their entirety herein by reference.

In one embodiment, the peptide can have the following formula: H-Met-Cys-Met-Pro-Cys-Phe-Thr-Thr-Asp-His-Gln-Met-Ala-Arg-$X_1$-Cys-Asp-Asp-Cys-Cys-Gly-Gly-$X_2$-Gly-Arg-Gly-$X_3$-Cys-Tyr-Gly-Pro-Gln-Cys-Leu-Cys-Arg-OH (SEQ ID NO: 482) acetate salt (disulfide bonds, air oxidized), wherein $X_1$, $X_2$, and $X_3$ can each independently be any amino acid.

In one embodiment, the peptide can have the following formula: H-Met-Cys-Met-Pro-Cys-Phe-Thr-Thr-Asp-His-Gln-Met-Ala-Arg-$X_1$-Cys-Asp-Asp-Cys-Cys-Gly-Gly-$X_2$-Gly-Arg-Gly-$X_3$-Cys-Tyr-Gly-Pro-Gln-Cys-Leu-Cys-Arg-OH (SEQ ID NO: 483) acetate salt (disulfide bonds, air oxidized), wherein $X_1$, $X_2$, and $X_3$ can each independently be Arg, Ala, or Lys.

In another embodiment, the all peptide can have the following formula: H-Met-Cys-Met-Pro-Cys-Phe-Thr-Thr-Asp-His-Gln-Met-Ala-Arg-$X_1$-Cys-Asp-Asp-Cys-Cys-Gly-Gly-$X_2$-Gly-Arg-Gly-$X_3$-Cys-Tyr-Gly-Pro-Gln-Cys-Leu-Cys-Arg-OH (SEQ ID NO: 484) acetate salt (disulfide bonds, air oxidized), wherein $X_1$, $X_2$, and $X_3$ can each independently be Arg or Ala.

In another embodiment, the all peptide can have the following formula: H-Met-Cys-Met-Pro-Cys-Phe-Thr-Thr-Asp-His-Gln-Met-Ala-Arg-$X_1$-Cys-Asp-Asp-Cys-Cys-Gly-Gly-$X_2$-Gly-Arg-Gly-Lys-Cys-Tyr-Gly-Pro-Gln-Cys-Leu-Cys-Arg-OH (SEQ ID NO: 485) acetate salt (disulfide bonds, air oxidized), wherein $X_1$ and $X_2$ can each independently be Arg or Ala.

In another embodiment, the peptide can have the following formula: H-Met-Cys-Met-Pro-Cys-Phe-Thr-Thr-Asp-His-Gln-Met-Ala-Arg-Arg-Cys-Asp-Asp-Cys-Cys-Gly-Gly-Arg-Gly-Arg-Gly-Lys-Cys-Tyr-Gly-Pro-Gln-Cys-Leu-Cys-Arg-OH (SEQ ID NO: 9) acetate salt (disulfide bonds, air oxidized).

In another embodiment, the peptide can have the following formula: H-Met-Cys-Met-Pro-Cys-Phe-Thr-Thr-Asp-His-Gln-Met-Ala-Arg-Arg-Cys-Asp-Asp-Cys-Cys-Gly-Gly-Ala-Gly-Arg-Gly-Lys-Cys-Tyr-Gly-Pro-Gln-Cys-Leu-Cys-Arg-OH (SEQ ID NO: 6) acetate salt (disulfide bonds, air oxidized).

In another embodiment, the peptide can have the following formula: H-Met-Cys-Met-Pro-Cys-Phe-Thr-Thr-Asp-His-Gln-Met-Ala-Arg-Ala-Cys-Asp-Asp-Cys-Cys-Gly-Gly-Arg-Gly-Arg-Gly-Lys-Cys-Tyr-Gly-Pro-Gln-Cys-Leu-Cys-Arg-OH (SEQ ID NO: 8) acetate salt (disulfide bonds, air oxidized).

In another embodiment, the peptide can have the following formula: H-Met-Cys-Met-Pro-Cys-Phe-Thr-Thr-Asp-His-Gln-Met-Ala-Arg-Ala-Cys-Asp-Asp-Cys-Cys-Gly-Gly-Ala-Gly-Arg-Gly-Lys-Cys-Tyr-Gly-Pro-Gln-Cys-Leu-Cys-Arg-OH (SEQ ID NO: 5) acetate salt (disulfide bonds, air oxidized).

Linkers

In some aspects, the peptides of the present disclosure are directly conjugated to a detectable label, such as a dye, fluorescent moiety or the like such that no additional amino acids, carbohydrates, nucleic acids, polymers, organic chains, or the like are added to the chlorotoxin or chlorotoxin variant and/or the dye, fluorescent moiety or the like to comprise the chlorotoxin conjugates described herein. In some other aspects, a linker is used to conjugate the chlorotoxin or chlorotoxin variant is not directly conjugated to a dye, fluorescent moiety or the like such that additional amino acids, carbohydrates, nucleic acids or the like are added to the chlorotoxin or chlorotoxin variant and/or the dye, fluorescent moiety or the like to comprise the chlorotoxin conjugates described herein. A "linker" as used herein refers to at least one compound comprising two functional groups that are capable of reacting specifically with other moieties to form covalent or non-covalent linkages. Such moieties can include, but are not limited to, the side groups on naturally occurring amino acids or non-natural amino acids or peptides which contain such natural or non-natural amino acids. By way of example, a linker has a functional group reactive with a group on a first peptide, and another functional group which is reactive with a group on a second peptide, whereby forming a conjugate that includes the first peptide, the linker and the second peptide. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; and 4,569,789 which are incorporated by reference herein in their entirety.

The term "linkage," as used herein refers to a bond or a chemical moiety formed from a chemical reaction between the functional group of a linker and another molecule. Such bonds can include, but are not limited to, covalent linkages and non-covalent bonds, while such chemical moieties include, but are not limited to, esters, carbonates, imines phosphate esters, hydrazones, acetals, orthoesters, peptide linkages, and oligonucleotide linkages. Hydrolytically stable linkages means that the linkages are substantially stable in water and do not react with water at neutral pH values, including but not limited to, under physiological conditions for an extended period of time, perhaps even indefinitely.

Hydrolytically unstable or degradable linkages mean that the linkages are degradable in water or in aqueous solutions, including for example, blood. Enzymatically unstable or degradable linkages mean that the linkage is often degraded by one or more enzymes. By way of example, PEG and related polymers include degradable linkages in the polymer backbone or in the linker group between the polymer backbone and one or more of the terminal functional groups of the polymer molecule. Such degradable linkages can include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable linkages can include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The conjugates for use in the method described herein can be conjugated by using any art-recognized method forming a complex including covalent, ionic, or hydrogen bonding of the ligand to the imaging agent, either directly or indirectly via a linking group such as a linker. The conjugate can typically be formed by covalent bonding of the ligand to the imaging agent through the formation of amide, ester or imino bonds between acid, aldehyde, hydroxy, amino, or hydrazo groups on the respective components of the complex or, for example, by the formation of disulfide bonds.

In addition, structural modifications of a linker portion of the conjugates are contemplated herein. For example, a number of amino acid substitutions are often made to the linker portion of the conjugate, including but not limited to naturally occurring amino acids, as well as those available from conventional synthetic methods. In one aspect, beta, gamma, and longer chain amino acids are used in place of one or more alpha amino acids. In another aspect, the stereochemistry of the chiral centers found in such molecules is selected to form various mixture of optical purity of the entire molecule, or only of a subset of the chiral centers present. In another aspect, the length of the peptide chain included in the linker is shortened or lengthened, either by changing the number of amino acids included therein, or by including more or fewer beta, gamma, or longer chain amino acids. In another aspect, the selection of amino acid side chains in the peptide portion is made to increase or decrease the relative hydrophilicity of the linker portion specifically or of the overall molecule generally.

Similarly, the length and shape of other chemical fragments of the linkers described herein can often be modified. In some aspects, the linker includes an alkylene chain. The alkylene chain can often vary in length, or can include branched groups, or can include a cyclic portion, which can be in line or spiro relative to the allylene chain. In another aspect, where the linker includes a beta thiol releasable fragment, it is appreciated that other intervening groups connecting the thiol end to the hydroxy or carbonate end are used in place of the ethylene bridge, such as but not limited to optionally substituted benzyl groups, where the hydroxy end is connected at the benzyl carbon and the thiol end is connected through the ortho or para phenyl position, and vice versa.

Direct attachment can be achieved by covalent attachment of a peptide to another molecule. For example, the peptide is attached to a terminus of the amino acid sequence of a larger polypeptide or peptide molecule, or could be attached to a side chain, such as the side chain of a lysine, serine, threonine, cysteine, tyrosine, aspartic acid, a non-natural amino acid residue, or glutamic acid residue. The attachment can be via an amide bond, an ester bond, an ether bond, a carbamate bond, a carbon-nitrogen bond, a triazole, a macrocycle, an oxime bond, a hydrazone bond, a carbon-carbon single double or triple bond, a disulfide bond, or a thioether bond. In some embodiments, similar regions of the disclosed peptide(s) itself (such as a terminus of the amino acid sequence, an amino acid side chain, such as the side chain of a lysine, serine, threonine, cysteine, tyrosine, aspartic acid, a non-natural amino acid residue, or glutamic acid residue, via an amide bond, an ester bond, an ether bond, a carbamate bond, a carbon-nitrogen bond, a triazole, a macrocycle, an oxime bond, a hydrazone bond, a carbon-carbon single double or triple bond, a disulfide bond, or a thioether bond, or linker as described herein) may be used to link other molecules.

Attachment via a linker can involve incorporation of a linker moiety between the other molecule and the peptide. The peptide and the other molecule can both be covalently attached to the linker. The linker can be cleavable, noncleavable, self-immolating, hydrophilic, or hydrophobic. The linker can have at least two functional groups, one bonded to the other molecule, one bonded to the peptide, and a linking portion between the two functional groups. The use of a cleavable linker can permit release of the conjugated moiety (e.g., a detectable agent or a therapeutic agent) from the peptide, e.g., after targeting to a tissue of interest. The cleavable linker can comprise a cleavage site for matrix metalloproteinases, thrombin, cathepsins, or beta-glucuronidase. In other aspects, the linker can be a hydrolytically labile linker. A hydrolytically labile linker, (amongst other cleavable linkers described herein) can be advantageous in terms of releasing a fluorophore molecule or other detectable or therapeutic agents from the peptide. For example, an agent (e.g., a detectable agent or a therapeutic agent) in a conjugate form with the peptide may not be active, but upon release from the conjugate after targeting to the cartilage, the agent can be active. In some cases the linker can be enzyme cleavable, e.g., a valine-citrulline linker. Alternatively or in combination, the linker can be cleavable by other mechanisms, such as via pH, reduction, or hydrolysis. Other cleavable linkers can include an ester bond using standard 1-ethyl-3-(3-dimethylaminopropyl)carbodiimide (EDC)-, dicylcohexylcarbodiimide (DCC)-, thionyl chloride-, or phosphorous chloride-based bioconjugation chemistries. These linkers can be cleaved by esterases, MMP, cathepsin B, a protease, or thrombin. In still other aspects, the peptide can be linked to the detectable agent via a noncleavable linker.

Non-limiting examples of the functional groups for attachment can include functional groups capable of forming, for example, an amide bond, an ester bond, an ether bond, a carbonate bond, a carbamate bond, or a thioether bond. Non-limiting examples of functional groups capable of forming such bonds can include amino groups; carboxyl groups; hydroxyl groups; aldehyde groups; azide groups; alkyne and alkene groups; ketones; hydrazides; acid halides such as acid fluorides, chlorides, bromides, and iodides; acid anhydrides, including symmetrical, mixed, and cyclic anhydrides; carbonates; carbonyl functionalities bonded to leaving groups such as cyano, succinimidyl, and N-hydroxysuccinimidyl; hydroxyl groups; sulfhydryl groups; and molecules possessing, for example, alkyl, alkenyl, alkynyl, allylic, or benzylic leaving groups, such as halides, mesylates, tosylates, triflates, epoxides, phosphate esters, sulfate esters, and besylates.

Non-limiting examples of the linking portion can include alkylene, alkenylene, alkynylene, polyether, such as polyethylene glycol (PEG), hydroxy carboxylic acids, polyester, polyamide, polyamino acids, polypeptides, cleavable peptides, valine-citrulline, aminobenzylcarbamates, D-amino acids, and polyamine, any of which being unsubstituted or substituted with any number of substituents, such as halogens, hydroxyl groups, sulfhydryl groups, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, epoxides, and ester groups.

Non-limiting examples of linkers can include:

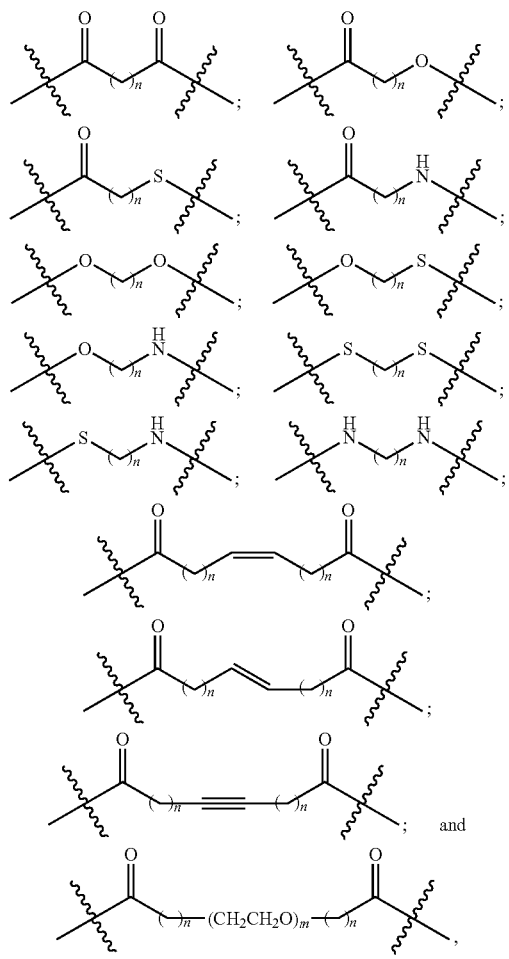

wherein each n is independently 0 to about 1,000; 1 to about 1,000; 0 to about 500; 1 to about 500; 0 to about 250; 1 to about 250; 0 to about 200; 1 to about 200; 0 to about 150; 1 to about 150; 0 to about 100; 1 to about 100; 0 to about 50; 1 to about 50; 0 to about 40; 1 to about 40; 0 to about 30; 1 to about 30; 0 to about 25; 1 to about 25; 0 to about 20; 1 to about 20; 0 to about 15; 1 to about 15; 0 to about 10; 1 to about 10; 0 to about 5; or 1 to about 5. In some embodiments, each n is independently 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50. In some embodiments, m is 1 to about 1,000; 1 to about 500; 1 to about 250; 1 to about 200; 1 to about 150; 1 to about 100; 1 to about 50; 1 to about 40; 1 to about 30; 1 to about 25; 1 to about 20; 1 to about 15; 1 to about 10; or 1 to about 5. In some embodiments, m is 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, 9, at 39, about 40, about 41, about 42, about 43, about 44, about 45, about 46, about 47, about 48, about 49, or about 50.

Formulations of Chlorotoxin Conjugates

In various aspects, the present disclosure provides compositions comprising the above-described compounds and a pharmaceutically acceptable carrier. In some aspects, the composition is formulated for parenteral administration. In further aspects, the composition is formulated for intravenous administration, intramuscular administration, subcutaneous administration, intratumor administration, or a combination thereof.

Certain methods described herein comprise administering to the subject an intravenous pharmaceutical composition comprising a chlorotoxin conjugate, for example, as described herein. Intravenous pharmaceutical compositions of chlorotoxin conjugates can include any formulation suitable for administration to a subject via any intravenous method, including a bolus, a slow-bolus, an infusion which occurs over time, or any other intravenous method known in the art, as discussed further herein. "Product" or "dosage form" as used herein refers to any solid, semi-solid, lyophilized, aqueous, liquid or frozen formulation or preparation used for administration. Upon administration, the rate of release of an active moiety from a product can often be greatly influenced by the excipients and/or product characteristics which make up the product itself. For example, an enteric coat on a tablet is designed to separate that tablet's contents from the stomach contents to prevent, for example, degradation of the stomach which often induces gastrointestinal discomfort or injury. According to the currently accepted conventional understanding, systemic exposure of the active moiety can be relatively insensitive to the small formulation changes.

As used herein "pharmaceutically acceptable" or "pharmacologically acceptable" includes molecular entities and compositions that do not produce an adverse, allergic or other untoward reaction when administered to a subject, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can often also be incorporated into the compositions.

In various aspects, the present compositions comprise a concentration of the compound as an active pharmaceutical ingredient having a concentration from 0.1 mg/mL to 100 mg/mL. In some aspects, the concentration of the compound is from 0.1 mg/mL to 5 mg/mL, from 0.1 mg/mL to 10 mg/mL, from 0.1 mg/mL to 15 mg/mL, from 0.1 mg/mL to 20 mg/mL, from 0.1 mg/mL to 30 mg/mL, from 0.1 mg/mL to 40 mg/mL, from 0.1 mg/mL to 50 mg/mL, from 0.1 mg/mL to 60 mg/mL, from 0.1 mg/mL to 70 mg/mL, from 0.1 mg/mL to 80 mg/mL, or from 0.1 mg/mL to 90 mg/mL. In further aspects, the concentration of the compound is from 1 mg/mL to 20 mg/mL. In still other aspects, the concentration of the compound is from 4 mg/mL to 10 mg/mL. In additional aspects, the concentration of the compound is from 5 mg/mL to 8 mg/mL. In yet further aspects, the concentration of the compound is from 5 mg/mL to 6 mg/mL. In other aspects, the concentration of the compound is from 15 mg/mL to 35 mg/mL. In still other aspects, the concentration of the compound is from 15 mg/mL to 25 mg/mL. In yet other aspects, the concentration of the compound is from 15 mg/mL to 50 mg/mL, from 15 mg/mL to 60 mg/mL, 15 mg/mL to 70 mg/mL, 15 mg/mL to 80 mg/mL, or 15 mg/mL to 90 mg/mL.

In some embodiments, the pharmaceutically acceptable carrier has a pH of about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In still other embodiments, the pharmaceutically acceptable carrier has a pH within a range from about 6.0 to about 7.5. In other embodiments, the pharmaceutically acceptable carrier has a pH within a range from about 5.0 to about 9.0.

In some embodiments, the composition has a pH of about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In still other embodiments, the composition has a pH within a range from about 6.0 to about 7.5. In other embodiments, the composition has a pH within a range from about 5.0 to about 9.0.

In some aspects, a pharmaceutically acceptable carrier comprises tris, D-mannitol, L-histidine, L-methionine, polysorbate 20, or a combination thereof. For example, in some aspects, a pharmaceutically acceptable carrier comprises tris and D-mannitol. In some aspects, a pharmaceutically acceptable carrier comprises L-histidine and D-mannitol. In some aspects, the pharmaceutically acceptable carrier comprises L-histidine and D-mannitol with polysorbate 20. In some aspects, the pharmaceutically acceptable carrier comprises L-histidine, D-mannitol, and L-methionine.

In some aspects, the pharmaceutically acceptable carrier comprises L-histidine, D-mannitol, polysorbate 20, and a pH of about 6.8. In some aspects, the pharmaceutically acceptable carrier comprises L-histidine, D-mannitol, polysorbate 20, and a pH within a range of about 6 to about 7.5. In some aspects, the pharmaceutically acceptable carrier comprises L-histidine, D-mannitol, polysorbate 20, and a pH within a range of about 5 to about 9. In some aspects, the pharmaceutically acceptable carrier comprises L-histidine, D-mannitol, and a pH of about 6.8. In some aspects, the pharma-ceutically acceptable carrier comprises L-histidine, D-mannitol, and a pH within a range of about 6 to about 7.5. In some aspects, the pharmaceutically acceptable carrier comprises L-histidine, D-mannitol, and a pH within a range of about 5 to about 9. In some aspects, the pharmaceutically acceptable carrier comprises L-histidine, D-mannitol, polysorbate 20, trehalose, and a pH of about 6.8. In some aspects, the pharmaceutically acceptable carrier comprises L-histidine, D-mannitol, polysorbate 20, trehalose, and a pH within a range of about 6 to about 7.5. In some aspects, the pharmaceutically acceptable carrier comprises L-histidine, D-mannitol, polysorbate 20, trehalose, and a pH within a range of about 5 to about 9.

A pharmaceutical composition comprising a chlorotoxin conjugate can be formulated according to known methods to prepare pharmaceutically useful compositions, for example, as found in "Excipient Selection in Parenteral Formulation Development" Pramanick et. al., Pharma Times, Vol. 45, No. 3, March 2013, incorporated in its entirety herein by reference. In some aspects, the chlorotoxin conjugate is combined with a pharmaceutically acceptable carrier. A composition is said to be a pharmaceutically acceptable carrier if its administration is tolerated by a recipient patient. Sterile phosphate-buffered saline is one example of a pharmaceutically acceptable carrier. Other suitable carriers are well-known to those in the art. See, for example, Gennaro (ed.), Remington's Pharmaceutical Sciences, 19th Edition (Mack Publishing Company 1995).

Formulations for administration of chlorotoxin conjugates are typically provided but are not limited to as liquid, solid or semi-solid products or dosage forms, exemplified by tablets, capsules, pellets, a powder or a lyophilized product. In some aspects, the chlorotoxin conjugate is formulated to comprise no additional materials except for a pharmaceutical carrier. In some other aspects, the chlorotoxin conjugate is formulated such that it comprises a core "matrix material" which encapsulates, binds to, coats or is adjacent to the chlorotoxin conjugate. In some other aspects, the chlorotoxin conjugate and matrix material further comprises a protective coatings. Various formulations are well-known to those in the art. See, for example, Gennaro (ed.), Remington's Pharmaceutical Sciences, 19th Edition (Mack Publishing Company 1995).

Suitable excipients for use with chlorotoxin conjugates are often included in formulations for intravenous use, for example, an injection. Injections are sterile, pyrogen-free solutions or dispersions (emulsions or suspensions) of one or more active ingredients in a suitable vehicle or carrier. Injections that are dispersions should remain sufficiently stable so that, after shaking, a homogeneous dose can be withdrawn. More specifically, formulations which can include chlorotoxin conjugates and one or more but not limited to suitable excipients, exemplified by matrix materials, binders, lubricants, glidants or disintegrants which aid in modulating the PK profile of administered chlorotoxin conjugates are preferred. In some aspects, compositions comprise chlorotoxin conjugates in combination with one or more suitable excipients and one or more specific product characteristics (such as dissolution or water content) which result in improved pharmacokinetic profiles of chlorotoxin conjugates in vivo. Thus, the in vivo performance of chlorotoxin conjugates dosage forms/products included herein can be based upon the composition of the excipients added during manufacturing and/or the final product characteristics generated through specific processing parameters and methods. Other excipients are well-known to those in the art. See, for example, Gennaro (ed.), Remington's Pharmaceutical Sciences, 19th Edition (Mack Publishing Company 1995).

Suitable carriers for intravenous administration can include, for example, but are not limited to, physiological saline or phosphate buffered saline (PBS), Tris, and solutions containing solubilizing agents, such as glucose, polyethylene glycol, polypropylene glycol, additional agents such as histidine, dextrose, mannitol and mixtures thereof. In some aspects, carriers for intravenous administration include a mixture of histidine and dextrose, Tris and dextrose or Tris and mannitol. Other carriers are well-known to those in the art. See, for example, Gennaro (ed.), Remington's Pharmaceutical Sciences, 19th Edition (Mack Publishing Company 1995).

The formulation can often include an aqueous vehicle. Aqueous vehicles include, by way of example and without limitation, sodium chloride solution, Ringers solution, isotonic dextrose solution, sterile water solution, dextrose and lactated Ringers solution. Nonaqueous vehicles can include, by way of example and without limitation, fixed oils of vegetable origin, cottonseed oil, corn oil, sesame oil and peanut oil, benzyl benzoate, castor oil, N,N-dimethylacetamide, ethanol, dehydrated ethanol, glycerin, glycerol, N-methyl-2-pyrrolidone, polyethylene glycol and any derivative thereof, propylene glycol, safflower oil and soybean oil. Other vehicles are well-known to those in the art. See, for example, Gennaro (ed.), Remington's Pharmaceutical Sciences, 19th Edition (Mack Publishing Company 1995).

In some aspects, the composition the pharmaceutically acceptable carrier comprises an osmolyte. In some aspects, the osmolyte comprises a sugar, a sugar alcohol, or a combination thereof.

In certain aspects, the composition comprises a sugar alcohol. In certain aspects, the composition comprises a sugar alcohol selected from sorbitol, inositol, mannitol, xylitol, glycerol, or a combination thereof. In further aspects, the sugar alcohol comprises mannitol. In certain aspects, the composition comprises from about 2% to about 20% (wt/vol %) sugar alcohol. In some aspects, the composition comprises from about 2% to about 10% (wt/vol %) sugar alcohol. In some aspects, the composition comprises from about 3% to about 10% (wt/vol %) sugar alcohol. In further aspects, the composition comprises about 5% (wt/vol %) sugar alcohol. In certain aspects, the composition comprises from about 2% to about 20% (wt/vol %) mannitol. In some aspects, the composition comprises from about 2% to about 10% (wt/vol %) mannitol. In further aspects, the composition comprises about 5% (wt/vol %) mannitol.

In other aspects, the composition comprises a sugar. In certain aspects, the sugar is selected from trehalose, lactose, sucrose, glucose, galactose, maltose, mannose, fructose, dextrose, or a combination thereof. In additional aspects, the sugar is selected from trehalose, sucrose, or a combination thereof. In some aspects, the composition comprises from about 1% to about 40% (wt/vol %) of sugar. In other aspects, the composition comprises from about 1% to about 20% (wt/vol %) of sugar. In additional aspects, the composition comprises about 2% (wt/vol %) of sugar. In some aspects, the composition comprises from about 1% to about 40% (wt/vol %) of trehalose, sucrose, or a combination of trehalose and sucrose. In other aspects, the composition comprises from about 1% to about 20% (wt/vol %) of trehalose, sucrose, or a combination of trehalose and sucrose. In additional aspects, the composition comprises about 2% (wt/vol %) of trehalose, sucrose, or a combination of trehalose and sucrose.

In certain aspects, the composition further comprises an osmolyte selected from glycine, carnitine, ethanolamine, their phosphates, mono sugars, or a combination thereof.

In some aspects, the present compositions are isotonic. In other aspects, the compositions are about isotonic.

In certain aspects, the ionic strength of the composition is less than or equal to 60 mM. In certain aspects, the composition comprises an ionic strength less than or equal to 50 mM. In certain aspects, the ionic strength of the composition is less than or equal to 40 mM. In certain aspects, the ionic strength of the composition is less than or equal to 30 mM. In certain aspects, the ionic strength of the composition is less than or equal to 20 mM. In other aspects, the ionic strength of the composition is less than or equal to 10 mM.

Antimicrobial agents in bacteriostatic or fungistatic concentrations can typically be added to preparations packaged in multiple dose containers which can include, by way of example and without limitation, phenols or cresols, mercurials, benzyl alcohol, chlorobutanol, methyl and propyl p-hydroxybenzoic acid esters, thimerosal, benzalkonium chloride and benzethonium chloride. Other antimicrobial agents are well-known to those in the art. See, for example, Gennaro (ed.), Remington's Pharmaceutical Sciences, 19th Edition (Mack Publishing Company 1995).

Buffers can include, by way of example and without limitation, acetate, ammonium sulfate, ammonium hydroxide, arginine, aspartic acid, benzene sulfonic acid, benzoate sodium, benzoate acid, carbonate, sodium carbonate, carbon dioxide, citrate, diethanolamine, glucono delta lactone, glycine, glycine HCl, histidine, histidine HCl, hydrochloric acid, hydrobromic acid, lysine maleic acid, meglumine, methanesulfonic acid, monoethanolamine, phosphate, sodium phosphate, citrate, succinate sodium, sulfuric acid, tartarate sodium, trimethamine, sodium citrate, hydroxide, sodium hydroxide, Tris base, Tris base-65, Tris acetate, Tris HCl, and Tris HCl-65.

In various aspects, the pharmaceutically acceptable carrier comprises a buffer. In some aspects, the buffer is selected from tris, HEPES, histidine, ethylene diamine, or a combination thereof. In other aspects, the buffer is selected from tris, histidine, or a combination thereof. In further aspects, the buffer comprises histidine, which is optionally L-histidine. In another aspect, the composition comprises a buffer comprising histidine, tris, HEPES, ethylene diamine, or a combination thereof. In additional aspects, the composition comprises at least 100 mM histidine. In further aspects, the composition comprises at least or equal to 50 mM histidine. In some aspects, the composition comprises at least or equal to 20 mM histidine. In additional aspects, the composition comprises 10 to 100 mM histidine. In other aspects, the composition comprises 10 to 20 mM histidine. In other aspects, the composition comprises 0 to 50 mM hisitidine. In further aspects, the composition comprises at least 100 mM tris. In some aspects, the composition comprises at least or equal to 50 mM tris. In additional aspects, the composition comprises at least or equal to 20 mM tris. In other aspects, the composition comprises 10 to 20 mM tris. In other aspects, the composition comprises 0 to 20 mM tris. In some aspects, the composition comprises from about 0 mM to about 50 mM histidine, from about 0 mM to about 20 mM tris, about 20 mM methionine, from about 3% to about 10% (wt/vol %) sugar alcohol, and a pH within a range from about 6 to about 7.5.

Antioxidants can include, by way of example and without limitation, sodium bisulfate, acetone sodium bisulfate, argon, ascorbyl palmitate, ascorbate sodium, ascorbate acid, butylated hydroxy anisole, butylated hydroxy toluene, cysteine, cystenate HCl, dithionite sodium, gentistic acid, gentistic acid ethanoloamine, glutamate monosodium, gluta-thione, formaldehyde solfoxylate sodium, metabisulfite potassium, metabisulfite sodium, methionine, monothio-glycerol, nitrogen, propyl gallate, sulfite sodium, tocopherol alpha, alpha tocopherol hydrogen succinate, and thioglycolyate sodium.

In some aspects, the compositions comprise an antioxidant, a free radical scavenger, a quencher, an antioxidant synergist, or a combination thereof.

In some aspects, the antioxidant is selected from methionine, butylated hydroxytoluene, butylated hydroxyanisole, propyl gallate, or a combination thereof. In other aspects, the antioxidant comprises methionine. In further aspects, the antioxidant is L-methionine. In certain aspects, the compositions comprise at least or equal to 20 mM methionine. In other aspects, the compositions comprise at least or equal to 5 mM methionine. In still other aspects, the compositions comprise at least or equal to 10 mM methionine. In further aspects, the compositions comprise at least or equal to 50 mM methionine. In other aspects, the compositions comprise 10 to 20 mM methionine. In other aspects, the compositions comprise 0 to 50 mM methionine.

Suspending, emulsifying and/or dispersing agents can include, by way of example and without limitation, sodium carboxymethylcelluose, hydroxypropyl methylcellulose, Polysorbate 80 (TWEEN® 80), and polyvinylpyrrolidone.

In various aspects, the compositions comprise a surfactant. In certain aspects, the surfactant is selected from polysorbate 20, polysorbate 80, a pluronic, polyoxyethylene sorbitan mono-oleate, polyethylene mono-laureate, N-actylglucoside, or a combination thereof. In certain aspects, the surfactant is polysorbate 20. In further aspects, the compositions comprise from 0.0001% to 0.1% (wt/vol %) polysorbate 20. In additional aspects, the compositions comprise cyclodextrin. In further aspects, the cyclodextrin comprises (2-hydroxypropyl)-j-cyclodextrin.

A sequestering or chelating agent of metal ions can include, by way of example and without limitation, calcium disodium EDTA, disodium EDTA, sodium EDTA, calcium versetaminde sodium, calteridol, and DPTA. In some aspects, the present compositions comprise a metal chelator. In certain aspects, the metal chelator is selected from EDTA, deferoxamine mesylate, EGTA, fumaric acid, and malic acid, salts thereof, or combinations thereof. In further aspects, the metal chelator comprises EDTA or salts thereof. In certain aspects, the compositions have an EDTA concentration of about 0.1 mg/ml to about 1.0 mg/ml.

Other isotonic agents, buffers, antioxidants, anesthetics, suspending and dispersing agents, emulsifying agents and chelating agents are well-known to those in the art. See, for example, Gennaro (ed.), Remington's Pharmaceutical Sciences, 19th Edition (Mack Publishing Company 1995).

Pharmaceutical carriers can also include, by way of example and without limitation, ethyl alcohol, polyethylene glycol and propylene glycol for water miscible vehicles and sodium hydroxide, hydrochloric acid, citric acid or lactic acid. Other pharmaceutical carriers are well-known to those in the art. See, for example, Gennaro (ed.), Remington's Pharmaceutical Sciences, 19th Edition (Mack Publishing Company 1995).

The chlorotoxin conjugates described herein can often be formulated using a variety of parameters, including by way of example and without limitation, pH, molarity, % weight/volume, % volume/volume, and the like. Other factors can be considered in the formulation of, stability of, storage of, shipping of chlorotoxin conjugates can include by way of example and without limitation, the gas environment, container material, container color, cap material, cap color, presence of additional aspects, such as antioxidants, stabilizers, photoprotective compounds, protectants, sugars, ion chelators, ion donors, or the like. Any factor which serves as any one of the above factors known to one of ordinary skill in the art can often be used with the chlorotoxin conjugates described herein but not limited as such.

The preparation of pharmaceutical or pharmacological compositions are known to those of skill in the art in light of the present disclosure. General techniques for formulation and administration can be found in "Remington: The Science and Practice of Pharmacy, Twentieth Edition," Lippincott Williams & Wilkins, Philadelphia, Pa. Tablets, capsules, pills, powders, granules, dragees, gels, slurries, ointments, solutions suppositories, injections, inhalants, and aerosols are examples of such formulations.

The chlorotoxin conjugates can often be stored at various temperatures, including by way of example and without limitation, freezing, for example at about −20° C., about −70° C., about −80° C., about −100° C., about −120° C., about −150° C., about −200° C. or more than about −200° C., cold storage, for example at about 10° C., about 5° C., about 4° C., about 2° C., about 0° C., about −2° C. or more than about −5° C., or any other suitable temperature such that the composition remains stable.

In some aspects, compositions comprising the compounds described herein are stored as lyophilized solids. In some aspects, the present disclosure provides methods for producing the lyophilized composition, the method comprising providing the composition, and lyophilizing the composition, thereby producing the lyophilized composition.

Using lyophilization, it can be possible to store the compounds in a manner that maintains physiological or otherwise optimal pH, isotonicity and stability. Such materials can include pH buffers, preservatives, tonicity adjusting agents, anti-oxidants, other polymers (e.g., viscosity adjusting agents or extenders) and excipients to stabilize the labile protein against the stresses of drying and storage of the dried product. Specific illustrative examples of such additives can include phosphate, citrate, or borate buffers; thimerosal; sorbic acid; methyl or propyl paraben, and chlorobutanol preservatives; sodium chloride: polyvinyl alcohol, polyvinyl pyrrolidone; mannitol, dextrose, dextran, lactose, sucrose, ethylene diamine tetra-acetic acid, and the like. Suitable formulations, known in the art, can be found in Remington's Pharmaceutical Sciences (latest edition), Mack Publishing Company, Easton, Pa.; Arakawa et al. (1990), supra; Carpenter et al. (1991), supra; and Pikal (1990), supra.

In certain aspects, the pharmaceutically acceptable carrier comprises a reconstitution stabilizer. In other aspects, the reconstitution stabilizer comprises a water-soluble polymer. In additional aspects, the water-soluble polymer is selected from a polaxamer, a polyol, a polyethylene glycol, a polyvinylalcohol, a hydroxyethyl starch, dextran, polyvinylpyrrolidene poly(acrylic acid), or a combination thereof.

The term "reconstitution stabilizer" means any excipient which is capable of preventing aggregation of a reconstituted protein in an aqueous medium. Excipients possessing the necessary characteristics for the present invention are well-known in the art and generally function by the mechanisms of charge repulsion, steric hindrance, hydrophobic binding or specific high-affinity binding to the dried protein. Exemplary excipients include various osmolytes, various salts, water soluble synthetic and natural polymers, surfactants, sulfated polysaccharides, carrier proteins, buffers and the like (Manning et al. (1989), Pharmaceutical Research, 6:903-918; and Paborji, et al. (1994), Pharmaceutical Research, 11:764-771).

The present compounds and an effective amount of the reconstitution stabilizer can be admixed under conditions effective to reduce aggregation of present compounds upon reconstitution with the reconstitution medium (e.g., a solvent and optionally other components such as antibacterials). The reconstitution stabilizer can be admixed with the compounds at a suitable time before, during or after reconstitution. In one aspect, the reconstitution stabilizer will be pre-dissolved in the reconstitution medium. The compound can be reconstituted at a temperature which is above the freezing point of the reconstitution medium, but which will not degrade the compound and which will not be deleterious to the reconstitution stabilizer. In one aspect, the temperature will be between about 2° C. to 50° C. The time taken to mix the reconstitution stabilizer and the dried compound should be for a sufficient period to prepare a suitable admixture. In one aspect, the mixing will be for between about 1 to 30 minutes. Generally, the reconstituted formulation can be used soon after reconstitution.

In certain aspects, the present compositions are reconstituted from a lyophilized form. In other aspects, the present disclosure provides methods for producing the reconstituted composition, the method comprising providing a lyophilized composition; and reconstituting the composition with a solution to produce a reconstituted composition. In various aspects, the reconstituting solution comprises water. In some aspects, the reconstituting solution is selected from sterile water, physiological saline solution, glucose solution or other aqueous solvents (e.g., alcohols such as ethyl, n-propyl or isopropyl, butyl alcohol), or a combination thereof, which are capable of dissolving the dried composition and compatible with the selected administration route and which does not negatively interfere with the compound and the reconstitution stabilizers employed.

Dosages and Methods of Administration of Chlorotoxin Conjugates

The product or dosage form characteristics which can result from processing methods and/or parameters for generating formulations such as powders, lyophilized compositions, and the like, and can include, but are not limited to, density, water content, friability, disintegration, dissolution profile(s), shape, size, weight, uniformity and composition of the particles. These product characteristics can often be modulated in a number of ways and affect the final in vitro and/or in vivo performance of the formulations. Product or dosage form characteristics can often be a consequence of excipient selection, excipient composition, manufacturing methods applied, or a combination of any of these. The combination of excipients as well as product characteristics (including processing methods or processing parameters) of the final dosage form can ultimately determine the pharmacokinetic profile of the active ingredient in vivo. The administered chlorotoxin conjugate formulations described herein can often be processed or manufactured under specific conditions such as, for example, mixing methods (including sieve size, rpm, and milling), drying time, conditions, environmental parameters (e.g., temperature, humidity and combinations thereof) which themselves can modulate the pharmacokinetic profile of chlorotoxin compositions in vivo (i.e., increase the average $C_{max}$ or AUC). In order to quantitatively compare one formulation to another, one can measure several of these product or dosage form characteristics. This can also necessary when attempting to duplicate multiple batches.

Dissolution and drug release from formulations can depend on many factors including the solubility and concentration of the active ingredient, the nature and composition of the excipients, content uniformity, water content, product shape and size, porosity, disintegration time, and other factors. The release of a drug or active ingredient from a final dosage form in vitro is typically characterized by its dissolution profile under standardized conditions (using United States Pharmacopeia (USP) or similar accepted methods for reference) and at the appropriate pH, often a neutral pH. The dissolution profile shows the amount of drug released over time into the test media under specified conditions. Standard conditions make use of buffers at an appropriate pH in order to best mimic the pH of a subject's blood.

Typically a therapeutically effective dosage can be formulated to contain a dose of at least about 0.1 mg up to about 100 mg or more, such as more than 100 mg of chlorotoxin conjugate. In some aspects, the effective dosage is formulated to contain a dose of at least about 0.01 mg, about 0.02 mg, about 0.03 mg, about 0.05 mg, about 0.07 mg, about 0.1 mg, about 0.2 mg, about 0.3 mg, about 0.35 mg, about 0.375 mg, about 0.4 mg, about 0.5 mg, about 0.6 mg, about 0.7 mg, about 0.75 mg, about 0.8 mg, about 0.9 mg, about 1 mg, about 1.3 mg, about 1.4 mg, about 1.5 mg, about 1.8 mg, about 1.9 mg, about 2 mg, about 2.4 mg, about 3 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 40 mg, about 45 mg, about 50 mg, about 55 mg, about 60 mg, about 70 mg, about 80 mg, about 90 mg, about 100 mg, about 150 mg or about 200 mg or more of chlorotoxin conjugate. In an exemplary aspect, the dose is 0.03 mg for a mouse, 1 mg for a dog, 0.3 mg for a rat, 0.6 mg for a monkey, and 6 mg or 12 mg for a human via intravenous administration.

In some exemplary aspects, a therapeutically effective dosage is formulated to contain a dose of 1 mg to 200 mg or more for a human. In other aspects, the effective dosage is formulated to contain a dose of 1 mg to 5 mg, of 1 mg to 10 mg, of 1 mg to 20 mg, of 1 mg to 30 mg, of 1 mg to 40 mg, of 1 mg to 50 mg, of 1 mg to 60 mg, of 1 mg to 70 mg, of 1 mg to 80 mg, of 1 mg to 90 mg, of 1 mg to 100 mg, of 1 mg to 120 mg, of 1 mg to 140 mg, of 1 mg to 160 mg, of 1 mg to 180 mg, 3 mg to 5 mg, of 3 mg to 10 mg, of 3 mg to 20 mg, of 3 mg to 30 mg, of 3 mg to 40 mg, of 3 mg to 50 mg, of 3 mg to 60 mg, of 3 mg to 70 mg, of 3 mg to 80 mg, of 3 mg to 90 mg, of 3 mg to 100 mg, of 3 mg to 120 mg, of 3 mg to 140 mg, of 3 mg to 160 mg, of 3 mg to 180 mg, of 3 mg to 200 mg, of 10 mg to 20 mg, of 10 mg to 30 mg, of 10 mg to 40 mg, of 10 mg to 50 mg, of 10 mg to 60 mg, of 10 mg to 70 mg, of 10 mg to 80 mg, of 10 mg to 90 mg, of 10 mg to 100 mg, of 10 mg to 120 mg, of 10 mg to 140 mg, of 10 mg to 160 mg, of 10 mg, to 180 mg, of 10 mg to 200 mg, of 20 mg to 50 mg, of 20 mg to 75 mg, of 20 mg to 100 mg, of 20 mg to 120 mg, of 20 mg, to 140 mg, of 20 mg to 160 mg, of 20 mg to 180 mg, of 20 mg to 200 mg, of 30 mg to 50 mg, of 30 mg to 75 mg, of 30 mg to 100 mg, of 30 mg to 120 mg, of 30 mg to 140 mg, of 30 mg to 160 mg, of 30 mg to 180 mg, of 30 mg to 200 mg, of 50 mg to 60 mg, of 50 mg to 75 mg, of 50 mg to 100 mg, of 50 mg to 120 mg, of 50 mg to 140 mg, of 50 mg to 160 mg, of 50 mg to 180 mg, of 50 mg to 200 mg, of 75 mg to 80 mg, of 75 mg to 90 mg, of 75 mg to 100 mg, of 75 mg to 120 mg, of 75 mg to 140 mg, of 75 mg to 160 mg, of 75 mg to 180 mg, of 75 mg to 200 mg, of 100 mg to 120 mg, of 100 mg to 140 mg, of 100 mg to 160 mg, of 100 mg to 180 mg, of 100 mg to 200 mg, of 120 mg to 140 mg, of 120 mg to 160 mg, of 120 mg to 180 mg, of 120 mg to 200 mg, of 140 mg to 160 mg, of 140 mg to 180 mg, of 140 mg to 200 mg, of 160 mg to 180 mg, of 160 mg to 200 mg, or of 180 mg to 200 mg.

The amount of chlorotoxin conjugate administered to a subject can often be the total about amount listed herein. In some aspects, the amount of chlorotoxin conjugate administered to a subject is often the about per milligram, gram or kilogram of subject weight for each amount listed herein. In other aspects, the amount of chlorotoxin conjugate administered to a subject is often the about per milliliter or liter of fluid volume for each amount listed herein. In yet other aspects, the amount of chlorotoxin conjugate administered to a subject is often the about per square millimeter, square centimeter or square meter of subject surface body area or subject body area for each amount listed herein.

As used herein a "dosage regimen" refers to the protocol used to administer an intravenous pharmaceutical formulation comprising chlorotoxin conjugate to a subject. In some aspects, the dosage regimen comprises a dose amount and dosing interval. In some aspects, the dosage regimen further comprises a dosing duration. As used herein "dosing duration" refers to the period of time over which a dose is administered. Furthermore, the dosage regimen comprises a method of administration. In some aspects, a method of administration comprises a bolus, a slow bolus, or an infusion.

As used herein, a "bolus" may refer to an intravenous injection administered over a short period of time. In one aspect, a bolus is manually administered over a short period of time. In other aspects, a bolus is administered via a pump or other automated mechanism over a short period of time. In some aspects, a bolus is administered over a period of time less than or equal to 5 seconds, less than or equal to 10 seconds, less than or equal to 15 seconds, less than or equal to 20 seconds, less than or equal to 25 seconds, less than or equal to 30 seconds, less than or equal to 35 seconds, less than or equal to 40 seconds, less than or equal to 45 seconds, less than or equal to 50 seconds, less than or equal to 55 seconds, less than or equal to 60 seconds, less than or equal to 65 seconds, less than or equal to 70 seconds, less than or equal to 75 seconds, less than or equal to 80 seconds, less than or equal to 85 seconds, less than or equal to 90 seconds, less than or equal to 95 seconds, less than or equal 100 seconds, less than or equal to 105 seconds, less than or equal to 110 seconds, less than or equal to 115 seconds, or less than or equal to 120 seconds.

As used herein, a "slow bolus" may refer to an intravenous injection administered over longer period of time than a bolus, but a shorter period of time than an infusion. In one aspect, a slow bolus is manually administered over a longer period of time than a bolus, but a shorter period of time than an infusion. In other aspects, a slow bolus is administered via a pump or other automated mechanism over a longer period of time than a bolus, but a shorter period of time than an infusion. In one aspect, a slow bolus is administered over a period of time within a range from about 2 minutes to about 5 minutes. In other aspects, a slow bolus is administered over a period of time within a range from about 2 minutes to about 4.9 minutes, about 2 minutes to about 4.8 minutes, about 2 minutes to about 4.8 minutes, about 2 minutes to about 4.7 minutes, about 2 minutes to about 4.6 minutes, about 2 minutes to about 4.5 minutes, about 2 minutes to about 4.4 minutes, about 2 minutes to about 4.3 minutes, about 2 minutes to about 4.4 minutes, about 2 minutes to about 4.3 minutes, about 2 minutes to about 4.2 minutes, about 2 minutes to about 4.1 minutes, about 2 minutes to about 4 minutes, about 2 minutes to about 3.9 minutes, about 2 minutes to about 3.8 minutes, about 2 minutes to about 3.7 minutes, about 2 minutes to about 3.6 minutes, about 2 minutes to about 3.5 minutes, about 2 minutes to about 3.4 minutes, about 2 minutes to about 3.3 minutes, about 2 minutes to about 3.2 minutes, about 2 minutes to about 3.1 minutes, about 2 minutes to about 3 minutes, about 2 minutes to about 2.9 minutes, about 2 minutes to about 2.8 minutes, about 2 minutes to about 2.7 minutes, about 2 minutes to about 2.6 minutes, about 2 minutes to about 2.5 minutes, about 2 minutes to about 2.4 minutes, about 2 minutes to about 2.3 minutes, about 2 minutes to about 2.2 minutes, or about 2 minutes to about 2.1 minutes. In other aspects, a slow bolus is administered over a period of time within the range of about 2.5 minutes to about 3 minutes, about 2.5 minutes to about 3.5 minutes, about 2.5 minutes to about 4 minutes, about 2.5 minutes to about 4.5 minutes, about 2.5 minutes to about 5 minutes, about 3 minutes to about 3.5 minutes, about 3 minutes to about 4 minutes, about 3 minutes to about 4.5 minutes, about 3 minutes to about 5 minutes, about 3.5 minutes to about 4 minutes, about 3.5 minutes to about 4.5 minutes, about 3.5 minutes to about 5 minutes, about 4 minutes to about 4.5 minutes, about 4 minutes about 5 minutes, or about 4.5 minutes to about 5 minutes.

As used herein, an "infusion" may refer to an intravenous injection administered over longer period of time than a bolus or a slow bolus. In one aspect, an infusion is administered via a pump or other automated mechanism over longer period of time than a bolus or a slow bolus. In other aspects, an infusion is manually administered over longer period of time than a bolus or a slow bolus. In other aspects, the infusion is administered over a period of time that is greater than or equal to 5 minutes, greater than or equal to 5.5 minutes, greater than or equal to 6 minutes, greater than or equal to 6.5 minutes, greater than or equal to 7 minutes, greater than or equal to 7.5 minutes, greater than or equal to 8 minutes, greater than or equal to 8.5 minutes, greater than or equal to 9 minutes, greater than or equal to 9.5 minutes, greater than or equal to 10 minutes, greater than or equal to 10.5 minutes, greater than or equal to 11 minutes, greater than or equal to 11.5 minutes, greater than or equal to 12 minutes, greater than or equal to 12.5 minutes, greater than or equal to 13 minutes, greater than or equal to 13.5 minutes, greater than or equal to 14 minutes, greater than or equal to 14.5 minutes, greater than or equal to 15 minutes, greater than or equal to 15.5 minutes greater than or equal to 16 minutes, greater than or equal to 16.5 minutes, greater than or equal to 17 minutes, greater than or equal to 17.5 minutes, greater than or equal to 18 minutes, greater than or equal to 18.5 minutes, greater than or equal to 19 minutes, greater than or equal to 19.5 minutes, greater than or equal to 20 minutes, greater than or equal to 30 minutes, greater than or equal to 45 minutes, greater than or equal to 60 minutes, greater than or equal to 75 minutes, greater than or equal to 90 minutes, greater than or equal to 105 minutes, greater than or equal to 120 minutes, greater than or equal to 150 minutes, greater than or equal to 180 minutes, greater than or equal to 210 minutes, greater than or equal to 240 minutes, greater than or equal to 270 minutes, greater than or equal to 300 minutes. In still other aspects, the infusion is administered over a period of time that is within a range of about 5 minutes to about 20 minutes, about 5 minutes to about 19 minutes, about 5 minutes to about 18 minutes, about 5 minutes to about 17 minutes, about 5 minutes to about 16 minutes, about 5 minutes to about 15 minutes, about 5 minutes to about 14 minutes, about 5 minutes to about 13 minutes, about 5 minutes to about 12 minutes, about 5 minutes to about 10 minutes, about 5 minutes to about 9 minutes, about 5 minutes to about 8 minutes, about 5 minutes to about 7 minutes, or about 5 minutes to about 6 minutes. In yet still further aspects, the infusion is administered over a period of time that is within the range of about 5 minutes to about 10 minutes, about 5 minutes to about 15 minutes, about 5 minutes to about 20 minutes, about 5 minutes to about 25 minutes, about 5 minutes to about 30 minutes, about 5 minutes to about 45 minutes, about 5 minutes to about 60 minutes, about 5 minutes to about 90 minutes, about 5 minutes to about 120 minutes, about 5 minutes to about 150 minutes, about 5 minutes to about 180 minutes, about 5 minutes to about 210 minutes, about 240 minutes to about 270 minutes, about 5 minutes to about 300 minutes, about 30 minutes to about 75 minutes, about 30 minutes to about 90 minutes, about 30 minutes to about 120 minutes, about 30 minutes to about 150 minutes, about 30 minutes to about 180 minutes, about 30 minutes to about 210 minutes, about 30 minutes to about 240 minutes, about 30 minutes to about 270 minutes, about 30 minutes to about 300 minutes, about 60 minutes to about 90 minutes, about 60 minutes to about 120 minutes, about 60 minutes to about 150 minutes, about 60 minutes to about 180 minutes, about 60 minutes to about 210 minutes, about 60 minutes to about 240 minutes, about 60 minutes to about 270 minutes, about 60 minutes to about 300 minutes, about 90 minutes to about 120 minutes, about 90 minutes to about 180 minutes, about 90 minutes to about 240 minutes, about 60 minutes to about 300 minutes, about 120 minutes to about 180 minutes, about 120 minutes to about 240 minutes, about 120 minutes to about 300 minutes, about 180 minutes to about 240 minutes, about 180 minutes to about 300 minutes, or about 240 minutes to about 300 minutes.

In some aspects, the dose of chlorotoxin conjugate is administered to a subject using either a fixed or a scaling dosing scheme. For example, a fixed dosing scheme can include administration of a bolus, a slow bolus or an infusion of chlorotoxin conjugate to a subject via an intravenous administration route wherein the fixed dose is, for example and without limitation, 0.1 mg to 100 mg and does not account or adjust for a subject's age, weight, height, body mass index, metabolism, or the like, or 1 mg to 30 mg and does not account or adjust for a subject's age, weight, height, body mass index, metabolism, or the like. For example, a scaling dosing scheme can include administration of a bolus, a slow bolus or an infusion of chlorotoxin conjugate to a subject via an intravenous administration route wherein the scaled dose is, for example and without limitation, 0.1 mg to 100 mg and accounts or adjusts for a subject's age, weight, height, body mass index, metabolism, or the like, or 1 mg to 30 mg and accounts or adjusts for a subject's age, weight, height, body mass index, metabolism, or the like. In some aspects, the fixed dose and/or the scaled dose are determined for one subject based upon the dose administered to a different subject wherein the subjects are or are not the same species, for example a mouse and a human, a rat and a human, a dog and a human, a monkey and a human, or a non-human primate and a human. Often in a fixed dose, the same dose or about the same dose can be administered to all subjects, for example a mouse and a human, a rat and a human, a dog and a human, a monkey and a human, or a non-human primate and a human. In some aspects, the scaled dose to be administered to a subject is determined from the dose administered to a different subject wherein the subjects are or are not the same species, for example a mouse and a human, a rat and a human, a dog and a human, a monkey and a human, or a non-human primate and a human. The scaled dose can therefore be increased from the dose administered to the mouse, rat, dog, monkey, or non-human primate to the dose administered to the human based upon the difference between the mouse, rat, dog, monkey, or non-human primate and the human, such as subject age, weight, height, body surface area, metabolism, size, physiological influences on pharmacokinetics, or the like. In one aspect, the dose is scaled from a rat to a human.

In some aspects, the compounds and compositions described herein, are used for detecting the presence or absence of the compound in a tissue or cell, wherein the presence of the compound in the tissue or cell indicates the presence of a cancerous tissue or cancer cell. In some embodiments, the compound binds to a site expressed by the cancerous tissue or cancer cell. In some aspects, the detecting of the cancerous tissue or cancer cell is performed using fluorescence imaging. In some aspects, the cancerous tissue or cancer cell is associated with one or more of DCIS, IDC, LCIS, ILC, or TNBC.

In further aspects, the compounds and compositions described herein, are used for detecting the presence or absence of the compound in a tissue or cell, wherein the presence of the compound in the tissue or cell indicates the presence of a cancerous tissue or cancer cell, and wherein the detecting allows for surgically removing the cancerous tissue or cancer cell from the human subject. In some aspects, the compound is administered at a dosage sufficient to treat breast cancer in the human subject. In some aspects, the compound binds to a site expressed by a cancerous tissue or cancer cell. In some aspects, the breast cancer being treated comprises one or more of DCIS, IDC, LCIS, ILC, or TNBC. Furthermore, the compounds and compositions described herein can be administered to a subject before surgery and/or during surgery, in which the excised tissue from the subject is contacted with compositions of the chlorotoxin conjugates. In some aspects, the compositions of the chlorotoxin conjugates are administered during surgery. In certain aspects, compositions of chlorotoxin conjugates are intravenously administered to a subject about 0.25 hours, about 0.5 hours, about 0.75 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 36 hours, about 48 hours, about 60 hours, or about 72 hours prior to performing surgery on a human subject. In some aspects, compositions of chlorotoxin conjugates are intravenously administered to a subject between 0 and 1 hours, between 1 and 2 hours, between 2 and 3 hours, between 3 and 4 hours, between 4 and 5 hours, between 5 and 6 hours, between 6 and 9 hours, between 9 and 12 hours, between 12 and 24 hours, between 24 and 36 hours, between 36 and 48 hours or between 48 and 72 hours (inclusive) before surgery.

Tissue or fluid samples, such as blood, normal tissue, and tumor tissue, can often be isolated from a subject prior to administration of a chlorotoxin conjugate, sometimes as a baseline reference. Samples can also be isolated from a subject after administration of the compounds of the present disclosure, often less than about 1 minute after, less than about 2 minutes after, less than about 3 minutes after, less than about 4 minutes after, less than about 5 minutes after, less than about 6 minutes after, less than about 7 minutes after, less than about 8 minutes after, less than about 9 minutes after, less than about 10 minutes after, less than about 11 minutes after, less than about 12 minutes after, less than about 13 minutes after, less than about 14 minutes after, less than about 15 minutes after, less than about 20 minutes after, less than about 30 minutes after, less than about 40 minutes after, less than about 50 minutes after, less than about 60 minutes after, less than about 1 hour after, less than about 2 hours after, less than about 3 hours after, less than about 4 hours after, less than about 5 hours after, less than about 6 hours after, less than about 12 hours after, less than about 18 hours after, less than about 24 hours after, less than about 36 hours after, less than about 48 hours after, less than about 72 hours after, less than about 96 hours after, less than about 5 days after, less than about 7 days after, less than about 10 days after, less than about 14 days after, less than about 21 days after, less than about 4 weeks after, less than about 6 weeks after, less than about 8 weeks after, less than about 12 weeks after, less than about 16 weeks after, less than about 20 weeks after or more than 20 weeks after.

Imaging and Surgical Methods

The present invention can provide methods for detection, intraoperative imaging, and resection of some types of breast cancer tumors with a chlorotoxin conjugate. The chlorotoxin can be a targeting agent that directs the conjugate to the type of breast cancer tissue. In one embodiment, the chlorotoxin conjugate of the invention includes one or more labeling agents. In a further embodiment, the labeling agent comprises a fluorescent moiety (e.g., red or near infrared emitting fluorescent moieties) covalently coupled to the chlorotoxin. In another embodiment, the labeling agent comprises a radionuclide. Imaging methods for detection of a certain type of breast cancer foci disclosed herein can be applicable to dog and other animal models of cancer as well as to veterinary practice.

As used herein, the term "red or near infrared emitting fluorescent moiety" refers to a fluorescent moiety having a fluorescence emission maximum greater than about 600 nm.

In certain embodiments of the chlorotoxin conjugate, the fluorescent moieties are derived from fluorescent compounds characterized by emission wavelength maxima greater than about 600 nm to avoid autofluorescence, emission that travels through millimeters to one centimeter of tissue/blood/fluids, emission that is not absorbed by hemoglobin, other blood components, or proteins in human or animal tissue. In some aspects, the emission wavelength maximum is greater than 600 nm, greater than 650 nm, greater than 700 nm, greater than 750 nm, greater than 800 nm, greater than 850 nm, greater than 900 nm, or greater than 950 nm.

The fluorescent moiety can be covalently coupled to the chlorotoxin to allow for the visualization of the conjugate by fluorescence imaging. The fluorescent moiety can be derived from a fluorescent compound. Suitable fluorescent compounds can be those that can be covalently coupled to a chlorotoxin without substantially adversely affecting the targeting and binding function of the chlorotoxin conjugate. Similarly, suitable fluorescent compounds can retain their fluorescent properties after conjugation to the chlorotoxin.

The chlorotoxin conjugates described herein can be used for detection and treatment of certain types of breast cancers, for example imaging, resection of, diagnosis of and treatment of certain types of breast cancer tumors. In some aspects, tumors amenable to detection with a chlorotoxin conjugate of the present disclosure are DCIS, IDC, LCIS, ILC, or TNBC.

Intraoperative resection of tumor types can vary depending on the type of tumor. Intraoperative visualization of solid breast cancer tumors in real-time can enable more complete resection while sparing surrounding normal tissue. Improvement in intraoperative tumor visualization can be of benefit for any resectable solid tumor, as it can enable surgeons to better determine the extent of local invasion as well as the presence of metastatic spread in nearby lymph nodes and fatty tissue. Surgeons who specialize in human breast cancer surgery have indicated that the surgical approach is generally a wide excision with 0.2-1 cm margins on all sides. However, it is difficult for surgeons to obtain wide margins using only white light and preoperative imaging information. In 20-50% of breast cancer surgeries, failure to obtain clean margins leads to second surgeries.

The chlorotoxin conjugates described herein can be used for detection and imaging of tumors that originated in breast tissue and metastasized to other organs or anatomical locations, including but not limited to, lung, brain, colon, rectum, prostate, head, neck, stomach, anus, and/or vaginal tissues, for example. As used herein, the term "metastasis" refers to the spread of tumor cells from one organ or tissue to another location, and also refers to tumor tissue that forms in a new location as a result of metastasis. Tumors of any grade or stage known to one of skill in the art, including low-grade tumors, can often be detected by the chlorotoxin conjugates described herein. In some aspects, tumor detection includes imaging, resection, diagnostics, and treatment.

In certain aspects, the present compounds are capable of passing across the blood brain barrier. Passing across the blood brain barrier is advantageous when detecting or treating a cancer cell in the brain or other region of the body after breast cancer metastasis.

In certain other aspects, the chlorotoxin conjugate can be used alone or in combination with other detection agents, to detect, image, visualize, or analyze the tumor in advance of, during, or following anti-tumor treatments, which can include surgery and surgical resection, chemotherapy, radiation therapy, and immunotherapy. In addition, the chlorotoxin conjugate can be used alone or with other detection agents for follow-up monitoring post treatment as well as for general monitoring for full-body screening.

In some embodiments, various fluorescence imaging systems can be used to image excised specimens ex vivo or can be used to perform intraoperative imaging. Any system capable of scanning for fluorescence in the infrared and near infrared range can be used, such as the SIRIS or Spectrum instruments.

Methods of Treatment

The present disclosure can provide methods for treating some types of breast cancer by administering a chlorotoxin variant. In one embodiment, the method includes administering an effective amount of a modified chlorotoxin peptide of the invention to a subject in need thereof. Subjects can include, but are not limited to humans, non-human primates, monkeys, cows, dogs, cats, rabbits, pigs, sheep, horses, guinea pigs, rats, and mice. The methods of treatment of the invention can be applicable to human and animal subjects in need of such treatment.

The term "effective amount," as used herein, refers to a sufficient amount of an agent or a compound being administered which will relieve to some extent one or more of the symptoms of breast cancer. The result can be reduction and/or alleviation of the signs, symptoms, or causes of breast cancer, the ablation, shrinkage, minimization, reduction, inhibition or killing of breast cancer cells, tissues, and tumors, or any other desired alteration of a biological system. Compositions containing such agents or compounds can be administered for prophylactic, enhancing, and/or therapeutic treatments. An appropriate "effective" amount in any individual case may be determined using techniques, such as a dose escalation study.

The chlorotoxin conjugates described herein can be used for treatment of breast cancers. In some aspects, certain tumors amenable to treatment with a chlorotoxin conjugate of the present disclosure include, but are not limited to DCIS, IDC, LCIS, ILC, or TNBC.

In certain aspects, the chlorotoxin conjugate is administered to an individual having or suspected of having a breast cancer tumor, such that the conjugate binds specifically to the tumor. Such methods can be useful in reducing the likelihood that the individual will develop a tumor, that one or more tumors in the individual will increase in size, that one or more tumors in the individual will metastasize, and/or that the cancer will progress by some other measure. As used herein, the term "metastasis" refers to the spread of tumor cells from one organ or tissue to another location, and also refers to tumor tissue that forms in a new location as a result of metastasis.

The chlorotoxin conjugates described herein can be used for treatment of tumors that originated in breast tissue and metastasized to other organs or anatomical locations, including but not limited to, lymph nodes, lung, brain, colon, rectum, prostate, head, neck, stomach, anus, and/or vaginal tissues, for example. In certain aspects, the present compounds are capable of passing across the blood brain barrier. Passing across the blood brain barrier is advantageous when treating a cancer cell in the brain after breast cancer metastasis. In further aspects, tumors of any grade or stage known to one of skill in the art, including low-grade tumors, can be treated by the chlorotoxin variants or their conjugates described herein. In some aspects, tumor treatment includes the chlorotoxin conjugated to a therapeutic agent.

The chlorotoxin can be a targeting agent that directs the conjugate to a type of breast cancer tissue. In one embodiment, the chlorotoxin conjugate of the invention includes one or more a therapeutic agents. In a further embodiment, a therapeutic agent is covalently coupled to the chlorotoxin. The therapeutic agent can be coupled to the chlorotoxin to allow for chlorotoxin directed delivery of the therapeutic agent to the breast cancer. Suitable therapeutic agents can be those that can be covalently coupled to a chlorotoxin without substantially adversely affecting the targeting and binding function of the chlorotoxin conjugate. Similarly, suitable therapeutic agents can retain their therapeutic properties after conjugation to the chlorotoxin.

Therapeutic agents coupled to the chlorotoxin conjugate can be any chemical compound or treatment method that induces DNA damage when applied to a cell. For example, a therapeutic agent can emit radiation and waves that induce DNA damage such as, irradiation, microwaves, electronic emissions, and the like. In other embodiments, a therapeutic agent can be a variety of chemotherapeutic agents including, but limited to, selective estrogen receptor antagonists such as Tamoxifen, 4-hydroxy Tamoxifen (Afimoxfene), Falsodex, Raloxifene, Bazedoxifene, Clomifene, Femarelle, Lasofoxifene, Ormeloxifene, Toremifene; camptothecin, actinomycin-D, mitomycin C; cisplatin or other agents that directly cross-link DNA or form adducts; inhibitors of HSP90 such as Geldanamycin, 17-(Allylamino)-17-demethoxygeldanamycin, PU-H71 and Rifabutin; compounds interfere with DNA replication, mitosis and chromosomal segregation such as doxorubicin, etoposide, verapamil, podophyllotoxin; compounds that inhibit microtubules paclitaxel, docetaxel, and other taxanes; cytokines such as TNF-alpha; compounds that are hormonal therapies such as tamoxifen or an aromatase inhibitor, trastuzumab, lapatinib, bevacizumab, and estrogen receptor downregulators; alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (for example, bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin gammall and calicheamicin omegall); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran;

spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP); carboplatin, procarbazine; mechlorethamine; cyclophosphamide; camptothecin; ifosfamide; melphalan; chlorambucil; busulfan; nitrosurea; dactinomycin; daunorubicin; doxorubicin; bleomycin; plicomycin; mitomycin; etoposide (VP 16); tamoxifen; raloxifene; estrogen receptor binding agents; taxol; paclitaxel; docetaxel; gemcitabine; navelbine; farnesyl-protein tansferase inhibitors; transplatinum; 5-fluorouracil; vincristine; vinblastine; methotrexate; bevacizumab; vorozol and other aromatase inhibitors; lapitinib; cetuximab; panitumumab; bicalutamide; anthracyclines; platinums; poly(ADP-ribose) polymerase (PARP) inhibitors (such as olaparib, veliparib, iniparib, niraparib, rucaparib); trastuzumab; lapatinib; carboplatin; taxane; gemcitabine; epirubicin; apatinib; cediranib; capecitabine; 7-hydroxystaurosporine (UCN-01); bortezomib; denaciclib; panobinostat; dasatinib; LGK974; and pharmaceutically acceptable salts, acids, or derivatives of any of the above.

Treatment of the types of breast cancer with a chlorotoxin conjugate as described herein can be combined with other treatments and therapies. Other treatments and therapies can consist of, but are not limited to, radiation therapy, surgery, chemotherapy, immunotherapy, or any other treatment part of the standard of care for a breast cancer patient.

Generally, the dosage of administered chlorotoxin conjugates can vary depending upon such factors as the patient's age, weight, height, sex, general medical condition and previous medical history. Typically, it can be desirable to provide the recipient with a dosage of chlorotoxin conjugated to a chemotherapeutic, an anti-cancer agent, or an anti-cancer drug that is effective to achieve the ablation, shrinkage, minimization, reduction, inhibition or killing of breast cancer cells, tissues, or tumors, or prevention of and ablation, shrinkage, minimization, reduction, inhibition or killing of breast cancer cells, tissues or tumors associated with metastasis. In many cases, it is desirable to provide the recipient with a dosage of a chlorotoxin conjugate that is in the range of from about 0.1 mg to about 100 mg, although a lower or higher dosage also may be administered as circumstances dictate.

Administration of a chlorotoxin conjugate to a subject can be topical, inhalant, intravenous, intraarterial, intraperitoneal, intramuscular, subcutaneous, intrapleural, intrathecal, by perfusion through a regional catheter, or by direct intralesional injection. When administering conjugates by injection, the administration may be by continuous infusion or by single or multiple boluses.

Additional routes of administration can include oral, mucosal-membrane, pulmonary, and transcutaneous. Oral deliverycan be suitable for polyester microspheres, zein microspheres, proteinoid microspheres, polycyanoacrylate microspheres, and lipid-based systems (see, for example, DiBase and Morrel, "Oral Delivery of Microencapsulated Proteins," in Protein Delivery: Physical Systems, Sanders and Hendren (eds.), pages 255-288 (Plenum Press 1997)). The feasibility of an intranasal delivery can exemplified by such a mode of insulin administration (see, for example, Hinchcliffe and Ilium, Adv. Drug Deliv. Rev. 35:199 (1999)). Dry or liquid particles comprising a chlorotoxin conjugate can be prepared and inhaled with the aid of dry-powder dispersers, liquid aerosol generators, or nebulizers (e.g., Pettit and Gombotz, TIBTECH 16:343 (1998); Patton et al., Adv. Drug Deliv. Rev. 35:235 (1999)). This approach can be illustrated by the AERX diabetes management system, which is a hand-held electronic inhaler that delivers aerosolized insulin into the lungs. Transdermal delivery using electroporation can provide another means to administer a chlorotoxin conjugate.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the disclosure provided herein.

All features discussed in connection with an aspect or embodiment herein can be readily adapted for use in other aspects and embodiments herein. The use of different terms or reference numerals for similar features in different embodiments does not necessarily imply differences other than those expressly set forth. Accordingly, the present invention is intended to be described solely by reference to the appended claims, and not limited to the embodiments disclosed herein.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The invention is further illustrated by the following non-limiting examples.

Example 1

Ex Vivo Imaging

This example describes ex vivo imaging of breast tissue from six human subjects diagnosed with breast cancer, wherein the breast tissue was excised at least two hours after administration of a single slow bolus of 12 mg Compound 76.

In all cases, areas of suspected tumors showed fluorescent signal. The Synchronized Infrared Imaging System (SIRIS) was used to detect Compound 76 in tumor tissue immediately following excision. Intact tissue was imaged, then cut into about 5 mm sections according to standard methods. Sections were imaged, and areas of gross tumor were noted by the pathologist. Fluorescent areas were noted to enable correlation of fluorescence with histopathologic analysis after tissue fixatiation. Images were analyzed using ImageJ software. The relative fluorescence signal (RFU) per pixel was measured in a region of interest in the tumor area and an adjacent non-tumor region and tumor to background ratio (TBR) was calculated. Immunohistochemistry analysis for expression of HER2, ER, and PR was conducted as part of standard clinical practice.

All subjects had invasive ductal carcinoma (IDC) and/or ductal carcinoma in situ (DCIS). More specifically, subject B001 was diagnosed with DCIS with small focus microinvasive carcinoma, columnar cell hyperplasia, and apocrine metaplasia, and which was further classified as ER positive, PR negative, HER2 equivocal, and 20% Ki67 positive. subject B002 was diagnosed with IDC and DCIS, which was further classified as ER negative, PR negative, HER2 negative, and 17% Ki67 positive. Subject B003 was diagnosed with IDC and DCIS, which was further classified as ER positive, PR positive, HER2 negative, and 10% Ki67 positive. Subject B004 was diagnosed with IDC and DCIS, which was further classified as ER positive, PR positive, HER2 negative, and 15% Ki67 positive. Subject B005 was diagnosed with DCIS, which further was classified as ER positive and HER2 negative. Subject B006 was diagnosed with IDC and DCIS, which was further classified as ER positive, PR negative, HER2 negative, and 10% Ki67 positive.

Contrast between confirmed areas of DCIS and adjacent normal tissues was seen in cases where DCIS was the only diagnosed lesion. Two DCIS lesions were missed in cases where IDC was the primary diagnosis. The IDC cases showed contrast between areas confirmed as tumor and adjacent normal breast tissue.

Figure 3:
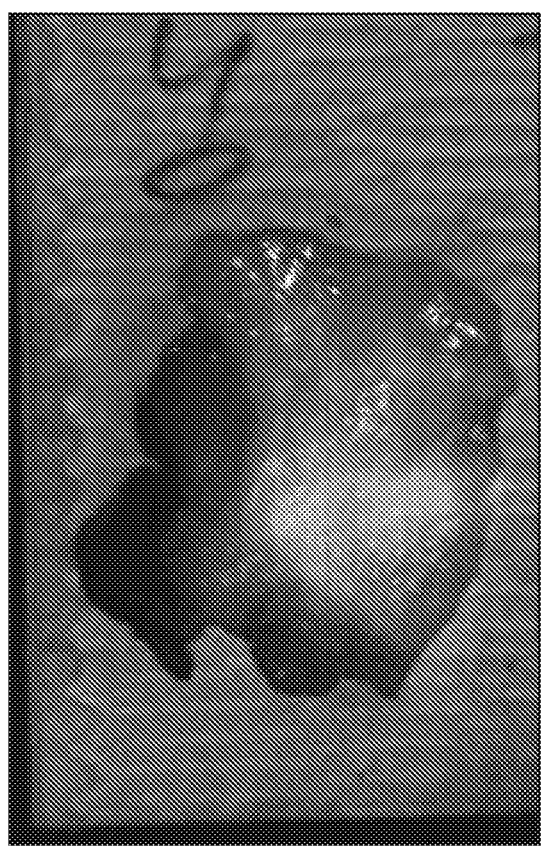
FIG. 3 shows a NIR image overlay with a white light image of ex vivo breast tissue that had been formalin fixed from a human subject (subject B003) diagnosed with breast cancer, wherein 12 mg of Compound 76 was administered to the human subject (subject B003) before excision of the breast tissue using a 180 ms calculated exposure time. Increased exposure time was required because the tissue was fixed prior to imaging. Fluorescence signal, corresponding to lighter and brighter areas in the NIR image, is indicative of the presence of Compound 76 in tumor tissues.
Figure 4:
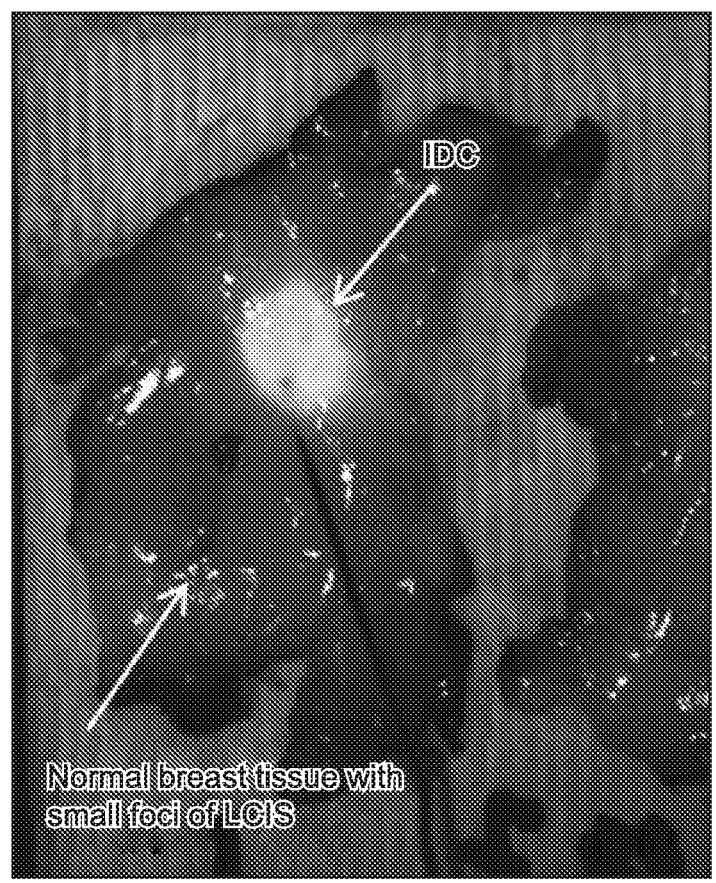
FIG. 4 shows a NIR image overlay with a white light image of ex vivo breast tissue from a human subject (subject B004) diagnosed with breast cancer, wherein 12 mg of Compound 76 was administered to the human subject (subject B004) before excision of the breast tissue using a 30 ms calculated exposure time. Strong, focal fluorescence signal, corresponding to the bright area in the NIR image, is indicative of the presence of Compound 76 in tumor tissues.
Figure 5:
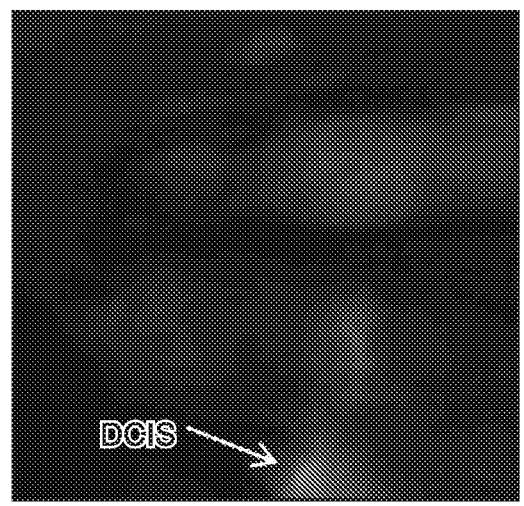
FIG. 5 shows a NIR image of ex vivo breast tissue from a human subject (subject B005) diagnosed with breast cancer, wherein 12 mg of Compound 76 was administered to the human subject (subject B005) before excision of the breast tissue using a 30 ms calculated exposure time. Fluorescence signal, corresponding to lighter and brighter areas in the NIR image, is indicative of the presence of Compound 76 in tumor tissues. Fluorescence signal is likely DCIS.
Figure 6:
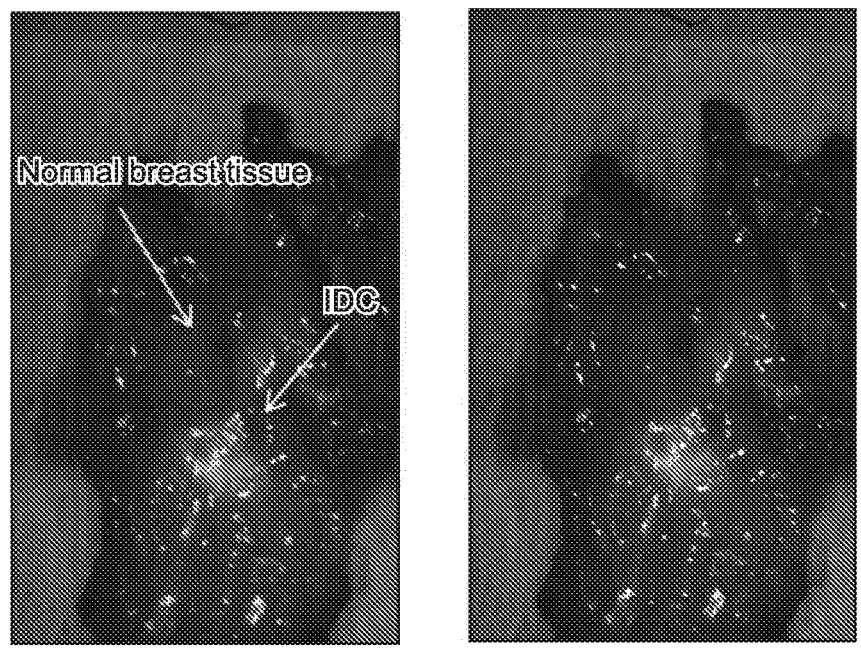
FIG. 6 shows a NIR image overlay with a white light image of ex vivo breast tissue from a human subject (subject B006) diagnosed with breast cancer, wherein 12 mg of Compound 76 was administered to the human subject (subject B006) before excision of the breast tissue using a 30 ms calculated exposure time. Strong, focal fluorescence signal, corresponding the bright area in the NIR images, is indicative of the presence of Compound 76 in tumor tissues.

The main tumor mass, lymph node tissue, and the tumor margin of subject B001 were excised and imaged. FIG. 1 shows images and graphs of fluorescent signal intensity of ex vivo tissue, wherein 12 mg of Compound 76 was administered to the human subject (subject B001) before excision of the tissue. FIG. 1A shows near-infrared (NIR) images of the ex vivo lumpectomy specimen on the left, and corresponding white light images of the lumpectomy specimen on the right, which were taken prior to gross sectioning. Fluorescence signal, corresponding to lighter and brighter areas in the NIR images, is indicative of the presence of Compound 76 in tumor tissues. FIG. 1B shows an NIR image overlay with the white light image of ex vivo gross sectioned lumpectomy specimen from subject B001 at a 30 millisecond (ms) calculated exposure time, in which the fluorescence indicates tumor. Fluorescence signal, corresponding to lighter and brighter areas in the NIR images, is indicative of the presence of Compound 76 in tumor tissues. The Ds with accompanying arrows indicate areas of DCIS. The MI with accompanying arrow indicates an area with microinvasive carcinoma. The B indicates the biopsy site. The fluorescent signal as seen in FIG. 1B was determined to be DCIS by tissue pathology using H&E staining, as shown in FIGS. 1C, 1D, and 1F, and to be microinvasive carcinoma by tissue pathology using H&E staining, as shown in FIG. 1E. FIG. 1G shows a line plot analysis graph of the ex vivo lumpectomy specimen as shown in FIG. 1B, which shows the fluorescent signal intensity (through the line on the above NIR image of the tumor mass) was increased in the microinvasive carcinoma "M" and DCIS "D" compared to the non-tumor adipose tissue "A". The biopsy site is marked "B". NIR image above the line plot analysis graph used a 30 ms calculated exposure time. This demonstrates that there was an increase in signal within the DCIS regions. FIG. 1H shows on the left, an NIR image of the tumor margin and the corresponding visible light image, and the lumpectomy specimen NIR image on the right, which were taken prior to gross sectioning using a 30 ms calculated exposure time. Fluorescence signal, corresponding to lighter and brighter areas in the NIR images, is indicative of the presence of Compound 76 in tumor tissues. Tissue pathology showed the tumor margin was mostly fat cells, and showed no evidence of tumor cells. FIG. 1I shows a line plot analysis of the fluorescent signal intensity of tumor margin tissue through the line. FIG. 1J shows a line plot analysis of the fluorescent signal intensity of the lumpectomy specimen through the line. Comparison of FIG. 1I to FIG. 1J shows the fluorescent signal intensity from the lumpectomy specimen is four-fold higher than the signal from the tumor margin. FIG. 2 shows images of ex vivo breast tissue after administration of Compound 76 to a human subject (subject B002) diagnosed with breast cancer. FIG. 2A shows an image of the excised breast tissue from subject B002 under white light. FIG. 2B shows a NIR image overlay of the excised breast tissue from subject B002 on the white light image from FIG. 2A, in which the fluorescence indicates tumor. Fluorescence signal, corresponding to lighter and brighter areas in the NIR image, is indicative of the presence of Compound 76 in tumor tissues. FIG. 2C shows a NIR image overlay on a white light image of excised breast tissue from subject B002, in which the fluorescence indicates tumor. The circle indicates a region with small foci of DCIS. FIG. 3 shows a NIR image overlay on a white light image of excised breast tissue from subject B003, in which the fluorescence indicates tumor. Fluorescence signal, corresponding to lighter and brighter areas in the NIR image, is indicative of the presence of Compound 76 in tumor tissues. FIG. 4 shows a NIR image overlay on a white light image of excised breast tissue from subject B004, in which the fluorescence indicates tumor. Strong, focal fluorescence signal, corresponding to the bright area in the NIR image, is indicative of the presence of Compound 76 in tumor tissues. The arrow indicates an area of IDC. FIG. 5 shows a NIR image of excised breast tissue from subject B005, in which the fluorescence indicates tumor. Fluorescence signal, corresponding to lighter and brighter areas in the NIR image, is indicative of the presence of Compound 76 in tumor tissues. The arrow indicates an area of fluorescence that is likely DCIS. FIG. 6 shows a NIR image overlay on a white light image of excised breast tissue from subject B006, in which the fluorescence indicates tumor. Strong, focal fluorescence signal, corresponding to the bright area in the NIR images, is indicative of the presence of Compound 76 in tumor tissues. NIR images were made using the Synchronized Infra-Red Imaging System (SIRIS) device and calculations of exposure time based thereon. It is understood that exposure times can vary depending on the different devices used to detect fluorescence in the tumor.

The TBR's ranged from 4.7 to 8.4. The case with the highest contrast was triple negative.

TABLE 5

Marker Expression and Imaging Results for Three Subjects with IDC

|  | Subject B002 | Subject B004 | Subject B006 |
|---|---|---|---|
| Marker expression | Her2−, ER−, PR− | Her2−, ER+, PR+ | Her2−, ER+, PR− |
| TBR | 8.4 | 4.7 | 4.9 |

Control breast tissues were also imaged to show tumor fluorescence occurs after administration of Compound 76, and to show Compound 76 fluorescence is specific to tumor tissue. To show tumor fluorescence occurs after administration of Compound 76, a human subject with breast cancer did not receive an injection of Compound 76 before breast tissue was excised. FIG. 7 shows images of breast tissue from a human subject diagnosed with breast cancer, wherein no Compound 76 was administered to the human subject before excision of the breast tissue. FIG. 7A shows a white light image of excised breast tissue from this subject. FIG. 7B shows a NIR image of excised breast tissue from this subject, in which the image was exposed for 30 ms calculated exposure time. FIG. 7C show a NIR image of excised breast tissue from this subject, in which the image exposed for 135 ms calculated exposure time. Both FIGS. 7B & 7C show no fluorescence, indicating tumor tissue does not fluorescence in the absence of Compound 76. To show Compound 76 fluorescence is specific to tumor tissue, normal breast tissue excised from a human subject who received an injection of Compound 76 was imaged. FIG. 8 shows ex vivo images of normal breast tissue from a human subject, wherein 12 mg of Compound 76 was administered to the human subject before excision of the normal breast tissue. FIG. 8A shows an white light image of excised normal breast tissue from this subject. FIG. 8B shows an H&E staining of the normal breast tissue from this subject to confirm that there is no tumor pathology in the excised breast tissue. FIG. 8C shows a NIR image of excised normal breast tissue from this subject, in which the image was exposed for 30 ms calculated exposure time. FIG. 8D shows a NIR image of excised normal breast tissue from this subject, in which the image was exposed for 135 ms calculated exposure time. Both FIGS. 8C & 8D show no fluorescence, indicating Compound 76 fluorescence is specific to tumor tissue.

Example 2

Mouse Xenograft Models of Breast Cancer and Imaging with Compound 76

This example demonstrates fluorescence of breast cancer tumors in mouse xenograft models after administration of Compound 76.

Xenograft of Breast Cancer Cell Lines

The human breast cancer cell lines MDA-MB-231 (MB231) and MDA-MB-468 (MB468) were purchased from American Type Culture Collection. Both cell lines are estrogen receptor negative, progesterone receptor negative, and HER2 negative, which classifies these cell lines as triple-negative breast cancers. MB231 and MB468 are both mestastatic breast adenocarcinoma derived from a pleural effusion. Subcutaneous flank xenografts of MB231 were generated in 3 female nude mice. Subcutaneous flank xenografts of MB468 were generated in 4 female nude mice. After 4-7 weeks of growth, both sets of mice received a single IV bolus dose of 0.03 mg of Compound 76 through the tail vein. The mice were euthanized one day after injection, and the tumor and quadriceps muscles were dissected. Ex vivo imaging was performed on an Odyssey CLx near-infrared scanner (LI-COR) at 21 micron resolution, autointensity, on the 800 nm channel. Images were analyzed using Image Studio software (LI-COR) by drawing regions of interest within each tissue. Background subtracted signal in tumor was then compared to signal in normal muscle and reported as tumor to background ratios (TBR).

Figure 9:
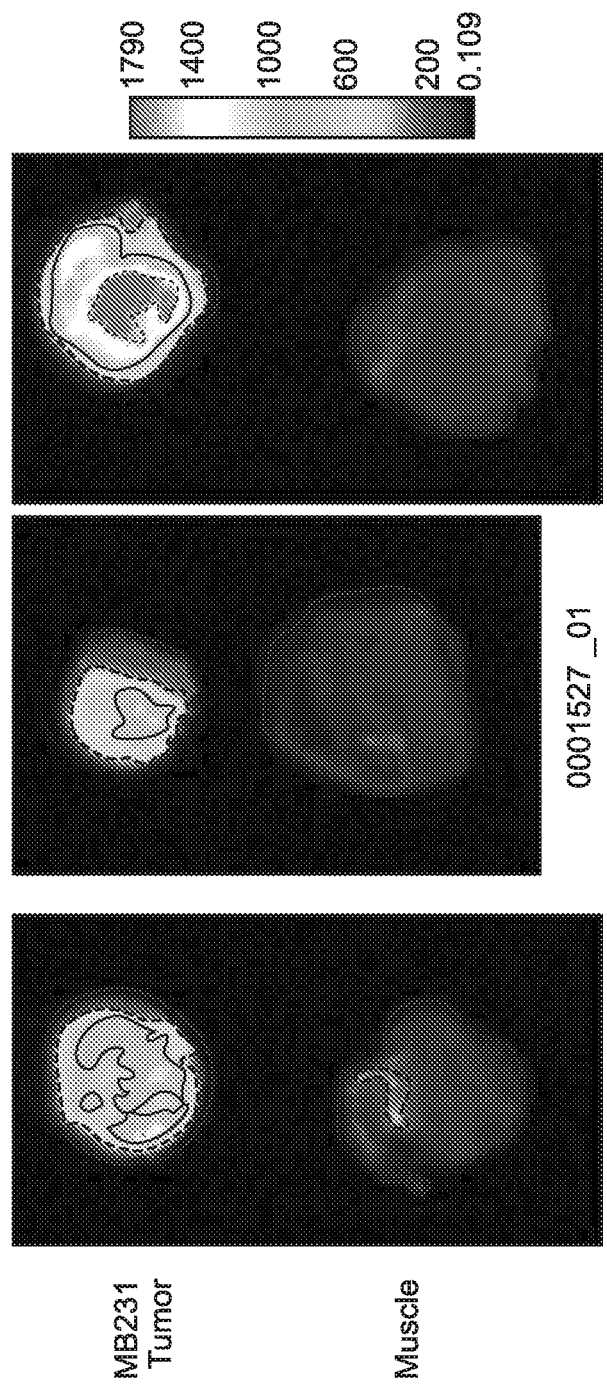
FIG. 9 shows NIR images of the MB231 xenografts from mice on the top row with control NIR images of corresponding normal muscle below in the bottom row.
Figure 10:
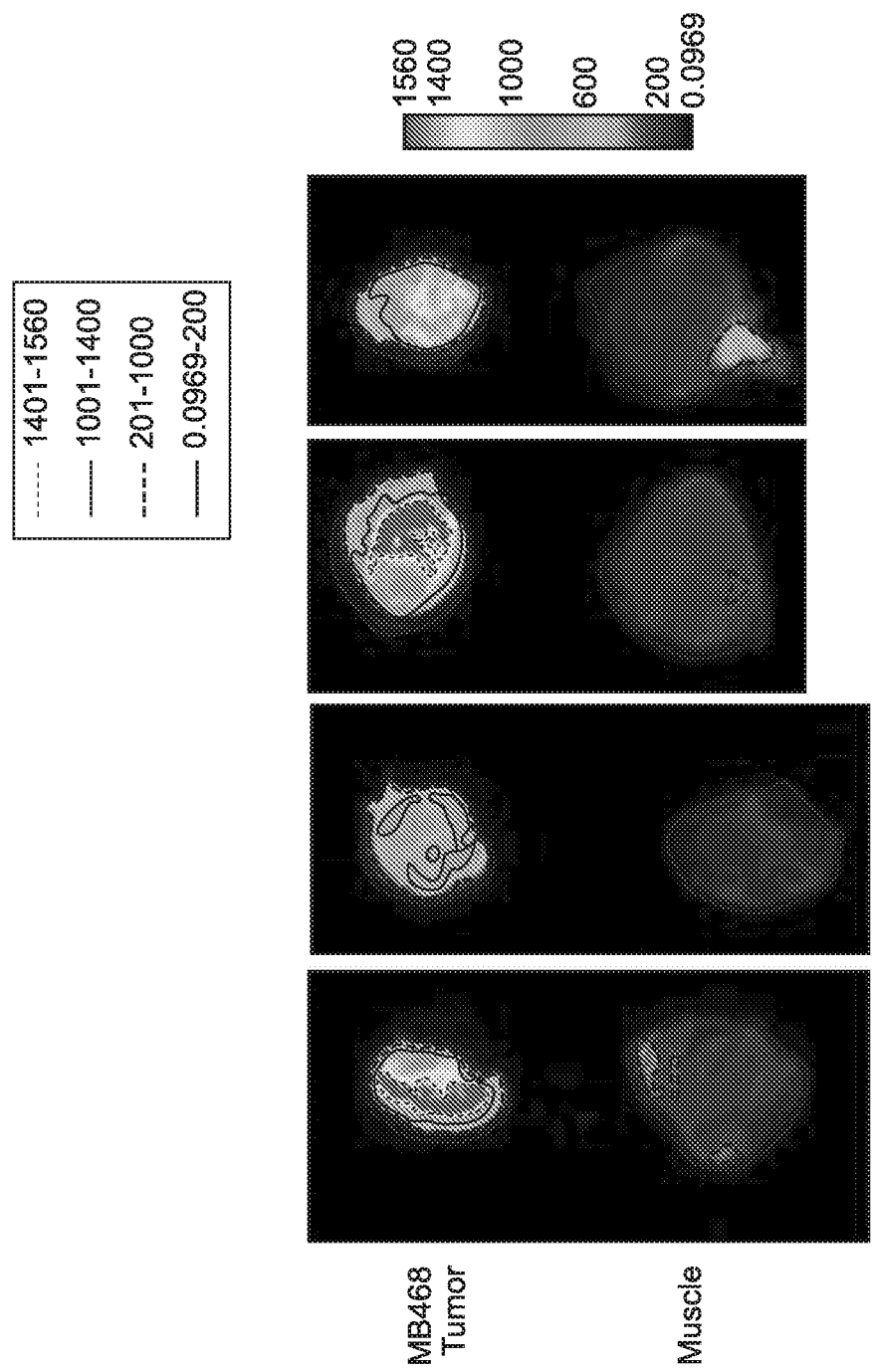
FIG. 10 shows NIR images of the MB468 xenografts from mice on the top row with NIR images of corresponding normal muscle below in the bottom row.

Compound 76 uptake was detected in all mice with MB231 xenografts and with MB468 xenografts one day after injection. FIG. 9 shows near infrared (NIR) images of the MB231 xenografts from mice on the top row with NIR images of corresponding normal muscle below in the bottom row. TBR in MB231 tumors compared to normal muscle was between 5 and 19. FIG. 10 shows NIR images of the MB468 xenografts from mice on the top row with NIR images of corresponding normal muscle below in the bottom row. The TBR in MB231 tumors compared to normal muscle is between 5 and 19. Fluorescence signal in MB468 tumors was between 3.6 and 10.5 times higher than normal muscle. These results indicate that Compound 76 can be readily detected in human breast cancer cell line xenograft models in mice with good contrast between normal and tumor tissue.

Xenograft of Breast Cancer Derived From a Patient

Additionally, the TM00089 patient-derived xenograft model was tested in mice through The Jackson Laboratory. This model was established from a human triple-negative/grade T2NOMX breast cancer. Tumor fragments were transplanted from mouse to mouse as subcutaneous flank xenografts in NOD-scid IL2Rgamma$^{null}$ mice. When the tumors reached 500-750 mm$^3$, the five mice received a single IV bolus dose of 0.03 mg of Compound 76 through the tail vein. The mice were euthanized one day after injection, and the tumor, mammary tissue, and quadriceps muscle were dissected. Half of each tissue was fixed in 10% neutral buffered formalin, and the other half was frozen in Optimal Cutting Temperature Compound (OCT). Whole fixed tissue was scanned on the Odyssey scanner using 21 micron resolution, autointensity, and the 800 nm channel. Analysis was conducted using Image studio software by drawing regions of interest within the tissue. Background subtracted signal in tumor was then compared to normal mammary tissue and muscle and reported as tumor to background ratios. Fixed tumor and mammary tissue is paraffin embedded, processed, and stained with Hematoxylin and Eosin (H&E) according to standard histology protocols (Histology Consultation Services).

Compound 76 uptake was detected in all five tumor xenografts. Compound 76 signal is significantly higher in tumor compared to normal mammary fat pads (p=0.01 two-tailed t-test of unequal variance) and compared to normal muscle (P<0.01 two-tailed T-test of unequal variance). TBR's were between 1.8 and 8.1 (1.8, 4.6, 8.1, 4.1, and 6.3) when compared to normal mammary tissue, and were between 5.1 and 23 (5.1, 19, 11.5, 7.1, and 23) when compared to muscle. FIG. 11 shows images of tumor, muscle, and mammary tissue from mice that received a xenograft of breast cancer tissue derived from a patient with breast cancer. FIG. 11A shows NIR images of the tumor xenografts from mice on the top row with NIR images of corresponding normal muscle below in the middle row and corresponding normal mammary fat pad below in the bottom row. The first five panels on the left are from mice that received an injection of Compound 76, and the panel on right is from a mouse that did not receive an injection of Compound 76. Variability in signal within the tumor may be due to areas of necrosis and the presence of cysts that are observed in some samples. FIG. 11B shows H&E staining of each tumor below the tumor it corresponds to in FIG. 11A, which confirms these tissues show tumor pathology.

The data obtained from these studies show Compound 76 can be used as an imaging agent for breast cancer surgery.

Example 3

Treatment of Triple-Negative Breast Cancer with a Peptide-Active Agent Conjugate This example describes the use of chlorotoxin variants described herein to treat triple-negative breast cancer. A peptide of the disclosure is expressed recombinantly or chemically synthesized and then is conjugated to a cytotoxic drug, such as iniparib, capecitabine, carboplatin, cisplatin, docetaxel, gemcitabine, irinotecan, or paclitaxel. The cytotoxic drug is conjugated to SEQ ID NO: 9 peptide at K27. Alternatively, the cytotoxic drug is conjugated to any one of SEQ ID NO: 1-SEQ ID NO: 481 peptide. Triple-negative breast cancer is targeted by the conjugate, and therefore, the conjugate is administered to a human or animal to treat triple-negative breast cancer.

Example 4

Treatment of Invasive Ductal Carcinoma Breast Cancer with a Peptide-Active Agent Conjugate This example describes the use of chlorotoxin variants described herein to treat invasive ductal carcinoma breast cancer. A peptide of the disclosure is expressed recombinantly or chemically synthesized and then is conjugated to a cytotoxic drug, such as lapatinib, doxorubicin, epirubicin, cyclophosphamide, docetaxel, paclitaxel, capecitabine, ixabepilone, methotrexate, or 5-fluorouracil. The cytotoxic drug is conjugated to SEQ ID NO: 9 peptide at K27. Alternatively, the cytotoxic drug is conjugated to any one of SEQ ID NO: 1-SEQ ID NO: 481 peptide. Invasive ductal carcinoma breast cancer is targeted by the conjugate, and therefore, the conjugate is administered to a human or animal to treat invasive ductal carcinoma breast cancer.

Example 5

Treatment of Ductal Carcinoma In Situ Breast Cancer with a Peptide-Active Agent Conjugate This example describes the use of chlorotoxin variants described herein to treat ductal carcinoma in situ breast cancer. A peptide of the disclosure is expressed recombinantly or chemically synthesized and then is conjugated to a radioactive moiety or a radiosensitizer. The cytotoxic drug is conjugated to SEQ ID NO: 9 peptide at K27. Alternatively, the cytotoxic drug is conjugated to any one of SEQ ID NO: 1-SEQ ID NO: 481 peptide. Ductal carcinoma in situ breast cancer is targeted by the conjugate, and therefore, the conjugate is administered to a human or animal to treat ductal carcinoma in situ breast cancer.

Example 6

Serum Pharmacokinetics of 6 mg and 12 mg Doses of Compound 76

This example describes a Phase I clinical study (BB-005) of Compound 76 dosing by intravenous (IV) bolus injection in adult subjects with breast cancer before surgical excision of breast cancer from subjects. The Phase I clinical study of Compound 76 included dose evaluation after intravenous injection of Compound 76 by fluorescence imaging and research pathology assessment.

Figure 12:
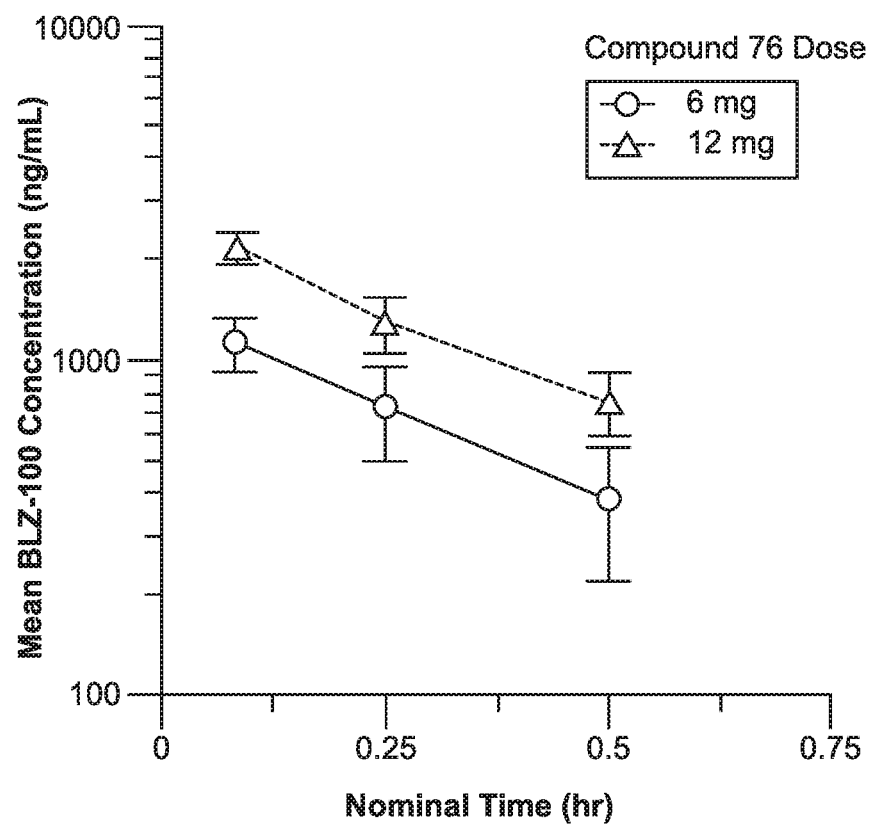
FIG. 12 illustrates mean serum concentration of Compound 76 at the time points measured above versus nominal time profiles in the 6 mg dosing cohort and the 12 mg dosing cohort.

Each subject was given a single bolus IV injection of Compound 76. Each single bolus IV injection was given over the course of 3-4 minutes. Eleven subjects were given a 6 mg dose. Four subjects were given a 12 mg dose. Following the single bolus IV injection, blood samples were collected at 5, 15, and 30 minutes post-injection from each subject. Samples were analyzed for Compound 76 serum concentration using a validated liquid chromatography/mass spectrometry (LC/MS) method. FIG. 12 illustrates mean serum concentration of Compound 76 at the time points measured above versus nominal time profiles in the 6 mg dosing cohort and the 12 mg dosing cohort.

Example 7

Phase I Clinical Study of Compound 76 Dosing in Adult Subjects with Breast Cancer (BB-005 Clinical Trial)

This example describes a Phase I clinical study of Compound 76 dosing in adult subjects with breast cancer. The Phase I clinical study of Compound 76 included dose evaluation after intravenous injection of Compound 76 by fluorescence imaging and research pathology assessment.

Clinical Imaging

Intact lumpectomy or mastectomy specimens were excised and imaged for Compound 76 fluorescence using the Synchronized Infrared Imaging System (SIRIS) (Butte 2014). Excised specimens were positioned under the SIRIS imaging head at a fixed focal distance of 35-40 cm. A black fabric covering was utilized to enclose the imaging head and platform to minimize interference from ambient light. Near infrared (NIR) images, visible light images and NIR/visible light composite images were acquired. NIR images were taken by varying exposure times and digital gain settings to optimize for Compound 76-specific fluorescence without reaching saturation levels. Excised lumpectomy specimens were roughly spherical and were rolled in all directions to image superficial, deep, lateral, medial, superior, and inferior sections of the tissue. Excised mastectomy specimens were imaged in the superficial section and posterior/deep aspects (farthest from the surface, adjacent to muscle) of the tissue.

After SIRIS imaging of intact lumpectomy and mastectomy specimens, tissues were gross sectioned using standard techniques and imaged as described above. Areas of gross tumor and areas of fluorescence not within the gross tumor were noted. Samples were further analyzed using standard histopathology methods.

Imaging with either the Spectrum (Quest Medical Imaging) or SIRIS was additionally carried out during surgery for a subset of subjects. Ambient light was minimized during imaging by turning off overhead lights and directing surgical lamps away from the field of view. In this subset of subjects, images of the intact specimens immediately after excision, the tumor bed, and any additional margin tissue after specimen excision were acquired. Additionally, lymph nodes were excised before or after specimen excision and were imaged.

Clinical Image Analysis

Intact lumpectomy and mastectomy specimens were subjectively scored for diffuse fluorescence, which can indicate tumor tissue beneath an adequate margin of normal tissue, or for bright fluorescence with sharp edges, which can indicate tumor tissue at or near the surface of the excised specimen.

Sectioned tissues were analyzed for tumor location using standard gross assessment techniques. Pathology confirmed tumor and non-tumor tissue regions, which were generally apparent within the same field of view. The ImageJ image analysis software was utilized to quantify the relative fluorescence intensity in tumor tissues and surrounding tissues (contrast). A region of interest (ROI) was drawn around the tumor region within a region of grossly normal tissue in the same field of view when possible. The integrated fluorescence intensity was quantified with the image analysis software within each ROI and the tumor to background ratio (TBR) was calculated.

ROI analysis as described above was also carried out for other regions of fluorescence not identified as tumor tissues by pathology assessment.

Image Correlation to Pathology

Hematoxylin and eosin (H&E) staining was used to analyze tissue sections from fluorescent and non-fluorescence regions of gross sectioned tissues. Photomicrographs of H&E stained tissues was compared to fluorescence images of the same regions.

Odyssey Imaging and Histopathology

In some cases, a small area of fluorescent and non-fluorescent tissue of the gross sectioned images was excised and frozen in optimum cutting temperature (OCT) compound. These tissues were cryosectioned and imaged with an Odyssey CLx near-infrared scanner (Li-Cor). Instrument settings were as follows: 800 nm channel, auto intensity, 21 µm resolution, 1 mm offset. Continuous, serial sections were H&E stained and the following regions were marked: tumor regions, necrotic regions, non-tumor abnormal tissue, and normal tissue. Fluorescence signal in each region was analyzed with the ImageJ v1.48 with Bio_Format plugin. Mean intensity per $mm^2$ was used to compare different regions and samples.

Subject Enrollment

Subjects were recruited at Overlake Hospital (Site 1) and the University of Washington Medical Center (Site 2). Ten subjects had been diagnosed with invasive ductal carcinoma (IDC), invasive lobular carcinomas (ILC), ductal carcinoma in situ (DCIS), or lobular carcinoma in situ (LCIS). DCIS and LCIS often occurred along with invasive carcinoma. Subjects were scheduled for lumpectomy or mastectomy. Subjects received either 12 mg or 6 mg of Compound 76 at least two hours prior to surgery. TABLE 6 summarizes the details for each enrolled subject and image acquisition details.

TABLE 6

Summary of Subject Information and Images Acquired

| Subject number | Site | Diagnosis | Procedure | Grade Inv[1]/ in situ[2] | Dose (mg) | Time from dose to surgery (h) | Intraop images Spectrum | Intraop images SIRIS | Ex vivo images SIRIS | Odyssey |
|---|---|---|---|---|---|---|---|---|---|---|
| B001 | 1 | microinvasive carcinoma, DCIS | Lumpectomy | 2/2 | 12 | 6 | No | No | Yes | No |
| B002 | 1 | IDC, DCIS | Lumpectomy | 2/2 | 12 | 3.25 | No | No | Yes | Yes |
| B003 | 1 | IDC with DCIS | Mastectomy | 2/2 | 12 | 3.25 | No | No | Yes | Yes |
| B004 | 1 | IDC with DCIS and LCIS | Lumpectomy | 1/2 | 12 | 2 | No | No | Yes | Yes |
| B005 | 1 | DCIS | Mastectomy | NA/2 | 12 | 3.25 | No | No | Yes | No |
| B006 | 1 | IDC, DCIS | Lumpectomy | 2/3 | 12 | 6 | No | No | Yes | Yes |
| B007 | 1 | bilateral IDC, DCIS | Bilateral Lumpectomy | 1/NA, 2/2 | 12 | 4.5 | Yes | No | Yes | Yes |
| B008 | 1 | IDC, DCIS | Lumpectomy | 2/1-2 | 12 | 3.5 | Yes | No | Yes | Yes |
| B009 | 1 | IDC | Mastectomy | 2/NA | 12 | 2 | Yes | No | Yes | Yes |
| B010 | 2 | IDC, DCIS | Lumpectomy | 2/1 | 12 | 23 | No | Yes | No | No |
| B011 | 1 | Mucinous carcinoma[3], DCIS | Lumpectomy | 2/2 | 12 | 4 | Yes | No | Yes | No |
| B012 | 2 | IDC, DCIS | Mastectomy | 3/3 | 12 | 23 | No | Yes | No | No |
| B013 | 2 | DCIS | Lumpectomy | NA/3 | 6 | 25.5 | No | Yes | Yes | No |
| B014 | 2 | bilateral carcinoma-ILC, LCIS, IDC[4], DCIS | Bilateral Mastectomy | 1/NA, 3/3 | 6 | 16.5 | No | Yes | Yes | No |
| B015 | 1 | IDC, DCIS | Lumpectomy | 1-2/2-3 | 6 | 3 | Yes | No | Yes | No |
| B016 | 2 | DCIS | Mastectomy | NA/3 | 6 | 17 | No | Yes | Yes | No |
| B017[5] | 1 | IDC, DCIS[5] | Mastectomy | 3/UK | 6 | 2.25 | Yes | No | Yes | No |
| B018[6] | 2 | IDC, DCIS | Mastectomy | 1/2 | 6 | 16 | No | Yes | Yes | No |
| B019 | 2 | DCIS | Lumpectomy | NA/2 | 6 | 19 | No | Yes | Yes | No |
| B020 | 1 | Bilateral IDC, DCIS | Bilateral Lumpectomy | 1/NA, 1/2 | 6 | 1 | Yes | No | Yes | No |

TABLE 6-continued

Summary of Subject Information and Images Acquired

| Subject number | Site | Diagnosis | Procedure | Grade Inv[1]/ in situ[2] | Dose (mg) | Time from dose to surgery (h) | Intraop images Spectrum | Intraop images SIRIS | Ex vivo images SIRIS | Odyssey |
|---|---|---|---|---|---|---|---|---|---|---|
| B021 | 2 | ILC, LCIS | Lumpectomy | 2/1-3 | 6 | 26 | No | Yes | yes | No |
| B022 | 1 | bilateral ILC, LCIS IDC, DCIS | Bilateral Mastectomy | 1/NA, 1/2 | 6 | 2 | Yes | No | Yes | No |
| B023[7] | 2 | IDC, DCIS | Mastectomy | 3/3 | 6 | 26 | No | Yes | Yes | No |

[1]Nottingham grade of the invasive carcinoma.
[2]Nuclear grade of the in situ carcinoma.
[3]Mucinous carcinoma was present in the previous biopsy. Residual invasive carcinoma was not present in the lumpectomy specimen.
[4]The invasive ductal carcinoma was present in the needle core biopsy. Residual invasive carcinoma was not present in the mastectomy specimen.
[5]Subject received pre-surgical neoadjuvant therapy. No residual invasive or in situ carcinoma was present in the mastectomy specimen.
[6]Subject had a lumpectomy approximately 2 months prior to this procedure.
[7]Subject received pre-surgical neoadjuvant therapy. Residual IDC and DCIS was present in the mastectomy specimen.
IDC—invasive ductal carcinoma
DCIS—ductal carcinoma in situ;
LCIS—lobular carcinoma in situ
ILC—invasive lobular carcinoma
UK—unknown Dose Analysis—12 mg Cohort A total of 12 subjects were intravenously administered 12 mg of Compound 76 (TABLE 6). Eleven subjects underwent surgery for invasive carcinoma (8 subjects received a lumpectomy and 4 subjects received a mastectomy). Subject B005 was only diagnosed with DCIS and received a mastectomy. Subject B007 had invasive carcinoma in the left and right breast and received a bilateral lumpectomy. Whole tissue specimens and gross sectioned specimens from 10 subjects were imaged ex vivo with the SIRIS. Intra-operative imaging was performed on 4 subjects with the Spectrum and on 2 subjects with the SIRIS (TABLE 6).

Figure 13:
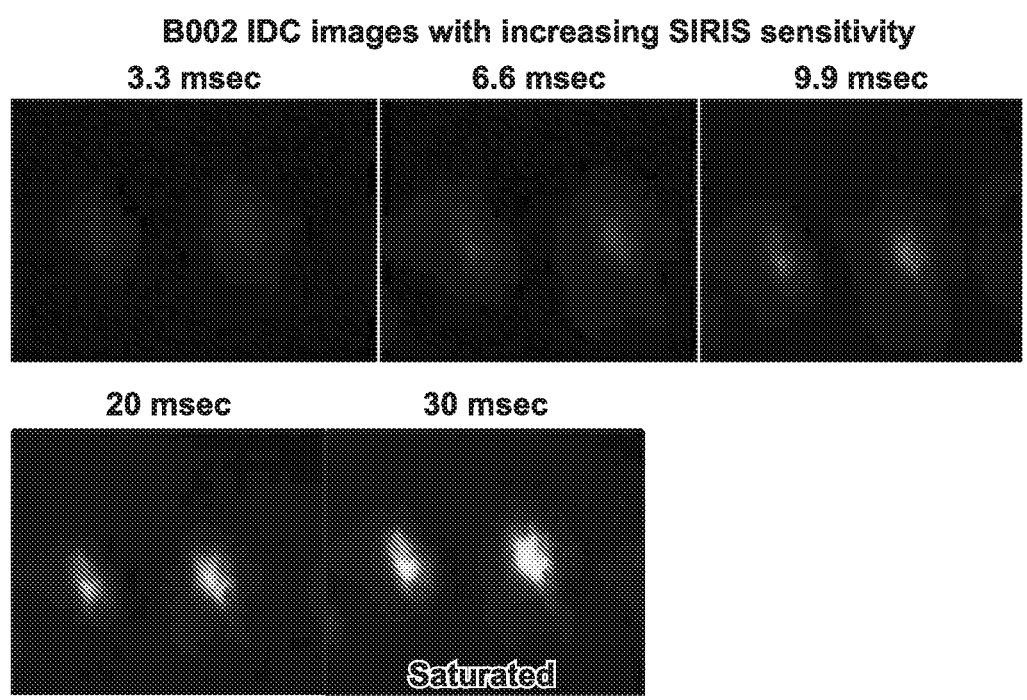
FIG. 13 illustrates the ex vivo NIR images of invasive ductal carcinoma (IDC) in subject B002 taken using the Synchronized Infra-Red Imaging System (SIRIS) at 3.3 msec, 6.6 msec, 9.9 msec, 20 msec, and 30 msec exposure settings. Fluorescence signal, corresponding to lighter and brighter areas in the NIR images, is indicative of the presence of Compound 76 in tumor tissues.
Figure 14:
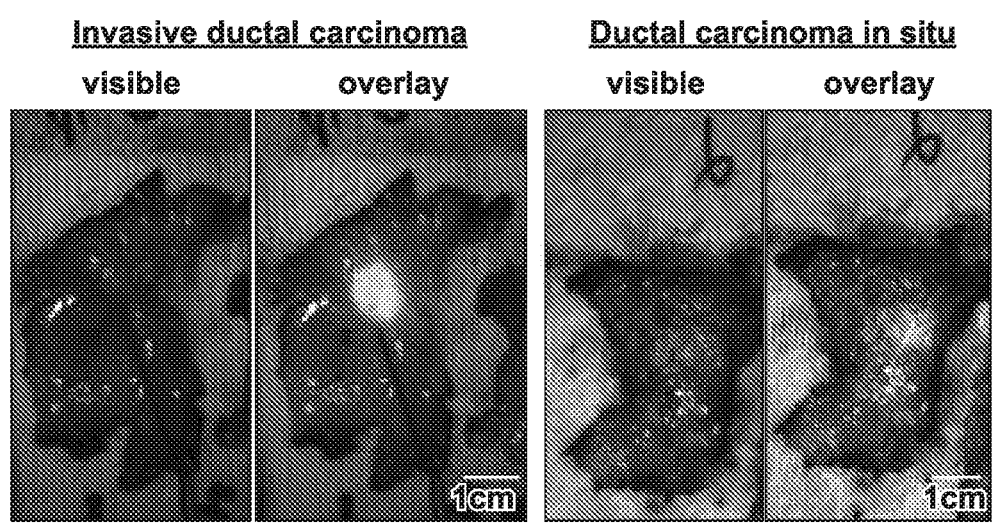
FIG. 14 illustrates representative images of IDC and DCIS carcinoma specimens imaged ex vivo after excision using the SIRIS imaging system. Fluorescence signal, corresponding to lighter and brighter areas in the NIR image, is indicative of the presence of Compound 76 in tumor tissues. Visible light images are shown on the left and visible/NIR overlay images are shown to the right.
Figure 15:
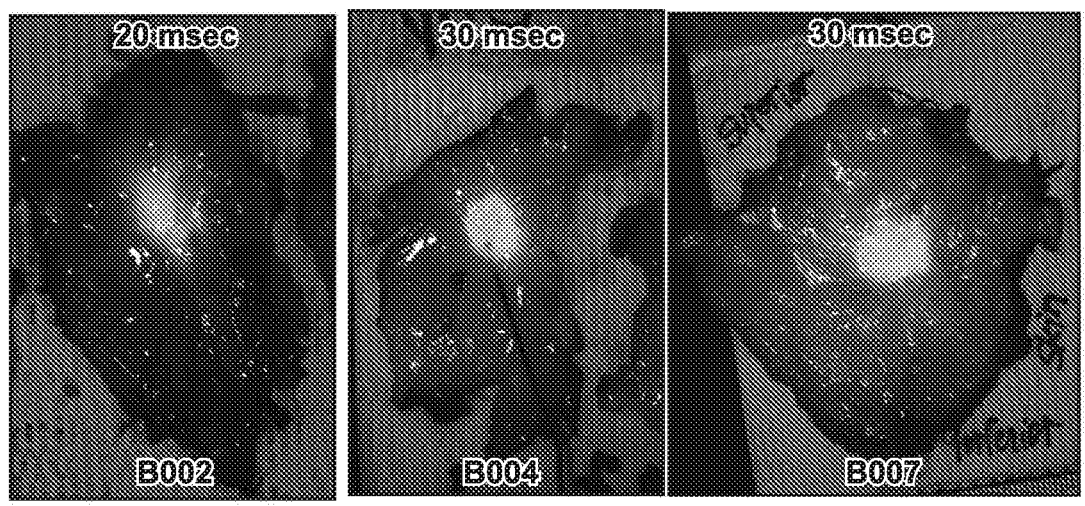
FIG. 15 illustrates representative gross sectioned images from invasive carcinoma (subjects B002, B004, B007) and in situ carcinoma (B001, B004, B008). Fluorescence signal, corresponding to lighter and brighter areas in the NIR image, is indicative of the presence of Compound 76 in tumor tissues. The abbreviation MI in this figure refers to microinvasive carcinoma, LCIS refers to lobular carcinoma in situ (LCIS), and B refers to biopsy.
Figure 15:
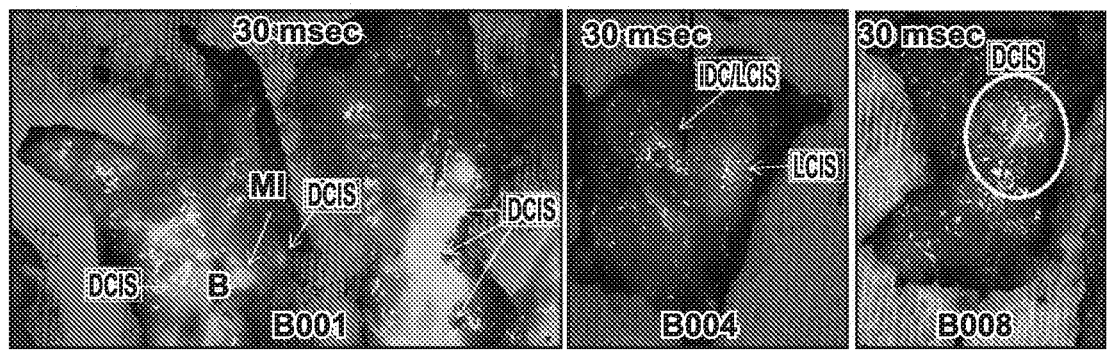

Fluorescent signal was detected in in situ and invasive carcinomas. Exposure times of tissues to imaging was at the lower end of the SIRIS sensitivity settings. FIG. 13 illustrates the ex vivo NIR images of IDC in subject B002 taken using the SIRIS at 3.3 msec to 30 msec exposure settings. Fluorescence signal, corresponding to lighter and brighter areas in the NIR images, is indicative of the presence of Compound 76 in tumor tissues. Tumor fluorescence was visible at the lowest exposure setting (3.3 msec) and was saturated at 30 msec, demonstrating that the IDC can be imaged within the SIRIS detection limits, which range from 3 msec to 1 sec. FIG. 14 illustrates representative images of IDC and DCIS carcinoma specimens imaged ex vivo using the SIRIS imaging system. Visible light images are shown on the left and visible/NIR overlay images are shown to the right. IDC specimens are from subject B004 and DCIS specimens are from B008. Fluorescence signal, corresponding to lighter and brighter areas in the NIR image, is indicative of the presence of Compound 76 in tumor tissues. FIG. 15 illustrates representative gross sectioned visible/NIR overlay images from invasive carcinoma (subjects B002, B004, B007) and in situ carcinoma (B001, B004, B008). The abbreviation MI in this figure refers to micro-invasive carcinoma and B refers to biopsy. Fluorescence signal was observed in specimens from eight subjects where invasive carcinoma was present in the specimen and gross sectioned tissue was imaged ex vivo. Fluorescence signal, corresponding to lighter and brighter areas in the NIR image, is indicative of the presence of Compound 76 in tumor tissues. Specimens from subjects B010 and B012 were not imaged ex vivo. Subject B011 was diagnosed with invasive mucinous carcinoma, which was found in a previous biopsy. Residual invasive carcinoma was not present in the lumpectomy specimen that was excised from subject B011. Tissue in subject B003 was fixed prior to ex vivo imaging and while fluorescence was observed, longer exposure times were required.

Lumpectomy/mastectomy specimens (in situ and ex vivo), the surgical cavity, additional margin tissue, and lymph nodes were imaged in subjects B007 through B012 in the 12 mg dosing cohort. Subjects B007, B008, B009, and B011 were imaged intraoperatively with the Spectrum and subjects B010 and B012 were imaged with the SIRIS. FIG. 16 illustrates representative Spectrum and SIRIS images from intra-operative imaging. FIG. 16A illustrates fluorescence signal from intra-operative imaging using the Spectrum in subject B009. Fluorescence signal, corresponding to lighter and brighter areas in the mastectomy tissue in situ, is indicative of the presence of Compound 76 in tumor tissues and was observed faintly towards the middle of the image. FIG. 16B illustrates fluorescence signal from intra-operative imaging using the SIRIS on lumpectomy specimens ex vivo and at the surgical site in subject B010. Fluorescence signal, corresponding to lighter and brighter areas in the NIR images, is indicative of the presence of Compound 76 in tumor tissues.

Figures 21, 21A, 21B:
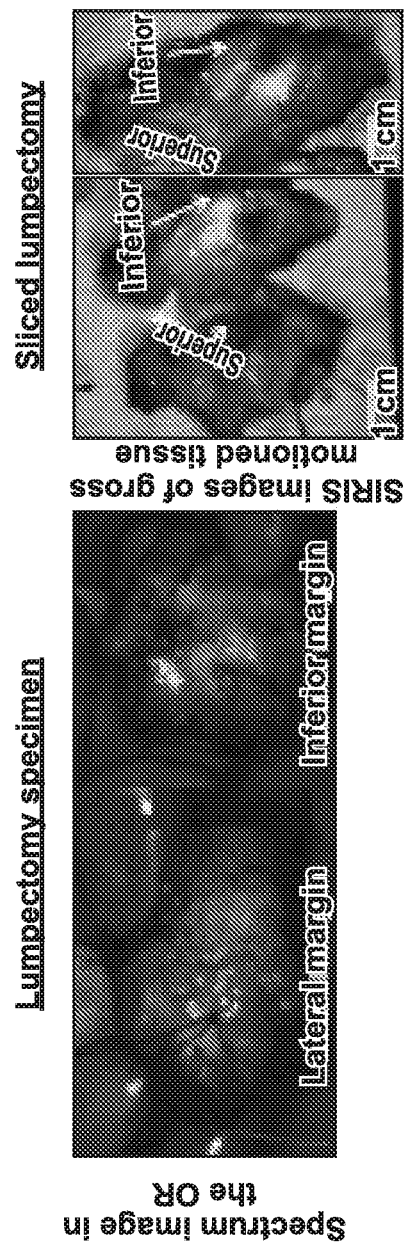
FIG. 21 shows multiple points of intraoperative imaging in subject B0008 in the 12 mg dosing cohort.
FIG. 21A illustrates fluorescence signal in Spectrum-obtained images of the lateral margin and inferior margin in lumpectomy specimens. Fluorescence signal, corresponding to lighter and brighter areas in the NIR images, is indicative of the presence of Compound 76 in tumor tissues.
FIG. 21B illustrates fluorescence signal in SIRIS-obtained sliced lumpectomy images. Fluorescence signal, corresponding to lighter and brighter areas in the NIR images, is indicative of the presence of Compound 76 in tumor tissues.
Figure 22:
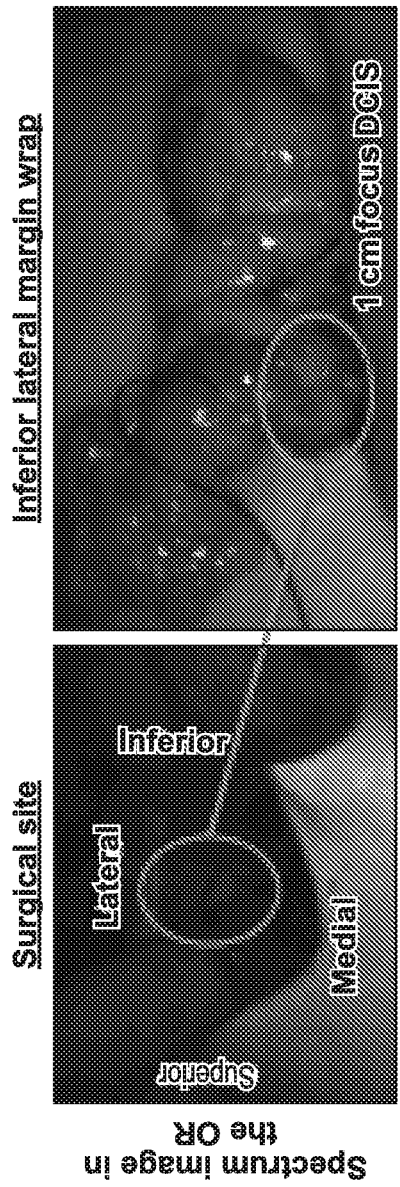
FIG. 22 show multiple points of intraoperative imaging in subject B0008 in the 12 mg dosing cohort.

FIG. 21 and FIG. 22 show multiple points of intraoperative imaging in subject B008 in the 12 mg dosing cohort. FIG. 21A illustrates fluorescence signal in Spectrum-obtained images of the lateral margin and inferior margin in lumpectomy specimens. Fluorescence signal, corresponding to lighter and brighter areas in the NIR images, is indicative of the presence of Compound 76 in tumor tissues. FIG. 21B illustrates fluorescence signal in SIRIS-obtained sliced lumpectomy images. Fluorescence signal, corresponding to lighter and brighter areas in the NIR images, is indicative of the presence of Compound 76 in tumor tissues. FIG. 22A illustrates fluorescence signal in the surgical site. Fluorescence signal, corresponding to lighter and brighter areas in the NIR images, is indicative of the presence of Compound 76 in tumor tissues. FIG. 22B illustrates fluorescence signal in the inferior lateral margin wrap that was excised from the surgical site in FIG. 22A. Fluorescence signal, corresponding to lighter and brighter areas in the NIR image, is indicative of the presence of Compound 76 in tumor tissues. Fluorescence signal in the inferior lateral margin wrap was concentrated in a 1 cm region of DCIS confirmed by histopathology analysis. Pathologic assessment of the excised lumpectomy specimen showed IDC and DCIS. The closet margin in the IDC samples was 2.0 mm (inferior) and the closest margin in the DCIS samples was 2.5 mm (inferior). The inferior-lateral cavity specimen showed a 1.0 cm area of residual DCIS characterized by small foci.

In three of the subjects, fluorescence signal was not observed in excised tissue specimens or in the tumor bed. In subject B008, fluorescence signal was observed in a lumpectomy specimen where margins were determined to be less than 5 mm by pathology consultation. Fluorescence signal was also observed in the surgical cavity of subject B008, corresponding to residual DCIS. Subject B010 was determined to have a 1 mm inferior margin on the lumpectomy specimen, but the margin was not captured in SIRIS images.

Dose Analysis—6 mg Dose Cohort

A total of 11 subjects were intravenously administered 6 mg of Compound 76 (TABLE 6). Eight subjects had invasive carcinoma. Three of these subjects received a lumpectomy and five subjects received a mastectomy. Three subjects were diagnosed with only in situ carcinoma. Two of these subjects underwent a lumpectomy and one subject underwent a mastectomy. Subjects B014, B020, and B022 had bilateral invasive carcinoma. Subjects B014 and B022 underwent a bilateral mastectomy and subject B020 underwent bilateral lumpectomy.

Figure 17:
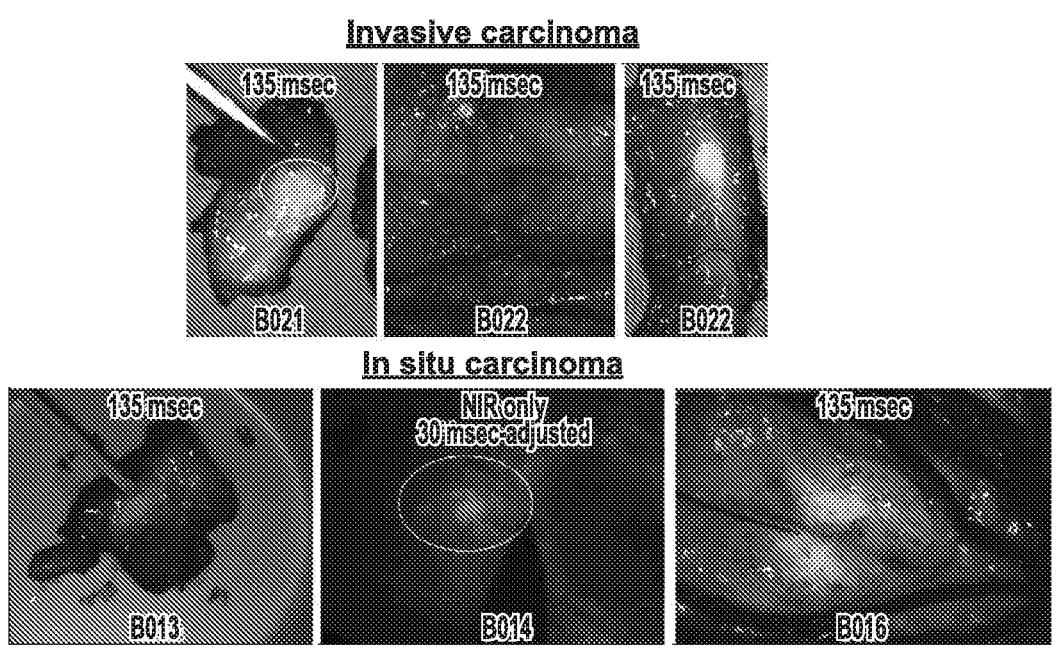
FIG. 17 illustrates representative images from tissue specimens with invasive and in situ carcinoma. Fluorescence signal, corresponding to lighter and brighter areas in the NIR images, is indicative of the presence of Compound 76 in tumor tissues. Invasive carcinoma NIR/visible light overlay images are shown in subjects B021, B022, and B015. In situ carcinoma NIR/visible light overlay images are shown in subjects B013 and B016. An NIR light image (brightened from original image) of the in situ carcinoma is shown for subject B014. Circles and arrows/pointer indicate tumor regions.
Figure 18:
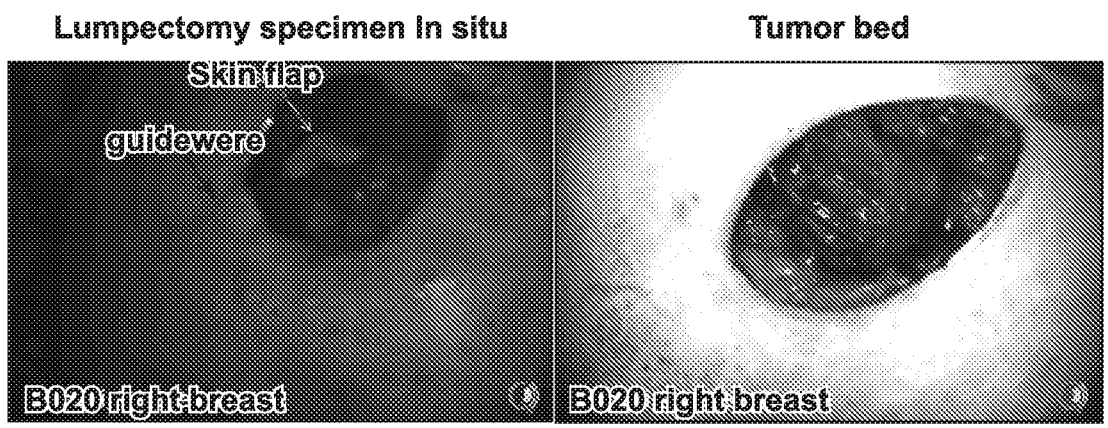
FIG. 18 illustrates a representative intraoperative SIRIS image of subject B020 including the lumpectomy specimen in situ and the tumor bed. Fluorescence signal was not observed in the surgical site.
Figure 19:
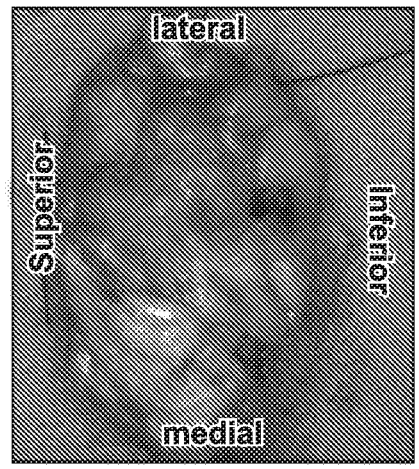
FIG. 19 illustrates representative intraoperative Spectrum images from subject B021 including the lumpectomy specimen ex vivo and the surgical site. Fluorescence signal, corresponding to lighter and brighter areas in the NIR images, is indicative of the presence of Compound 76 in tumor tissues. The NIR only image of the lumpectomy specimen contains an outline region where increased fluorescence was observed and the margin was less than 5 mm.
Figure 19:
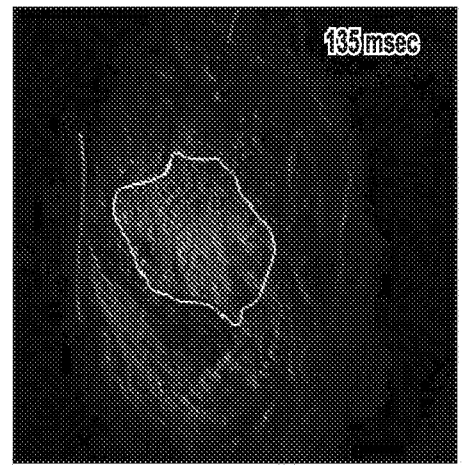
Figure 19:
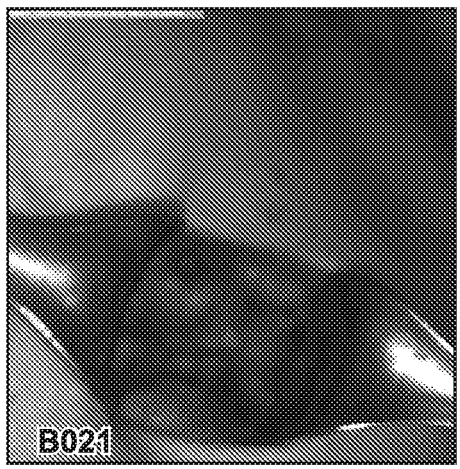
Figure 19:

All subjects in this dose cohort were imaged intraoperatively with the SIRIS (7 subjects) or the Spectrum (4 subjects) and gross sectioned tissue from all subjects were imaged ex vivo with the SIRIS. Fluorescence signal was observed in all subjects with invasive and in situ carcinoma. Exposure times of 135 msec were needed to image samples, which was higher than the exposure time used to image the above 12 mg dose cohort. Subject B022 underwent a bilateral mastectomy for lobular and invasive carcinoma and two invasive lesions were found in the right breast. One of these lesions exhibited negative fluorescence; however, the lesion may have been out of the range of the limit of detection. FIG. 17 illustrates representative images from tissue specimens with invasive and in situ carcinoma. Invasive carcinoma NIR/visible light overlay images were produced for subjects B021, B022, and B015. In situ carcinoma NIR/visible light overlay images were produced for subjects B013 and B016. An NIR light image only of the in situ carcinoma were produced for subject B014. Circles and arrows/pointer indicate tumor regions. Fluorescence signal, corresponding to lighter and brighter areas in the NIR images, is indicative of the presence of Compound 76 in tumor tissues. FIGS. 18-19 illustrate representative intraoperative images from the 6 mg dose cohort. FIG. 18 illustrates a representative intraoperative SIRIS image of subject B020 including the lumpectomy specimen in situ and the tumor bed. Fluorescence signal was not observed in the surgical site in any of these subjects. FIG. 19 illustrates representative intraoperative Spectrum images from subject B021 including the lumpectomy specimen ex vivo and the surgical site. The NIR only image of the lumpectomy specimen contains an outline region where increased fluorescence was observed and the margin was less than 5 mm. Fluorescence signal, corresponding to lighter and brighter areas in the NIR images, is indicative of the presence of Compound 76 in tumor tissues.

Figure 20:
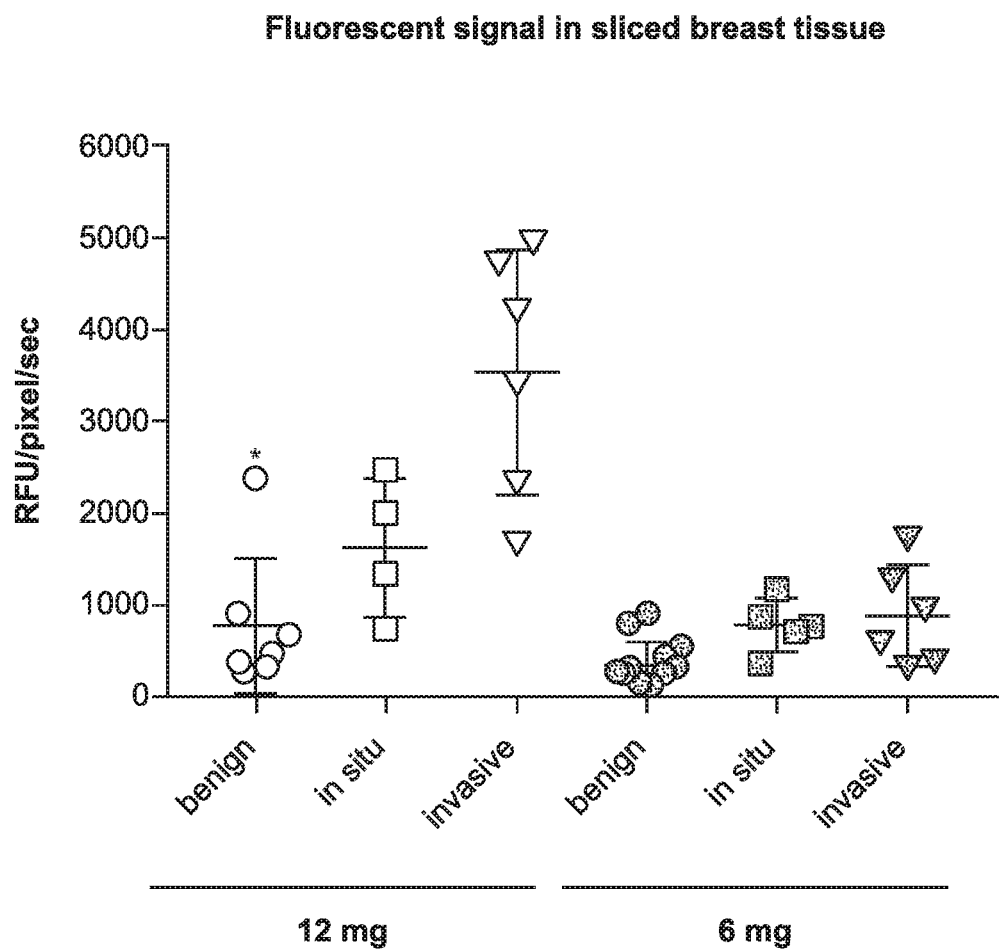
FIG. 20 illustrates a graph of relative fluorescence units (RFU)/pixel/sec for benign, in situ, and invasive breast tissues (as confirmed by pathology assessment) for the 12 mg and 6 mg dose cohorts. The asterisk indicates a false positive. Fluorescence signal intensity was measured within a region of interest (ROI) by ImageJ software analysis.

Overall the data showed that fluorescence signal intensity in invasive and in situ carcinoma was higher than benign tissue in the 12 mg dose cohort. Furthermore, the fluorescence signal was sufficiently strong such that invasive and in situ carcinoma were visually distinguishable in 7 out of 9 lesions evaluated. FIG. 20 illustrates a graph of relative fluorescence units (RFU)/pixel/sec for benign, in situ, and invasive breast tissues (as confirmed by pathology assessment) for the 12 mg and 6 mg dose cohorts. The asterisk indicates a false positive. The data showed the fluorescence signal intensity in the 6 mg dose cohort was lower than the 12 mg dose cohort in all three tissue types. The data showed that fluorescence signal intensity in subjects with invasive and in situ carcinoma was higher than benign tissue in the 6 mg dose cohort as well. However, exposure times were longer and the fluorescence signal was not as bright as the 12 mg dose cohort. Finally, although fluorescence in benign tissue in the 12 mg dose cohort was higher than in the 6 mg dose cohort, this analysis included a false positive outlier in the 12 mg dose cohort, indicated with an asterisk in FIG. 20. Fluorescence signal intensity was measured within a region of interest (ROI) by ImageJ software analysis. As seen in FIG. 20, fluorescence signal in invasive carcinoma was three fold higher (range of 1.4-4.4; n=6 subjects) than benign breast tissue in the 6 mg dose cohort. Fluorescence signal in invasive carcinoma was seven fold higher (range of 5-10; n=6 subjects) than benign breast tissue in the 12 mg dose cohort. Thus, the 6 mg dose level was effective in detecting breast cancer, but the higher 12 mg dose level exhibited better contrast between fluorescence in carcinoma versus benign breast tissue.

Fluorescence Correlation with Histopathology

Figure 23:
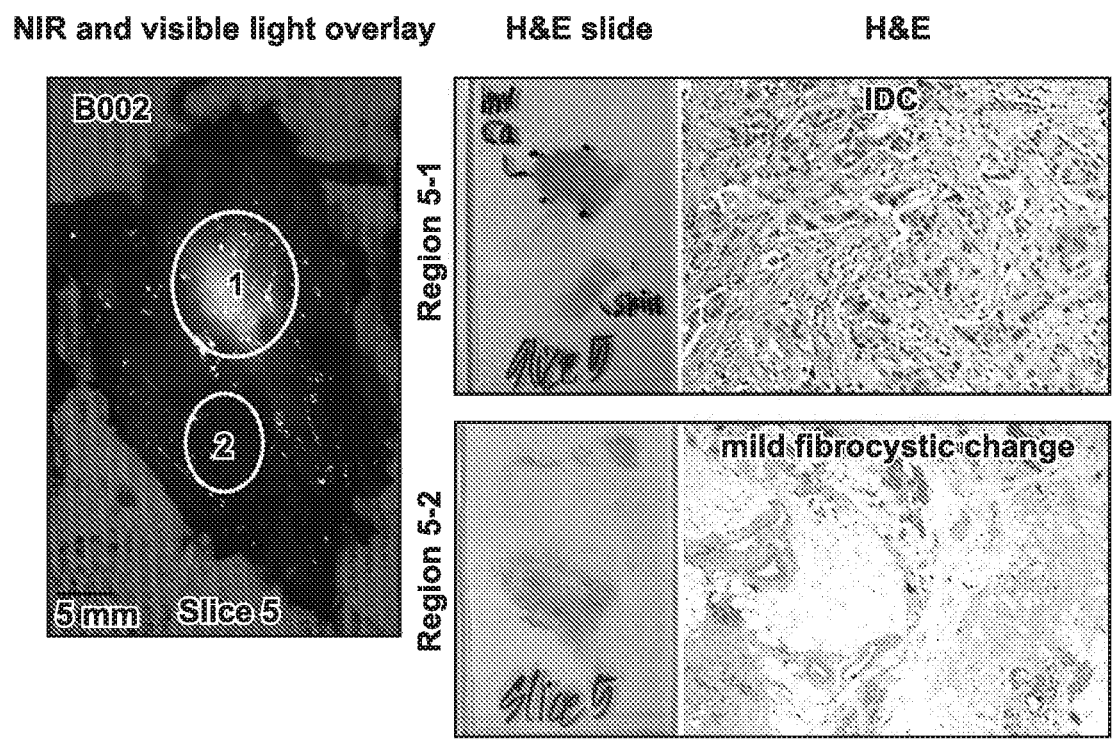
FIG. 23 illustrates fluorescence and histopathology H&E images in subject B002 (same subject as FIG. 2) with invasive ductal carcinoma. Fluorescence signal, corresponding to lighter and brighter areas in the NIR images, is indicative of the presence of Compound 76 in tumor tissues.
Figure 24:
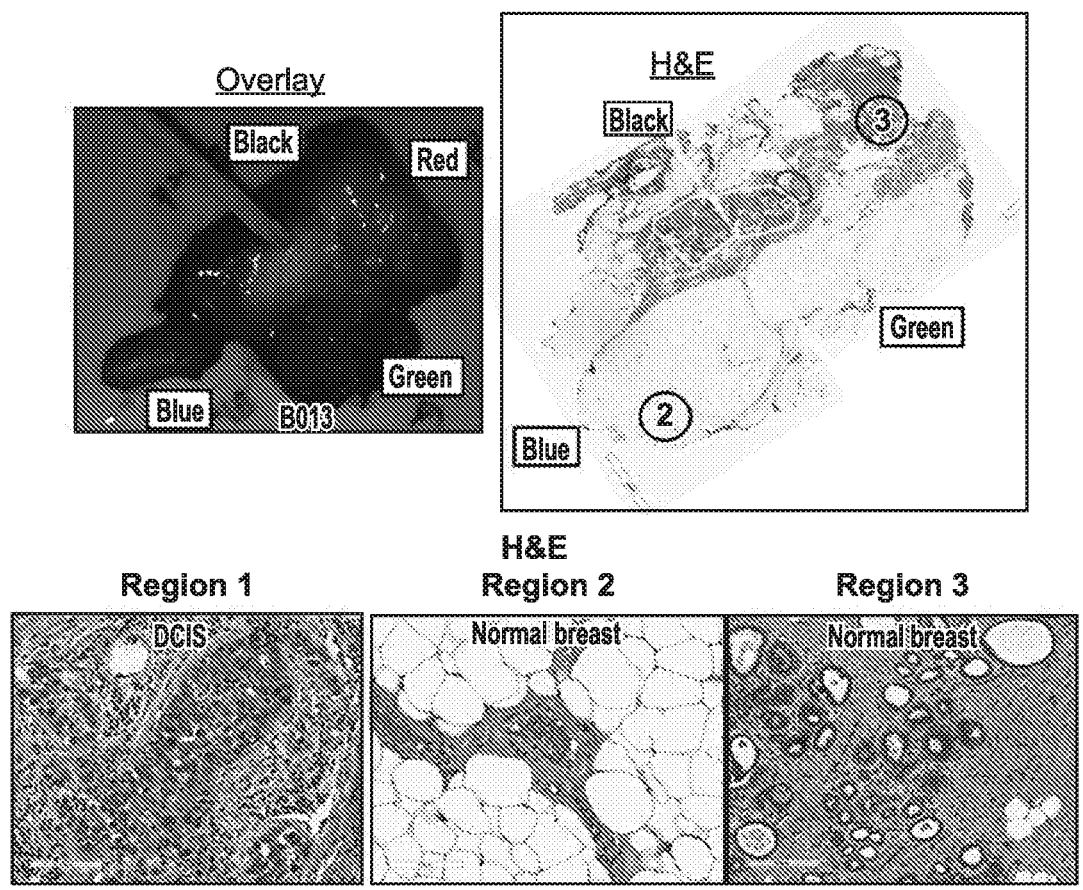
FIG. 24 illustrates diffuse fluorescence in subject B013 with in situ ductal carcinoma (see pointer in image), which corresponds to a region of ductal carcinoma in situ (DCIS) outlined in white in the H&E image on the right. The site of a previous biopsy is indicated in a circle. Fluorescence signal, corresponding to lighter and brighter areas in the NIR image, is indicative of the presence of Compound 76 in tumor tissues.

Fluorescence signal relevant to pathology was correlated to H&E histopathological analysis using microscopy. Bright focal fluorescence signal was correlated to invasive carcinoma in eight of eight subjects in the 12 mg dose cohort as shown in FIG. 23. For example, this correlation was exhibited by specimens from subject B001 with microinvasive carcinoma and subject B003. In the 6 mg dose cohort, seven of eight invasive carcinoma lesions were detected. In the 12 mg dose cohort, regions containing diffuse fluorescence signal were observed in five of seven DCIS lesions. In the 6 mg dose cohort, five out of five in situ lesions were detected as shown in FIG. 24. FIG. 23 illustrates fluorescence and histopathology images in subject B002 with invasive carcinoma. Fluorescence signal, corresponding to lighter and brighter areas in the NIR images, is indicative of the presence of Compound 76 in tumor tissues. Bright, focal fluorescence was observed in invasive carcinoma regions (2) of lumpectomy specimens imaged ex vivo and corresponded well to the H&E image to the right. No fluorescence signal was observed in benign breast tissue (1) and corresponded well to the H&E image to the right. FIG. 24 illustrates diffuse fluorescence in subject B013 with in situ carcinoma (see pointer in image) and corresponded to a region of DCIS outlined in the light color in the H&E image to the right. Fluorescence signal, corresponding to lighter and brighter areas in the NIR image, is indicative of the presence of Compound 76 in tumor tissues. Benign breast tissue, as illustrated by H&E staining, exhibited no fluorescence signal in Region 2 and light fluorescence in Region 3. The site of a previous biopsy is indicated in the dark circle.

Margin Analysis

Margin analysis was conducted on ten subjects with ex vivo images on whole specimens and final pathologic margin data. Eight subjects had IDC and/or DCIS or LCIS. Two subjects had ILC and/or LCIS. TABLE 8 shows results from the diagnosis, the NIR imaging result, and the closest pathologic margin in each subject.

TABLE 8

Whole Specimen Imaging Results and Final Pathologic Margins

| Subject | Diagnosis | Suspected close margin on NIR imaging | Closest pathologic margin (mm) |
|---|---|---|---|
| B001 | DCIS with microinvasion | Yes | 1 |
| B002 | IDC, DCIS | No | 6 |
| B004 | IDC, LCIS | No | >10 |
| B007 | IDC | Yes | 4 |
| B008 | IDC, DCIS | Yes | 2 |
| B011 | DCIS | No | 5 |
| B015 | IDC | Yes | 2 |
| B018 | DCIS, IDC | Yes | 1 |
| B021 | ILC, LCIS | Yes | 3 |
| B022 | ILC | No | 4 |

Six specimens were observed to be suspicious of a close margin based on NIR imaging results and four were not suspicious of a close margin. The mean closest margin was 2.2 mm for specimens suspicious of a close margin and 6.25 mm for specimens not suspicious of a close margin (P<0.05).

Breast density was assessed by radiologists using mammograms and was classified into four categories. Low density breast tissues were described as "almost entirely fatty" and "scattered areas of fibroglandular density." Dense breast tissues were described as "heterogeneously dense" and "extremely dense." Higher density breast tissues makes mammographic detection difficult (Freer, 2015). Breast density data was collected for eight subjects in the 12 mg dose cohort. Seven of these subjects were in the 6 mg dose cohort and one of these subjects was in the 12 mg dose cohort. Fluorescence signal intensity and pathology assessments were determined for five subjects. These five subjects included two subjects with lobular carcinoma and three subjects with ductal carcinoma in situ. These subjects were determined to have dense breast tissues; however fluorescence was still observed in all five subjects, indicating that fluorescence detection with Compound 76 was not hindered by dense breast tissue.

Lobular and Ductal Carcinoma

Figure 25:
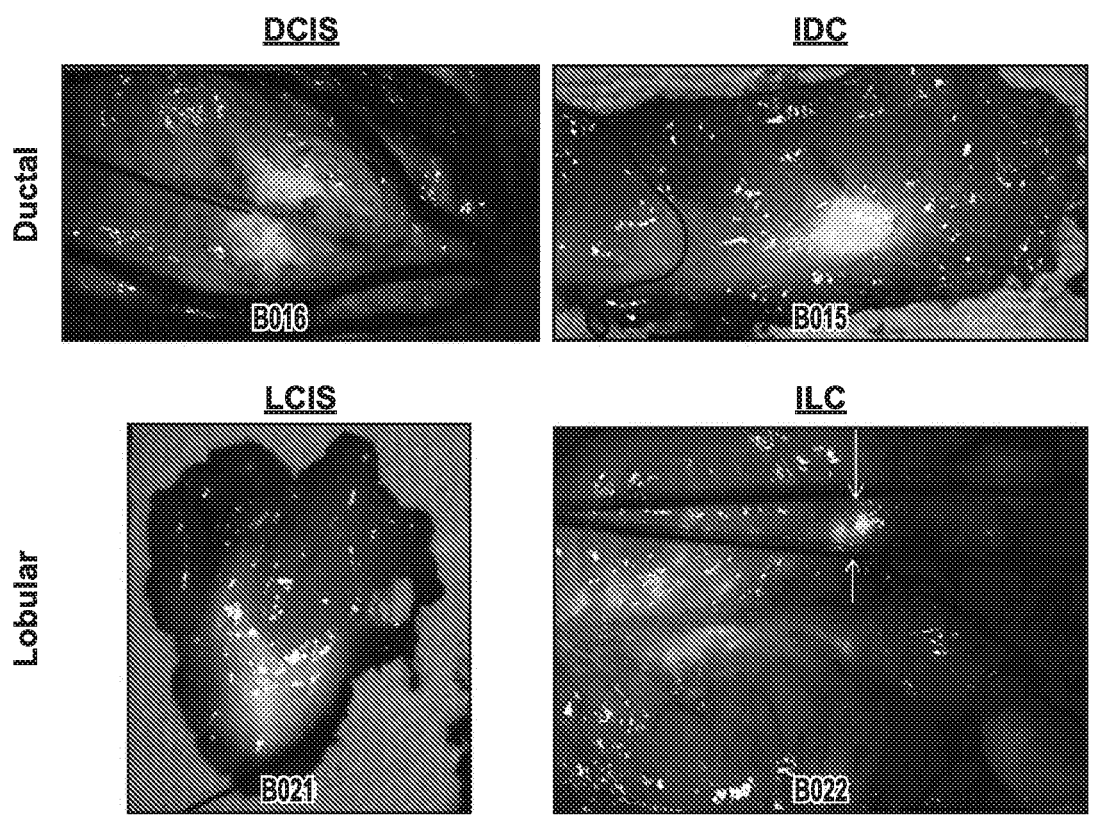
FIG. 25 illustrates fluorescence patterns in ductal carcinoma in situ (DCIS) in subject B016 and invasive ductal carcinoma (IDC) in subject B015 as well as lobular carcinoma in situ (LCIS) in subject B021 and invasive lobular carcinoma (ILC) in subject B022. Fluorescence signal, corresponding to lighter and brighter areas in the NIR images, is indicative of the presence of Compound 76 in tumor tissues.

Most subjects enrolled in this Phase I study had a ductal histological type of carcinoma. Of 27 specimens (four enrolled subjects underwent bilateraly lumpectomy or mastectomy), 24 were ductal carcinomas and three were lobular carcinomas. Subject B011 was diagnosed with mucinous carcinoma confirmed by a previous biopsy, but mucinous carcinoma was not found in the lumpectomy specimen. Subject B011 had a focus of DCIS, which exhibited fluorescence. In situ disease was characterized by a diffuse, lower fluorescence signal, and invasive disease was characterized by bright, focal fluorescence signal for both lobular (ILC and LCIS) and ductal carcinomas (IDC and DCIS). FIG. 25 illustrates fluorescence patterns in DCIS in subject B016 and IDC in subject B015 as well as LCIS in subject B021 and ILC in subject B022. Fluorescence signal, corresponding to lighter and brighter areas in the NIR images, is indicative of the presence of Compound 76 in tumor tissues. These subjects received 6 mg of Compound 76, and NIR and visible light overlays were acquired using the SIRIS at a 135 msec exposure setting. Similar patterns were observed in the 12 mg dose cohort.

Hormone Receptors and HER2 Expression

Hormone receptor and HER2 expression was determined for 22 of 23 subjects enrolled in this Phase I clinical study. Data for subject B013 was not available. TABLE 11 and TABLE 12 summarize these results.

TABLE 11

Hormone Receptor and Molecular Markers in the 12 mg Dose Group

| Subject Number | Post-Surgical Diagnosis | Receptor Status |
|---|---|---|
| B001 | DCIS with small focus microinvasion | ER+, PR−, HER2 equivocal |
| B002 | IDC with some DCIS | ER−, PR−, HER2− |
| B003 | IDC with some DCIS, some LCIS | ER+, PR+, HER2− |
| B004 | IDC with some DCIS | ER+, PR+, HER2− |
| B005 | DCIS | ER+ |
| B006 | IDC with some DCIS | ER+, PR−, HER2− |
| B007 | L: IDC with some DCIS R: IDC | L: ER+, PR+, HER2− R: ER+, PR+, HER2− |
| B008 | IDC with some DCIS | ER+, PR+, HER2− |
| B009 | IDC | ER+, PR+, HER2− |
| B010 | IDC with some DCIS | ER+, PR+, HER2− |
| B011 | IDC with some DCIS | ER+, PR+, HER2− |
| B012 | IDC with DCIS | ER+, PR−, HER2− |

TABLE 12

Hormone Receptor and Molecular Markers in the 6 mg Dose Group

| Subject Number | Post-Surgical Diagnosis | Receptor Status |
|---|---|---|
| B013 | R: DCIS L: LCIS | Unknown |
| B014 | R: DCIS L: ILC with LCIS present | R: ER−, PR−, HER2− L: ER+, PR+, HER2− |
| B015 | IDC (multifocal) with DCIS | ER+, PR+, HER2− |
| B016 | DCIS | ER+, remaining unknown |
| B017 | Negative for residual carcinoma after neoadjuvant treatment (IDC prior Dx) | ER+, PR+, HER2+ |
| B018 | IDC with some DCIS | ER+, PR+, HER2− |
| B019 | DCIS | ER+, remaining unknown |
| B020 | R: IDC with DCIS L: IDC | R: ER+, PR+, HER2− L: ER+, PR+, HER2− |
| B021 | ILC with LCIS | ER+, PR+, HER2− |
| B022 | R: ILC (multifocal) L: IDC (multifocal) | R: ER+, PR+, HER2− L: ER+, PR+, HER2− |
| B023 | R: mild fibrocystic changes, negative for carcinoma L: IDC, DCIS present | L: ER+, PR+, HER2− |

Figure 26:
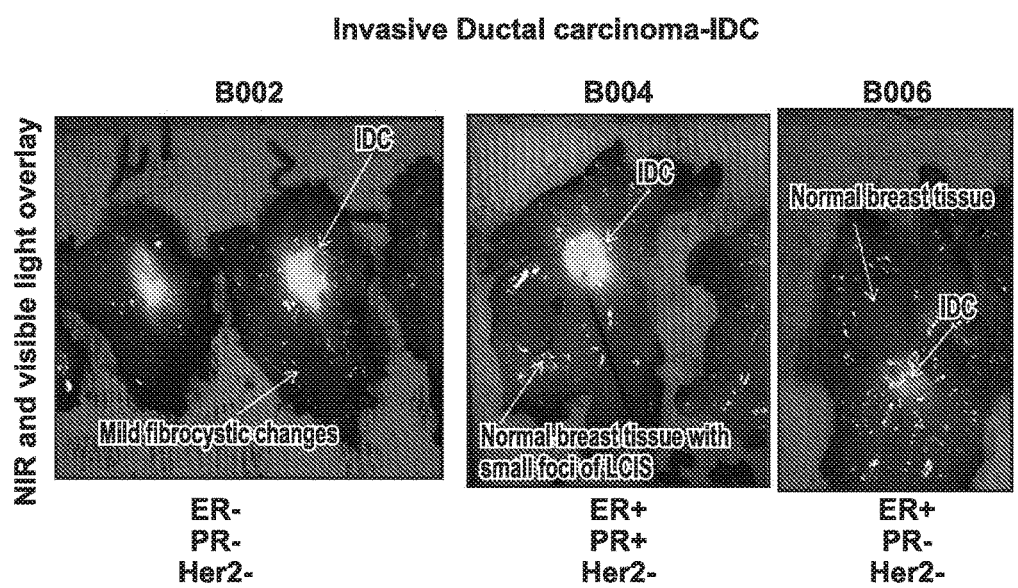
FIG. 26 illustrates a SIRIS image of invasive ductal carcinoma in subjects B002, B004, and B006. Molecular marker subtype expression is shown below each image. Fluorescence signal, corresponding to lighter and brighter areas in the NIR images, is indicative of the presence of Compound 76 in tumor tissues.

Subjects B002 and B014 were ER−, PR−, and HER2− (triple negative). All other subjects were ER+, and all but three subjects were PR+. Only B017 was HER2+, all other subjects were HER2−. Subject B017 was treated prior to surgery and residual IDC was not detected in the mastectomy specimen. FIG. 26 illustrates a SIRIS image of invasive ductal carcinoma in subjects B002, B004, and B006. Molecular marker subtype expression is shown below each image. Fluorescence signal, corresponding to lighter and brighter areas in the NIR images, is indicative of the presence of Compound 76 in tumor tissues. Compound 76 was detected in subjects with IDC and fluorescence signal was not hindered by expression or lack of expression of ER or PR. A seven-fold difference in fluorescence signal between tumor and non-tumor regions was observed in the subject with triple-negative breast cancer.

Example 8

Treatment of Invasive Lobular Carcinoma Breast Cancer with a Peptide-Active Agent Conjugate This example describes the use of chlorotoxin variants described herein to treat invasive lobular carcinoma breast cancer. A peptide of the disclosure is expressed recombinantly or chemically synthesized and then is conjugated to a cytotoxic drug, such as lapatinib, doxorubicin, epirubicin, cyclophosphamide, docetaxel, paclitaxel, capecitabine, ixabepilone, methotrexate, or 5-fluorouracil. The cytotoxic drug is conjugated to SEQ ID NO: 9 peptide at K27. Alternatively, the cytotoxic drug is conjugated to any one of SEQ ID NO: 1-SEQ ID NO: 481 peptide. Invasive lobular carcinoma breast cancer is targeted by the conjugate, and therefore, the conjugate is administered to a human or animal to treat invasive lobular carcinoma breast cancer.

Example 9

Treatment of Lobular Carcinoma In Situ Breast Cancer with a Peptide-Active Agent Conjugate This example describes the use of chlorotoxin variants described herein to treat lobular carcinoma in situ breast cancer. A peptide of the disclosure is expressed recombinantly or chemically synthesized and then is conjugated to a radioactive moiety or a radiosensitizer. The cytotoxic drug is conjugated to SEQ ID NO: 9 peptide at K27. Alternatively, the cytotoxic drug is conjugated to any one of SEQ ID NO: 1-SEQ ID NO: 481 peptide. Lobular carcinoma in situ breast cancer is targeted by the conjugate, and therefore, the conjugate is administered to a human or animal to treat lobular carcinoma in situ breast cancer.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a subject with breast cancer, the method comprising:
   administering a compound to the subject, wherein the compound comprises a polypeptide conjugated to a detectable agent, wherein the polypeptide has at least 80% sequence identity with SEQ ID NO: 9, or the polypeptide has at least 80% sequence identity with a fragment of SEQ ID NO: 9, wherein the fragment of SEQ ID NO: 9 is at least 29 amino acid residues in length;
   selectively labeling a breast cancer tissue in the subject with the compound; and
   performing image guided excision of the breast cancer tissue from the subject with a tumor margin of from 0.2 cm to 1 cm,
   wherein the breast cancer is a triple-negative breast cancer.

2. The method of claim 1, wherein the compound further comprises a therapeutic agent selected from the group consisting of a radiosensitizer, a radioisotope, an antibody, an antibody fragment, a chemotherapeutic agent, a hormone, Olaparib, veliparib, iniparib, niraparib, rucaparib, doxorubicin, etoposide, verapamil, podophyllotoxin, and Herceptin.

3. The method of claim 2, wherein the chemotherapeutic agent is selected from the group consisting of an anthracycline, a taxane, a platinum agent, 5-fluorouracil, cyclophosphamide, vinorelbine, capecitabine, gemcitabine, ixabepilone, tamoxifen, 4-hydroxy tamoxifen, falsodex, raloxifene, bazedoxifene, clomifene, femarelle, lasofoxifene, ormeloxifene, toremifene, and everolimus.

4. The method of claim 2 wherein the chemotherapeutic agent is palbociclib.

5. The method of claim 2, wherein the chemotherapeutic agent is lapatinib.

6. The method of claim 2, wherein the chemotherapeutic agent is doxorubicin or epirubicin.

7. The method of claim 3, wherein the taxane is paclitaxel or docetaxel.

8. The method of claim 3, wherein the platinum agent is cisplatin or carboplatin.

9. The method of claim 2, wherein the therapeutic agent is olaparib.

10. The method of claim 1, wherein the polypeptide is SEQ ID NO: 9.

11. The method of claim 1, wherein the polypeptide contains no lysine residues.

12. The method of claim 1, wherein the polypeptide contains a single lysine residue.

13. The method of claim 12, wherein the single lysine residue is located at a position corresponding to residue 27, residue 23, or residue 15 of SEQ ID NO: 9.

14. The method of claim 1, wherein the compound further comprises polyethylene glycol (PEG), hydroxyethyl starch, polyvinyl alcohol, a water soluble polymer, a zwitterionic water soluble polymer, a water soluble poly(amino acid), an albumin derivative, or a fatty acid conjugated to the polypeptide.

15. The method of claim 1, wherein each amino acid of the polypeptide is independently selected as an L- or D-enantiomer.

16. The method of claim 1, wherein one, two, or three methionine residues of the polypeptide are replaced with other amino acids.

17. The method of claim 1, wherein the polypeptide comprises at least 2 disulfide bonds.

18. The method of claim 1, wherein the presence of the compound in the subject indicates the presence of the breast cancer tissue.

19. The method of claim 1, wherein the image guided excision further comprises fluorescence imaging.

20. The method of claim 1, wherein the compound comprises a structure of Formula (IV), or a pharmaceutically acceptable salt thereof:

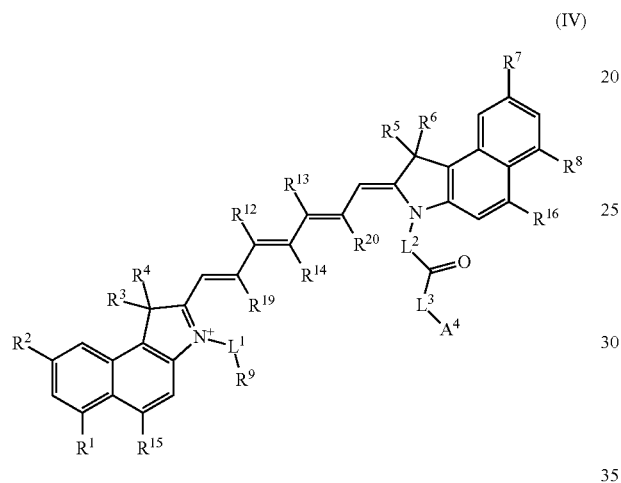

(IV)

wherein:
- $R^1$, $R^2$, $R^3$, $R^4$, $R^5$, $R^6$, $R^7$, $R^8$, $R^{15}$, and $R^{16}$ are each independently selected from hydrogen, $C_1$-$C_6$ alkyl, $C_1$-$C_6$ alkylene-COOH, sulfonate, $C_1$-$C_6$ alkylene-sulfonate, —COOH, —$SO_2$—$NH_2$, or $C_1$-$C_6$ alkoxy;
- $R^9$ is hydrogen, sulfonate, amine, or —COOH;
- $L^1$ is $C_3$-$C_6$ alkylene;
- $L^2$ is $C_1$-$C_{10}$ alkylene;
- $L^3$ is a bond, –O—, —$NR^{10}$—, —$NR^{10}$—$C_1$-$C_6$ alkylene-, —O—$NR^{10}$—, —$NR^{10}$—$C_1$-$C_6$ alkylene-(O—$C_1$-$C_6$ alkylene)$_n$-, —$NR^{10}$-$L^4$-, —$NR^{10}$—$C_1$-$C_6$ alkylene-$NR^{11}$—(C(=O)—$C_1$-$C_6$ alkylene-O—)$_m$—, or —$NR^{10}$—$C_1$-$C_6$ alkylene-$NR^{10}$—$C_1$-$C_6$ alkylene-$NR^{10}$—$C_1$-$C_6$ alkylene-;
- $L^4$ is a bond, -heterocyclyl-, or -heterocyclyl-$C_1$-$C_6$ alkylene-;
- $R^{10}$ is hydrogen or $C_1$-$C_6$ alkyl;
- $R^{11}$ is hydrogen or $C_1$-$C_6$ alkyl;
- $R^{12}$ and $R^{13}$ are independently selected from hydrogen, $C_1$-$C_6$ alkyl, or $R^{12}$ and $R^{13}$ are joined together along with the other atoms to which they are attached to form a 5-membered or 6-membered carbocyclic or heterocyclic ring;
- $R^{14}$ is hydrogen or $C_1$-$C_6$ alkylene, -($L^5$)-aryl, -($L^5$)-aryl-$R^{21}$, -($L^5$)-heteroaryl, -($L^5$)-heteroaryl-$R^{21}$, —$NR^{17}$ $R^{18}$, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;
- $L^5$ is a bond, $C_1$-$C_{10}$ alkylene, —O—, —$NR^{10}$—;
- $R^{17}$ and $R^{18}$ are each independently hydrogen or aryl;
- $R^{19}$ and $R^{20}$ are independently selected from hydrogen, $C_1$-$C_6$ alkyl, $R^{14}$ and $R^{19}$ are joined together along with the other atoms to which they are attached to form a 5-membered or 6-membered carbocyclic or heterocyclic ring, or $R^{14}$ and $R^{20}$ are joined together along with the other atoms to which they are attached to form a 5-membered or 6-membered carbocyclic or heterocyclic ring;
- $R^{21}$ is hydrogen, sulfonate, or —COOH;
- n is 0, 1, 2, or 3;
- m is 0, 1, 2, or 3;
- p is 0, 1, 2, or 3;
- q is 0, 1, 2, or 3; and
- $A^4$ is the polypeptide having at least 80% sequence identity with SEQ ID NO: 9 or at least 80% sequence identity with the fragment of SEQ ID NO: 9.

21. The method of claim 19, wherein:
- $R^3$, $R^4$, $R^5$, $R^6$ are each independently methyl;
- $R^1$, $R^2$, $R^7$, $R^8$, $R^{15}$, and $R^{16}$ are each independently hydrogen;
- $R^{12}$, $R^{13}$, $R^{14}$, $R^{19}$, and $R^{20}$ are each independently hydrogen;
- $R^9$ is sulfonate;
- $R^{10}$ is hydrogen;
- $L^1$ is butylene;
- $L^2$ is pentylene; or
- $L^3$ is selected from a bond, —O—, —$NR^{10}$—, —$NR^{10}$—$C_1$-$C_6$ alkylene-, —O—$NR^{10}$—, or —$NR^{10}$-$L^4$-.

22. The method of claim 19, wherein the compound has a structure of any one of Formulas (IX), (X), (XI), (XII), (XIII), (XIV), (XV), or (XVI), wherein $A^4$ is the polypeptide:

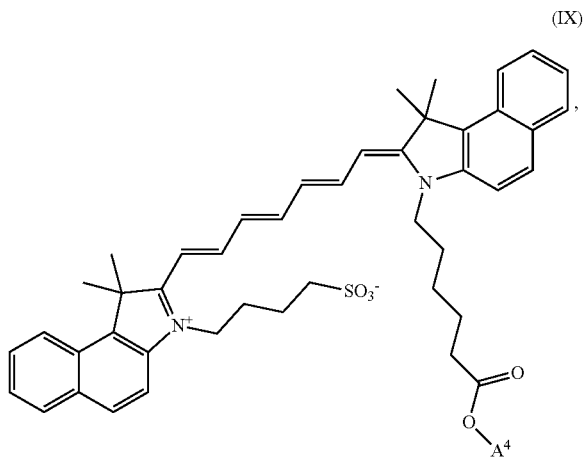

(IX)

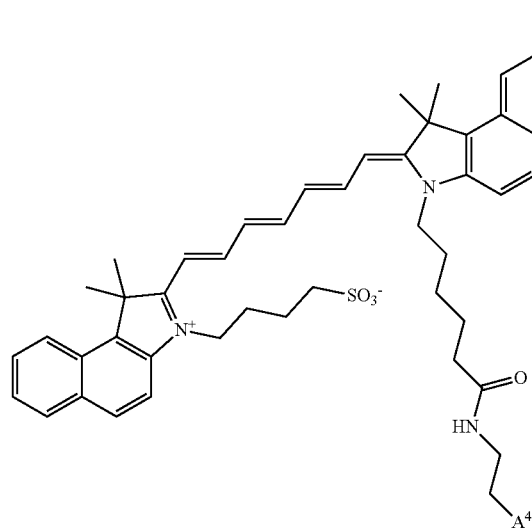
(X)
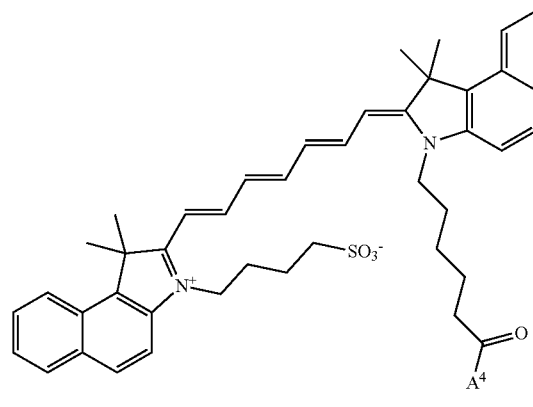
(XI)
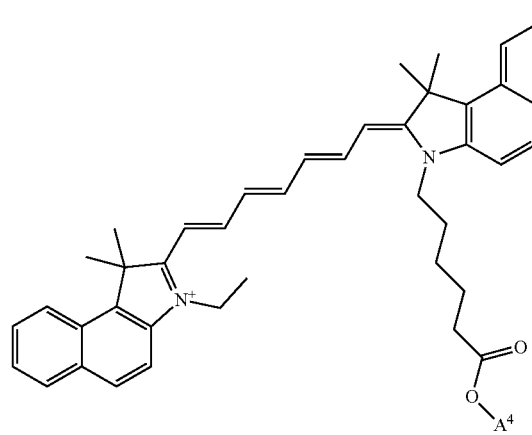
(XII)
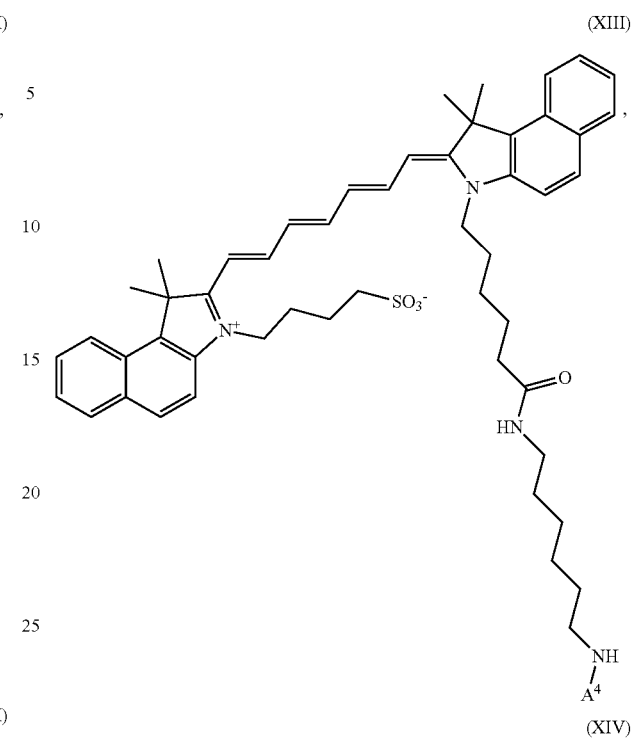
(XIII)
(XIV)
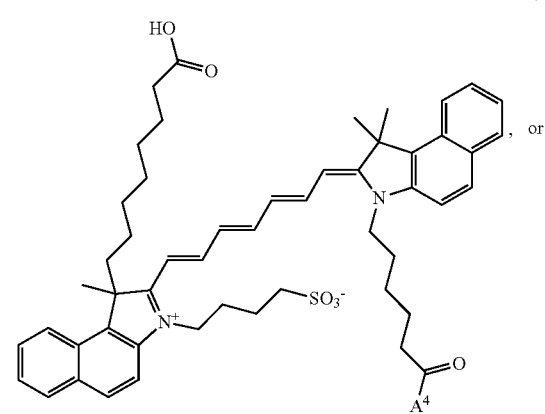
(XV)

-continued (XVI)

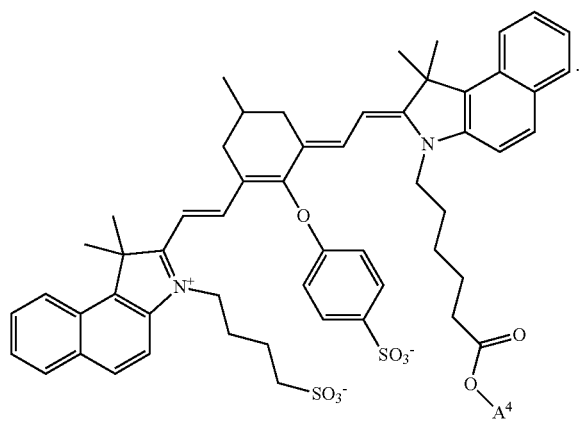

23. The method of claim 1, wherein the detectable agent is selected from the group consisting of a dye, a fluorophore, a fluorescent biotin compound, a luminescent compound, a chemiluminescent compound, a radioisotope, and a paramagnetic metal ion, or combinations thereof.

24. The method of claim 1, wherein the administering is intravenous administration.

25. The method of claim 1, comprising administering the compound at least 2 hours prior to surgically removing the breast cancer.

26. The method of claim 1, comprising administering the compound at a dose of from 1 mg to 30 mg.

27. A method of imaging an organ or body region of a subject, the method comprising:
   administering to the subject a compound comprising a polypeptide conjugated to a detectable agent, wherein the polypeptide has at least 80% sequence identity with SEQ ID NO: 9, or the polypeptide has at least 80% sequence identity with a fragment of SEQ ID NO: 9, wherein the fragment of SEQ ID NO: 9 is at least 29 amino acid residues in length;
   imaging a breast tissue excised from the subject;
   detecting the presence or absence of the compound in a tissue or cell, wherein the presence of the compound in the tissue or cell indicates the presence of a breast cancer; and
   detecting a tumor margin of from 0.2 cm to 1 cm in the breast tissue excised from the subject using image guided excision,
wherein the breast cancer is a triple-negative breast cancer.

28. The method of claim 1, further comprising imaging the breast cancer tissue after the image guided excision.

29. The method of claim 1, further comprising imaging a tumor bed of the subject.

30. The method of claim 29, further comprising detecting residual breast cancer tissue in the tumor bed by detecting residual compound in the tumor bed.

31. The method of claim 30, further comprising surgically removing the residual breast cancer tissue in the tumor bed.

32. The method of claim 1, wherein the tumor margin is from 0.2 cm to 0.5 cm.

* * * * *

```
                        SEQUENCE LISTING

<160> NUMBER OF SEQ ID NOS: 485

<210> SEQ ID NO 1
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Cys Met Pro Cys Phe Thr Thr Asp His Gln Met Ala Arg Ala Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 3
<211> LENGTH: 36
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 3

Met Cys Met Pro Cys Phe Thr Thr Asp His Gln Met Ala Arg Arg Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Cys Met Pro Cys Phe Thr Thr Asp His Gln Met Ala Arg Lys Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 5
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Cys Met Pro Cys Phe Thr Thr Asp His Gln Met Ala Arg Ala Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 6
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Cys Met Pro Cys Phe Thr Thr Asp His Gln Met Ala Arg Arg Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 7
<211> LENGTH: 36
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 7

Met Cys Met Pro Cys Phe Thr Thr Asp His Gln Met Ala Arg Lys Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Cys Met Pro Cys Phe Thr Thr Asp His Gln Met Ala Arg Ala Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 9
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Cys Met Pro Cys Phe Thr Thr Asp His Gln Met Ala Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 10
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Cys Met Pro Cys Phe Thr Thr Asp His Gln Met Ala Arg Lys Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 11
<211> LENGTH: 36

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Cys Met Pro Cys Phe Thr Thr Asp His Gln Met Ala Arg Ala Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 12
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Cys Met Pro Cys Phe Thr Thr Asp His Gln Met Ala Arg Arg Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 13
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Cys Met Pro Cys Phe Thr Thr Asp His Gln Met Ala Arg Lys Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Cys Met Pro Cys Phe Thr Thr Asp His Gln Met Ala Arg Ala Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 15
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Cys Met Pro Cys Phe Thr Thr Asp His Gln Met Ala Arg Arg Cys
1               5                   10                  15

Asp Asp Cys Cys Gly Gly Ala Gly Arg Gly Ala Cys Tyr Gly Pro Gln
            20                  25                  30

Cys Leu Cys Arg
            35

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Cys Met Pro Cys Phe Thr Thr Asp His Gln Met Ala Arg Lys Cys
1               5                   10                  15

Asp Asp Cys Cys Gly Gly Arg Gly Arg Gly Ala Cys Tyr Gly Pro Gln
            20                  25                  30

Cys Leu Cys Arg
            35

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Cys Met Pro Cys Phe Thr Thr Asp His Gln Met Ala Arg Ala Cys
1               5                   10                  15

Asp Asp Cys Cys Gly Gly Arg Gly Arg Gly Ala Cys Tyr Gly Pro Gln
            20                  25                  30

Cys Leu Cys Arg
            35

<210> SEQ ID NO 18
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Cys Met Pro Cys Phe Thr Thr Asp His Gln Met Ala Arg Arg Cys
1               5                   10                  15

Asp Asp Cys Cys Gly Gly Arg Gly Arg Gly Ala Cys Tyr Gly Pro Gln
            20                  25                  30

Cys Leu Cys Arg
            35
```

```
<210> SEQ ID NO 19
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Cys Met Pro Cys Phe Thr Thr Asp His Gln Met Ala Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 20
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Cys Met Pro Cys Phe Thr Thr Asp His Gln Met Ala Arg Ala Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 21
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Cys Met Pro Cys Phe Thr Thr Asp His Gln Met Ala Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Cys Met Pro Cys Phe Thr Thr Asp His Gln Met Ala Arg Lys Cys
1               5                   10                  15

Asp Asp Cys Cys Gly Gly Ala Gly Arg Gly Arg Cys Tyr Gly Pro Gln
            20                  25                  30

Cys Leu Cys Arg
        35
```

```
<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Cys Met Pro Cys Phe Thr Thr Asp His Gln Met Ala Arg Ala Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 24
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Cys Met Pro Cys Phe Thr Thr Asp His Gln Met Ala Arg Arg Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Cys Met Pro Cys Phe Thr Thr Asp His Gln Met Ala Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 26
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Cys Met Pro Cys Phe Thr Thr Asp His Gln Met Ala Arg Ala Cys
1               5                   10                  15

Asp Asp Cys Cys Gly Gly Arg Gly Arg Gly Arg Cys Tyr Gly Pro Gln
            20                  25                  30

Cys Leu Cys Arg
        35
```

```
<210> SEQ ID NO 27
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Cys Met Pro Cys Phe Thr Thr Asp His Gln Met Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 28
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Cys Met Pro Cys Phe Thr Thr Asp His Gln Met Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 29
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Lys Cys Met Pro Cys Phe Thr Thr Asp His Gln Met Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 30
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
```

```
<210> SEQ ID NO 31
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Lys Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 32

Met Cys Met Pro Cys Phe Thr Thr Asp His Gln Met Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 33

Met Cys Met Pro Cys Phe Thr Thr Asp His Gln Met Ala Arg Xaa Cys
1               5                   10                  15

Asp Asp Cys Cys Gly Gly Xaa Gly Arg Gly Xaa Cys Tyr Gly Pro Gln
            20                  25                  30
```

Cys Leu Cys Arg
        35

<210> SEQ ID NO 34
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 34

Lys Cys Met Pro Cys Phe Thr Thr Asp His Gln Met Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 35

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

```
<220> FEATURE:
<221> NAME/KEY: MOD_RES
<222> LOCATION: (27)..(27)
<223> OTHER INFORMATION: Citrulline

<400> SEQUENCE: 36

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
            35

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 37

Lys Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
            35

<210> SEQ ID NO 38
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Gly Ala Gly Ala Ala Gly Gly
            35                  40

<210> SEQ ID NO 39
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39
```

```
Met Cys Met Pro Cys Phe Thr Thr Asp His Gln Met Ala Arg Ala Cys
1               5                   10                  15

Asp Asp Cys Cys Gly Gly Lys Gly Arg Gly Lys Cys Tyr Gly Pro Gln
            20                  25                  30

Cys Leu Cys Arg Gly Ala Gly Ala Ala Gly Gly
        35                  40
```

<210> SEQ ID NO 40
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Met Cys Met Pro Cys Phe Thr Thr Asp His Gln Met Ala Arg Arg Cys
1               5                   10                  15

Asp Asp Cys Cys Gly Gly Lys Gly Arg Gly Lys Cys Tyr Gly Pro Gln
            20                  25                  30

Cys Leu Cys Arg Gly Ala Gly Ala Ala Gly Gly
        35                  40
```

<210> SEQ ID NO 41
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Met Cys Met Pro Cys Phe Thr Thr Asp His Gln Met Ala Arg Lys Cys
1               5                   10                  15

Asp Asp Cys Cys Gly Gly Ala Gly Arg Gly Lys Cys Tyr Gly Pro Gln
            20                  25                  30

Cys Leu Cys Arg Gly Ala Gly Ala Ala Gly Gly
        35                  40
```

<210> SEQ ID NO 42
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Met Cys Met Pro Cys Phe Thr Thr Asp His Gln Met Ala Arg Ala Cys
1               5                   10                  15

Asp Asp Cys Cys Gly Gly Ala Gly Arg Gly Lys Cys Tyr Gly Pro Gln
            20                  25                  30

Cys Leu Cys Arg Gly Ala Gly Ala Ala Gly Gly
        35                  40
```

<210> SEQ ID NO 43
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Met Cys Met Pro Cys Phe Thr Thr Asp His Gln Met Ala Arg Arg Cys
1               5                   10                  15

Asp Asp Cys Cys Gly Gly Ala Gly Arg Gly Lys Cys Tyr Gly Pro Gln
            20                  25                  30

Cys Leu Cys Arg Gly Ala Gly Ala Ala Gly Gly
        35                  40
```

<210> SEQ ID NO 44
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Met Cys Met Pro Cys Phe Thr Thr Asp His Gln Met Ala Arg Lys Cys
1               5                   10                  15

Asp Asp Cys Cys Gly Gly Arg Gly Arg Gly Lys Cys Tyr Gly Pro Gln
            20                  25                  30

Cys Leu Cys Arg Gly Ala Gly Ala Ala Gly Gly
        35                  40
```

<210> SEQ ID NO 45
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Met Cys Met Pro Cys Phe Thr Thr Asp His Gln Met Ala Arg Ala Cys
1               5                   10                  15

Asp Asp Cys Cys Gly Gly Arg Gly Arg Gly Lys Cys Tyr Gly Pro Gln
            20                  25                  30

Cys Leu Cys Arg Gly Ala Gly Ala Ala Gly Gly
        35                  40
```

<210> SEQ ID NO 46
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Met Cys Met Pro Cys Phe Thr Thr Asp His Gln Met Ala Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg Gly Ala Gly Ala Ala Gly Gly
        35                  40
```

<210> SEQ ID NO 47
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 47

Met Cys Met Pro Cys Phe Thr Thr Asp His Gln Met Ala Arg Lys Cys
1               5                   10                  15

Asp Asp Cys Cys Gly Gly Lys Gly Arg Gly Ala Cys Tyr Gly Pro Gln
            20                  25                  30

Cys Leu Cys Arg Gly Ala Gly Ala Ala Gly Gly
        35                  40

<210> SEQ ID NO 48
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Cys Met Pro Cys Phe Thr Thr Asp His Gln Met Ala Arg Ala Cys
1               5                   10                  15

Asp Asp Cys Cys Gly Gly Lys Gly Arg Gly Ala Cys Tyr Gly Pro Gln
            20                  25                  30

Cys Leu Cys Arg Gly Ala Gly Ala Ala Gly Gly
        35                  40

<210> SEQ ID NO 49
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Cys Met Pro Cys Phe Thr Thr Asp His Gln Met Ala Arg Arg Cys
1               5                   10                  15

Asp Asp Cys Cys Gly Gly Lys Gly Arg Gly Ala Cys Tyr Gly Pro Gln
            20                  25                  30

Cys Leu Cys Arg Gly Ala Gly Ala Ala Gly Gly
        35                  40

<210> SEQ ID NO 50
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Cys Met Pro Cys Phe Thr Thr Asp His Gln Met Ala Arg Lys Cys
1               5                   10                  15

Asp Asp Cys Cys Gly Gly Ala Gly Arg Gly Ala Cys Tyr Gly Pro Gln
            20                  25                  30

Cys Leu Cys Arg Gly Ala Gly Ala Ala Gly Gly
        35                  40

<210> SEQ ID NO 51
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 51

Met Cys Met Pro Cys Phe Thr Thr Asp His Gln Met Ala Arg Ala Cys
1               5                   10                  15

Asp Asp Cys Cys Gly Gly Ala Gly Arg Gly Ala Cys Tyr Gly Pro Gln
            20                  25                  30

Cys Leu Cys Arg Gly Ala Gly Ala Ala Gly Gly
        35                  40

<210> SEQ ID NO 52
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Cys Met Pro Cys Phe Thr Thr Asp His Gln Met Ala Arg Arg Cys
1               5                   10                  15

Asp Asp Cys Cys Gly Gly Ala Gly Arg Gly Ala Cys Tyr Gly Pro Gln
            20                  25                  30

Cys Leu Cys Arg Gly Ala Gly Ala Ala Gly Gly
        35                  40

<210> SEQ ID NO 53
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Cys Met Pro Cys Phe Thr Thr Asp His Gln Met Ala Arg Lys Cys
1               5                   10                  15

Asp Asp Cys Cys Gly Gly Arg Gly Arg Gly Ala Cys Tyr Gly Pro Gln
            20                  25                  30

Cys Leu Cys Arg Gly Ala Gly Ala Ala Gly Gly
        35                  40

<210> SEQ ID NO 54
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Cys Met Pro Cys Phe Thr Thr Asp His Gln Met Ala Arg Ala Cys
1               5                   10                  15

Asp Asp Cys Cys Gly Gly Arg Gly Arg Gly Ala Cys Tyr Gly Pro Gln
            20                  25                  30

Cys Leu Cys Arg Gly Ala Gly Ala Ala Gly Gly
        35                  40

<210> SEQ ID NO 55
<211> LENGTH: 43
<212> TYPE: PRT
<213> ORGANISM: Artificial Sequence
<220> FEATURE:
<223> OTHER INFORMATION: Description of Artificial Sequence: Synthetic

```
                      polypeptide

<400> SEQUENCE: 55

Met Cys Met Pro Cys Phe Thr Thr Asp His Gln Met Ala Arg Arg Cys
1               5                   10                  15

Asp Asp Cys Cys Gly Gly Arg Gly Arg Gly Ala Cys Tyr Gly Pro Gln
            20                  25                  30

Cys Leu Cys Arg Gly Ala Gly Ala Ala Gly Gly
        35                  40

<210> SEQ ID NO 56
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Cys Met Pro Cys Phe Thr Thr Asp His Gln Met Ala Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 57
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Cys Met Pro Cys Phe Thr Thr Asp His Gln Met Ala Arg Ala Cys
1               5                   10                  15

Asp Asp Cys Cys Gly Gly Lys Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 58
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Cys Met Pro Cys Phe Thr Thr Asp His Gln Met Ala Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 59
<211> LENGTH: 43
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 59

Met Cys Met Pro Cys Phe Thr Thr Asp His Gln Met Ala Arg Lys Cys
1               5                   10                  15

Asp Asp Cys Cys Gly Gly Ala Gly Gly Arg Cys Tyr Gly Pro Gln
            20                  25                  30

Cys Leu Cys Arg Gly Ala Gly Ala Ala Gly Gly
        35                  40

<210> SEQ ID NO 60
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Cys Met Pro Cys Phe Thr Thr Asp His Gln Met Ala Arg Ala Cys
1               5                   10                  15

Asp Asp Cys Cys Gly Gly Ala Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 61
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Cys Met Pro Cys Phe Thr Thr Asp His Gln Met Ala Arg Arg Cys
1               5                   10                  15

Asp Asp Cys Cys Gly Gly Ala Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 62
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Cys Met Pro Cys Phe Thr Thr Asp His Gln Met Ala Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 63
<211> LENGTH: 43
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 63

Met Cys Met Pro Cys Phe Thr Thr Asp His Gln Met Ala Arg Ala Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 64
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Cys Met Pro Cys Phe Thr Thr Asp His Gln Met Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 65
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Cys Met Pro Cys Phe Thr Thr Asp His Gln Met Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 66
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Lys Cys Met Pro Cys Phe Thr Thr Asp His Gln Met Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 67
<211> LENGTH: 43
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 67

Ala Cys Ala Pro Cys Phe Thr Thr Asp His Gln Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 68
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Lys Cys Ala Pro Cys Phe Thr Thr Asp His Gln Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 69
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 69

Met Cys Met Pro Cys Phe Thr Thr Asp His Gln Met Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg Gly Ala Gly Ala Ala Gly Gly
        35                  40

<210> SEQ ID NO 70
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
```

```
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 70

Met Cys Met Pro Cys Phe Thr Thr Asp His Gln Met Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg Gly Ala Gly Ala Ala Gly Gly
        35                  40

<210> SEQ ID NO 71
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 71

Lys Cys Met Pro Cys Phe Thr Thr Asp His Gln Met Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg Gly Ala Gly Ala Ala Gly Gly
        35                  40

<210> SEQ ID NO 72
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 72

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg Gly Ala Gly Ala Ala Gly Gly
        35                  40

<210> SEQ ID NO 73
```

```
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 73

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg Gly Ala Gly Ala Ala Gly Gly
        35                  40

<210> SEQ ID NO 74
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 74

Lys Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg Gly Ala Gly Ala Ala Gly Gly
        35                  40

<210> SEQ ID NO 75
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Cys Met Pro Cys Phe Thr Thr Asp His Gln Met Val Arg Lys Cys
1               5                   10                  15

Asp Asp Cys Cys Gly Gly Lys Gly Arg Gly Lys Cys Tyr Gly Pro Gln
            20                  25                  30
```

Cys Leu Cys Arg
        35

<210> SEQ ID NO 76
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Cys Met Pro Cys Phe Thr Thr Asp His Gln Met Val Arg Val Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 77
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Cys Met Pro Cys Phe Thr Thr Asp His Gln Met Val Arg Arg Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 78
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Cys Met Pro Cys Phe Thr Thr Asp His Gln Met Val Arg Lys Cys
1               5                   10                  15

Asp Asp Cys Cys Gly Gly Val Gly Arg Gly Lys Cys Tyr Gly Pro Gln
            20                  25                  30

Cys Leu Cys Arg
        35

<210> SEQ ID NO 79
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Cys Met Pro Cys Phe Thr Thr Asp His Gln Met Val Arg Val Cys
1               5                   10                  15

Asp Asp Cys Cys Gly Gly Val Gly Arg Gly Lys Cys Tyr Gly Pro Gln
            20                  25                  30

```
Cys Leu Cys Arg
        35

<210> SEQ ID NO 80
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Cys Met Pro Cys Phe Thr Thr Asp His Gln Met Val Arg Arg Cys
1               5                   10                  15

Asp Asp Cys Cys Gly Gly Val Gly Arg Gly Lys Cys Tyr Gly Pro Gln
            20                  25                  30

Cys Leu Cys Arg
        35

<210> SEQ ID NO 81
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Cys Met Pro Cys Phe Thr Thr Asp His Gln Met Val Arg Lys Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 82
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Cys Met Pro Cys Phe Thr Thr Asp His Gln Met Val Arg Val Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 83
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Cys Met Pro Cys Phe Thr Thr Asp His Gln Met Val Arg Arg Cys
1               5                   10                  15

Asp Asp Cys Cys Gly Gly Arg Gly Arg Gly Lys Cys Tyr Gly Pro Gln
```

```
                 20                  25                  30

Cys Leu Cys Arg
        35

<210> SEQ ID NO 84
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Cys Met Pro Cys Phe Thr Thr Asp His Gln Met Val Arg Lys Cys
1               5                   10                  15

Asp Asp Cys Cys Gly Gly Lys Gly Arg Gly Val Cys Tyr Gly Pro Gln
                 20                  25                  30

Cys Leu Cys Arg
        35

<210> SEQ ID NO 85
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Cys Met Pro Cys Phe Thr Thr Asp His Gln Met Val Arg Val Cys
1               5                   10                  15

Asp Asp Cys Cys Gly Gly Lys Gly Arg Gly Val Cys Tyr Gly Pro Gln
                 20                  25                  30

Cys Leu Cys Arg
        35

<210> SEQ ID NO 86
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Cys Met Pro Cys Phe Thr Thr Asp His Gln Met Val Arg Arg Cys
1               5                   10                  15

Asp Asp Cys Cys Gly Gly Lys Gly Arg Gly Val Cys Tyr Gly Pro Gln
                 20                  25                  30

Cys Leu Cys Arg
        35

<210> SEQ ID NO 87
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Cys Met Pro Cys Phe Thr Thr Asp His Gln Met Val Arg Lys Cys
1               5                   10                  15
```

Asp Asp Cys Cys Gly Gly Val Gly Arg Gly Val Cys Tyr Gly Pro Gln
            20                  25                  30

Cys Leu Cys Arg
        35

<210> SEQ ID NO 88
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Cys Met Pro Cys Phe Thr Thr Asp His Gln Met Val Arg Val Cys
1               5                   10                  15

Asp Asp Cys Cys Gly Gly Val Gly Arg Gly Val Cys Tyr Gly Pro Gln
            20                  25                  30

Cys Leu Cys Arg
        35

<210> SEQ ID NO 89
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Cys Met Pro Cys Phe Thr Thr Asp His Gln Met Val Arg Arg Cys
1               5                   10                  15

Asp Asp Cys Cys Gly Gly Val Gly Arg Gly Val Cys Tyr Gly Pro Gln
            20                  25                  30

Cys Leu Cys Arg
        35

<210> SEQ ID NO 90
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Cys Met Pro Cys Phe Thr Thr Asp His Gln Met Val Arg Lys Cys
1               5                   10                  15

Asp Asp Cys Cys Gly Gly Arg Gly Arg Gly Val Cys Tyr Gly Pro Gln
            20                  25                  30

Cys Leu Cys Arg
        35

<210> SEQ ID NO 91
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Cys Met Pro Cys Phe Thr Thr Asp His Gln Met Val Arg Val Cys
1               5                   10                  15

```
Asp Asp Cys Cys Gly Gly Arg Gly Arg Gly Val Cys Tyr Gly Pro Gln
            20                  25                  30

Cys Leu Cys Arg
        35

<210> SEQ ID NO 92
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Cys Met Pro Cys Phe Thr Thr Asp His Gln Met Val Arg Arg Cys
1               5                   10                  15

Asp Asp Cys Cys Gly Gly Arg Gly Arg Gly Val Cys Tyr Gly Pro Gln
            20                  25                  30

Cys Leu Cys Arg
        35

<210> SEQ ID NO 93
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Cys Met Pro Cys Phe Thr Thr Asp His Gln Met Val Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 94
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Cys Met Pro Cys Phe Thr Thr Asp His Gln Met Val Arg Val Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 95
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Cys Met Pro Cys Phe Thr Thr Asp His Gln Met Val Arg Arg Cys
```

```
                1               5                  10                 15
Asp Asp Cys Cys Gly Gly Lys Gly Arg Gly Arg Cys Tyr Gly Pro Gln
                            20                 25                 30

Cys Leu Cys Arg
            35

<210> SEQ ID NO 96
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Cys Met Pro Cys Phe Thr Thr Asp His Gln Met Val Arg Lys Cys
1               5                  10                 15

Asp Asp Cys Cys Gly Gly Val Gly Arg Gly Arg Cys Tyr Gly Pro Gln
                            20                 25                 30

Cys Leu Cys Arg
            35

<210> SEQ ID NO 97
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Cys Met Pro Cys Phe Thr Thr Asp His Gln Met Val Arg Val Cys
1               5                  10                 15

Asp Asp Cys Cys Gly Gly Val Gly Arg Gly Arg Cys Tyr Gly Pro Gln
                            20                 25                 30

Cys Leu Cys Arg
            35

<210> SEQ ID NO 98
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Cys Met Pro Cys Phe Thr Thr Asp His Gln Met Val Arg Arg Cys
1               5                  10                 15

Asp Asp Cys Cys Gly Gly Val Gly Arg Gly Arg Cys Tyr Gly Pro Gln
                            20                 25                 30

Cys Leu Cys Arg
            35

<210> SEQ ID NO 99
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99
```

Met Cys Met Pro Cys Phe Thr Thr Asp His Gln Met Val Arg Lys Cys
1               5                   10                  15

Asp Asp Cys Cys Gly Gly Arg Gly Arg Gly Arg Cys Tyr Gly Pro Gln
                20                  25                  30

Cys Leu Cys Arg
        35

<210> SEQ ID NO 100
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Cys Met Pro Cys Phe Thr Thr Asp His Gln Met Val Arg Val Cys
1               5                   10                  15

Asp Asp Cys Cys Gly Gly Arg Gly Arg Gly Arg Cys Tyr Gly Pro Gln
                20                  25                  30

Cys Leu Cys Arg
        35

<210> SEQ ID NO 101
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Cys Met Pro Cys Phe Thr Thr Asp His Gln Met Val Arg Arg Cys
1               5                   10                  15

Asp Asp Cys Cys Gly Gly Arg Gly Arg Gly Arg Cys Tyr Gly Pro Gln
                20                  25                  30

Cys Leu Cys Arg
        35

<210> SEQ ID NO 102
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Met Cys Met Pro Cys Phe Thr Thr Asp His Gln Met Val Arg Arg Cys
1               5                   10                  15

Asp Asp Cys Cys Gly Gly Arg Gly Arg Gly Arg Cys Tyr Gly Pro Gln
                20                  25                  30

Cys Leu Cys Arg
        35

<210> SEQ ID NO 103
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Lys Cys Met Pro Cys Phe Thr Thr Asp His Gln Met Val Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 104
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Val Cys Val Pro Cys Phe Thr Thr Asp His Gln Val Val Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 105
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Lys Cys Val Pro Cys Phe Thr Thr Asp His Gln Val Val Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 106
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 106

Met Cys Met Pro Cys Phe Thr Thr Asp His Gln Met Val Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

```
<210> SEQ ID NO 107
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 107

Met Cys Met Pro Cys Phe Thr Thr Asp His Gln Met Val Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 108
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 108

Lys Cys Met Pro Cys Phe Thr Thr Asp His Gln Met Val Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 109
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
```

```
<400> SEQUENCE: 109

Val Cys Val Pro Cys Phe Thr Thr Asp His Gln Val Val Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 110
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 110

Val Cys Val Pro Cys Phe Thr Thr Asp His Gln Val Val Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 111
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 111

Lys Cys Val Pro Cys Phe Thr Thr Asp His Gln Val Val Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 112
<211> LENGTH: 43
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Cys Met Pro Cys Phe Thr Thr Asp His Gln Met Val Arg Lys Cys
1               5                   10                  15

Asp Asp Cys Cys Gly Gly Lys Gly Arg Gly Lys Cys Tyr Gly Pro Gln
                20                  25                  30

Cys Leu Cys Arg Gly Ala Gly Ala Ala Gly Gly
            35                  40

<210> SEQ ID NO 113
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Cys Met Pro Cys Phe Thr Thr Asp His Gln Met Val Arg Val Cys
1               5                   10                  15

Asp Asp Cys Cys Gly Gly Lys Gly Arg Gly Lys Cys Tyr Gly Pro Gln
                20                  25                  30

Cys Leu Cys Arg Gly Ala Gly Ala Ala Gly Gly
            35                  40

<210> SEQ ID NO 114
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Cys Met Pro Cys Phe Thr Thr Asp His Gln Met Val Arg Arg Cys
1               5                   10                  15

Asp Asp Cys Cys Gly Gly Lys Gly Arg Gly Lys Cys Tyr Gly Pro Gln
                20                  25                  30

Cys Leu Cys Arg Gly Ala Gly Ala Ala Gly Gly
            35                  40

<210> SEQ ID NO 115
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Met Cys Met Pro Cys Phe Thr Thr Asp His Gln Met Val Arg Lys Cys
1               5                   10                  15

Asp Asp Cys Cys Gly Gly Val Gly Arg Gly Lys Cys Tyr Gly Pro Gln
                20                  25                  30

Cys Leu Cys Arg Gly Ala Gly Ala Ala Gly Gly
            35                  40

<210> SEQ ID NO 116
```

```
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Cys Met Pro Cys Phe Thr Thr Asp His Gln Met Val Arg Val Cys
1               5                   10                  15

Asp Asp Cys Cys Gly Gly Val Gly Arg Gly Lys Cys Tyr Gly Pro Gln
            20                  25                  30

Cys Leu Cys Arg Gly Ala Gly Ala Ala Gly Gly
            35                  40

<210> SEQ ID NO 117
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Met Cys Met Pro Cys Phe Thr Thr Asp His Gln Met Val Arg Arg Cys
1               5                   10                  15

Asp Asp Cys Cys Gly Gly Val Gly Arg Gly Lys Cys Tyr Gly Pro Gln
            20                  25                  30

Cys Leu Cys Arg Gly Ala Gly Ala Ala Gly Gly
            35                  40

<210> SEQ ID NO 118
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Cys Met Pro Cys Phe Thr Thr Asp His Gln Met Val Arg Lys Cys
1               5                   10                  15

Asp Asp Cys Cys Gly Gly Arg Gly Arg Gly Lys Cys Tyr Gly Pro Gln
            20                  25                  30

Cys Leu Cys Arg Gly Ala Gly Ala Ala Gly Gly
            35                  40

<210> SEQ ID NO 119
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Cys Met Pro Cys Phe Thr Thr Asp His Gln Met Val Arg Val Cys
1               5                   10                  15

Asp Asp Cys Cys Gly Gly Arg Gly Arg Gly Lys Cys Tyr Gly Pro Gln
            20                  25                  30

Cys Leu Cys Arg Gly Ala Gly Ala Ala Gly Gly
            35                  40
```

```
<210> SEQ ID NO 120
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Cys Met Pro Cys Phe Thr Thr Asp His Gln Met Val Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg Gly Ala Gly Ala Ala Gly Gly
        35                  40

<210> SEQ ID NO 121
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Cys Met Pro Cys Phe Thr Thr Asp His Gln Met Val Arg Lys Cys
1               5                   10                  15

Asp Asp Cys Cys Gly Gly Lys Gly Arg Gly Val Cys Tyr Gly Pro Gln
            20                  25                  30

Cys Leu Cys Arg Gly Ala Gly Ala Ala Gly Gly
        35                  40

<210> SEQ ID NO 122
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Met Cys Met Pro Cys Phe Thr Thr Asp His Gln Met Val Arg Val Cys
1               5                   10                  15

Asp Asp Cys Cys Gly Gly Lys Gly Arg Gly Val Cys Tyr Gly Pro Gln
            20                  25                  30

Cys Leu Cys Arg Gly Ala Gly Ala Ala Gly Gly
        35                  40

<210> SEQ ID NO 123
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Met Cys Met Pro Cys Phe Thr Thr Asp His Gln Met Val Arg Arg Cys
1               5                   10                  15

Asp Asp Cys Cys Gly Gly Lys Gly Arg Gly Val Cys Tyr Gly Pro Gln
            20                  25                  30

Cys Leu Cys Arg Gly Ala Gly Ala Ala Gly Gly
        35                  40
```

<210> SEQ ID NO 124
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Cys Met Pro Cys Phe Thr Thr Asp His Gln Met Val Arg Lys Cys
1               5                   10                  15

Asp Asp Cys Cys Gly Gly Val Gly Arg Gly Val Cys Tyr Gly Pro Gln
            20                  25                  30

Cys Leu Cys Arg Gly Ala Gly Ala Ala Gly Gly
        35                  40

<210> SEQ ID NO 125
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Cys Met Pro Cys Phe Thr Thr Asp His Gln Met Val Arg Val Cys
1               5                   10                  15

Asp Asp Cys Cys Gly Gly Val Gly Arg Gly Val Cys Tyr Gly Pro Gln
            20                  25                  30

Cys Leu Cys Arg Gly Ala Gly Ala Ala Gly Gly
        35                  40

<210> SEQ ID NO 126
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met Cys Met Pro Cys Phe Thr Thr Asp His Gln Met Val Arg Arg Cys
1               5                   10                  15

Asp Asp Cys Cys Gly Gly Val Gly Arg Gly Val Cys Tyr Gly Pro Gln
            20                  25                  30

Cys Leu Cys Arg Gly Ala Gly Ala Ala Gly Gly
        35                  40

<210> SEQ ID NO 127
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Cys Met Pro Cys Phe Thr Thr Asp His Gln Met Val Arg Lys Cys
1               5                   10                  15

Asp Asp Cys Cys Gly Gly Arg Gly Arg Gly Val Cys Tyr Gly Pro Gln
            20                  25                  30

Cys Leu Cys Arg Gly Ala Gly Ala Ala Gly Gly
        35                  40

<210> SEQ ID NO 128
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Cys Met Pro Cys Phe Thr Thr Asp His Gln Met Val Arg Val Cys
1               5                   10                  15

Asp Asp Cys Cys Gly Gly Arg Gly Arg Gly Val Cys Tyr Gly Pro Gln
            20                  25                  30

Cys Leu Cys Arg Gly Ala Gly Ala Ala Gly Gly
        35                  40

<210> SEQ ID NO 129
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Cys Met Pro Cys Phe Thr Thr Asp His Gln Met Val Arg Arg Cys
1               5                   10                  15

Asp Asp Cys Cys Gly Gly Arg Gly Arg Gly Val Cys Tyr Gly Pro Gln
            20                  25                  30

Cys Leu Cys Arg Gly Ala Gly Ala Ala Gly Gly
        35                  40

<210> SEQ ID NO 130
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Cys Met Pro Cys Phe Thr Thr Asp His Gln Met Val Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 131
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Met Cys Met Pro Cys Phe Thr Thr Asp His Gln Met Val Arg Val Cys
1               5                   10                  15

Asp Asp Cys Cys Gly Gly Lys Gly Arg Gly Arg Cys Tyr Gly Pro Gln
            20                  25                  30

Cys Leu Cys Arg Gly Ala Gly Ala Ala Gly Gly 35                  40

<210> SEQ ID NO 132
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Cys Met Pro Cys Phe Thr Thr Asp His Gln Met Val Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg Gly Ala Gly Ala Ala Gly Gly
            35                  40

<210> SEQ ID NO 133
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Met Cys Met Pro Cys Phe Thr Thr Asp His Gln Met Val Arg Lys Cys
1               5                   10                  15

Asp Asp Cys Cys Gly Gly Val Gly Arg Gly Arg Cys Tyr Gly Pro Gln
            20                  25                  30

Cys Leu Cys Arg Gly Ala Gly Ala Ala Gly Gly
            35                  40

<210> SEQ ID NO 134
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Cys Met Pro Cys Phe Thr Thr Asp His Gln Met Val Arg Val Cys
1               5                   10                  15

Asp Asp Cys Cys Gly Gly Val Gly Arg Gly Arg Cys Tyr Gly Pro Gln
            20                  25                  30

Cys Leu Cys Arg Gly Ala Gly Ala Ala Gly Gly
            35                  40

<210> SEQ ID NO 135
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Cys Met Pro Cys Phe Thr Thr Asp His Gln Met Val Arg Arg Cys
1               5                   10                  15

Asp Asp Cys Cys Gly Gly Val Gly Arg Gly Arg Cys Tyr Gly Pro Gln
            20                  25                  30

Cys Leu Cys Arg Gly Ala Gly Ala Ala Gly Gly
            35                  40

<210> SEQ ID NO 136
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Met Cys Met Pro Cys Phe Thr Thr Asp His Gln Met Val Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
            35                  40

<210> SEQ ID NO 137
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Met Cys Met Pro Cys Phe Thr Thr Asp His Gln Met Val Arg Val Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
            35                  40

<210> SEQ ID NO 138
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Cys Met Pro Cys Phe Thr Thr Asp His Gln Met Val Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
            35                  40

<210> SEQ ID NO 139
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Cys Met Pro Cys Phe Thr Thr Asp His Gln Met Val Arg Arg Cys
1               5                   10                  15

Asp Asp Cys Cys Gly Gly Arg Gly Arg Gly Arg Cys Tyr Gly Pro Gln
            20                  25                  30

```
Cys Leu Cys Arg Gly Ala Gly Ala Ala Gly Gly
        35                  40

<210> SEQ ID NO 140
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Lys Cys Met Pro Cys Phe Thr Thr Asp His Gln Met Val Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 141
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Val Cys Val Pro Cys Phe Thr Thr Asp His Gln Val Val Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 142
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Lys Cys Val Pro Cys Phe Thr Thr Asp His Gln Val Val Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 143
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
```

```
<223> OTHER INFORMATION: Citrulline

<400> SEQUENCE: 143

Met Cys Met Pro Cys Phe Thr Thr Asp His Gln Met Val Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg Gly Ala Gly Ala Ala Gly Gly
        35                  40

<210> SEQ ID NO 144
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 144

Met Cys Met Pro Cys Phe Thr Thr Asp His Gln Met Val Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg Gly Ala Gly Ala Ala Gly Gly
        35                  40

<210> SEQ ID NO 145
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 145

Lys Cys Met Pro Cys Phe Thr Thr Asp His Gln Met Val Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg Gly Ala Gly Ala Ala Gly Gly
        35                  40

<210> SEQ ID NO 146
```

```
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 146

Val Cys Val Pro Cys Phe Thr Thr Asp His Gln Val Val Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg Gly Ala Gly Ala Ala Gly Gly
        35                  40

<210> SEQ ID NO 147
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 147

Val Cys Val Pro Cys Phe Thr Thr Asp His Gln Val Val Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg Gly Ala Gly Ala Ala Gly Gly
        35                  40

<210> SEQ ID NO 148
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline
```

```
<400> SEQUENCE: 148

Lys Cys Val Pro Cys Phe Thr Thr Asp His Gln Val Val Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg Gly Ala Gly Ala Ala Gly Gly
        35                  40

<210> SEQ ID NO 149
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Met Cys Met Pro Cys Phe Thr Thr Asp His Gln Met Leu Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 150
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Met Cys Met Pro Cys Phe Thr Thr Asp His Gln Met Leu Arg Leu Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 151
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Cys Met Pro Cys Phe Thr Thr Asp His Gln Met Leu Arg Arg Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 152
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 152

Met Cys Met Pro Cys Phe Thr Thr Asp His Gln Met Leu Arg Lys Cys
1               5                   10                  15

Asp Asp Cys Cys Gly Gly Leu Gly Arg Gly Lys Cys Tyr Gly Pro Gln
                20                  25                  30

Cys Leu Cys Arg
            35

<210> SEQ ID NO 153
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Cys Met Pro Cys Phe Thr Thr Asp His Gln Met Leu Arg Leu Cys
1               5                   10                  15

Asp Asp Cys Cys Gly Gly Leu Gly Arg Gly Lys Cys Tyr Gly Pro Gln
                20                  25                  30

Cys Leu Cys Arg
            35

<210> SEQ ID NO 154
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Cys Met Pro Cys Phe Thr Thr Asp His Gln Met Leu Arg Arg Cys
1               5                   10                  15

Asp Asp Cys Cys Gly Gly Leu Gly Arg Gly Lys Cys Tyr Gly Pro Gln
                20                  25                  30

Cys Leu Cys Arg
            35

<210> SEQ ID NO 155
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Cys Met Pro Cys Phe Thr Thr Asp His Gln Met Leu Arg Lys Cys
1               5                   10                  15

Asp Asp Cys Cys Gly Gly Arg Gly Arg Gly Lys Cys Tyr Gly Pro Gln
                20                  25                  30

Cys Leu Cys Arg
            35

<210> SEQ ID NO 156
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

Met Cys Met Pro Cys Phe Thr Thr Asp His Gln Met Leu Arg Leu Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 157
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Cys Met Pro Cys Phe Thr Thr Asp His Gln Met Leu Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 158
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Cys Met Pro Cys Phe Thr Thr Asp His Gln Met Leu Arg Lys Cys
1               5                   10                  15

Asp Asp Cys Cys Gly Gly Lys Gly Arg Gly Leu Cys Tyr Gly Pro Gln
            20                  25                  30

Cys Leu Cys Arg
        35

<210> SEQ ID NO 159
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Cys Met Pro Cys Phe Thr Thr Asp His Gln Met Leu Arg Leu Cys
1               5                   10                  15

Asp Asp Cys Cys Gly Gly Lys Gly Arg Gly Leu Cys Tyr Gly Pro Gln
            20                  25                  30

Cys Leu Cys Arg
        35

<210> SEQ ID NO 160
<211> LENGTH: 36
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 160

Met Cys Met Pro Cys Phe Thr Thr Asp His Gln Met Leu Arg Arg Cys
1               5                   10                  15

Asp Asp Cys Cys Gly Gly Lys Gly Arg Gly Leu Cys Tyr Gly Pro Gln
            20                  25                  30

Cys Leu Cys Arg
        35

<210> SEQ ID NO 161
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Cys Met Pro Cys Phe Thr Thr Asp His Gln Met Leu Arg Lys Cys
1               5                   10                  15

Asp Asp Cys Cys Gly Gly Leu Gly Arg Gly Leu Cys Tyr Gly Pro Gln
            20                  25                  30

Cys Leu Cys Arg
        35

<210> SEQ ID NO 162
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Met Cys Met Pro Cys Phe Thr Thr Asp His Gln Met Leu Arg Leu Cys
1               5                   10                  15

Asp Asp Cys Cys Gly Gly Leu Gly Arg Gly Leu Cys Tyr Gly Pro Gln
            20                  25                  30

Cys Leu Cys Arg
        35

<210> SEQ ID NO 163
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Met Cys Met Pro Cys Phe Thr Thr Asp His Gln Met Leu Arg Arg Cys
1               5                   10                  15

Asp Asp Cys Cys Gly Gly Leu Gly Arg Gly Leu Cys Tyr Gly Pro Gln
            20                  25                  30

Cys Leu Cys Arg
        35

<210> SEQ ID NO 164
<211> LENGTH: 36
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 164

Met Cys Met Pro Cys Phe Thr Thr Asp His Gln Met Leu Arg Lys Cys
1               5                   10                  15

Asp Asp Cys Cys Gly Gly Arg Gly Arg Gly Leu Cys Tyr Gly Pro Gln
            20                  25                  30

Cys Leu Cys Arg
        35

<210> SEQ ID NO 165
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Met Cys Met Pro Cys Phe Thr Thr Asp His Gln Met Leu Arg Leu Cys
1               5                   10                  15

Asp Asp Cys Cys Gly Gly Arg Gly Arg Gly Leu Cys Tyr Gly Pro Gln
            20                  25                  30

Cys Leu Cys Arg
        35

<210> SEQ ID NO 166
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Met Cys Met Pro Cys Phe Thr Thr Asp His Gln Met Leu Arg Arg Cys
1               5                   10                  15

Asp Asp Cys Cys Gly Gly Arg Gly Arg Gly Leu Cys Tyr Gly Pro Gln
            20                  25                  30

Cys Leu Cys Arg
        35

<210> SEQ ID NO 167
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Met Cys Met Pro Cys Phe Thr Thr Asp His Gln Met Leu Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 168
<211> LENGTH: 36
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 168

Met Cys Met Pro Cys Phe Thr Thr Asp His Gln Met Leu Arg Leu Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 169
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Met Cys Met Pro Cys Phe Thr Thr Asp His Gln Met Leu Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 170
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Met Cys Met Pro Cys Phe Thr Thr Asp His Gln Met Leu Arg Lys Cys
1               5                   10                  15

Asp Asp Cys Cys Gly Gly Leu Gly Arg Gly Arg Cys Tyr Gly Pro Gln
            20                  25                  30

Cys Leu Cys Arg
        35

<210> SEQ ID NO 171
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Met Cys Met Pro Cys Phe Thr Thr Asp His Gln Met Leu Arg Leu Cys
1               5                   10                  15

Asp Asp Cys Cys Gly Gly Leu Gly Arg Gly Arg Cys Tyr Gly Pro Gln
            20                  25                  30

Cys Leu Cys Arg
        35

<210> SEQ ID NO 172
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Met Cys Met Pro Cys Phe Thr Thr Asp His Gln Met Leu Arg Arg Cys
1               5                   10                  15

Asp Asp Cys Cys Gly Gly Leu Gly Arg Gly Arg Cys Tyr Gly Pro Gln
            20                  25                  30

Cys Leu Cys Arg
        35

<210> SEQ ID NO 173
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Met Cys Met Pro Cys Phe Thr Thr Asp His Gln Met Leu Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 174
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Met Cys Met Pro Cys Phe Thr Thr Asp His Gln Met Leu Arg Leu Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 175
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Met Cys Met Pro Cys Phe Thr Thr Asp His Gln Met Leu Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 176
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Met Cys Met Pro Cys Phe Thr Thr Asp His Gln Met Leu Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 177
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Lys Cys Met Pro Cys Phe Thr Thr Asp His Gln Met Leu Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 178
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Leu Cys Leu Pro Cys Phe Thr Thr Asp His Gln Leu Leu Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 179
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Lys Cys Leu Pro Cys Phe Thr Thr Asp His Gln Leu Leu Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35
```

```
<210> SEQ ID NO 180
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 180

Met Cys Met Pro Cys Phe Thr Thr Asp His Gln Met Leu Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 181
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 181

Met Cys Met Pro Cys Phe Thr Thr Asp His Gln Met Leu Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 182
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline
```

-continued

<400> SEQUENCE: 182

Lys Cys Met Pro Cys Phe Thr Thr Asp His Gln Met Leu Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 183
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 183

Leu Cys Leu Pro Cys Phe Thr Thr Asp His Gln Leu Leu Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 184
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 184

Leu Cys Leu Pro Cys Phe Thr Thr Asp His Gln Leu Leu Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 185
<211> LENGTH: 36
<212> TYPE: PRT
<213> ORGANISM: Artificial Sequence
<220> FEATURE:
<223> OTHER INFORMATION: Description of Artificial Sequence: Synthetic

```
                               polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 185

Lys Cys Leu Pro Cys Phe Thr Thr Asp His Gln Leu Leu Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 186
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Met Cys Met Pro Cys Phe Thr Thr Asp His Gln Met Leu Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Gly Ala Gly Ala Ala Gly Gly
        35                  40

<210> SEQ ID NO 187
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Met Cys Met Pro Cys Phe Thr Thr Asp His Gln Met Leu Arg Leu Cys
1               5                   10                  15

Asp Asp Cys Cys Gly Gly Lys Gly Arg Gly Lys Cys Tyr Gly Pro Gln
            20                  25                  30

Cys Leu Cys Arg Gly Ala Gly Ala Ala Gly Gly
        35                  40

<210> SEQ ID NO 188
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Met Cys Met Pro Cys Phe Thr Thr Asp His Gln Met Leu Arg Arg Cys
1               5                   10                  15
```

```
Asp Asp Cys Cys Gly Gly Lys Gly Arg Gly Lys Cys Tyr Gly Pro Gln
            20                  25                  30

Cys Leu Cys Arg Gly Ala Gly Ala Ala Gly Gly
        35                  40
```

<210> SEQ ID NO 189
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

```
Met Cys Met Pro Cys Phe Thr Thr Asp His Gln Met Leu Arg Lys Cys
1               5                   10                  15

Asp Asp Cys Cys Gly Gly Leu Gly Arg Gly Lys Cys Tyr Gly Pro Gln
            20                  25                  30

Cys Leu Cys Arg Gly Ala Gly Ala Ala Gly Gly
        35                  40
```

<210> SEQ ID NO 190
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

```
Met Cys Met Pro Cys Phe Thr Thr Asp His Gln Met Leu Arg Leu Cys
1               5                   10                  15

Asp Asp Cys Cys Gly Gly Leu Gly Arg Gly Lys Cys Tyr Gly Pro Gln
            20                  25                  30

Cys Leu Cys Arg Gly Ala Gly Ala Ala Gly Gly
        35                  40
```

<210> SEQ ID NO 191
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

```
Met Cys Met Pro Cys Phe Thr Thr Asp His Gln Met Leu Arg Arg Cys
1               5                   10                  15

Asp Asp Cys Cys Gly Gly Leu Gly Arg Gly Lys Cys Tyr Gly Pro Gln
            20                  25                  30

Cys Leu Cys Arg Gly Ala Gly Ala Ala Gly Gly
        35                  40
```

<210> SEQ ID NO 192
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

```
Met Cys Met Pro Cys Phe Thr Thr Asp His Gln Met Leu Arg Lys Cys
1               5                   10                  15
```

Asp Asp Cys Cys Gly Gly Arg Gly Arg Gly Lys Cys Tyr Gly Pro Gln
            20                  25                  30

Cys Leu Cys Arg Gly Ala Gly Ala Ala Gly Gly
        35                  40

<210> SEQ ID NO 193
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Met Cys Met Pro Cys Phe Thr Thr Asp His Gln Met Leu Arg Leu Cys
1               5                   10                  15

Asp Asp Cys Cys Gly Gly Arg Gly Arg Gly Lys Cys Tyr Gly Pro Gln
            20                  25                  30

Cys Leu Cys Arg Gly Ala Gly Ala Ala Gly Gly
        35                  40

<210> SEQ ID NO 194
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Met Cys Met Pro Cys Phe Thr Thr Asp His Gln Met Leu Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg Gly Ala Gly Ala Ala Gly Gly
        35                  40

<210> SEQ ID NO 195
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Cys Met Pro Cys Phe Thr Thr Asp His Gln Met Leu Arg Lys Cys
1               5                   10                  15

Asp Asp Cys Cys Gly Gly Lys Gly Arg Gly Leu Cys Tyr Gly Pro Gln
            20                  25                  30

Cys Leu Cys Arg Gly Ala Gly Ala Ala Gly Gly
        35                  40

<210> SEQ ID NO 196
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Met Cys Met Pro Cys Phe Thr Thr Asp His Gln Met Leu Arg Leu Cys

```
                1               5                  10                  15
Asp Asp Cys Cys Gly Gly Lys Gly Arg Gly Leu Cys Tyr Gly Pro Gln
                       20                  25                  30

Cys Leu Cys Arg Gly Ala Gly Ala Ala Gly Gly
            35                  40

<210> SEQ ID NO 197
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Met Cys Met Pro Cys Phe Thr Thr Asp His Gln Met Leu Arg Arg Cys
1               5                  10                  15

Asp Asp Cys Cys Gly Gly Lys Gly Arg Gly Leu Cys Tyr Gly Pro Gln
                       20                  25                  30

Cys Leu Cys Arg Gly Ala Gly Ala Ala Gly Gly
            35                  40

<210> SEQ ID NO 198
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Met Cys Met Pro Cys Phe Thr Thr Asp His Gln Met Leu Arg Lys Cys
1               5                  10                  15

Asp Asp Cys Cys Gly Gly Leu Gly Arg Gly Leu Cys Tyr Gly Pro Gln
                       20                  25                  30

Cys Leu Cys Arg Gly Ala Gly Ala Ala Gly Gly
            35                  40

<210> SEQ ID NO 199
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Met Cys Met Pro Cys Phe Thr Thr Asp His Gln Met Leu Arg Leu Cys
1               5                  10                  15

Asp Asp Cys Cys Gly Gly Leu Gly Arg Gly Leu Cys Tyr Gly Pro Gln
                       20                  25                  30

Cys Leu Cys Arg Gly Ala Gly Ala Ala Gly Gly
            35                  40

<210> SEQ ID NO 200
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200
```

Met Cys Met Pro Cys Phe Thr Thr Asp His Gln Met Leu Arg Arg Cys
1               5                   10                  15

Asp Asp Cys Cys Gly Gly Leu Gly Arg Gly Leu Cys Tyr Gly Pro Gln
            20                  25                  30

Cys Leu Cys Arg Gly Ala Gly Ala Ala Gly Gly
            35                  40

<210> SEQ ID NO 201
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Met Cys Met Pro Cys Phe Thr Thr Asp His Gln Met Leu Arg Lys Cys
1               5                   10                  15

Asp Asp Cys Cys Gly Gly Arg Gly Arg Gly Leu Cys Tyr Gly Pro Gln
            20                  25                  30

Cys Leu Cys Arg Gly Ala Gly Ala Ala Gly Gly
            35                  40

<210> SEQ ID NO 202
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Met Cys Met Pro Cys Phe Thr Thr Asp His Gln Met Leu Arg Leu Cys
1               5                   10                  15

Asp Asp Cys Cys Gly Gly Arg Gly Arg Gly Leu Cys Tyr Gly Pro Gln
            20                  25                  30

Cys Leu Cys Arg Gly Ala Gly Ala Ala Gly Gly
            35                  40

<210> SEQ ID NO 203
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Met Cys Met Pro Cys Phe Thr Thr Asp His Gln Met Leu Arg Arg Cys
1               5                   10                  15

Asp Asp Cys Cys Gly Gly Arg Gly Arg Gly Leu Cys Tyr Gly Pro Gln
            20                  25                  30

Cys Leu Cys Arg Gly Ala Gly Ala Ala Gly Gly
            35                  40

<210> SEQ ID NO 204
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Met Cys Met Pro Cys Phe Thr Thr Asp His Gln Met Leu Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 205
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Met Cys Met Pro Cys Phe Thr Thr Asp His Gln Met Leu Arg Leu Cys
1               5                   10                  15

Asp Asp Cys Cys Gly Gly Lys Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 206
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Met Cys Met Pro Cys Phe Thr Thr Asp His Gln Met Leu Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 207
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Met Cys Met Pro Cys Phe Thr Thr Asp His Gln Met Leu Arg Lys Cys
1               5                   10                  15

Asp Asp Cys Cys Gly Gly Leu Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 208
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Met Cys Met Pro Cys Phe Thr Thr Asp His Gln Met Leu Arg Leu Cys
1               5                   10                  15

Asp Asp Cys Cys Gly Gly Leu Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 209
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Met Cys Met Pro Cys Phe Thr Thr Asp His Gln Met Leu Arg Arg Cys
1               5                   10                  15

Asp Asp Cys Cys Gly Gly Leu Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 210
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Met Cys Met Pro Cys Phe Thr Thr Asp His Gln Met Leu Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 211
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Met Cys Met Pro Cys Phe Thr Thr Asp His Gln Met Leu Arg Leu Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 212
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 212

Met Cys Met Pro Cys Phe Thr Thr Asp His Gln Met Leu Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 213
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Met Cys Met Pro Cys Phe Thr Thr Asp His Gln Met Leu Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 214
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Lys Cys Met Pro Cys Phe Thr Thr Asp His Gln Met Leu Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 215
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Leu Cys Leu Pro Cys Phe Thr Thr Asp His Gln Leu Leu Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 216
<211> LENGTH: 43
<212> TYPE: PRT
<213> ORGANISM: Artificial Sequence
<220> FEATURE:
<223> OTHER INFORMATION: Description of Artificial Sequence: Synthetic
```

-continued

```
      polypeptide

<400> SEQUENCE: 216

Lys Cys Leu Pro Cys Phe Thr Thr Asp His Gln Leu Leu Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Gly Ala Gly Ala Ala Gly Gly
        35                  40

<210> SEQ ID NO 217
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 217

Met Cys Met Pro Cys Phe Thr Thr Asp His Gln Met Leu Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg Gly Ala Gly Ala Ala Gly Gly
        35                  40

<210> SEQ ID NO 218
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 218

Met Cys Met Pro Cys Phe Thr Thr Asp His Gln Met Leu Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg Gly Ala Gly Ala Ala Gly Gly
        35                  40

<210> SEQ ID NO 219
<211> LENGTH: 43
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 219

Lys Cys Met Pro Cys Phe Thr Thr Asp His Gln Met Leu Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg Gly Ala Gly Ala Ala Gly Gly
        35                  40

<210> SEQ ID NO 220
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 220

Leu Cys Leu Pro Cys Phe Thr Thr Asp His Gln Leu Leu Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg Gly Ala Gly Ala Ala Gly Gly
        35                  40

<210> SEQ ID NO 221
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 221

Leu Cys Leu Pro Cys Phe Thr Thr Asp His Gln Leu Leu Arg Xaa Cys
1               5                   10                  15

```
Asp Asp Cys Cys Gly Gly Xaa Gly Arg Gly Xaa Cys Tyr Gly Pro Gln
            20                  25                  30

Cys Leu Cys Arg Gly Ala Gly Ala Ala Gly Gly
            35                  40
```

<210> SEQ ID NO 222
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 222

```
Lys Cys Leu Pro Cys Phe Thr Thr Asp His Gln Leu Leu Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg Gly Ala Gly Ala Ala Gly Gly
            35                  40
```

<210> SEQ ID NO 223
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

```
Gly Cys Gly Pro Cys Phe Thr Thr Asp His Gln Gly Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
            35
```

<210> SEQ ID NO 224
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

```
Gly Cys Gly Pro Cys Phe Thr Thr Asp His Gln Gly Ala Arg Ala Cys
1               5                   10                  15

Asp Asp Cys Cys Gly Gly Lys Gly Arg Gly Lys Cys Tyr Gly Pro Gln
            20                  25                  30

Cys Leu Cys Arg
            35
```

<210> SEQ ID NO 225
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gly Cys Gly Pro Cys Phe Thr Thr Asp His Gln Gly Ala Arg Arg Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 226
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gly Cys Gly Pro Cys Phe Thr Thr Asp His Gln Gly Ala Arg Lys Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 227
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gly Cys Gly Pro Cys Phe Thr Thr Asp His Gln Gly Ala Arg Ala Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 228
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Gly Cys Gly Pro Cys Phe Thr Thr Asp His Gln Gly Ala Arg Arg Cys
1               5                   10                  15

Asp Asp Cys Cys Gly Gly Ala Gly Arg Gly Lys Cys Tyr Gly Pro Gln
            20                  25                  30

Cys Leu Cys Arg
        35

```
<210> SEQ ID NO 229
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gly Cys Gly Pro Cys Phe Thr Thr Asp His Gln Gly Ala Arg Lys Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 230
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Gly Cys Gly Pro Cys Phe Thr Thr Asp His Gln Gly Ala Arg Ala Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 231
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gly Cys Gly Pro Cys Phe Thr Thr Asp His Gln Gly Ala Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 232
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gly Cys Gly Pro Cys Phe Thr Thr Asp His Gln Gly Ala Arg Lys Cys
1               5                   10                  15

Asp Asp Cys Cys Gly Gly Lys Gly Arg Gly Ala Cys Tyr Gly Pro Gln
            20                  25                  30

Cys Leu Cys Arg
```

<210> SEQ ID NO 233
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gly Cys Gly Pro Cys Phe Thr Thr Asp His Gln Gly Ala Arg Ala Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 234
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gly Cys Gly Pro Cys Phe Thr Thr Asp His Gln Gly Ala Arg Arg Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 235
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gly Cys Gly Pro Cys Phe Thr Thr Asp His Gln Gly Ala Arg Lys Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 236
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Gly Cys Gly Pro Cys Phe Thr Thr Asp His Gln Gly Ala Arg Ala Cys
1               5                   10                  15

Asp Asp Cys Cys Gly Gly Ala Gly Arg Gly Ala Cys Tyr Gly Pro Gln
            20                  25                  30

```
Cys Leu Cys Arg
        35

<210> SEQ ID NO 237
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gly Cys Gly Pro Cys Phe Thr Thr Asp His Gln Gly Ala Arg Arg Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 238
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Gly Cys Gly Pro Cys Phe Thr Thr Asp His Gln Gly Ala Arg Lys Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 239
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gly Cys Gly Pro Cys Phe Thr Thr Asp His Gln Gly Ala Arg Ala Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 240
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gly Cys Gly Pro Cys Phe Thr Thr Asp His Gln Gly Ala Arg Arg Cys
1               5                   10                  15

Asp Asp Cys Cys Gly Gly Arg Gly Arg Gly Ala Cys Tyr Gly Pro Gln
            20                  25                  30
```

Cys Leu Cys Arg
        35

<210> SEQ ID NO 241
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gly Cys Gly Pro Cys Phe Thr Thr Asp His Gln Gly Ala Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 242
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Gly Cys Gly Pro Cys Phe Thr Thr Asp His Gln Gly Ala Arg Ala Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 243
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Gly Cys Gly Pro Cys Phe Thr Thr Asp His Gln Gly Ala Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 244
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gly Cys Gly Pro Cys Phe Thr Thr Asp His Gln Gly Ala Arg Lys Cys
1               5                   10                  15

Asp Asp Cys Cys Gly Gly Ala Gly Arg Gly Arg Cys Tyr Gly Pro Gln

```
                    20                  25                  30

Cys Leu Cys Arg
        35

<210> SEQ ID NO 245
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Gly Cys Gly Pro Cys Phe Thr Thr Asp His Gln Gly Ala Arg Ala Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 246
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Gly Cys Gly Pro Cys Phe Thr Thr Asp His Gln Gly Ala Arg Arg Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 247
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gly Cys Gly Pro Cys Phe Thr Thr Asp His Gln Gly Ala Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 248
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gly Cys Gly Pro Cys Phe Thr Thr Asp His Gln Gly Ala Arg Ala Cys
1               5                   10                  15
```

Asp Asp Cys Cys Gly Gly Arg Gly Arg Gly Arg Cys Tyr Gly Pro Gln
            20                  25                  30

Cys Leu Cys Arg
        35

<210> SEQ ID NO 249
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Gly Cys Gly Pro Cys Phe Thr Thr Asp His Gln Gly Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 250
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gly Cys Gly Pro Cys Phe Thr Thr Asp His Gln Gly Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 251
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Lys Cys Gly Pro Cys Phe Thr Thr Asp His Gln Gly Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 252
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Ala Cys Ala Pro Cys Phe Thr Thr Asp His Gln Ala Ala Arg Arg Cys
1               5                   10                  15

```
Asp Asp Cys Cys Gly Gly Arg Gly Arg Gly Arg Cys Tyr Gly Pro Gln
            20                  25                  30

Cys Leu Cys Arg
        35

<210> SEQ ID NO 253
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Lys Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 254
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 254

Gly Cys Gly Pro Cys Phe Thr Thr Asp His Gln Gly Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 255
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 255

Gly Cys Gly Pro Cys Phe Thr Thr Asp His Gln Gly Ala Arg Xaa Cys
```

```
1               5                  10                 15
Asp Asp Cys Cys Gly Gly Xaa Gly Arg Gly Xaa Cys Tyr Gly Pro Gln
            20                 25                 30

Cys Leu Cys Arg
        35

<210> SEQ ID NO 256
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 256

Lys Cys Gly Pro Cys Phe Thr Thr Asp His Gln Gly Ala Arg Xaa Cys
1               5                  10                 15

Asp Asp Cys Cys Gly Gly Xaa Gly Arg Gly Xaa Cys Tyr Gly Pro Gln
            20                 25                 30

Cys Leu Cys Arg
        35

<210> SEQ ID NO 257
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 257

Ala Cys Ala Pro Cys Phe Thr Thr Asp His Gln Ala Ala Arg Xaa Cys
1               5                  10                 15

Asp Asp Cys Cys Gly Gly Xaa Gly Arg Gly Lys Cys Tyr Gly Pro Gln
            20                 25                 30

Cys Leu Cys Arg
        35

<210> SEQ ID NO 258
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
```

```
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 258

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 259
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 259

Lys Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 260
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Ala Cys Ala Pro Cys Phe Thr Thr Asp His Gln Ala Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 261
<211> LENGTH: 36
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 261

Ala Cys Ala Pro Cys Phe Thr Thr Asp His Gln Ala Ala Arg Ala Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 262
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Ala Cys Ala Pro Cys Phe Thr Thr Asp His Gln Ala Ala Arg Arg Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 263
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Ala Cys Ala Pro Cys Phe Thr Thr Asp His Gln Ala Ala Arg Lys Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 264
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Ala Cys Ala Pro Cys Phe Thr Thr Asp His Gln Ala Ala Arg Ala Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 265
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Ala Cys Ala Pro Cys Phe Thr Thr Asp His Gln Ala Ala Arg Arg Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 266
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Ala Cys Ala Pro Cys Phe Thr Thr Asp His Gln Ala Ala Arg Lys Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 267
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Ala Cys Ala Pro Cys Phe Thr Thr Asp His Gln Ala Ala Arg Ala Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 268
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Ala Cys Ala Pro Cys Phe Thr Thr Asp His Gln Ala Ala Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 269
<211> LENGTH: 36
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 269

Ala Cys Ala Pro Cys Phe Thr Thr Asp His Gln Ala Ala Arg Lys Cys
1               5                   10                  15
Asp Asp Cys Cys Gly Gly Lys Gly Arg Gly Ala Cys Tyr Gly Pro Gln
            20                  25                  30
Cys Leu Cys Arg
        35

<210> SEQ ID NO 270
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Ala Cys Ala Pro Cys Phe Thr Thr Asp His Gln Ala Ala Arg Ala Cys
1               5                   10                  15
Asp Asp Cys Cys Gly Gly Lys Gly Arg Gly Ala Cys Tyr Gly Pro Gln
            20                  25                  30
Cys Leu Cys Arg
        35

<210> SEQ ID NO 271
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Ala Cys Ala Pro Cys Phe Thr Thr Asp His Gln Ala Ala Arg Arg Cys
1               5                   10                  15
Asp Asp Cys Cys Gly Gly Lys Gly Arg Gly Ala Cys Tyr Gly Pro Gln
            20                  25                  30
Cys Leu Cys Arg
        35

<210> SEQ ID NO 272
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Ala Cys Ala Pro Cys Phe Thr Thr Asp His Gln Ala Ala Arg Lys Cys
1               5                   10                  15
Asp Asp Cys Cys Gly Gly Ala Gly Arg Gly Ala Cys Tyr Gly Pro Gln
            20                  25                  30
Cys Leu Cys Arg
        35

<210> SEQ ID NO 273
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Ala Cys Ala Pro Cys Phe Thr Thr Asp His Gln Ala Ala Arg Ala Cys
1               5                   10                  15
Asp Asp Cys Cys Gly Gly Ala Gly Arg Gly Ala Cys Tyr Gly Pro Gln
            20                  25                  30
Cys Leu Cys Arg
        35

<210> SEQ ID NO 274
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Ala Cys Ala Pro Cys Phe Thr Thr Asp His Gln Ala Ala Arg Arg Cys
1               5                   10                  15
Asp Asp Cys Cys Gly Gly Ala Gly Arg Gly Ala Cys Tyr Gly Pro Gln
            20                  25                  30
Cys Leu Cys Arg
        35

<210> SEQ ID NO 275
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Ala Cys Ala Pro Cys Phe Thr Thr Asp His Gln Ala Ala Arg Lys Cys
1               5                   10                  15
Asp Asp Cys Cys Gly Gly Arg Gly Arg Gly Ala Cys Tyr Gly Pro Gln
            20                  25                  30
Cys Leu Cys Arg
        35

<210> SEQ ID NO 276
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Ala Cys Ala Pro Cys Phe Thr Thr Asp His Gln Ala Ala Arg Ala Cys
1               5                   10                  15
Asp Asp Cys Cys Gly Gly Arg Gly Arg Gly Ala Cys Tyr Gly Pro Gln
            20                  25                  30
Cys Leu Cys Arg
        35

<210> SEQ ID NO 277
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Ala Cys Ala Pro Cys Phe Thr Thr Asp His Gln Ala Ala Arg Arg Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 278
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Ala Cys Ala Pro Cys Phe Thr Thr Asp His Gln Ala Ala Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 279
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Ala Cys Ala Pro Cys Phe Thr Thr Asp His Gln Ala Ala Arg Ala Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 280
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Ala Cys Ala Pro Cys Phe Thr Thr Asp His Gln Ala Ala Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg
        35
```

```
<210> SEQ ID NO 281
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Ala Cys Ala Pro Cys Phe Thr Thr Asp His Gln Ala Ala Arg Lys Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 282
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Ala Cys Ala Pro Cys Phe Thr Thr Asp His Gln Ala Ala Arg Ala Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 283
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Ala Cys Ala Pro Cys Phe Thr Thr Asp His Gln Ala Ala Arg Arg Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 284
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Ala Cys Ala Pro Cys Phe Thr Thr Asp His Gln Ala Ala Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg
        35
```

<210> SEQ ID NO 285
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Ala Cys Ala Pro Cys Phe Thr Thr Asp His Gln Ala Ala Arg Ala Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 286
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Ala Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 287
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Ala Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 288
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Lys Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 289
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Ala Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 290
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Lys Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 291
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 291

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 292
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES

```
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 292

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 293
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 293

Lys Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 294
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 294

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Lys Cys Tyr Gly Pro Gln
            20                  25                  30
```

Cys Leu Cys Arg
        35

<210> SEQ ID NO 295
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 295

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 296
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 296

Lys Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 297
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Ile Cys Ile Pro Cys Phe Thr Thr Asp His Gln Ile Ala Arg Lys Cys

```
                1               5                  10                  15
Asp Asp Cys Cys Gly Gly Lys Gly Arg Gly Lys Cys Tyr Gly Pro Gln
                20                  25                  30

Cys Leu Cys Arg
        35

<210> SEQ ID NO 298
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Ile Cys Ile Pro Cys Phe Thr Thr Asp His Gln Ile Ala Arg Ala Cys
1               5                  10                  15

Asp Asp Cys Cys Gly Gly Lys Gly Arg Gly Lys Cys Tyr Gly Pro Gln
                20                  25                  30

Cys Leu Cys Arg
        35

<210> SEQ ID NO 299
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Ile Cys Ile Pro Cys Phe Thr Thr Asp His Gln Ile Ala Arg Arg Cys
1               5                  10                  15

Asp Asp Cys Cys Gly Gly Lys Gly Arg Gly Lys Cys Tyr Gly Pro Gln
                20                  25                  30

Cys Leu Cys Arg
        35

<210> SEQ ID NO 300
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Ile Cys Ile Pro Cys Phe Thr Thr Asp His Gln Ile Ala Arg Lys Cys
1               5                  10                  15

Asp Asp Cys Cys Gly Gly Ala Gly Arg Gly Lys Cys Tyr Gly Pro Gln
                20                  25                  30

Cys Leu Cys Arg
        35

<210> SEQ ID NO 301
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301
```

Ile Cys Ile Pro Cys Phe Thr Thr Asp His Gln Ile Ala Arg Ala Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 302
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Ile Cys Ile Pro Cys Phe Thr Thr Asp His Gln Ile Ala Arg Arg Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 303
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Ile Cys Ile Pro Cys Phe Thr Thr Asp His Gln Ile Ala Arg Lys Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 304
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Ile Cys Ile Pro Cys Phe Thr Thr Asp His Gln Ile Ala Arg Ala Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 305
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

```
Ile Cys Ile Pro Cys Phe Thr Thr Asp His Gln Ile Ala Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 306
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Ile Cys Ile Pro Cys Phe Thr Thr Asp His Gln Ile Ala Arg Lys Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 307
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Ile Cys Ile Pro Cys Phe Thr Thr Asp His Gln Ile Ala Arg Ala Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 308
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Ile Cys Ile Pro Cys Phe Thr Thr Asp His Gln Ile Ala Arg Arg Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 309
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 309

Ile Cys Ile Pro Cys Phe Thr Thr Asp His Gln Ile Ala Arg Lys Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 310
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Ile Cys Ile Pro Cys Phe Thr Thr Asp His Gln Ile Ala Arg Ala Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 311
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Ile Cys Ile Pro Cys Phe Thr Thr Asp His Gln Ile Ala Arg Arg Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 312
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Ile Cys Ile Pro Cys Phe Thr Thr Asp His Gln Ile Ala Arg Lys Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 313
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 313

Ile Cys Ile Pro Cys Phe Thr Thr Asp His Gln Ile Ala Arg Ala Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 314
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Ile Cys Ile Pro Cys Phe Thr Thr Asp His Gln Ile Ala Arg Arg Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 315
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Ile Cys Ile Pro Cys Phe Thr Thr Asp His Gln Ile Ala Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 316
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Ile Cys Ile Pro Cys Phe Thr Thr Asp His Gln Ile Ala Arg Ala Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 317
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 317

Ile Cys Ile Pro Cys Phe Thr Thr Asp His Gln Ile Ala Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 318
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Ile Cys Ile Pro Cys Phe Thr Thr Asp His Gln Ile Ala Arg Lys Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 319
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Ile Cys Ile Pro Cys Phe Thr Thr Asp His Gln Ile Ala Arg Ala Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 320
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Ile Cys Ile Pro Cys Phe Thr Thr Asp His Gln Ile Ala Arg Arg Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 321
<211> LENGTH: 36
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 321

Ile Cys Ile Pro Cys Phe Thr Thr Asp His Gln Ile Ala Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 322
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Ile Cys Ile Pro Cys Phe Thr Thr Asp His Gln Ile Ala Arg Ala Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 323
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Ile Cys Ile Pro Cys Phe Thr Thr Asp His Gln Ile Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 324
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Ile Cys Ile Pro Cys Phe Thr Thr Asp His Gln Ile Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 325
<211> LENGTH: 36
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 325

Lys Cys Ile Pro Cys Phe Thr Thr Asp His Gln Ile Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 326
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Ala Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 327
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Lys Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 328
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 328

Ile Cys Ile Pro Cys Phe Thr Thr Asp His Gln Ile Ala Arg Xaa Cys
1               5                   10                  15

Asp Asp Cys Cys Gly Gly Xaa Gly Arg Gly Lys Cys Tyr Gly Pro Gln
            20                  25                  30
```

Cys Leu Cys Arg
        35

<210> SEQ ID NO 329
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 329

Ile Cys Ile Pro Cys Phe Thr Thr Asp His Gln Ile Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 330
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 330

Lys Cys Ile Pro Cys Phe Thr Thr Asp His Gln Ile Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 331
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)

<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 331

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 332
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 332

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 333
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 333

Lys Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg

```
<210> SEQ ID NO 334
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Thr Cys Thr Pro Cys Phe Thr Thr Asp His Gln Thr Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 335
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Thr Cys Thr Pro Cys Phe Thr Thr Asp His Gln Thr Ala Arg Ala Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 336
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Thr Cys Thr Pro Cys Phe Thr Thr Asp His Gln Thr Ala Arg Arg Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 337
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Thr Cys Thr Pro Cys Phe Thr Thr Asp His Gln Thr Ala Arg Lys Cys
1               5                   10                  15

Asp Asp Cys Cys Gly Gly Ala Gly Arg Gly Lys Cys Tyr Gly Pro Gln
            20                  25                  30
```

Cys Leu Cys Arg
        35

<210> SEQ ID NO 338
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Thr Cys Thr Pro Cys Phe Thr Thr Asp His Gln Thr Ala Arg Ala Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 339
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Thr Cys Thr Pro Cys Phe Thr Thr Asp His Gln Thr Ala Arg Arg Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 340
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Thr Cys Thr Pro Cys Phe Thr Thr Asp His Gln Thr Ala Arg Lys Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 341
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Thr Cys Thr Pro Cys Phe Thr Thr Asp His Gln Thr Ala Arg Ala Cys
1               5                   10                  15

Asp Asp Cys Cys Gly Gly Arg Gly Arg Gly Lys Cys Tyr Gly Pro Gln
            20                  25                  30

```
Cys Leu Cys Arg
        35

<210> SEQ ID NO 342
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Thr Cys Thr Pro Cys Phe Thr Thr Asp His Gln Thr Ala Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 343
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Thr Cys Thr Pro Cys Phe Thr Thr Asp His Gln Thr Ala Arg Lys Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 344
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Thr Cys Thr Pro Cys Phe Thr Thr Asp His Gln Thr Ala Arg Ala Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 345
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Thr Cys Thr Pro Cys Phe Thr Thr Asp His Gln Thr Ala Arg Arg Cys
1               5                   10                  15

Asp Asp Cys Cys Gly Gly Lys Gly Arg Gly Ala Cys Tyr Gly Pro Gln
```

```
                  20                  25                  30

Cys Leu Cys Arg
         35

<210> SEQ ID NO 346
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Thr Cys Thr Pro Cys Phe Thr Thr Asp His Gln Thr Ala Arg Lys Cys
1               5                   10                  15

Asp Asp Cys Cys Gly Gly Ala Gly Arg Gly Ala Cys Tyr Gly Pro Gln
            20                  25                  30

Cys Leu Cys Arg
         35

<210> SEQ ID NO 347
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Thr Cys Thr Pro Cys Phe Thr Thr Asp His Gln Thr Ala Arg Ala Cys
1               5                   10                  15

Asp Asp Cys Cys Gly Gly Ala Gly Arg Gly Ala Cys Tyr Gly Pro Gln
            20                  25                  30

Cys Leu Cys Arg
         35

<210> SEQ ID NO 348
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Thr Cys Thr Pro Cys Phe Thr Thr Asp His Gln Thr Ala Arg Arg Cys
1               5                   10                  15

Asp Asp Cys Cys Gly Gly Ala Gly Arg Gly Ala Cys Tyr Gly Pro Gln
            20                  25                  30

Cys Leu Cys Arg
         35

<210> SEQ ID NO 349
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Thr Cys Thr Pro Cys Phe Thr Thr Asp His Gln Thr Ala Arg Lys Cys
1               5                   10                  15
```

Asp Asp Cys Cys Gly Gly Arg Gly Arg Gly Ala Cys Tyr Gly Pro Gln
            20                  25                  30

Cys Leu Cys Arg
        35

<210> SEQ ID NO 350
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Thr Cys Thr Pro Cys Phe Thr Thr Asp His Gln Thr Ala Arg Ala Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 351
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Thr Cys Thr Pro Cys Phe Thr Thr Asp His Gln Thr Ala Arg Arg Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 352
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Thr Cys Thr Pro Cys Phe Thr Thr Asp His Gln Thr Ala Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 353
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Thr Cys Thr Pro Cys Phe Thr Thr Asp His Gln Thr Ala Arg Ala Cys
1               5                   10                  15

```
Asp Asp Cys Cys Gly Gly Lys Gly Arg Gly Arg Cys Tyr Gly Pro Gln
            20                  25                  30

Cys Leu Cys Arg
        35

<210> SEQ ID NO 354
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Thr Cys Thr Pro Cys Phe Thr Thr Asp His Gln Thr Ala Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 355
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Thr Cys Thr Pro Cys Phe Thr Thr Asp His Gln Thr Ala Arg Lys Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 356
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Thr Cys Thr Pro Cys Phe Thr Thr Asp His Gln Thr Ala Arg Ala Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 357
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Thr Cys Thr Pro Cys Phe Thr Thr Asp His Gln Thr Ala Arg Arg Cys
```

```
                1               5                   10                  15
Asp Asp Cys Cys Gly Gly Ala Gly Arg Gly Arg Cys Tyr Gly Pro Gln
                        20                  25                  30

Cys Leu Cys Arg
            35

<210> SEQ ID NO 358
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Thr Cys Thr Pro Cys Phe Thr Thr Asp His Gln Thr Ala Arg Lys Cys
1               5                   10                  15

Asp Asp Cys Cys Gly Gly Arg Gly Arg Gly Arg Cys Tyr Gly Pro Gln
                        20                  25                  30

Cys Leu Cys Arg
            35

<210> SEQ ID NO 359
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Thr Cys Thr Pro Cys Phe Thr Thr Asp His Gln Thr Ala Arg Ala Cys
1               5                   10                  15

Asp Asp Cys Cys Gly Gly Arg Gly Arg Gly Arg Cys Tyr Gly Pro Gln
                        20                  25                  30

Cys Leu Cys Arg
            35

<210> SEQ ID NO 360
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Thr Cys Thr Pro Cys Phe Thr Thr Asp His Gln Thr Ala Arg Arg Cys
1               5                   10                  15

Asp Asp Cys Cys Gly Gly Arg Gly Arg Gly Arg Cys Tyr Gly Pro Gln
                        20                  25                  30

Cys Leu Cys Arg
            35

<210> SEQ ID NO 361
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361
```

Thr Cys Thr Pro Cys Phe Thr Thr Asp His Gln Thr Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 362
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

Lys Cys Thr Pro Cys Phe Thr Thr Asp His Gln Thr Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 363
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Ala Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 364
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Lys Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 365
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES

```
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 365

Thr Cys Thr Pro Cys Phe Thr Thr Asp His Gln Thr Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 366
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 366

Thr Cys Thr Pro Cys Phe Thr Thr Asp His Gln Thr Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 367
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 367

Lys Cys Thr Pro Cys Phe Thr Thr Asp His Gln Thr Ala Arg Xaa Cys
1               5                   10                  15

Asp Asp Cys Cys Gly Gly Xaa Gly Arg Gly Xaa Cys Tyr Gly Pro Gln
            20                  25                  30
```

Cys Leu Cys Arg
        35

<210> SEQ ID NO 368
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 368

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 369
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 369

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 370
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

```
<220> FEATURE:
<221> NAME/KEY: MOD_RES
<222> LOCATION: (27)..(27)
<223> OTHER INFORMATION: Citrulline

<400> SEQUENCE: 370

Lys Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
            35

<210> SEQ ID NO 371
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Val Cys Val Pro Cys Phe Thr Thr Asp His Gln Val Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
            35

<210> SEQ ID NO 372
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

Val Cys Val Pro Cys Phe Thr Thr Asp His Gln Val Ala Arg Ala Cys
1               5                   10                  15

Asp Asp Cys Cys Gly Gly Lys Gly Arg Gly Lys Cys Tyr Gly Pro Gln
            20                  25                  30

Cys Leu Cys Arg
            35

<210> SEQ ID NO 373
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Val Cys Val Pro Cys Phe Thr Thr Asp His Gln Val Ala Arg Arg Cys
1               5                   10                  15

Asp Asp Cys Cys Gly Gly Lys Gly Arg Gly Lys Cys Tyr Gly Pro Gln
            20                  25                  30

Cys Leu Cys Arg
            35

<210> SEQ ID NO 374
<211> LENGTH: 36
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

Val Cys Val Pro Cys Phe Thr Thr Asp His Gln Val Ala Arg Lys Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 375
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Val Cys Val Pro Cys Phe Thr Thr Asp His Gln Val Ala Arg Ala Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 376
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Val Cys Val Pro Cys Phe Thr Thr Asp His Gln Val Ala Arg Arg Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 377
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Val Cys Val Pro Cys Phe Thr Thr Asp His Gln Val Ala Arg Lys Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 378

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Val Cys Val Pro Cys Phe Thr Thr Asp His Gln Val Ala Arg Ala Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 379
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Val Cys Val Pro Cys Phe Thr Thr Asp His Gln Val Ala Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 380
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Val Cys Val Pro Cys Phe Thr Thr Asp His Gln Val Ala Arg Lys Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 381
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Val Cys Val Pro Cys Phe Thr Thr Asp His Gln Val Ala Arg Ala Cys
1               5                   10                  15

Asp Asp Cys Cys Gly Gly Lys Gly Arg Gly Ala Cys Tyr Gly Pro Gln
            20                  25                  30

Cys Leu Cys Arg
        35
```

```
<210> SEQ ID NO 382
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382

Val Cys Val Pro Cys Phe Thr Thr Asp His Gln Val Ala Arg Arg Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 383
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 383

Val Cys Val Pro Cys Phe Thr Thr Asp His Gln Val Ala Arg Lys Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 384
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384

Val Cys Val Pro Cys Phe Thr Thr Asp His Gln Val Ala Arg Ala Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 385
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

Val Cys Val Pro Cys Phe Thr Thr Asp His Gln Val Ala Arg Arg Cys
1               5                   10                  15

Asp Asp Cys Cys Gly Gly Ala Gly Arg Gly Ala Cys Tyr Gly Pro Gln
            20                  25                  30

Cys Leu Cys Arg
        35
```

<210> SEQ ID NO 386
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 386

Val Cys Val Pro Cys Phe Thr Thr Asp His Gln Val Ala Arg Lys Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 387
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387

Val Cys Val Pro Cys Phe Thr Thr Asp His Gln Val Ala Arg Ala Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 388
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 388

Val Cys Val Pro Cys Phe Thr Thr Asp His Gln Val Ala Arg Arg Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 389
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Val Cys Val Pro Cys Phe Thr Thr Asp His Gln Val Ala Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg
        35

```
<210> SEQ ID NO 390
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 390

Val Cys Val Pro Cys Phe Thr Thr Asp His Gln Val Ala Arg Ala Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 391
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

Val Cys Val Pro Cys Phe Thr Thr Asp His Gln Val Ala Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 392
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 392

Val Cys Val Pro Cys Phe Thr Thr Asp His Gln Val Ala Arg Lys Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 393
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

Val Cys Val Pro Cys Phe Thr Thr Asp His Gln Val Ala Arg Ala Cys
1               5                   10                  15

Asp Asp Cys Cys Gly Gly Ala Gly Arg Gly Arg Cys Tyr Gly Pro Gln
            20                  25                  30

Cys Leu Cys Arg
```

35

<210> SEQ ID NO 394
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 394

Val Cys Val Pro Cys Phe Thr Thr Asp His Gln Val Ala Arg Arg Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 395
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

Val Cys Val Pro Cys Phe Thr Thr Asp His Gln Val Ala Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 396
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Val Cys Val Pro Cys Phe Thr Thr Asp His Gln Val Ala Arg Ala Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 397
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Val Cys Val Pro Cys Phe Thr Thr Asp His Gln Val Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 398
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

Val Cys Val Pro Cys Phe Thr Thr Asp His Gln Val Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 399
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

Lys Cys Val Pro Cys Phe Thr Thr Asp His Gln Val Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 400
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Ala Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 401
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Lys Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

```
Cys Leu Cys Arg
        35

<210> SEQ ID NO 402
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 402

Val Cys Val Pro Cys Phe Thr Thr Asp His Gln Val Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 403
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 403

Val Cys Val Pro Cys Phe Thr Thr Asp His Gln Val Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 404
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
```

```
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 404

Lys Cys Val Pro Cys Phe Thr Thr Asp His Gln Val Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 405
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 405

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 406
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 406

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 407
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 407

Lys Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 408
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Leu Cys Leu Pro Cys Phe Thr Thr Asp His Gln Leu Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 409
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Leu Cys Leu Pro Cys Phe Thr Thr Asp His Gln Leu Ala Arg Ala Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 410
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 410

Leu Cys Leu Pro Cys Phe Thr Thr Asp His Gln Leu Ala Arg Arg Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 411
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Leu Cys Leu Pro Cys Phe Thr Thr Asp His Gln Leu Ala Arg Lys Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 412
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Leu Cys Leu Pro Cys Phe Thr Thr Asp His Gln Leu Ala Arg Ala Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 413
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Leu Cys Leu Pro Cys Phe Thr Thr Asp His Gln Leu Ala Arg Arg Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 414
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 414

Leu Cys Leu Pro Cys Phe Thr Thr Asp His Gln Leu Ala Arg Lys Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 415
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Leu Cys Leu Pro Cys Phe Thr Thr Asp His Gln Leu Ala Arg Ala Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 416
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

Leu Cys Leu Pro Cys Phe Thr Thr Asp His Gln Leu Ala Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 417
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Leu Cys Leu Pro Cys Phe Thr Thr Asp His Gln Leu Ala Arg Lys Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 418
<211> LENGTH: 36
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 418

Leu Cys Leu Pro Cys Phe Thr Thr Asp His Gln Leu Ala Arg Ala Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 419
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Leu Cys Leu Pro Cys Phe Thr Thr Asp His Gln Leu Ala Arg Arg Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 420
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Leu Cys Leu Pro Cys Phe Thr Thr Asp His Gln Leu Ala Arg Lys Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 421
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Leu Cys Leu Pro Cys Phe Thr Thr Asp His Gln Leu Ala Arg Ala Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 422
<211> LENGTH: 36
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 422

Leu Cys Leu Pro Cys Phe Thr Thr Asp His Gln Leu Ala Arg Arg Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 423
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 423

Leu Cys Leu Pro Cys Phe Thr Thr Asp His Gln Leu Ala Arg Lys Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 424
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 424

Leu Cys Leu Pro Cys Phe Thr Thr Asp His Gln Leu Ala Arg Ala Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 425
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 425

Leu Cys Leu Pro Cys Phe Thr Thr Asp His Gln Leu Ala Arg Arg Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 426
<211> LENGTH: 36
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 426

Leu Cys Leu Pro Cys Phe Thr Thr Asp His Gln Leu Ala Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 427
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Leu Cys Leu Pro Cys Phe Thr Thr Asp His Gln Leu Ala Arg Ala Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 428
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Leu Cys Leu Pro Cys Phe Thr Thr Asp His Gln Leu Ala Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 429
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

Leu Cys Leu Pro Cys Phe Thr Thr Asp His Gln Leu Ala Arg Lys Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 430
<211> LENGTH: 36
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 430

Leu Cys Leu Pro Cys Phe Thr Thr Asp His Gln Leu Ala Arg Ala Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 431
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

Leu Cys Leu Pro Cys Phe Thr Thr Asp His Gln Leu Ala Arg Arg Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 432
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 432

Leu Cys Leu Pro Cys Phe Thr Thr Asp His Gln Leu Ala Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 433
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 433

Leu Cys Leu Pro Cys Phe Thr Thr Asp His Gln Leu Ala Arg Ala Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 434
<211> LENGTH: 36

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Leu Cys Leu Pro Cys Phe Thr Thr Asp His Gln Leu Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 435
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

Leu Cys Leu Pro Cys Phe Thr Thr Asp His Gln Leu Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 436
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 436

Lys Cys Leu Pro Cys Phe Thr Thr Asp His Gln Leu Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 437
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Ala Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 438
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

Lys Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 439
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 439

Leu Cys Leu Pro Cys Phe Thr Thr Asp His Gln Leu Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 440
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 440

Leu Cys Leu Pro Cys Phe Thr Thr Asp His Gln Leu Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35
```

```
<210> SEQ ID NO 441
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 441

Lys Cys Leu Pro Cys Phe Thr Thr Asp His Gln Leu Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 442
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 442

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 443
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline
```

<400> SEQUENCE: 443

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 444
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 444

Lys Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 445
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 445

Ser Cys Ser Pro Cys Phe Thr Thr Asp His Gln Ser Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 446
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Ser Cys Ser Pro Cys Phe Thr Thr Asp His Gln Ser Ala Arg Ala Cys
1               5                   10                  15

Asp Asp Cys Cys Gly Gly Lys Gly Arg Gly Lys Cys Tyr Gly Pro Gln

```
            20                  25                  30

Cys Leu Cys Arg
        35

<210> SEQ ID NO 447
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Ser Cys Ser Pro Cys Phe Thr Thr Asp His Gln Ser Ala Arg Arg Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 448
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Ser Cys Ser Pro Cys Phe Thr Thr Asp His Gln Ser Ala Arg Lys Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 449
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Ser Cys Ser Pro Cys Phe Thr Thr Asp His Gln Ser Ala Arg Ala Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 450
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Ser Cys Ser Pro Cys Phe Thr Thr Asp His Gln Ser Ala Arg Arg Cys
1               5                   10                  15
```

Asp Asp Cys Cys Gly Gly Ala Gly Arg Gly Lys Cys Tyr Gly Pro Gln
            20                  25                  30

Cys Leu Cys Arg
        35

<210> SEQ ID NO 451
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Ser Cys Ser Pro Cys Phe Thr Thr Asp His Gln Ser Ala Arg Lys Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 452
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Ser Cys Ser Pro Cys Phe Thr Thr Asp His Gln Ser Ala Arg Ala Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 453
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Ser Cys Ser Pro Cys Phe Thr Thr Asp His Gln Ser Ala Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg
        35

<210> SEQ ID NO 454
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Ser Cys Ser Pro Cys Phe Thr Thr Asp His Gln Ser Ala Arg Lys Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 455
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Ser Cys Ser Pro Cys Phe Thr Thr Asp His Gln Ser Ala Arg Ala Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 456
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Ser Cys Ser Pro Cys Phe Thr Thr Asp His Gln Ser Ala Arg Arg Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 457
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Ser Cys Ser Pro Cys Phe Thr Thr Asp His Gln Ser Ala Arg Lys Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 458
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Ser Cys Ser Pro Cys Phe Thr Thr Asp His Gln Ser Ala Arg Ala Cys

-continued

```
                1               5                  10                  15
Asp Asp Cys Cys Gly Gly Ala Gly Arg Gly Ala Cys Tyr Gly Pro Gln
                        20                  25                  30

Cys Leu Cys Arg
            35

<210> SEQ ID NO 459
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Ser Cys Ser Pro Cys Phe Thr Thr Asp His Gln Ser Ala Arg Arg Cys
1               5                  10                  15

Asp Asp Cys Cys Gly Gly Ala Gly Arg Gly Ala Cys Tyr Gly Pro Gln
                        20                  25                  30

Cys Leu Cys Arg
            35

<210> SEQ ID NO 460
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

Ser Cys Ser Pro Cys Phe Thr Thr Asp His Gln Ser Ala Arg Lys Cys
1               5                  10                  15

Asp Asp Cys Cys Gly Gly Arg Gly Arg Gly Ala Cys Tyr Gly Pro Gln
                        20                  25                  30

Cys Leu Cys Arg
            35

<210> SEQ ID NO 461
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Ser Cys Ser Pro Cys Phe Thr Thr Asp His Gln Ser Ala Arg Ala Cys
1               5                  10                  15

Asp Asp Cys Cys Gly Gly Arg Gly Arg Gly Ala Cys Tyr Gly Pro Gln
                        20                  25                  30

Cys Leu Cys Arg
            35

<210> SEQ ID NO 462
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462
```

Ser Cys Ser Pro Cys Phe Thr Thr Asp His Gln Ser Ala Arg Arg Cys
1               5                   10                  15

Asp Asp Cys Cys Gly Gly Arg Gly Arg Gly Ala Cys Tyr Gly Pro Gln
            20                  25                  30

Cys Leu Cys Arg
        35

<210> SEQ ID NO 463
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

Ser Cys Ser Pro Cys Phe Thr Thr Asp His Gln Ser Ala Arg Lys Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 464
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 464

Ser Cys Ser Pro Cys Phe Thr Thr Asp His Gln Ser Ala Arg Ala Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 465
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465

Ser Cys Ser Pro Cys Phe Thr Thr Asp His Gln Ser Ala Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg
        35

<210> SEQ ID NO 466
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 466

Ser Cys Ser Pro Cys Phe Thr Thr Asp His Gln Ser Ala Arg Lys Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 467
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

Ser Cys Ser Pro Cys Phe Thr Thr Asp His Gln Ser Ala Arg Ala Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 468
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

Ser Cys Ser Pro Cys Phe Thr Thr Asp His Gln Ser Ala Arg Arg Cys
1               5                   10                  15

Asp Asp Cys Cys Gly Gly Ala Gly Arg Gly Arg Cys Tyr Gly Pro Gln
            20                  25                  30

Cys Leu Cys Arg
        35

<210> SEQ ID NO 469
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469

Ser Cys Ser Pro Cys Phe Thr Thr Asp His Gln Ser Ala Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 470
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 470

Ser Cys Ser Pro Cys Phe Thr Thr Asp His Gln Ser Ala Arg Ala Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 471
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

Ser Cys Ser Pro Cys Phe Thr Thr Asp His Gln Ser Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 472
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

Ser Cys Ser Pro Cys Phe Thr Thr Asp His Gln Ser Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 473
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

Lys Cys Ser Pro Cys Phe Thr Thr Asp His Gln Ser Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 474
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 474

Ala Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 475
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

Lys Cys Ala Pro Cys Phe Thr Thr Asp His Gln Ala Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 476
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 476

Ser Cys Ser Pro Cys Phe Thr Thr Asp His Gln Ser Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 477
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
```

```
<223> OTHER INFORMATION: Citrulline

<400> SEQUENCE: 477

Ser Cys Ser Pro Cys Phe Thr Thr Asp His Gln Ser Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 478
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 478

Lys Cys Ser Pro Cys Phe Thr Thr Asp His Gln Ser Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 479
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline

<400> SEQUENCE: 479

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Lys Cys Tyr Gly Pro Gln
            20                  25                  30

Cys Leu Cys Arg
        35

<210> SEQ ID NO 480
<211> LENGTH: 36
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 480

Ala Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 481
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (27)..(27)
<223> OTHER INFORMATION: Citrulline

<400> SEQUENCE: 481

Lys Cys Ala Pro Cys Phe Thr Thr Asp His Gln Ala Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 482
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (27)..(27)
<223> OTHER INFORMATION: Any amino acid
```

<400> SEQUENCE: 482

Met Cys Met Pro Cys Phe Thr Thr Asp His Gln Met Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 483
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys, Ala or Arg
<220> FEATURE:
<221> NAME/KEY: MOD_RES
<222> LOCATION: (23)..(23)
<223> OTHER INFORMATION: Lys, Ala or Arg
<220> FEATURE:
<221> NAME/KEY: MOD_RES
<222> LOCATION: (27)..(27)
<223> OTHER INFORMATION: Lys, Ala or Arg

<400> SEQUENCE: 483

Met Cys Met Pro Cys Phe Thr Thr Asp His Gln Met Ala Arg Xaa Cys
1               5                   10                  15

Asp Asp Cys Cys Gly Gly Xaa Gly Arg Gly Xaa Cys Tyr Gly Pro Gln
            20                  25                  30

Cys Leu Cys Arg
        35

<210> SEQ ID NO 484
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Ala or Arg
<220> FEATURE:
<221> NAME/KEY: MOD_RES
<222> LOCATION: (23)..(23)
<223> OTHER INFORMATION: Ala or Arg
<220> FEATURE:
<221> NAME/KEY: MOD_RES
<222> LOCATION: (27)..(27)
<223> OTHER INFORMATION: Ala or Arg

```
<400> SEQUENCE: 484

Met Cys Met Pro Cys Phe Thr Thr Asp His Gln Met Ala Arg Xaa Cys
1               5                   10                  15

Asp Asp Cys Cys Gly Gly Xaa Gly Arg Gly Xaa Cys Tyr Gly Pro Gln
                20                  25                  30

Cys Leu Cys Arg
            35

<210> SEQ ID NO 485
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Ala or Arg
<220> FEATURE:
<221> NAME/KEY: MOD_RES
<222> LOCATION: (23)..(23)
<223> OTHER INFORMATION: Ala or Arg

<400> SEQUENCE: 485

Met Cys Met Pro Cys Phe Thr Thr Asp His Gln Met Ala Arg Xaa Cys
1               5                   10                  15

Asp Asp Cys Cys Gly Gly Xaa Gly Arg Gly Lys Cys Tyr Gly Pro Gln
                20                  25                  30

Cys Leu Cys Arg
            35
```